US011536724B2

(12) United States Patent
Garin et al.

(10) Patent No.: US 11,536,724 B2
(45) Date of Patent: Dec. 27, 2022

(54) BLADDER CANCER BIOMARKER PROTEINS

(71) Applicants: Polyquant GmbH, Bad Abbach (DE); COMMISSARIAT A L'ENERGIE ATOMIQUE ET AUX ENERGIES ALTERNATIVES, Paris (FR); BIOMEDICAL RESEARCH FOUNDATION OF THE ACADEMY OF ATHENS, Athens (GR); LUXEMBOURG INSTITUTE OF HEALTH, Luxembourg (LU); INSTITUT CURIE, Paris (FR); ASSISTANCE PUBLIQUE—HOPITAUX DE PARIS, Paris (FR); FUNDACION CENTRO NACIONAL DE INVESTIGACIONES ONCOLOGICAS CARLOS III, CNIO, Madrid (ES)

(72) Inventors: Jerome Garin, Paris (FR); Christophe Masselon, Paris (FR); Antonia Vlahou, Athens (GR); Manousos Makrydakis, Athens (GR); Ieronimos Zoidakis, Athens (GR); Bruno Domon, Luxembourg (LU); Elodie Duriez, Luxembourg (LU); Aurelie Kamoun, Paris (FR); Francois Radvanyi, Paris (FR); Yves Allory, Paris (FR); Nuria Malats Riera, Madrid (ES); Mirari Marquez Cid, Madrid (ES); Magali Court, Paris (FR)

(73) Assignees: POLYQUANT GMBH, Bad Abbach (DE); COMMISSARIAT A L'ENERGIE ATOMIQUE ET AUX ENERGIES ALTERNATIVES, Paris (FR); BIOMEDICAL RESEARCH FOUNDATION OF THE ACADEMY OF ATHENS, Athens (GR); LUXEMBOURG INSTITUTE OF HEALTH, Luxembourg (LU); INSTITUT CURIE, Paris (FR); ASSISTANCE PUBLIQUE—HOPITAUX DE PARIS, Paris (FR); FUNDACION CENTRO NACIONAL DE INVESTIGACIONES ONCOLOGICAS CARLOS III, CNIO, Madrid (ES)

( * ) Notice: Subject to any disclaimer, the term of this patent is extended or adjusted under 35 U.S.C. 154(b) by 363 days.

(21) Appl. No.: 16/065,663

(22) PCT Filed: Dec. 23, 2016

(86) PCT No.: PCT/EP2016/082558
§ 371 (c)(1),
(2) Date: Jun. 22, 2018

(87) PCT Pub. No.: WO2017/109171
PCT Pub. Date: Jun. 29, 2017

(65) Prior Publication Data
US 2018/0372754 A1    Dec. 27, 2018

(30) Foreign Application Priority Data
Dec. 23, 2015   (EP) .................................... 15202453

(51) Int. Cl.
| *G01N 31/00* | (2006.01) |
| *G01N 33/53* | (2006.01) |
| *G01N 33/68* | (2006.01) |
| *C07K 7/08* | (2006.01) |
| *G01N 33/574* | (2006.01) |

(Continued)

(52) U.S. Cl.
CPC ........... *G01N 33/6848* (2013.01); *C07K 7/08* (2013.01); *C07K 14/54* (2013.01); *C07K 16/30* (2013.01); *G01N 33/57407* (2013.01); *G01N 2800/52* (2013.01); *G01N 2800/56* (2013.01); *G01N 2800/60* (2013.01); *G01N 2800/7028* (2013.01)

(58) Field of Classification Search
None
See application file for complete search history.

(56) References Cited

FOREIGN PATENT DOCUMENTS

WO    2008134526 A2    11/2008

OTHER PUBLICATIONS

Yang et al. (Proteomics, 2011, vol. 8, pp. 832-851). (Year: 2011).*

(Continued)

*Primary Examiner* — Lisa V Cook
(74) *Attorney, Agent, or Firm* — Viksnins Harris Padys Malen LLP

(57) ABSTRACT

The invention relates to a collection of signature peptides representing at least 10 proteins for use in cancer diagnosis and/or prognosis, to an artificial protein comprising signature peptides representing at least 10 proteins and to a nucleic acid construct encoding for such an artificial protein. The invention further relates to a collection of at least 10 proteins for use in cancer diagnosis and/or prognosis. Additionally, the invention relates to a method for cancer diagnosis and/or prognosis comprising the step of analyzing at least 10 proteins in a urine sample of a subject. Finally, the invention relates to an immunoassay product comprising antibodies for detecting at least 10 proteins.

3 Claims, 1 Drawing Sheet
Specification includes a Sequence Listing.

(51) Int. Cl.
C07K 14/54 (2006.01)
C07K 16/30 (2006.01)

(56) References Cited

OTHER PUBLICATIONS

Court et al. (Proteomics, 2011, vol. 11, pp. 1160-1171, IDS filed Jan. 9, 2019, #8) (Year: 2019).*
Scott et al. (Methods in Enzymology, vol. 566, 2016, pp. 289-303, Published online Oct. 21, 2015) (Year: 2015).*
Court et al. (Proteomics, 2011, vol. 11, pp. 1160-1171, IDS filed Jan. 9, 2019, #8) (Year: 2011).*
Kreunin et al. (Journal of Proteome Research, 2007, vol. 6, pp. 2631-2639) (Year: 2007).*
Yang et al. (Proteomics, 2008, vol. 8, pp. 832-851). (Year: 2008).*
Abbatiello, et al., "Automated Detection of Inaccurate and Imprecise Transitions in Peptide Quantification by Multiple Reaction Monitoring Mass Spectrometry", Clin Chem 56(2), 291-305 (2010).
Allory, et al., "The DECanBIO European Project: Novel MS-based strategies to discover and evaluate cancer biomarkers in urine: Application to diagnosis of bladder cancer recurrence", Proteomics Research Unit, Oct. 5, 2010, XP055265687, retrieved from the internet: URL:http:/Avww.decanbio.eu/home/liblocal/docs/doc1/ESUR2010.pdf (retrieved on Apr. 15, 2016).
Babjuk, et al., "EAU Guidelines on Non-Muscle-Invasive Urothelial Carcinoma of the Bladder", European Urology 54, 303-314 (2008).
Carr, et al., "Targeted Peptide Measurements in Biology and Medicine: Best Practices for Mass Spectrometry-based Assay Development Using a Fit-for-Purpose Approach", Molecular & Cellular Proteomics 13.3, 907-917 (2014).
Cham Mead, et al., "Free computational resources for designing selected reaction monitoring transitions", Proteomics 10, 1106-1126 (2010).
Chen, et al., "Comparative and targeted proteomic analyses of urinary microparticles from bladder cancer and hernia patients", Journal of Proteome Reseach 11, 5611-5629 (2012).
Chen, et al., "Multiplexed quantification of 63 proteins in human urine by multiple reaction monitoring-based mass spectrometry for discovery of potential bladder cancer biomarkers", Journal of Proteomics 75, 3529-3545 (2012).
Court, et al., "Toward a standardized urine proteome analysis methodology", Proteomics 11, 1160-1171 (2011).
Duriez, et al., "Protein Quantification Using a Cleavable Reporter Peptide", J Proteome Res 14, 728-737 (2015).
Frantzi, et al., "Developing proteomic biomarkers for bladder cancer: towards clinical application", Nat Rev Urol 12, 317-330 (2015).
Guzman-Rojas, et al., "Cooperative effects of aminopeptidase N (CD13) expressed by nonmalignant and cancer cells within the tumor microenvironment", PNAS 109(5), 1637-1642 (2012).
Holman, et al., "The use of selected reaction monitoring in quantitative proteomics", Bioanalysis 4(14), 1763-1786 (2012).
Jebar, et al., "FGFR3 and Ras gene mutations are mutually exclusive genetic events in urothelial cell carcinoma", Oncogene 24, 5218-5225 (2005).
Jensen, et al., "Expression of the lysosomal-associated membrane protein-1 (LAMP-1) in astrocytomas", Int J Clin Exp Pathol 6(7), 1294-1305 (2013).
Kageyama, et al., "Identification by Proteomic Analysis of Calreticulin as a Marker for Bladder Cancer and Evaluation of the Diagnostic Accuracy of Its Detection in Urine", Clinical Chemistry 50(5), 857-866 (2004).
Kalantari, et al., "Urinary Prognostic Biomarkers and Classification of IgA Nephropathy by High Resolution Mass Spectrometry Coupled with Liquid Chromatography", PLOS One 8(12), e80830, 11 pages (2013).
Linden, et al., "Proteomic analysis of urinary biomarker candidates for nonmuscle invasive bladder cancer", Proteomics 12, 135-144 (2012).
Miyata, et al., "Thrombospondin-1 in Urological Cancer: Pathological Role, Clinical Significance, and Therapeutic Prospects", Int J Mol Sci 14, 12249-12272 (2013).
Ostergaard, et al., "Proteome Profiling of Bladder Squamous Cell Carcinomas: Identification of Markers That Define Their Degree of Differentiation", Cancer Research 57, 4111-4117 (1997).
Patent Cooperation Treaty, International Searching Authority, Search Report and Written Opinion for PCT/EP2016/08258, 13 pages, dated Feb. 22, 2017.
Peterson, et al., "Parallel Reaction Monitoring for High Resolution and High Mass Accuracy Quantitative, Targeted Proteomics", Molecular & Cellular Proteomics 11.11, 1475-1488 (2012).
Pratt, et al., "Multiplexed absolute quantification for proteomics using concatenated signature peptides encoded by QconCAT genes", Nature Protocols 1(2), 1029-1043 (2006).
Welsch, et al., "Eps8 is increased in pancreatic cancer and required for dynamic actin-based cell protrusions and intercellular cytoskeletal organization", Cancer Letters 255, 205-218 (2007).
Yang, et al., "Urinary Glycoprotein Biomarker Discovery for Bladder Cancer Detection Using LC/MS-MS and Label-Free Quantification", Clin Cancer Res 17(10), 3349-3359 (2011).
Zhao, et al., "Applications Of Selected Reaction Monitoring (SRM)-Mass Spectrometry (MS) For Quantitative Measurement Of Signaling Pathways", Methods 61(3), 313-322 (2013).

* cited by examiner

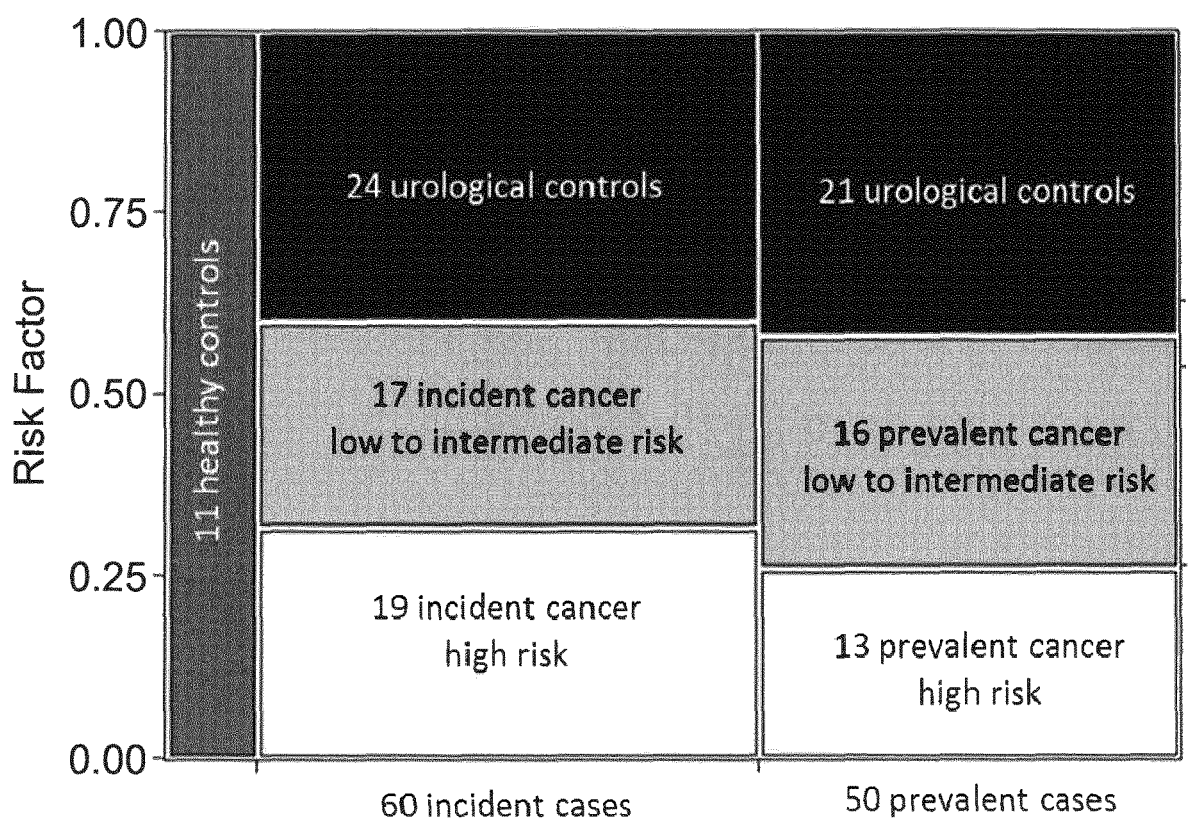

SEQUENCE LISTING

<160> NUMBER OF SEQ ID NOS: 945

<210> SEQ ID NO 1
<211> LENGTH: 10
<212> TYPE: PRT
<213> ORGANISM: Homo sapiens

<400> SEQUENCE: 1

Glu His Val Ala His Leu Leu Phe Leu Arg
1               5                   10

<210> SEQ ID NO 2
<211> LENGTH: 15
<212> TYPE: PRT
<213> ORGANISM: Homo sapiens

<400> SEQUENCE: 2

Asn Trp Gly Leu Ser Phe Tyr Ala Asp Lys Pro Glu Thr Thr Lys
1               5                   10                  15

<210> SEQ ID NO 3
<211> LENGTH: 9
<212> TYPE: PRT
<213> ORGANISM: Homo sapiens

<400> SEQUENCE: 3

Ser Asp Val Met Tyr Thr Asp Trp Lys
1               5

<210> SEQ ID NO 4
<211> LENGTH: 14
<212> TYPE: PRT
<213> ORGANISM: Homo sapiens

<400> SEQUENCE: 4

Ile Thr Pro Asn Leu Ala Glu Phe Ala Phe Ser Leu Tyr Arg
1               5                   10

<210> SEQ ID NO 5
<211> LENGTH: 15
<212> TYPE: PRT
<213> ORGANISM: Homo sapiens

<400> SEQUENCE: 5

Leu Gln His Leu Glu Asn Glu Leu Thr His Asp Ile Ile Thr Lys
1               5                   10                  15

<210> SEQ ID NO 6
<211> LENGTH: 10
<212> TYPE: PRT
<213> ORGANISM: Homo sapiens

<400> SEQUENCE: 6

Leu Ser Ile Thr Gly Thr Tyr Asp Leu Lys
1               5                   10

<210> SEQ ID NO 7
<211> LENGTH: 18
<212> TYPE: PRT
<213> ORGANISM: Homo sapiens

<400> SEQUENCE: 7

Leu Tyr His Ser Glu Ala Phe Thr Val Asn Phe Gly Asp Thr Glu Glu
1               5                   10                  15

Ala Lys

<210> SEQ ID NO 8
<211> LENGTH: 10
<212> TYPE: PRT
<213> ORGANISM: Homo sapiens

<400> SEQUENCE: 8

Ser Val Leu Gly Gln Leu Gly Ile Thr Lys
1               5                   10

<210> SEQ ID NO 9
<211> LENGTH: 11
<212> TYPE: PRT
<213> ORGANISM: Homo sapiens

<400> SEQUENCE: 9

Ala Thr Trp Ser Gly Ala Val Leu Ala Gly Arg
1               5                   10

<210> SEQ ID NO 10
<211> LENGTH: 12
<212> TYPE: PRT
<213> ORGANISM: Homo sapiens

<400> SEQUENCE: 10

His Gln Phe Leu Leu Thr Gly Asp Thr Gln Gly Arg
1               5                   10

<210> SEQ ID NO 11
<211> LENGTH: 10
<212> TYPE: PRT
<213> ORGANISM: Homo sapiens

<400> SEQUENCE: 11

Asp Leu Leu Leu Pro Gln Pro Asp Leu Arg
1               5                   10

<210> SEQ ID NO 12
<211> LENGTH: 9
<212> TYPE: PRT
<213> ORGANISM: Homo sapiens

<400> SEQUENCE: 12

Gly Gln Thr Leu Leu Ala Val Ala Lys
1               5

<210> SEQ ID NO 13
<211> LENGTH: 10
<212> TYPE: PRT
<213> ORGANISM: Homo sapiens

<400> SEQUENCE: 13

Val Ala Ala Gly Ala Phe Gln Gly Leu Arg
1               5                   10

<210> SEQ ID NO 14
<211> LENGTH: 13
<212> TYPE: PRT
<213> ORGANISM: Homo sapiens

<400> SEQUENCE: 14

Leu Val His Val Glu Glu Pro His Thr Glu Thr Val Arg
1               5                   10

<210> SEQ ID NO 15
<211> LENGTH: 12
<212> TYPE: PRT
<213> ORGANISM: Homo sapiens

<400> SEQUENCE: 15

Asn Glu Asp Ser Leu Val Phe Val Gln Thr Asp Lys
1               5                   10

<210> SEQ ID NO 16
<211> LENGTH: 10
<212> TYPE: PRT
<213> ORGANISM: Homo sapiens

<400> SEQUENCE: 16

Gln Gly Ile Pro Phe Phe Gly Gln Val Arg
1               5                   10

<210> SEQ ID NO 17
<211> LENGTH: 10
<212> TYPE: PRT
<213> ORGANISM: Homo sapiens

<400> SEQUENCE: 17

Asp Ala Asp Pro Asp Thr Phe Phe Ala Lys
1               5                   10

<210> SEQ ID NO 18
<211> LENGTH: 7
<212> TYPE: PRT
<213> ORGANISM: Homo sapiens

<400> SEQUENCE: 18

Phe Thr Phe Glu Tyr Ser Arg
1               5

<210> SEQ ID NO 19
<211> LENGTH: 16
<212> TYPE: PRT
<213> ORGANISM: Homo sapiens

<400> SEQUENCE: 19

Ile Ala Pro Gln Leu Ser Thr Glu Glu Leu Val Ser Leu Gly Glu Lys
1               5                   10                  15

<210> SEQ ID NO 20
<211> LENGTH: 14
<212> TYPE: PRT
<213> ORGANISM: Homo sapiens

<400> SEQUENCE: 20

Asp Ile Val Leu Val Ala His Ser Ala Leu Gly Thr Gln Arg
1               5                   10

<210> SEQ ID NO 21
<211> LENGTH: 19
<212> TYPE: PRT
<213> ORGANISM: Homo sapiens

<400> SEQUENCE: 21

His Ile Asp Ser Ala Tyr Leu Tyr Asn Asn Glu Glu Gln Val Gly Leu
1               5                   10                  15

Ala Ile Arg

-continued

<210> SEQ ID NO 22
<211> LENGTH: 12
<212> TYPE: PRT
<213> ORGANISM: Homo sapiens

<400> SEQUENCE: 22

Ala Asp Asp Gly Arg Pro Phe Pro Gln Val Ile Lys
1               5                   10

<210> SEQ ID NO 23
<211> LENGTH: 14
<212> TYPE: PRT
<213> ORGANISM: Homo sapiens

<400> SEQUENCE: 23

Gly Ile Leu Ala Ala Asp Glu Ser Thr Gly Ser Ile Ala Lys
1               5                   10

<210> SEQ ID NO 24
<211> LENGTH: 11
<212> TYPE: PRT
<213> ORGANISM: Homo sapiens

<400> SEQUENCE: 24

Glu Ala Thr Asp Val Ile Ile Ile His Ser Lys
1               5                   10

<210> SEQ ID NO 25
<211> LENGTH: 14
<212> TYPE: PRT
<213> ORGANISM: Homo sapiens

<400> SEQUENCE: 25

Phe Ser Thr Glu Tyr Glu Leu Gln Gln Leu Glu Gln Phe Lys
1               5                   10

<210> SEQ ID NO 26
<211> LENGTH: 9
<212> TYPE: PRT
<213> ORGANISM: Homo sapiens

<400> SEQUENCE: 26

Ser Ile Gln Leu Pro Thr Thr Val Arg
1               5

<210> SEQ ID NO 27
<211> LENGTH: 16
<212> TYPE: PRT
<213> ORGANISM: Homo sapiens

<400> SEQUENCE: 27

Leu Leu Leu Thr Ser Ala Pro Ser Leu Ala Thr Ser Pro Ala Phe Arg
1               5                   10                  15

<210> SEQ ID NO 28
<211> LENGTH: 13
<212> TYPE: PRT
<213> ORGANISM: Homo sapiens

<400> SEQUENCE: 28

Ile Val Thr Ala Thr Val Asn Asn Ser Val Leu Gln Lys
1               5                   10

<210> SEQ ID NO 29

```
<211> LENGTH: 11
<212> TYPE: PRT
<213> ORGANISM: Homo sapiens

<400> SEQUENCE: 29

Gln Ile Leu Asp Gln Thr Ser Glu Ile Asn Lys
1               5                   10

<210> SEQ ID NO 30
<211> LENGTH: 9
<212> TYPE: PRT
<213> ORGANISM: Homo sapiens

<400> SEQUENCE: 30

Ala Lys Pro Ala Leu Glu Asp Leu Arg
1               5

<210> SEQ ID NO 31
<211> LENGTH: 11
<212> TYPE: PRT
<213> ORGANISM: Homo sapiens

<400> SEQUENCE: 31

Ala Thr Glu His Leu Ser Thr Leu Ser Glu Lys
1               5                   10

<210> SEQ ID NO 32
<211> LENGTH: 13
<212> TYPE: PRT
<213> ORGANISM: Homo sapiens

<400> SEQUENCE: 32

Asp Tyr Val Ser Gln Phe Glu Gly Ser Ala Leu Gly Lys
1               5                   10

<210> SEQ ID NO 33
<211> LENGTH: 16
<212> TYPE: PRT
<213> ORGANISM: Homo sapiens

<400> SEQUENCE: 33

Glu Gln Leu Gly Pro Val Thr Gln Glu Phe Trp Asp Asn Leu Glu Lys
1               5                   10                  15

<210> SEQ ID NO 34
<211> LENGTH: 11
<212> TYPE: PRT
<213> ORGANISM: Homo sapiens

<400> SEQUENCE: 34

Gln Gly Leu Leu Pro Val Leu Glu Ser Phe Lys
1               5                   10

<210> SEQ ID NO 35
<211> LENGTH: 11
<212> TYPE: PRT
<213> ORGANISM: Homo sapiens

<400> SEQUENCE: 35

Thr His Leu Ala Pro Tyr Ser Asp Glu Leu Arg
1               5                   10

<210> SEQ ID NO 36
<211> LENGTH: 10
<212> TYPE: PRT
```

<213> ORGANISM: Homo sapiens

<400> SEQUENCE: 36

Val Gln Pro Tyr Leu Asp Asp Phe Gln Lys
1               5                   10

<210> SEQ ID NO 37
<211> LENGTH: 12
<212> TYPE: PRT
<213> ORGANISM: Homo sapiens

<400> SEQUENCE: 37

Val Ser Phe Leu Ser Ala Leu Glu Glu Tyr Thr Lys
1               5                   10

<210> SEQ ID NO 38
<211> LENGTH: 13
<212> TYPE: PRT
<213> ORGANISM: Homo sapiens

<400> SEQUENCE: 38

Leu Gly Glu Val Asn Thr Tyr Ala Gly Asp Leu Gln Lys
1               5                   10

<210> SEQ ID NO 39
<211> LENGTH: 14
<212> TYPE: PRT
<213> ORGANISM: Homo sapiens

<400> SEQUENCE: 39

Ser Glu Leu Thr Gln Gln Leu Asn Ala Leu Phe Gln Asp Lys
1               5                   10

<210> SEQ ID NO 40
<211> LENGTH: 12
<212> TYPE: PRT
<213> ORGANISM: Homo sapiens

<400> SEQUENCE: 40

Ser Leu Ala Pro Tyr Ala Gln Asp Thr Gln Glu Lys
1               5                   10

<210> SEQ ID NO 41
<211> LENGTH: 16
<212> TYPE: PRT
<213> ORGANISM: Homo sapiens

<400> SEQUENCE: 41

Glu Leu Glu Gly Trp Glu Pro Asp Asp Pro Ile Glu Glu His Lys
1               5                   10                  15

<210> SEQ ID NO 42
<211> LENGTH: 12
<212> TYPE: PRT
<213> ORGANISM: Homo sapiens

<400> SEQUENCE: 42

Gln Phe Glu Glu Leu Thr Leu Gly Glu Phe Leu Lys
1               5                   10

<210> SEQ ID NO 43
<211> LENGTH: 11
<212> TYPE: PRT
<213> ORGANISM: Homo sapiens

```
<400> SEQUENCE: 43

Glu Asp Val Tyr Val Val Gly Thr Val Leu Arg
1               5                   10

<210> SEQ ID NO 44
<211> LENGTH: 9
<212> TYPE: PRT
<213> ORGANISM: Homo sapiens

<400> SEQUENCE: 44

Gly Tyr Ile Leu Val Gly Gln Ala Lys
1               5

<210> SEQ ID NO 45
<211> LENGTH: 12
<212> TYPE: PRT
<213> ORGANISM: Homo sapiens

<400> SEQUENCE: 45

Leu Ser Leu Glu Ile Glu Gln Leu Glu Leu Gln Arg
1               5                   10

<210> SEQ ID NO 46
<211> LENGTH: 9
<212> TYPE: PRT
<213> ORGANISM: Homo sapiens

<400> SEQUENCE: 46

Gly Leu Gln Thr Ser Gln Asp Ala Arg
1               5

<210> SEQ ID NO 47
<211> LENGTH: 8
<212> TYPE: PRT
<213> ORGANISM: Homo sapiens

<400> SEQUENCE: 47

Gln Ile Asp Asn Pro Asp Tyr Lys
1               5

<210> SEQ ID NO 48
<211> LENGTH: 8
<212> TYPE: PRT
<213> ORGANISM: Homo sapiens

<400> SEQUENCE: 48

Val His Val Ile Phe Asn Tyr Lys
1               5

<210> SEQ ID NO 49
<211> LENGTH: 10
<212> TYPE: PRT
<213> ORGANISM: Homo sapiens

<400> SEQUENCE: 49

Glu Gln Trp Pro Gln Cys Pro Thr Ile Lys
1               5                   10

<210> SEQ ID NO 50
<211> LENGTH: 8
<212> TYPE: PRT
<213> ORGANISM: Homo sapiens

<400> SEQUENCE: 50
```

```
Leu Pro Ala Ser Phe Asp Ala Arg
1               5

<210> SEQ ID NO 51
<211> LENGTH: 18
<212> TYPE: PRT
<213> ORGANISM: Homo sapiens

<400> SEQUENCE: 51

Asn Gly Pro Val Glu Gly Ala Phe Ser Val Tyr Ser Asp Phe Leu Leu
1               5                   10                  15

Tyr Lys

<210> SEQ ID NO 52
<211> LENGTH: 18
<212> TYPE: PRT
<213> ORGANISM: Homo sapiens

<400> SEQUENCE: 52

Ser Gly Val Tyr Gln His Val Thr Gly Glu Met Met Gly Gly His Ala
1               5                   10                  15

Ile Arg

<210> SEQ ID NO 53
<211> LENGTH: 7
<212> TYPE: PRT
<213> ORGANISM: Homo sapiens

<400> SEQUENCE: 53

Thr Asp Gln Tyr Trp Glu Lys
1               5

<210> SEQ ID NO 54
<211> LENGTH: 17
<212> TYPE: PRT
<213> ORGANISM: Homo sapiens

<400> SEQUENCE: 54

Gly Gln Asp His Cys Gly Ile Glu Ser Glu Val Val Ala Gly Ile Pro
1               5                   10                  15

Arg

<210> SEQ ID NO 55
<211> LENGTH: 20
<212> TYPE: PRT
<213> ORGANISM: Homo sapiens

<400> SEQUENCE: 55

Asp Gln Gly Ser Cys Gly Ser Cys Trp Ala Phe Gly Ala Val Glu Ala
1               5                   10                  15

Ile Ser Asp Arg
            20

<210> SEQ ID NO 56
<211> LENGTH: 14
<212> TYPE: PRT
<213> ORGANISM: Homo sapiens

<400> SEQUENCE: 56

His Tyr Gly Tyr Asn Ser Tyr Ser Val Ser Asn Ser Glu Lys
1               5                   10
```

```
<210> SEQ ID NO 57
<211> LENGTH: 15
<212> TYPE: PRT
<213> ORGANISM: Homo sapiens

<400> SEQUENCE: 57

Gly Leu Val Ser Gly Gly Leu Tyr Glu Ser His Val Gly Cys Arg
1               5                   10                  15

<210> SEQ ID NO 58
<211> LENGTH: 22
<212> TYPE: PRT
<213> ORGANISM: Homo sapiens

<400> SEQUENCE: 58

His Tyr Gly Tyr Asn Ser Tyr Ser Val Ser Asn Ser Glu Lys Asp Ile
1               5                   10                  15

Met Ala Glu Ile Tyr Lys
            20

<210> SEQ ID NO 59
<211> LENGTH: 14
<212> TYPE: PRT
<213> ORGANISM: Homo sapiens

<400> SEQUENCE: 59

Ile Cys Glu Pro Gly Tyr Ser Pro Thr Tyr Lys Gln Asp Lys
1               5                   10

<210> SEQ ID NO 60
<211> LENGTH: 25
<212> TYPE: PRT
<213> ORGANISM: Homo sapiens

<400> SEQUENCE: 60

Gln Asp Lys His Tyr Gly Tyr Asn Ser Tyr Ser Val Ser Asn Ser Glu
1               5                   10                  15

Lys Asp Ile Met Ala Glu Ile Tyr Lys
            20                  25

<210> SEQ ID NO 61
<211> LENGTH: 11
<212> TYPE: PRT
<213> ORGANISM: Homo sapiens

<400> SEQUENCE: 61

Ile Cys Glu Pro Gly Tyr Ser Pro Thr Tyr Lys
1               5                   10

<210> SEQ ID NO 62
<211> LENGTH: 17
<212> TYPE: PRT
<213> ORGANISM: Homo sapiens

<400> SEQUENCE: 62

Gln Asp Lys His Tyr Gly Tyr Asn Ser Tyr Ser Val Ser Asn Ser Glu
1               5                   10                  15

Lys

<210> SEQ ID NO 63
<211> LENGTH: 8
<212> TYPE: PRT
<213> ORGANISM: Homo sapiens
```

```
<400> SEQUENCE: 63

Asp Ile Met Ala Glu Ile Tyr Lys
1               5

<210> SEQ ID NO 64
<211> LENGTH: 9
<212> TYPE: PRT
<213> ORGANISM: Homo sapiens

<400> SEQUENCE: 64

Ala Ala Ser Gln Pro Gly Glu Leu Lys
1               5

<210> SEQ ID NO 65
<211> LENGTH: 12
<212> TYPE: PRT
<213> ORGANISM: Homo sapiens

<400> SEQUENCE: 65

Asn Ser Leu Ile Ser Tyr Leu Glu Gln Ile His Arg
1               5                   10

<210> SEQ ID NO 66
<211> LENGTH: 10
<212> TYPE: PRT
<213> ORGANISM: Homo sapiens

<400> SEQUENCE: 66

Ser Asn Ala Gln Gly Ile Asp Leu Asn Arg
1               5                   10

<210> SEQ ID NO 67
<211> LENGTH: 9
<212> TYPE: PRT
<213> ORGANISM: Homo sapiens

<400> SEQUENCE: 67

Phe Ala Gly Val Phe His Val Glu Lys
1               5

<210> SEQ ID NO 68
<211> LENGTH: 12
<212> TYPE: PRT
<213> ORGANISM: Homo sapiens

<400> SEQUENCE: 68

Tyr Gly Phe Ile Glu Gly His Val Val Ile Pro Arg
1               5                   10

<210> SEQ ID NO 69
<211> LENGTH: 20
<212> TYPE: PRT
<213> ORGANISM: Homo sapiens

<400> SEQUENCE: 69

Ala Glu Glu Glu His Leu Gly Ile Leu Gly Pro Gln Leu His Ala Asp
1               5                   10                  15

Val Gly Asp Lys
            20

<210> SEQ ID NO 70
<211> LENGTH: 12
<212> TYPE: PRT
<213> ORGANISM: Homo sapiens
```

<400> SEQUENCE: 70

Ala Leu Tyr Leu Gln Tyr Thr Asp Glu Thr Phe Arg
1               5                   10

<210> SEQ ID NO 71
<211> LENGTH: 13
<212> TYPE: PRT
<213> ORGANISM: Homo sapiens

<400> SEQUENCE: 71

Gly Ala Tyr Pro Leu Ser Ile Glu Pro Ile Gly Val Arg
1               5                   10

<210> SEQ ID NO 72
<211> LENGTH: 16
<212> TYPE: PRT
<213> ORGANISM: Homo sapiens

<400> SEQUENCE: 72

Asn Asn Glu Gly Thr Tyr Tyr Ser Pro Asn Tyr Asn Pro Gln Ser Arg
1               5                   10                  15

<210> SEQ ID NO 73
<211> LENGTH: 12
<212> TYPE: PRT
<213> ORGANISM: Homo sapiens

<400> SEQUENCE: 73

Ala Ser Ser Ile Ile Asp Glu Leu Phe Gln Asp Arg
1               5                   10

<210> SEQ ID NO 74
<211> LENGTH: 11
<212> TYPE: PRT
<213> ORGANISM: Homo sapiens

<400> SEQUENCE: 74

Glu Leu Asp Glu Ser Leu Gln Val Ala Glu Arg
1               5                   10

<210> SEQ ID NO 75
<211> LENGTH: 9
<212> TYPE: PRT
<213> ORGANISM: Homo sapiens

<400> SEQUENCE: 75

Ile Asp Ser Leu Leu Glu Asn Asp Arg
1               5

<210> SEQ ID NO 76
<211> LENGTH: 17
<212> TYPE: PRT
<213> ORGANISM: Homo sapiens

<400> SEQUENCE: 76

Leu Phe Asp Ser Asp Pro Ile Thr Val Thr Val Pro Val Glu Val Ser
1               5                   10                  15

Arg

<210> SEQ ID NO 77
<211> LENGTH: 12
<212> TYPE: PRT
<213> ORGANISM: Homo sapiens

```
<400> SEQUENCE: 77

Gly Glu Pro Gly Asn Ile Gly Phe Pro Gly Pro Lys
1               5                   10

<210> SEQ ID NO 78
<211> LENGTH: 15
<212> TYPE: PRT
<213> ORGANISM: Homo sapiens

<400> SEQUENCE: 78

Gly Ile Pro Gly Pro Val Gly Ala Ala Gly Ala Thr Gly Ala Arg
1               5                   10                  15

<210> SEQ ID NO 79
<211> LENGTH: 10
<212> TYPE: PRT
<213> ORGANISM: Homo sapiens

<400> SEQUENCE: 79

Ile His Trp Glu Ser Ala Ser Leu Leu Arg
1               5                   10

<210> SEQ ID NO 80
<211> LENGTH: 16
<212> TYPE: PRT
<213> ORGANISM: Homo sapiens

<400> SEQUENCE: 80

Ser Asn Leu Asp Glu Asp Ile Ile Ala Glu Glu Asn Ile Val Ser Arg
1               5                   10                  15

<210> SEQ ID NO 81
<211> LENGTH: 12
<212> TYPE: PRT
<213> ORGANISM: Homo sapiens

<400> SEQUENCE: 81

Thr Ile Tyr Thr Pro Gly Ser Thr Val Leu Tyr Arg
1               5                   10

<210> SEQ ID NO 82
<211> LENGTH: 11
<212> TYPE: PRT
<213> ORGANISM: Homo sapiens

<400> SEQUENCE: 82

Leu Ser Ile Ile Ala Thr Asp His Thr Tyr Arg
1               5                   10

<210> SEQ ID NO 83
<211> LENGTH: 9
<212> TYPE: PRT
<213> ORGANISM: Homo sapiens

<400> SEQUENCE: 83

Ala Asp Gly Val Pro Val Tyr Leu Lys
1               5

<210> SEQ ID NO 84
<211> LENGTH: 9
<212> TYPE: PRT
<213> ORGANISM: Homo sapiens

<400> SEQUENCE: 84
```

```
Gly Leu Pro Asp Gln Met Leu Tyr Arg
1               5

<210> SEQ ID NO 85
<211> LENGTH: 13
<212> TYPE: PRT
<213> ORGANISM: Homo sapiens

<400> SEQUENCE: 85

Leu Thr Ser Asp Ser Thr Val Tyr Asp Tyr Ala Gly Lys
1               5                   10

<210> SEQ ID NO 86
<211> LENGTH: 16
<212> TYPE: PRT
<213> ORGANISM: Homo sapiens

<400> SEQUENCE: 86

Asp Phe Val Glu Ile Leu Asp Gly Gly His Glu Asp Ala Pro Leu Arg
1               5                   10                  15

<210> SEQ ID NO 87
<211> LENGTH: 17
<212> TYPE: PRT
<213> ORGANISM: Homo sapiens

<400> SEQUENCE: 87

Glu Gln Leu Ala Asn Pro Ile Val Ser Ser Gly Asn Ser Leu Phe Leu
1               5                   10                  15

Arg

<210> SEQ ID NO 88
<211> LENGTH: 13
<212> TYPE: PRT
<213> ORGANISM: Homo sapiens

<400> SEQUENCE: 88

Phe Val Thr Asp Gly Ser Val Thr Ala Ser Gly Phe Arg
1               5                   10

<210> SEQ ID NO 89
<211> LENGTH: 11
<212> TYPE: PRT
<213> ORGANISM: Homo sapiens

<400> SEQUENCE: 89

Ser Asp Asn Ser Pro Thr His Val Gly Phe Lys
1               5                   10

<210> SEQ ID NO 90
<211> LENGTH: 20
<212> TYPE: PRT
<213> ORGANISM: Homo sapiens

<400> SEQUENCE: 90

Ala Ala Gln Ala Ala Val Ala Ser Tyr Asn Met Gly Ser Asn Ser Ile
1               5                   10                  15

Tyr Tyr Phe Arg
            20

<210> SEQ ID NO 91
<211> LENGTH: 10
<212> TYPE: PRT
```

```
<213> ORGANISM: Homo sapiens

<400> SEQUENCE: 91

Ala Gln Ser Gln Leu Val Ala Gly Ile Lys
1               5                   10

<210> SEQ ID NO 92
<211> LENGTH: 6
<212> TYPE: PRT
<213> ORGANISM: Homo sapiens

<400> SEQUENCE: 92

Ala Arg Pro Gln Glu Arg
1               5

<210> SEQ ID NO 93
<211> LENGTH: 18
<212> TYPE: PRT
<213> ORGANISM: Homo sapiens

<400> SEQUENCE: 93

Cys Asp Phe Glu Val Leu Val Val Pro Trp Gln Asn Ser Ser Gln Leu
1               5                   10                  15

Leu Lys

<210> SEQ ID NO 94
<211> LENGTH: 11
<212> TYPE: PRT
<213> ORGANISM: Homo sapiens

<400> SEQUENCE: 94

Asp Leu Ser Pro Asp Asp Pro Gln Val Gln Lys
1               5                   10

<210> SEQ ID NO 95
<211> LENGTH: 6
<212> TYPE: PRT
<213> ORGANISM: Homo sapiens

<400> SEQUENCE: 95

Asp Thr His Ile Ile Lys
1               5

<210> SEQ ID NO 96
<211> LENGTH: 20
<212> TYPE: PRT
<213> ORGANISM: Homo sapiens

<400> SEQUENCE: 96

Leu Arg Cys Asp Phe Glu Val Leu Val Val Pro Trp Gln Asn Ser Ser
1               5                   10                  15

Gln Leu Leu Lys
                20

<210> SEQ ID NO 97
<211> LENGTH: 21
<212> TYPE: PRT
<213> ORGANISM: Homo sapiens

<400> SEQUENCE: 97

Ser Asn Leu Pro Leu Ala Leu Gly Leu Ala Leu Val Ala Phe Cys Leu
1               5                   10                  15

Leu Ala Leu Pro Arg
```

<210> SEQ ID NO 98
<211> LENGTH: 23
<212> TYPE: PRT
<213> ORGANISM: Homo sapiens

<400> SEQUENCE: 98

Thr Arg Val Thr Gly Asp His Val Asp Leu Thr Thr Cys Pro Leu Ala
1               5                   10                  15

Ala Gly Ala Gln Gln Glu Lys
            20

<210> SEQ ID NO 99
<211> LENGTH: 21
<212> TYPE: PRT
<213> ORGANISM: Homo sapiens

<400> SEQUENCE: 99

Val Thr Gly Asp His Val Asp Leu Thr Thr Cys Pro Leu Ala Ala Gly
1               5                   10                  15

Ala Gln Gln Glu Lys
            20

<210> SEQ ID NO 100
<211> LENGTH: 13
<212> TYPE: PRT
<213> ORGANISM: Homo sapiens

<400> SEQUENCE: 100

Tyr Phe Leu Thr Met Glu Met Gly Ser Thr Asp Cys Arg
1               5                   10

<210> SEQ ID NO 101
<211> LENGTH: 14
<212> TYPE: PRT
<213> ORGANISM: Homo sapiens

<400> SEQUENCE: 101

Tyr Phe Leu Thr Met Glu Met Gly Ser Thr Asp Cys Arg Lys
1               5                   10

<210> SEQ ID NO 102
<211> LENGTH: 14
<212> TYPE: PRT
<213> ORGANISM: Homo sapiens

<400> SEQUENCE: 102

Leu Gly Thr Phe Glu Val Glu Asp Gln Ile Glu Ala Ala Arg
1               5                   10

<210> SEQ ID NO 103
<211> LENGTH: 10
<212> TYPE: PRT
<213> ORGANISM: Homo sapiens

<400> SEQUENCE: 103

Val Leu Glu Asp Asn Ser Ala Leu Asp Lys
1               5                   10

<210> SEQ ID NO 104
<211> LENGTH: 11
<212> TYPE: PRT
<213> ORGANISM: Homo sapiens

<400> SEQUENCE: 104

Trp Glu Tyr Tyr Asp Ser Val Tyr Thr Glu Arg
1               5                   10

<210> SEQ ID NO 105
<211> LENGTH: 11
<212> TYPE: PRT
<213> ORGANISM: Homo sapiens

<400> SEQUENCE: 105

Ile Glu Ser Ser Ser Leu Gln Gly Leu Gly Arg
1               5                   10

<210> SEQ ID NO 106
<211> LENGTH: 8
<212> TYPE: PRT
<213> ORGANISM: Homo sapiens

<400> SEQUENCE: 106

Ile Tyr Trp Val Asp Leu Glu Arg
1               5

<210> SEQ ID NO 107
<211> LENGTH: 8
<212> TYPE: PRT
<213> ORGANISM: Homo sapiens

<400> SEQUENCE: 107

Leu Phe Trp Ile Gln Tyr Asn Arg
1               5

<210> SEQ ID NO 108
<211> LENGTH: 11
<212> TYPE: PRT
<213> ORGANISM: Homo sapiens

<400> SEQUENCE: 108

Asn Gln Val Thr Pro Leu Asp Ile Leu Ser Lys
1               5                   10

<210> SEQ ID NO 109
<211> LENGTH: 8
<212> TYPE: PRT
<213> ORGANISM: Homo sapiens

<400> SEQUENCE: 109

Leu Ala Ile Asn Leu Leu Ala Lys
1               5

<210> SEQ ID NO 110
<211> LENGTH: 20
<212> TYPE: PRT
<213> ORGANISM: Homo sapiens

<400> SEQUENCE: 110

Leu Leu Asp Ile Glu Ser Gln Glu Glu Leu Glu Asp Phe Pro Leu Pro
1               5                   10                  15

Thr Val Gln Arg
            20

<210> SEQ ID NO 111
<211> LENGTH: 18
<212> TYPE: PRT

<213> ORGANISM: Homo sapiens

<400> SEQUENCE: 111

Ser Gln Pro Val Ser Gln Pro Leu Thr Tyr Glu Ser Gly Pro Asp Glu
1               5                   10                  15

Val Arg

<210> SEQ ID NO 112
<211> LENGTH: 9
<212> TYPE: PRT
<213> ORGANISM: Homo sapiens

<400> SEQUENCE: 112

Gln Asp Gly Ser Val Asp Phe Phe Arg
1               5

<210> SEQ ID NO 113
<211> LENGTH: 9
<212> TYPE: PRT
<213> ORGANISM: Homo sapiens

<400> SEQUENCE: 113

Tyr Gly Ile Asp Trp Ala Ser Gly Arg
1               5

<210> SEQ ID NO 114
<211> LENGTH: 15
<212> TYPE: PRT
<213> ORGANISM: Homo sapiens

<400> SEQUENCE: 114

Asp Asn Glu Asn Val Val Asn Glu Tyr Ser Ser Glu Leu Glu Lys
1               5                   10                  15

<210> SEQ ID NO 115
<211> LENGTH: 18
<212> TYPE: PRT
<213> ORGANISM: Homo sapiens

<400> SEQUENCE: 115

His Gln Leu Tyr Ile Asp Glu Thr Val Asn Ser Asn Ile Pro Thr Asn
1               5                   10                  15

Leu Arg

<210> SEQ ID NO 116
<211> LENGTH: 8
<212> TYPE: PRT
<213> ORGANISM: Homo sapiens

<400> SEQUENCE: 116

Ile Arg Pro Phe Phe Pro Gln Gln
1               5

<210> SEQ ID NO 117
<211> LENGTH: 15
<212> TYPE: PRT
<213> ORGANISM: Homo sapiens

<400> SEQUENCE: 117

Ile His Leu Ile Ser Thr Gln Ser Ala Ile Pro Tyr Ala Leu Arg
1               5                   10                  15

<210> SEQ ID NO 118

-continued

```
<211> LENGTH: 11
<212> TYPE: PRT
<213> ORGANISM: Homo sapiens

<400> SEQUENCE: 118

Gln Ser Gly Leu Tyr Phe Ile Lys Pro Leu Lys
1               5                   10

<210> SEQ ID NO 119
<211> LENGTH: 13
<212> TYPE: PRT
<213> ORGANISM: Homo sapiens

<400> SEQUENCE: 119

Tyr Glu Ala Ser Ile Leu Thr His Asp Ser Ser Ile Arg
1               5                   10

<210> SEQ ID NO 120
<211> LENGTH: 12
<212> TYPE: PRT
<213> ORGANISM: Homo sapiens

<400> SEQUENCE: 120

Ala Ala Leu Pro Glu Gly Leu Pro Glu Ala Ser Arg
1               5                   10

<210> SEQ ID NO 121
<211> LENGTH: 9
<212> TYPE: PRT
<213> ORGANISM: Homo sapiens

<400> SEQUENCE: 121

Ala Ala Asn Met His Ala Gln Ile Lys
1               5

<210> SEQ ID NO 122
<211> LENGTH: 19
<212> TYPE: PRT
<213> ORGANISM: Homo sapiens

<400> SEQUENCE: 122

Ala Asn Gln Ser Trp Glu Asp Ser Asn Thr Asp Leu Val Pro Ala Pro
1               5                   10                  15

Ala Val Arg

<210> SEQ ID NO 123
<211> LENGTH: 16
<212> TYPE: PRT
<213> ORGANISM: Homo sapiens

<400> SEQUENCE: 123

Ala Ser Leu Glu Asp Leu Gly Trp Ala Asp Trp Val Leu Ser Pro Arg
1               5                   10                  15

<210> SEQ ID NO 124
<211> LENGTH: 16
<212> TYPE: PRT
<213> ORGANISM: Homo sapiens

<400> SEQUENCE: 124

Glu Val Gln Val Thr Met Cys Ile Gly Ala Cys Pro Ser Gln Phe Arg
1               5                   10                  15

<210> SEQ ID NO 125
```

```
<211> LENGTH: 7
<212> TYPE: PRT
<213> ORGANISM: Homo sapiens

<400> SEQUENCE: 125

Ile Leu Thr Pro Glu Val Arg
1               5

<210> SEQ ID NO 126
<211> LENGTH: 10
<212> TYPE: PRT
<213> ORGANISM: Homo sapiens

<400> SEQUENCE: 126

Leu Gly Ser Gly Gly His Leu His Leu Arg
1               5                   10

<210> SEQ ID NO 127
<211> LENGTH: 24
<212> TYPE: PRT
<213> ORGANISM: Homo sapiens

<400> SEQUENCE: 127

Leu Lys Pro Asp Thr Val Pro Ala Pro Cys Cys Val Pro Ala Ser Tyr
1               5                   10                  15

Asn Pro Met Val Leu Ile Gln Lys
            20

<210> SEQ ID NO 128
<211> LENGTH: 7
<212> TYPE: PRT
<213> ORGANISM: Homo sapiens

<400> SEQUENCE: 128

Leu Ser Pro Thr Ala Ser Arg
1               5

<210> SEQ ID NO 129
<211> LENGTH: 11
<212> TYPE: PRT
<213> ORGANISM: Homo sapiens

<400> SEQUENCE: 129

Asn Gly Asp His Cys Pro Leu Gly Pro Gly Arg
1               5                   10

<210> SEQ ID NO 130
<211> LENGTH: 15
<212> TYPE: PRT
<213> ORGANISM: Homo sapiens

<400> SEQUENCE: 130

Gln Leu Ser Leu Ala Arg Pro Gln Ala Pro Ala Leu His Leu Arg
1               5                   10                  15

<210> SEQ ID NO 131
<211> LENGTH: 9
<212> TYPE: PRT
<213> ORGANISM: Homo sapiens

<400> SEQUENCE: 131

Ser Trp Asp Val Thr Arg Pro Leu Arg
1               5
```

```
<210> SEQ ID NO 132
<211> LENGTH: 16
<212> TYPE: PRT
<213> ORGANISM: Homo sapiens

<400> SEQUENCE: 132

Thr Asp Thr Gly Val Ser Leu Gln Thr Tyr Asp Asp Leu Leu Ala Lys
1               5                   10                  15

<210> SEQ ID NO 133
<211> LENGTH: 21
<212> TYPE: PRT
<213> ORGANISM: Homo sapiens

<400> SEQUENCE: 133

Thr Asp Thr Gly Val Ser Leu Gln Thr Tyr Asp Asp Leu Leu Ala Lys
1               5                   10                  15

Asp Cys His Cys Ile
            20

<210> SEQ ID NO 134
<211> LENGTH: 7
<212> TYPE: PRT
<213> ORGANISM: Homo sapiens

<400> SEQUENCE: 134

Tyr Glu Asp Leu Leu Thr Arg
1               5

<210> SEQ ID NO 135
<211> LENGTH: 13
<212> TYPE: PRT
<213> ORGANISM: Homo sapiens

<400> SEQUENCE: 135

Ala Gly Ala Leu Asn Ser Asn Asp Ala Phe Val Leu Lys
1               5                   10

<210> SEQ ID NO 136
<211> LENGTH: 17
<212> TYPE: PRT
<213> ORGANISM: Homo sapiens

<400> SEQUENCE: 136

Gln Thr Gln Val Ser Val Leu Pro Glu Gly Gly Glu Thr Pro Leu Phe
1               5                   10                  15

Lys

<210> SEQ ID NO 137
<211> LENGTH: 9
<212> TYPE: PRT
<213> ORGANISM: Homo sapiens

<400> SEQUENCE: 137

Tyr Ile Glu Thr Asp Pro Ala Asn Arg
1               5

<210> SEQ ID NO 138
<211> LENGTH: 12
<212> TYPE: PRT
<213> ORGANISM: Homo sapiens

<400> SEQUENCE: 138

Phe Phe Asn Val Leu Thr Thr Asn Thr Asp Gly Lys
```

```
1               5                   10

<210> SEQ ID NO 139
<211> LENGTH: 14
<212> TYPE: PRT
<213> ORGANISM: Homo sapiens

<400> SEQUENCE: 139

Thr Ala Phe Tyr Leu Ala Glu Phe Phe Val Asn Glu Ala Arg
1               5                   10

<210> SEQ ID NO 140
<211> LENGTH: 12
<212> TYPE: PRT
<213> ORGANISM: Homo sapiens

<400> SEQUENCE: 140

Tyr Pro Val Tyr Gly Val Gln Trp His Pro Glu Lys
1               5                   10

<210> SEQ ID NO 141
<211> LENGTH: 9
<212> TYPE: PRT
<213> ORGANISM: Homo sapiens

<400> SEQUENCE: 141

Ala Ser Trp Met Pro Met Phe Gln Arg
1               5

<210> SEQ ID NO 142
<211> LENGTH: 7
<212> TYPE: PRT
<213> ORGANISM: Homo sapiens

<400> SEQUENCE: 142

Cys Gly Met Cys Cys Lys Thr
1               5

<210> SEQ ID NO 143
<211> LENGTH: 16
<212> TYPE: PRT
<213> ORGANISM: Homo sapiens

<400> SEQUENCE: 143

Asp Thr His Phe Pro Ile Cys Ile Phe Cys Cys Gly Cys Cys His Arg
1               5                   10                  15

<210> SEQ ID NO 144
<211> LENGTH: 9
<212> TYPE: PRT
<213> ORGANISM: Homo sapiens

<400> SEQUENCE: 144

Ser Lys Cys Gly Met Cys Cys Lys Thr
1               5

<210> SEQ ID NO 145
<211> LENGTH: 8
<212> TYPE: PRT
<213> ORGANISM: Homo sapiens

<400> SEQUENCE: 145

Leu Pro Gly Gly Leu Glu Pro Lys
1               5
```

```
<210> SEQ ID NO 146
<211> LENGTH: 14
<212> TYPE: PRT
<213> ORGANISM: Homo sapiens

<400> SEQUENCE: 146

His Glu Val Thr Gly Trp Val Leu Val Ser Pro Leu Ser Lys
1               5                   10

<210> SEQ ID NO 147
<211> LENGTH: 13
<212> TYPE: PRT
<213> ORGANISM: Homo sapiens

<400> SEQUENCE: 147

Ile Thr Val Val Asp Ala Leu His Glu Ile Pro Val Lys
1               5                   10

<210> SEQ ID NO 148
<211> LENGTH: 8
<212> TYPE: PRT
<213> ORGANISM: Homo sapiens

<400> SEQUENCE: 148

Thr Glu Leu Leu Pro Gly Asp Arg
1               5

<210> SEQ ID NO 149
<211> LENGTH: 15
<212> TYPE: PRT
<213> ORGANISM: Homo sapiens

<400> SEQUENCE: 149

Asp Val Ser Thr Pro Pro Thr Val Leu Pro Asp Asn Phe Pro Arg
1               5                   10                  15

<210> SEQ ID NO 150
<211> LENGTH: 14
<212> TYPE: PRT
<213> ORGANISM: Homo sapiens

<400> SEQUENCE: 150

Phe Asn Trp Tyr Val Asp Gly Val Glu Val His Asn Ala Lys
1               5                   10

<210> SEQ ID NO 151
<211> LENGTH: 12
<212> TYPE: PRT
<213> ORGANISM: Homo sapiens

<400> SEQUENCE: 151

Gly Pro Ser Val Phe Pro Leu Ala Pro Ser Ser Lys
1               5                   10

<210> SEQ ID NO 152
<211> LENGTH: 17
<212> TYPE: PRT
<213> ORGANISM: Homo sapiens

<400> SEQUENCE: 152

Thr Thr Pro Pro Val Leu Asp Ser Asp Gly Ser Phe Phe Leu Tyr Ser
1               5                   10                  15

Lys
```

<210> SEQ ID NO 153
<211> LENGTH: 11
<212> TYPE: PRT
<213> ORGANISM: Homo sapiens

<400> SEQUENCE: 153

Ala Val Val Glu Val Asp Glu Ser Gly Thr Arg
1               5                   10

<210> SEQ ID NO 154
<211> LENGTH: 10
<212> TYPE: PRT
<213> ORGANISM: Homo sapiens

<400> SEQUENCE: 154

Glu Asp Gln Tyr His Tyr Leu Leu Asp Arg
1               5                   10

<210> SEQ ID NO 155
<211> LENGTH: 15
<212> TYPE: PRT
<213> ORGANISM: Homo sapiens

<400> SEQUENCE: 155

Val Glu Asp Leu His Val Gly Ala Thr Val Ala Pro Ser Ser Arg
1               5                   10                  15

<210> SEQ ID NO 156
<211> LENGTH: 11
<212> TYPE: PRT
<213> ORGANISM: Homo sapiens

<400> SEQUENCE: 156

Phe Tyr Asn Gln Val Ser Thr Pro Leu Leu Arg
1               5                   10

<210> SEQ ID NO 157
<211> LENGTH: 15
<212> TYPE: PRT
<213> ORGANISM: Homo sapiens

<400> SEQUENCE: 157

Ile Gln Pro Ser Gly Gly Thr Asn Ile Asn Glu Ala Leu Leu Arg
1               5                   10                  15

<210> SEQ ID NO 158
<211> LENGTH: 10
<212> TYPE: PRT
<213> ORGANISM: Homo sapiens

<400> SEQUENCE: 158

Thr Glu Val Asn Val Leu Pro Gly Ala Lys
1               5                   10

<210> SEQ ID NO 159
<211> LENGTH: 9
<212> TYPE: PRT
<213> ORGANISM: Homo sapiens

<400> SEQUENCE: 159

Phe Ala His Thr Val Val Thr Ser Arg
1               5

<210> SEQ ID NO 160

```
<211> LENGTH: 12
<212> TYPE: PRT
<213> ORGANISM: Homo sapiens

<400> SEQUENCE: 160

Gly Pro Asp Val Leu Thr Ala Thr Val Ser Gly Lys
1               5                   10

<210> SEQ ID NO 161
<211> LENGTH: 9
<212> TYPE: PRT
<213> ORGANISM: Homo sapiens

<400> SEQUENCE: 161

Leu Gly Val Tyr Glu Leu Leu Leu Lys
1               5

<210> SEQ ID NO 162
<211> LENGTH: 16
<212> TYPE: PRT
<213> ORGANISM: Homo sapiens

<400> SEQUENCE: 162

Ser Pro Glu Gln Gln Glu Thr Val Leu Asp Gly Asn Leu Ile Ile Arg
1               5                   10                  15

<210> SEQ ID NO 163
<211> LENGTH: 13
<212> TYPE: PRT
<213> ORGANISM: Homo sapiens

<400> SEQUENCE: 163

Ala Ala Leu Glu Asp Thr Leu Ala Glu Thr Glu Ala Arg
1               5                   10

<210> SEQ ID NO 164
<211> LENGTH: 10
<212> TYPE: PRT
<213> ORGANISM: Homo sapiens

<400> SEQUENCE: 164

Ile Leu Gly Ala Thr Ile Glu Asn Ser Arg
1               5                   10

<210> SEQ ID NO 165
<211> LENGTH: 17
<212> TYPE: PRT
<213> ORGANISM: Homo sapiens

<400> SEQUENCE: 165

Ser Leu Leu Glu Gly Gln Glu Asp His Tyr Asn Asn Leu Ser Ala Ser
1               5                   10                  15

Lys

<210> SEQ ID NO 166
<211> LENGTH: 12
<212> TYPE: PRT
<213> ORGANISM: Homo sapiens

<400> SEQUENCE: 166

Leu Ser Glu Pro Ala Glu Leu Thr Asp Ala Val Lys
1               5                   10

<210> SEQ ID NO 167
```

```
<211> LENGTH: 12
<212> TYPE: PRT
<213> ORGANISM: Homo sapiens

<400> SEQUENCE: 167

Leu Asn Ala Glu Asn Asn Ala Thr Phe Tyr Phe Lys
1               5                   10

<210> SEQ ID NO 168
<211> LENGTH: 11
<212> TYPE: PRT
<213> ORGANISM: Homo sapiens

<400> SEQUENCE: 168

Thr Val Gly Ser Asp Thr Phe Tyr Ser Phe Lys
1               5                   10

<210> SEQ ID NO 169
<211> LENGTH: 8
<212> TYPE: PRT
<213> ORGANISM: Homo sapiens

<400> SEQUENCE: 169

Tyr Phe Ile Asp Phe Val Ala Arg
1               5

<210> SEQ ID NO 170
<211> LENGTH: 15
<212> TYPE: PRT
<213> ORGANISM: Homo sapiens

<400> SEQUENCE: 170

Tyr Asn Ser Gln Asn Gln Ser Asn Asn Gln Phe Val Leu Tyr Arg
1               5                   10                  15

<210> SEQ ID NO 171
<211> LENGTH: 15
<212> TYPE: PRT
<213> ORGANISM: Homo sapiens

<400> SEQUENCE: 171

Ala Gly Gln Ser Pro Gln Leu Leu Ile Tyr Thr Leu Ser Tyr Arg
1               5                   10                  15

<210> SEQ ID NO 172
<211> LENGTH: 12
<212> TYPE: PRT
<213> ORGANISM: Homo sapiens

<400> SEQUENCE: 172

Leu Glu Ile Pro Tyr Thr Phe Gly Gln Gly Thr Lys
1               5                   10

<210> SEQ ID NO 173
<211> LENGTH: 11
<212> TYPE: PRT
<213> ORGANISM: Homo sapiens

<400> SEQUENCE: 173

Asp Ala Pro Ser Trp Asp Pro Val Ala Leu Lys
1               5                   10

<210> SEQ ID NO 174
<211> LENGTH: 8
<212> TYPE: PRT
```

<213> ORGANISM: Homo sapiens

<400> SEQUENCE: 174

Leu Ile Thr Glu Glu Ala Asn Arg
1               5

<210> SEQ ID NO 175
<211> LENGTH: 14
<212> TYPE: PRT
<213> ORGANISM: Homo sapiens

<400> SEQUENCE: 175

Ser Gly Val Leu Ser Val Ser Ser Gly Ala Ala Ala His Arg
1               5                   10

<210> SEQ ID NO 176
<211> LENGTH: 11
<212> TYPE: PRT
<213> ORGANISM: Homo sapiens

<400> SEQUENCE: 176

Ala Leu Gln Ala Thr Val Gly Asn Ser Tyr Lys
1               5                   10

<210> SEQ ID NO 177
<211> LENGTH: 16
<212> TYPE: PRT
<213> ORGANISM: Homo sapiens

<400> SEQUENCE: 177

Phe Phe Leu Gln Gly Ile Gln Leu Asn Thr Ile Leu Pro Asp Ala Arg
1               5                   10                  15

<210> SEQ ID NO 178
<211> LENGTH: 10
<212> TYPE: PRT
<213> ORGANISM: Homo sapiens

<400> SEQUENCE: 178

Gly His Thr Leu Thr Leu Asn Phe Thr Arg
1               5                   10

<210> SEQ ID NO 179
<211> LENGTH: 12
<212> TYPE: PRT
<213> ORGANISM: Homo sapiens

<400> SEQUENCE: 179

Gly Ile Leu Thr Val Asp Glu Leu Leu Ala Ile Arg
1               5                   10

<210> SEQ ID NO 180
<211> LENGTH: 9
<212> TYPE: PRT
<213> ORGANISM: Homo sapiens

<400> SEQUENCE: 180

Tyr Leu Asp Phe Val Phe Ala Val Lys
1               5

<210> SEQ ID NO 181
<211> LENGTH: 15
<212> TYPE: PRT
<213> ORGANISM: Homo sapiens -continued

<400> SEQUENCE: 181

Asp Leu Ala Asp Glu Leu Ala Leu Val Asp Val Ile Glu Asp Lys
1               5                   10                  15

<210> SEQ ID NO 182
<211> LENGTH: 10
<212> TYPE: PRT
<213> ORGANISM: Homo sapiens

<400> SEQUENCE: 182

Ser Ala Asp Thr Leu Trp Gly Ile Gln Lys
1               5                   10

<210> SEQ ID NO 183
<211> LENGTH: 10
<212> TYPE: PRT
<213> ORGANISM: Homo sapiens

<400> SEQUENCE: 183

Val Thr Leu Thr Ser Glu Glu Glu Ala Arg
1               5                   10

<210> SEQ ID NO 184
<211> LENGTH: 14
<212> TYPE: PRT
<213> ORGANISM: Homo sapiens

<400> SEQUENCE: 184

Glu Leu Ser Glu Ala Leu Gly Gln Ile Phe Asp Ser Gln Arg
1               5                   10

<210> SEQ ID NO 185
<211> LENGTH: 9
<212> TYPE: PRT
<213> ORGANISM: Homo sapiens

<400> SEQUENCE: 185

Ile Asp Ile Thr Leu Ser Ser Val Lys
1               5

<210> SEQ ID NO 186
<211> LENGTH: 11
<212> TYPE: PRT
<213> ORGANISM: Homo sapiens

<400> SEQUENCE: 186

Leu Ala Asp Gly Gly Ala Thr Asn Gln Gly Arg
1               5                   10

<210> SEQ ID NO 187
<211> LENGTH: 13
<212> TYPE: PRT
<213> ORGANISM: Homo sapiens

<400> SEQUENCE: 187

Ser Asp Leu Ala Val Pro Ser Glu Leu Ala Leu Leu Lys
1               5                   10

<210> SEQ ID NO 188
<211> LENGTH: 13
<212> TYPE: PRT
<213> ORGANISM: Homo sapiens

<400> SEQUENCE: 188

```
Tyr Ser Ser Asp Tyr Phe Gln Ala Pro Ser Asp Tyr Arg
1               5                   10
```

<210> SEQ ID NO 189
<211> LENGTH: 10
<212> TYPE: PRT
<213> ORGANISM: Homo sapiens

<400> SEQUENCE: 189

```
Glu Leu Ala Pro Leu Phe Glu Glu Leu Arg
1               5                   10
```

<210> SEQ ID NO 190
<211> LENGTH: 15
<212> TYPE: PRT
<213> ORGANISM: Homo sapiens

<400> SEQUENCE: 190

```
Leu Pro Ser Val Glu Gly Leu His Ala Ile Val Val Ser Asp Arg
1               5                   10                  15
```

<210> SEQ ID NO 191
<211> LENGTH: 11
<212> TYPE: PRT
<213> ORGANISM: Homo sapiens

<400> SEQUENCE: 191

```
Gly Ala Tyr Thr Gln Val Ile Phe Leu Ala Arg
1               5                   10
```

<210> SEQ ID NO 192
<211> LENGTH: 16
<212> TYPE: PRT
<213> ORGANISM: Homo sapiens

<400> SEQUENCE: 192

```
Gly Glu Leu Phe Trp Asp Asp Gly Glu Ser Leu Glu Val Leu Glu Arg
1               5                   10                  15
```

<210> SEQ ID NO 193
<211> LENGTH: 10
<212> TYPE: PRT
<213> ORGANISM: Homo sapiens

<400> SEQUENCE: 193

```
Trp Gly Tyr Ser Ser Thr Ala Ile Thr Arg
1               5                   10
```

<210> SEQ ID NO 194
<211> LENGTH: 9
<212> TYPE: PRT
<213> ORGANISM: Homo sapiens

<400> SEQUENCE: 194

```
Asp Phe Ala Asp Ile Pro Asn Leu Arg
1               5
```

<210> SEQ ID NO 195
<211> LENGTH: 11
<212> TYPE: PRT
<213> ORGANISM: Homo sapiens

<400> SEQUENCE: 195

```
Ala Ala Tyr Glu Asp Phe Asn Val Gln Leu Arg
1               5                   10
```

```
<210> SEQ ID NO 196
<211> LENGTH: 14
<212> TYPE: PRT
<213> ORGANISM: Homo sapiens

<400> SEQUENCE: 196

Ala Val Thr Leu Ser Leu Asp Gly Gly Asp Thr Ala Ile Arg
1               5                   10

<210> SEQ ID NO 197
<211> LENGTH: 9
<212> TYPE: PRT
<213> ORGANISM: Homo sapiens

<400> SEQUENCE: 197

Asp Gly Asn Val Phe Leu Val Pro Lys
1               5

<210> SEQ ID NO 198
<211> LENGTH: 12
<212> TYPE: PRT
<213> ORGANISM: Homo sapiens

<400> SEQUENCE: 198

Glu Gln Phe Asn Glu Ala Gln Leu Ala Leu Ile Arg
1               5                   10

<210> SEQ ID NO 199
<211> LENGTH: 8
<212> TYPE: PRT
<213> ORGANISM: Homo sapiens

<400> SEQUENCE: 199

Asp Gly Val Val Ser Val Asn Lys
1               5

<210> SEQ ID NO 200
<211> LENGTH: 12
<212> TYPE: PRT
<213> ORGANISM: Homo sapiens

<400> SEQUENCE: 200

Glu Ser Tyr Asn Val Gln Leu Gln Leu Pro Ala Arg
1               5                   10

<210> SEQ ID NO 201
<211> LENGTH: 12
<212> TYPE: PRT
<213> ORGANISM: Homo sapiens

<400> SEQUENCE: 201

His Ala Gln Ala Gln Tyr Ala Tyr Pro Gly Ala Arg
1               5                   10

<210> SEQ ID NO 202
<211> LENGTH: 17
<212> TYPE: PRT
<213> ORGANISM: Homo sapiens

<400> SEQUENCE: 202

Ala Ile Pro Val Ala Gln Asp Leu Asn Ala Pro Ser Asp Trp Asp Ser
1               5                   10                  15

Arg
```

<210> SEQ ID NO 203
<211> LENGTH: 19
<212> TYPE: PRT
<213> ORGANISM: Homo sapiens

<400> SEQUENCE: 203

Ala Asn Asp Glu Ser Asn Glu His Ser Asp Val Ile Asp Ser Gln Glu
1               5                   10                  15

Leu Ser Lys

<210> SEQ ID NO 204
<211> LENGTH: 16
<212> TYPE: PRT
<213> ORGANISM: Homo sapiens

<400> SEQUENCE: 204

Tyr Pro Asp Ala Val Ala Thr Trp Leu Asn Pro Asp Pro Ser Gln Lys
1               5                   10                  15

<210> SEQ ID NO 205
<211> LENGTH: 10
<212> TYPE: PRT
<213> ORGANISM: Homo sapiens

<400> SEQUENCE: 205

Leu Gly Phe Leu His Ser Gly Thr Ala Lys
1               5                   10

<210> SEQ ID NO 206
<211> LENGTH: 18
<212> TYPE: PRT
<213> ORGANISM: Homo sapiens

<400> SEQUENCE: 206

Leu Leu Glu Ile Asp Ser Val Gly Ser Glu Asp Ser Leu Asp Thr Ser
1               5                   10                  15

Leu Arg

<210> SEQ ID NO 207
<211> LENGTH: 8
<212> TYPE: PRT
<213> ORGANISM: Homo sapiens

<400> SEQUENCE: 207

Thr Val Ile Tyr Glu Ile Pro Arg
1               5

<210> SEQ ID NO 208
<211> LENGTH: 11
<212> TYPE: PRT
<213> ORGANISM: Homo sapiens

<400> SEQUENCE: 208

Ile Gln Ala Ile Glu Leu Glu Asp Leu Leu Arg
1               5                   10

<210> SEQ ID NO 209
<211> LENGTH: 14
<212> TYPE: PRT
<213> ORGANISM: Homo sapiens

<400> SEQUENCE: 209

Leu Leu Gln Val Val Tyr Leu His Ser Asn Asn Ile Thr Lys
1               5                   10

<210> SEQ ID NO 210
<211> LENGTH: 18
<212> TYPE: PRT
<213> ORGANISM: Homo sapiens

<400> SEQUENCE: 210

Asn His Leu Val Glu Ile Pro Pro Asn Leu Pro Ser Ser Leu Val Glu
1               5                   10                  15

Leu Arg

<210> SEQ ID NO 211
<211> LENGTH: 18
<212> TYPE: PRT
<213> ORGANISM: Homo sapiens

<400> SEQUENCE: 211

Ala Ser Pro Ala Thr Leu Leu Leu Val Leu Cys Leu Gln Leu Gly Ala
1               5                   10                  15

Asn Lys

<210> SEQ ID NO 212
<211> LENGTH: 15
<212> TYPE: PRT
<213> ORGANISM: Homo sapiens

<400> SEQUENCE: 212

Glu Leu Gly Ile Cys Pro Asp Asp Ala Ala Val Ile Pro Ile Lys
1               5                   10                  15

<210> SEQ ID NO 213
<211> LENGTH: 18
<212> TYPE: PRT
<213> ORGANISM: Homo sapiens

<400> SEQUENCE: 213

Glu Leu Gly Ile Cys Pro Asp Asp Ala Ala Val Ile Pro Ile Lys Asn
1               5                   10                  15

Asn Arg

<210> SEQ ID NO 214
<211> LENGTH: 8
<212> TYPE: PRT
<213> ORGANISM: Homo sapiens

<400> SEQUENCE: 214

Phe Tyr Thr Ile Glu Ile Leu Lys
1               5

<210> SEQ ID NO 215
<211> LENGTH: 10
<212> TYPE: PRT
<213> ORGANISM: Homo sapiens

<400> SEQUENCE: 215

Phe Tyr Thr Ile Glu Ile Leu Lys Val Glu
1               5                   10

<210> SEQ ID NO 216
<211> LENGTH: 7
<212> TYPE: PRT

<213> ORGANISM: Homo sapiens

<400> SEQUENCE: 216

Leu Leu Gln Leu Leu Phe Arg
1               5

<210> SEQ ID NO 217
<211> LENGTH: 6
<212> TYPE: PRT
<213> ORGANISM: Homo sapiens

<400> SEQUENCE: 217

Asn Phe Asp Ile Pro Lys
1               5

<210> SEQ ID NO 218
<211> LENGTH: 19
<212> TYPE: PRT
<213> ORGANISM: Homo sapiens

<400> SEQUENCE: 218

Ser Val Arg Pro Asn Asp Glu Val Thr Ala Val Leu Ala Val Gln Thr
1               5                   10                  15

Glu Leu Lys

<210> SEQ ID NO 219
<211> LENGTH: 25
<212> TYPE: PRT
<213> ORGANISM: Homo sapiens

<400> SEQUENCE: 219

Ser Val Arg Pro Asn Asp Glu Val Thr Ala Val Leu Ala Val Gln Thr
1               5                   10                  15

Glu Leu Lys Glu Cys Met Val Val Lys
            20                  25

<210> SEQ ID NO 220
<211> LENGTH: 10
<212> TYPE: PRT
<213> ORGANISM: Homo sapiens

<400> SEQUENCE: 220

Thr Phe Tyr Trp Asp Phe Tyr Thr Asn Arg
1               5                   10

<210> SEQ ID NO 221
<211> LENGTH: 12
<212> TYPE: PRT
<213> ORGANISM: Homo sapiens

<400> SEQUENCE: 221

Thr Val Gln Ile Ala Ala Val Val Asp Val Ile Arg
1               5                   10

<210> SEQ ID NO 222
<211> LENGTH: 16
<212> TYPE: PRT
<213> ORGANISM: Homo sapiens

<400> SEQUENCE: 222

Thr Tyr Leu Ile Ser Ser Ile Pro Leu Gln Gly Ala Phe Asn Tyr Lys
1               5                   10                  15

```
<210> SEQ ID NO 223
<211> LENGTH: 11
<212> TYPE: PRT
<213> ORGANISM: Homo sapiens

<400> SEQUENCE: 223

Tyr Thr Ala Cys Leu Cys Asp Asp Asn Pro Lys
1               5                   10

<210> SEQ ID NO 224
<211> LENGTH: 12
<212> TYPE: PRT
<213> ORGANISM: Homo sapiens

<400> SEQUENCE: 224

Ala Gly Ala Leu Gln Leu Leu Leu Val Gly Asp Lys
1               5                   10

<210> SEQ ID NO 225
<211> LENGTH: 20
<212> TYPE: PRT
<213> ORGANISM: Homo sapiens

<400> SEQUENCE: 225

Ala Thr Tyr Phe Gly Ser Ile Val Leu Leu Ser Pro Ala Val Ile Asp
1               5                   10                  15

Ser Pro Leu Lys
            20

<210> SEQ ID NO 226
<211> LENGTH: 12
<212> TYPE: PRT
<213> ORGANISM: Homo sapiens

<400> SEQUENCE: 226

Glu Gly His Phe Tyr Tyr Asn Ile Ser Glu Val Lys
1               5                   10

<210> SEQ ID NO 227
<211> LENGTH: 15
<212> TYPE: PRT
<213> ORGANISM: Homo sapiens

<400> SEQUENCE: 227

Glu Leu Ser Glu Leu Ser Leu Leu Ser Leu Tyr Gly Ile His Lys
1               5                   10                  15

<210> SEQ ID NO 228
<211> LENGTH: 10
<212> TYPE: PRT
<213> ORGANISM: Homo sapiens

<400> SEQUENCE: 228

Phe Gln Glu Leu Glu Ser Glu Thr Leu Lys
1               5                   10

<210> SEQ ID NO 229
<211> LENGTH: 12
<212> TYPE: PRT
<213> ORGANISM: Homo sapiens

<400> SEQUENCE: 229

Ser Pro Ile Asp Thr Phe Pro Thr Asp Pro Ile Lys
1               5                   10
```

```
<210> SEQ ID NO 230
<211> LENGTH: 12
<212> TYPE: PRT
<213> ORGANISM: Homo sapiens

<400> SEQUENCE: 230

Ala Asp Leu His Ala Val Gln Gly Trp Ala Ala Arg
1               5                   10

<210> SEQ ID NO 231
<211> LENGTH: 11
<212> TYPE: PRT
<213> ORGANISM: Homo sapiens

<400> SEQUENCE: 231

Met Leu Leu Gln Ala Thr Asp Asp Val Leu Arg
1               5                   10

<210> SEQ ID NO 232
<211> LENGTH: 16
<212> TYPE: PRT
<213> ORGANISM: Homo sapiens

<400> SEQUENCE: 232

Ser Trp Leu Pro Ala Gly Cys Glu Thr Ala Ile Leu Phe Pro Met Arg
1               5                   10                  15

<210> SEQ ID NO 233
<211> LENGTH: 14
<212> TYPE: PRT
<213> ORGANISM: Homo sapiens

<400> SEQUENCE: 233

Ala Glu Gln Trp Asn Val Asn Tyr Val Glu Thr Ser Ala Lys
1               5                   10

<210> SEQ ID NO 234
<211> LENGTH: 13
<212> TYPE: PRT
<213> ORGANISM: Homo sapiens

<400> SEQUENCE: 234

Glu Asp Glu Asn Val Pro Phe Leu Leu Val Gly Asn Lys
1               5                   10

<210> SEQ ID NO 235
<211> LENGTH: 9
<212> TYPE: PRT
<213> ORGANISM: Homo sapiens

<400> SEQUENCE: 235

Gly Gln Asn Ser Leu Ala Leu His Lys
1               5

<210> SEQ ID NO 236
<211> LENGTH: 9
<212> TYPE: PRT
<213> ORGANISM: Homo sapiens

<400> SEQUENCE: 236

Ser Phe Glu Asp Ile His His Tyr Arg
1               5

<210> SEQ ID NO 237
```

```
<211> LENGTH: 10
<212> TYPE: PRT
<213> ORGANISM: Homo sapiens

<400> SEQUENCE: 237

Val Glu Asp Ala Phe Tyr Thr Leu Val Arg
1               5                   10

<210> SEQ ID NO 238
<211> LENGTH: 9
<212> TYPE: PRT
<213> ORGANISM: Homo sapiens

<400> SEQUENCE: 238

Ser Phe Ala Asp Ile Asn Leu Tyr Arg
1               5

<210> SEQ ID NO 239
<211> LENGTH: 11
<212> TYPE: PRT
<213> ORGANISM: Homo sapiens

<400> SEQUENCE: 239

Asp Pro Asn Gly Leu Pro Pro Glu Ala Gln Lys
1               5                   10

<210> SEQ ID NO 240
<211> LENGTH: 14
<212> TYPE: PRT
<213> ORGANISM: Homo sapiens

<400> SEQUENCE: 240

Asp Pro Asn Gly Leu Pro Pro Glu Ala Gln Lys Ile Val Arg
1               5                   10

<210> SEQ ID NO 241
<211> LENGTH: 10
<212> TYPE: PRT
<213> ORGANISM: Homo sapiens

<400> SEQUENCE: 241

Phe Ser Gly Thr Trp Tyr Ala Met Ala Lys
1               5                   10

<210> SEQ ID NO 242
<211> LENGTH: 22
<212> TYPE: PRT
<213> ORGANISM: Homo sapiens

<400> SEQUENCE: 242

Gly Asn Asp Asp His Trp Ile Val Asp Thr Asp Tyr Asp Thr Tyr Ala
1               5                   10                  15

Val Gln Tyr Ser Cys Arg
            20

<210> SEQ ID NO 243
<211> LENGTH: 29
<212> TYPE: PRT
<213> ORGANISM: Homo sapiens

<400> SEQUENCE: 243

Lys Asp Pro Glu Gly Leu Phe Leu Gln Asp Asn Ile Val Ala Glu Phe
1               5                   10                  15

Ser Val Asp Glu Thr Gly Gln Met Ser Ala Thr Ala Lys
```

<210> SEQ ID NO 244
<211> LENGTH: 11
<212> TYPE: PRT
<213> ORGANISM: Homo sapiens

<400> SEQUENCE: 244

Leu Ile Val His Asn Gly Tyr Cys Asp Gly Arg
1               5                   10

<210> SEQ ID NO 245
<211> LENGTH: 14
<212> TYPE: PRT
<213> ORGANISM: Homo sapiens

<400> SEQUENCE: 245

Leu Ile Val His Asn Gly Tyr Cys Asp Gly Arg Ser Glu Arg
1               5                   10

<210> SEQ ID NO 246
<211> LENGTH: 18
<212> TYPE: PRT
<213> ORGANISM: Homo sapiens

<400> SEQUENCE: 246

Leu Leu Asn Leu Asp Gly Thr Cys Ala Asp Ser Tyr Ser Phe Val Phe
1               5                   10                  15

Ser Arg

<210> SEQ ID NO 247
<211> LENGTH: 23
<212> TYPE: PRT
<213> ORGANISM: Homo sapiens

<400> SEQUENCE: 247

Leu Leu Asn Asn Trp Asp Val Cys Ala Asp Met Val Gly Thr Phe Thr
1               5                   10                  15

Asp Thr Glu Asp Pro Ala Lys
            20

<210> SEQ ID NO 248
<211> LENGTH: 25
<212> TYPE: PRT
<213> ORGANISM: Homo sapiens

<400> SEQUENCE: 248

Leu Leu Asn Asn Trp Asp Val Cys Ala Asp Met Val Gly Thr Phe Thr
1               5                   10                  15

Asp Thr Glu Asp Pro Ala Lys Phe Lys
            20                  25

<210> SEQ ID NO 249
<211> LENGTH: 12
<212> TYPE: PRT
<213> ORGANISM: Homo sapiens

<400> SEQUENCE: 249

Met Lys Tyr Trp Gly Val Ala Ser Phe Leu Gln Lys
1               5                   10

<210> SEQ ID NO 250
<211> LENGTH: 8

```
<212> TYPE: PRT
<213> ORGANISM: Homo sapiens

<400> SEQUENCE: 250

Gln Glu Glu Leu Cys Leu Ala Arg
1               5

<210> SEQ ID NO 251
<211> LENGTH: 10
<212> TYPE: PRT
<213> ORGANISM: Homo sapiens

<400> SEQUENCE: 251

Gln Arg Gln Glu Glu Leu Cys Leu Ala Arg
1               5                   10

<210> SEQ ID NO 252
<211> LENGTH: 9
<212> TYPE: PRT
<213> ORGANISM: Homo sapiens

<400> SEQUENCE: 252

Val Lys Glu Asn Phe Asp Lys Ala Arg
1               5

<210> SEQ ID NO 253
<211> LENGTH: 15
<212> TYPE: PRT
<213> ORGANISM: Homo sapiens

<400> SEQUENCE: 253

Trp Val Trp Ala Leu Leu Leu Ala Ala Leu Gly Ser Gly Arg
1               5                   10                  15

<210> SEQ ID NO 254
<211> LENGTH: 10
<212> TYPE: PRT
<213> ORGANISM: Homo sapiens

<400> SEQUENCE: 254

Tyr Trp Gly Val Ala Ser Phe Leu Gln Lys
1               5                   10

<210> SEQ ID NO 255
<211> LENGTH: 11
<212> TYPE: PRT
<213> ORGANISM: Homo sapiens

<400> SEQUENCE: 255

Ile Gln Glu Val Ala Gly Ser Leu Ile Phe Arg
1               5                   10

<210> SEQ ID NO 256
<211> LENGTH: 10
<212> TYPE: PRT
<213> ORGANISM: Homo sapiens

<400> SEQUENCE: 256

Asp Lys Asp Ala Val Asp Lys Leu Leu Lys
1               5                   10

<210> SEQ ID NO 257
<211> LENGTH: 28
<212> TYPE: PRT
<213> ORGANISM: Homo sapiens
```

```
<400> SEQUENCE: 257

Asp Leu Asp Ala Asn Gly Asp Ala Gln Val Asp Phe Ser Glu Phe Ile
1               5                   10                  15
Val Phe Val Ala Ala Ile Thr Ser Ala Cys His Lys
            20                  25

<210> SEQ ID NO 258
<211> LENGTH: 10
<212> TYPE: PRT
<213> ORGANISM: Homo sapiens

<400> SEQUENCE: 258

Glu Leu Pro Gly Phe Leu Gln Ser Gly Lys
1               5                   10

<210> SEQ ID NO 259
<211> LENGTH: 17
<212> TYPE: PRT
<213> ORGANISM: Homo sapiens

<400> SEQUENCE: 259

Glu Leu Pro Gly Phe Leu Gln Ser Gly Lys Asp Lys Asp Ala Val Asp
1               5                   10                  15
Lys

<210> SEQ ID NO 260
<211> LENGTH: 17
<212> TYPE: PRT
<213> ORGANISM: Homo sapiens

<400> SEQUENCE: 260

Met Thr Glu Leu Glu Thr Ala Met Gly Met Ile Ile Asp Val Phe Ser
1               5                   10                  15
Arg

<210> SEQ ID NO 261
<211> LENGTH: 16
<212> TYPE: PRT
<213> ORGANISM: Homo sapiens

<400> SEQUENCE: 261

Thr Glu Leu Glu Thr Ala Met Gly Met Ile Ile Asp Val Phe Ser Arg
1               5                   10                  15

<210> SEQ ID NO 262
<211> LENGTH: 13
<212> TYPE: PRT
<213> ORGANISM: Homo sapiens

<400> SEQUENCE: 262

Tyr Ser Gly Ser Glu Gly Ser Thr Gln Thr Leu Thr Lys
1               5                   10

<210> SEQ ID NO 263
<211> LENGTH: 17
<212> TYPE: PRT
<213> ORGANISM: Homo sapiens

<400> SEQUENCE: 263

Tyr Ser Gly Ser Glu Gly Ser Thr Gln Thr Leu Thr Lys Gly Glu Leu
1               5                   10                  15
```

Lys

<210> SEQ ID NO 264
<211> LENGTH: 7
<212> TYPE: PRT
<213> ORGANISM: Homo sapiens

<400> SEQUENCE: 264

Leu Met Glu Asp Leu Asp Arg
1               5

<210> SEQ ID NO 265
<211> LENGTH: 8
<212> TYPE: PRT
<213> ORGANISM: Homo sapiens

<400> SEQUENCE: 265

Leu Gln Asp Ala Glu Ile Ala Arg
1               5

<210> SEQ ID NO 266
<211> LENGTH: 9
<212> TYPE: PRT
<213> ORGANISM: Homo sapiens

<400> SEQUENCE: 266

Ala Ala Asp Leu Leu His Ser Lys
1               5

<210> SEQ ID NO 267
<211> LENGTH: 13
<212> TYPE: PRT
<213> ORGANISM: Homo sapiens

<400> SEQUENCE: 267

Ile Thr Thr Val Ser Leu Ser Ala Pro Asp Ala Leu Lys
1               5                   10

<210> SEQ ID NO 268
<211> LENGTH: 12
<212> TYPE: PRT
<213> ORGANISM: Homo sapiens

<400> SEQUENCE: 268

Thr Asn Val Tyr Ile Ser Ser Ser Ala Gly Ala Arg
1               5                   10

<210> SEQ ID NO 269
<211> LENGTH: 15
<212> TYPE: PRT
<213> ORGANISM: Homo sapiens

<400> SEQUENCE: 269

Glu Leu Gln Glu Leu Val Gln Tyr Pro Val Glu His Pro Asp Lys
1               5                   10                  15

<210> SEQ ID NO 270
<211> LENGTH: 10
<212> TYPE: PRT
<213> ORGANISM: Homo sapiens

<400> SEQUENCE: 270

Gly Asp Asp Leu Ser Thr Ala Ile Leu Lys
1               5                   10

```
<210> SEQ ID NO 271
<211> LENGTH: 20
<212> TYPE: PRT
<213> ORGANISM: Homo sapiens

<400> SEQUENCE: 271

Leu Ile Val Asp Glu Ala Ile Asn Glu Asp Asn Ser Val Val Ser Leu
1               5                   10                  15

Ser Gln Pro Lys
            20

<210> SEQ ID NO 272
<211> LENGTH: 17
<212> TYPE: PRT
<213> ORGANISM: Homo sapiens

<400> SEQUENCE: 272

Gly Gln Gly Cys Pro Ser Thr His Val Leu Thr His Thr Ile Ser
1               5                   10                  15

Arg

<210> SEQ ID NO 273
<211> LENGTH: 8
<212> TYPE: PRT
<213> ORGANISM: Homo sapiens

<400> SEQUENCE: 273

Val Asn Leu Leu Ser Ala Ile Lys
1               5

<210> SEQ ID NO 274
<211> LENGTH: 10
<212> TYPE: PRT
<213> ORGANISM: Homo sapiens

<400> SEQUENCE: 274

Asp Gly Ala Gly Asp Val Ala Phe Val Lys
1               5                   10

<210> SEQ ID NO 275
<211> LENGTH: 11
<212> TYPE: PRT
<213> ORGANISM: Homo sapiens

<400> SEQUENCE: 275

Glu Gly Tyr Tyr Gly Tyr Thr Gly Ala Phe Arg
1               5                   10

<210> SEQ ID NO 276
<211> LENGTH: 11
<212> TYPE: PRT
<213> ORGANISM: Homo sapiens

<400> SEQUENCE: 276

Ser Ala Ser Asp Leu Thr Trp Asp Asn Leu Lys
1               5                   10

<210> SEQ ID NO 277
<211> LENGTH: 15
<212> TYPE: PRT
<213> ORGANISM: Homo sapiens

<400> SEQUENCE: 277
```

```
Gly Gly Val Asn Asp Asn Phe Gln Gly Val Leu Gln Asn Val Arg
1               5                   10                  15

<210> SEQ ID NO 278
<211> LENGTH: 11
<212> TYPE: PRT
<213> ORGANISM: Homo sapiens

<400> SEQUENCE: 278

Thr Ile Val Thr Thr Leu Gln Asp Ser Ile Arg
1               5                   10

<210> SEQ ID NO 279
<211> LENGTH: 16
<212> TYPE: PRT
<213> ORGANISM: Homo sapiens

<400> SEQUENCE: 279

Asp Ser Thr Ile Gln Val Val Glu Asn Gly Glu Ser Ser Gln Gly Arg
1               5                   10                  15

<210> SEQ ID NO 280
<211> LENGTH: 10
<212> TYPE: PRT
<213> ORGANISM: Homo sapiens

<400> SEQUENCE: 280

Asp Trp Val Ser Val Val Thr Pro Ala Arg
1               5                   10

<210> SEQ ID NO 281
<211> LENGTH: 13
<212> TYPE: PRT
<213> ORGANISM: Homo sapiens

<400> SEQUENCE: 281

Glu Asp Phe Thr Ser Leu Ser Leu Val Leu Tyr Ser Arg
1               5                   10

<210> SEQ ID NO 282
<211> LENGTH: 10
<212> TYPE: PRT
<213> ORGANISM: Homo sapiens

<400> SEQUENCE: 282

Thr His Leu Pro Glu Val Phe Leu Ser Lys
1               5                   10

<210> SEQ ID NO 283
<211> LENGTH: 7
<212> TYPE: PRT
<213> ORGANISM: Homo sapiens

<400> SEQUENCE: 283

Tyr Thr Phe Glu Leu Ser Arg
1               5

<210> SEQ ID NO 284
<211> LENGTH: 16
<212> TYPE: PRT
<213> ORGANISM: Homo sapiens

<400> SEQUENCE: 284

Glu Ile Pro Ala Trp Val Pro Phe Asp Pro Ala Ala Gln Ile Thr Lys
1               5                   10                  15
```

<210> SEQ ID NO 285
<211> LENGTH: 10
<212> TYPE: PRT
<213> ORGANISM: Homo sapiens

<400> SEQUENCE: 285

Trp Glu Ala Glu Pro Val Tyr Val Gln Arg
1               5                   10

<210> SEQ ID NO 286
<211> LENGTH: 12
<212> TYPE: PRT
<213> ORGANISM: Homo sapiens

<400> SEQUENCE: 286

Tyr Ser Leu Thr Tyr Ile Tyr Thr Gly Leu Ser Lys
1               5                   10

<210> SEQ ID NO 287
<211> LENGTH: 12
<212> TYPE: PRT
<213> ORGANISM: Homo sapiens

<400> SEQUENCE: 287

Thr Leu Met Phe Gly Ser Tyr Leu Asp Asp Glu Lys
1               5                   10

<210> SEQ ID NO 288
<211> LENGTH: 17
<212> TYPE: PRT
<213> ORGANISM: Homo sapiens

<400> SEQUENCE: 288

Glu Gln Leu Gly Glu Phe Tyr Glu Ala Leu Asp Cys Leu Cys Ile Pro
1               5                   10                  15

Arg

<210> SEQ ID NO 289
<211> LENGTH: 15
<212> TYPE: PRT
<213> ORGANISM: Homo sapiens

<400> SEQUENCE: 289

Gln Asn Gln Cys Phe Tyr Asn Ser Ser Tyr Leu Asn Val Gln Arg
1               5                   10                  15

<210> SEQ ID NO 290
<211> LENGTH: 8
<212> TYPE: PRT
<213> ORGANISM: Homo sapiens

<400> SEQUENCE: 290

Leu Leu Glu Leu Thr Gly Pro Lys
1               5

<210> SEQ ID NO 291
<211> LENGTH: 16
<212> TYPE: PRT
<213> ORGANISM: Homo sapiens

<400> SEQUENCE: 291

Asn Gly Val Ala Gln Glu Pro Val His Leu Asp Ser Pro Ala Ile Lys
1               5                   10                  15

```
<210> SEQ ID NO 292
<211> LENGTH: 12
<212> TYPE: PRT
<213> ORGANISM: Homo sapiens

<400> SEQUENCE: 292

Ser Gly Leu Ser Thr Gly Trp Thr Gln Leu Ser Lys
1               5                   10

<210> SEQ ID NO 293
<211> LENGTH: 16
<212> TYPE: PRT
<213> ORGANISM: Homo sapiens

<400> SEQUENCE: 293

Glu Asn Gln Leu Glu Val Leu Glu Val Ser Trp Leu His Gly Leu Lys
1               5                   10                  15

<210> SEQ ID NO 294
<211> LENGTH: 7
<212> TYPE: PRT
<213> ORGANISM: Homo sapiens

<400> SEQUENCE: 294

Gly Pro Leu Gln Leu Glu Arg
1               5

<210> SEQ ID NO 295
<211> LENGTH: 10
<212> TYPE: PRT
<213> ORGANISM: Homo sapiens

<400> SEQUENCE: 295

Gly His Phe Ser Ile Ser Ile Pro Val Lys
1               5                   10

<210> SEQ ID NO 296
<211> LENGTH: 12
<212> TYPE: PRT
<213> ORGANISM: Homo sapiens

<400> SEQUENCE: 296

His Tyr Asp Gly Ser Tyr Ser Thr Phe Gly Glu Arg
1               5                   10

<210> SEQ ID NO 297
<211> LENGTH: 9
<212> TYPE: PRT
<213> ORGANISM: Homo sapiens

<400> SEQUENCE: 297

Ala Ile Pro Val Thr Gln Tyr Leu Lys
1               5

<210> SEQ ID NO 298
<211> LENGTH: 9
<212> TYPE: PRT
<213> ORGANISM: Homo sapiens

<400> SEQUENCE: 298

Leu Pro Asn Asn Val Leu Gln Glu Lys
1               5
```

```
<210> SEQ ID NO 299
<211> LENGTH: 7
<212> TYPE: PRT
<213> ORGANISM: Homo sapiens

<400> SEQUENCE: 299

Val Leu Asp Gly Leu Asn Arg
1               5

<210> SEQ ID NO 300
<211> LENGTH: 17
<212> TYPE: PRT
<213> ORGANISM: Homo sapiens

<400> SEQUENCE: 300

Val Ile Phe Asp Thr Val Asp Leu Ser Ala Thr Trp Glu Val Met Glu
1               5                   10                  15

Lys

<210> SEQ ID NO 301
<211> LENGTH: 10
<212> TYPE: PRT
<213> ORGANISM: Homo sapiens

<400> SEQUENCE: 301

Asp His Ser Ala Ile Pro Val Ile Asn Arg
1               5                   10

<210> SEQ ID NO 302
<211> LENGTH: 7
<212> TYPE: PRT
<213> ORGANISM: Homo sapiens

<400> SEQUENCE: 302

Glu Leu Trp Ile Leu Asn Arg
1               5

<210> SEQ ID NO 303
<211> LENGTH: 15
<212> TYPE: PRT
<213> ORGANISM: Homo sapiens

<400> SEQUENCE: 303

Ala Gln Ile Ile Asn Asp Ala Phe Asn Leu Ala Ser Ala His Lys
1               5                   10                  15

<210> SEQ ID NO 304
<211> LENGTH: 7
<212> TYPE: PRT
<213> ORGANISM: Homo sapiens

<400> SEQUENCE: 304

Ile Gln Thr Gln Leu Gln Arg
1               5

<210> SEQ ID NO 305
<211> LENGTH: 16
<212> TYPE: PRT
<213> ORGANISM: Homo sapiens

<400> SEQUENCE: 305

Leu Leu Gly Pro Gly Pro Ala Ala Asp Phe Ser Val Ser Val Glu Arg
1               5                   10                  15
```

<210> SEQ ID NO 306
<211> LENGTH: 11
<212> TYPE: PRT
<213> ORGANISM: Homo sapiens

<400> SEQUENCE: 306

Phe Leu Leu Gly Ser Trp Leu Glu Gln Ala Arg
1               5                   10

<210> SEQ ID NO 307
<211> LENGTH: 8
<212> TYPE: PRT
<213> ORGANISM: Homo sapiens

<400> SEQUENCE: 307

Tyr Asp Leu Leu Asp Leu Thr Arg
1               5

<210> SEQ ID NO 308
<211> LENGTH: 8
<212> TYPE: PRT
<213> ORGANISM: Homo sapiens

<400> SEQUENCE: 308

Ser Asp Val Phe Glu Ala Trp Arg
1               5

<210> SEQ ID NO 309
<211> LENGTH: 9
<212> TYPE: PRT
<213> ORGANISM: Homo sapiens

<400> SEQUENCE: 309

Val Asn Ser Phe Phe Ser Thr Phe Lys
1               5

<210> SEQ ID NO 310
<211> LENGTH: 10
<212> TYPE: PRT
<213> ORGANISM: Homo sapiens

<400> SEQUENCE: 310

Ala Leu Val Gln Gln Met Glu Gln Leu Arg
1               5                   10

<210> SEQ ID NO 311
<211> LENGTH: 9
<212> TYPE: PRT
<213> ORGANISM: Homo sapiens

<400> SEQUENCE: 311

Leu Gly Pro Leu Val Glu Gln Gly Arg
1               5

<210> SEQ ID NO 312
<211> LENGTH: 15
<212> TYPE: PRT
<213> ORGANISM: Homo sapiens

<400> SEQUENCE: 312

Ser Glu Leu Glu Glu Gln Leu Thr Pro Val Ala Glu Glu Thr Arg
1               5                   10                  15

<210> SEQ ID NO 313
<211> LENGTH: 10

```
<212> TYPE: PRT
<213> ORGANISM: Homo sapiens

<400> SEQUENCE: 313

Gln Gln Thr Glu Trp Gln Ser Gly Gln Arg
1               5                   10

<210> SEQ ID NO 314
<211> LENGTH: 7
<212> TYPE: PRT
<213> ORGANISM: Homo sapiens

<400> SEQUENCE: 314

Trp Glu Leu Ala Leu Gly Arg
1               5

<210> SEQ ID NO 315
<211> LENGTH: 9
<212> TYPE: PRT
<213> ORGANISM: Homo sapiens

<400> SEQUENCE: 315

Leu Glu Glu Gln Ala Gln Gln Ile Arg
1               5

<210> SEQ ID NO 316
<211> LENGTH: 9
<212> TYPE: PRT
<213> ORGANISM: Homo sapiens

<400> SEQUENCE: 316

Leu Ala Val Tyr Gln Ala Gly Ala Arg
1               5

<210> SEQ ID NO 317
<211> LENGTH: 9
<212> TYPE: PRT
<213> ORGANISM: Homo sapiens

<400> SEQUENCE: 317

His Asp Leu Gly His Phe Met Leu Arg
1               5

<210> SEQ ID NO 318
<211> LENGTH: 10
<212> TYPE: PRT
<213> ORGANISM: Homo sapiens

<400> SEQUENCE: 318

Leu Gln Ala Val Thr Asp Asp His Ile Arg
1               5                   10

<210> SEQ ID NO 319
<211> LENGTH: 15
<212> TYPE: PRT
<213> ORGANISM: Homo sapiens

<400> SEQUENCE: 319

Thr Val Ala Gly Gln Asp Ala Val Ile Val Leu Leu Gly Thr Arg
1               5                   10                  15

<210> SEQ ID NO 320
<211> LENGTH: 14
<212> TYPE: PRT
<213> ORGANISM: Homo sapiens
```

```
<400> SEQUENCE: 320

Asn Asp Leu Ser Pro Thr Thr Val Met Ser Glu Gly Ala Arg
1               5                   10

<210> SEQ ID NO 321
<211> LENGTH: 15
<212> TYPE: PRT
<213> ORGANISM: Homo sapiens

<400> SEQUENCE: 321

Val Val Ala Cys Thr Ser Ala Phe Leu Leu Trp Asp Pro Thr Lys
1               5                   10                  15

<210> SEQ ID NO 322
<211> LENGTH: 15
<212> TYPE: PRT
<213> ORGANISM: Homo sapiens

<400> SEQUENCE: 322

Gly Val Gly Trp Ser His Pro Leu Pro Gln Cys Glu Ile Val Lys
1               5                   10                  15

<210> SEQ ID NO 323
<211> LENGTH: 10
<212> TYPE: PRT
<213> ORGANISM: Homo sapiens

<400> SEQUENCE: 323

Leu Asn Asn Gly Glu Ile Thr Gln His Arg
1               5                   10

<210> SEQ ID NO 324
<211> LENGTH: 9
<212> TYPE: PRT
<213> ORGANISM: Homo sapiens

<400> SEQUENCE: 324

Glu Glu Ile Ile Tyr Glu Cys Asp Lys
1               5

<210> SEQ ID NO 325
<211> LENGTH: 12
<212> TYPE: PRT
<213> ORGANISM: Homo sapiens

<400> SEQUENCE: 325

Gly Ser Ser Val Ile His Cys Asp Ala Asp Ser Lys
1               5                   10

<210> SEQ ID NO 326
<211> LENGTH: 18
<212> TYPE: PRT
<213> ORGANISM: Homo sapiens

<400> SEQUENCE: 326

Asp Thr Ala Asn Trp Leu Glu Ile Asn Pro Asp Thr Gly Ala Ile Ser
1               5                   10                  15

Thr Arg

<210> SEQ ID NO 327
<211> LENGTH: 16
<212> TYPE: PRT
<213> ORGANISM: Homo sapiens
```

<400> SEQUENCE: 327

Gly Gln Val Pro Glu Asn Glu Ala Asn Val Val Ile Thr Thr Leu Lys
1               5                   10                  15

<210> SEQ ID NO 328
<211> LENGTH: 14
<212> TYPE: PRT
<213> ORGANISM: Homo sapiens

<400> SEQUENCE: 328

Asn Thr Gly Val Ile Ser Val Val Thr Thr Gly Leu Asp Arg
1               5                   10

<210> SEQ ID NO 329
<211> LENGTH: 10
<212> TYPE: PRT
<213> ORGANISM: Homo sapiens

<400> SEQUENCE: 329

Val Gly Thr Asp Gly Val Ile Thr Val Lys
1               5                   10

<210> SEQ ID NO 330
<211> LENGTH: 7
<212> TYPE: PRT
<213> ORGANISM: Homo sapiens

<400> SEQUENCE: 330

Val Thr Glu Pro Leu Asp Arg
1               5

<210> SEQ ID NO 331
<211> LENGTH: 12
<212> TYPE: PRT
<213> ORGANISM: Homo sapiens

<400> SEQUENCE: 331

Glu Gln Phe Leu Asp Gly Asp Gly Trp Thr Ser Arg
1               5                   10

<210> SEQ ID NO 332
<211> LENGTH: 11
<212> TYPE: PRT
<213> ORGANISM: Homo sapiens

<400> SEQUENCE: 332

Gly Gln Thr Leu Val Val Gln Phe Thr Val Lys
1               5                   10

<210> SEQ ID NO 333
<211> LENGTH: 14
<212> TYPE: PRT
<213> ORGANISM: Homo sapiens

<400> SEQUENCE: 333

Phe Tyr Ala Leu Ser Ala Ser Phe Glu Pro Phe Ser Asn Lys
1               5                   10

<210> SEQ ID NO 334
<211> LENGTH: 13
<212> TYPE: PRT
<213> ORGANISM: Homo sapiens

<400> SEQUENCE: 334

-continued

His Glu Gln Asn Ile Asp Cys Gly Gly Gly Tyr Val Lys
1               5                   10

<210> SEQ ID NO 335
<211> LENGTH: 18
<212> TYPE: PRT
<213> ORGANISM: Homo sapiens

<400> SEQUENCE: 335

Tyr Ser Gln Ala Val Pro Ala Val Thr Glu Gly Pro Ile Pro Glu Val
1               5                   10                  15

Leu Lys

<210> SEQ ID NO 336
<211> LENGTH: 13
<212> TYPE: PRT
<213> ORGANISM: Homo sapiens

<400> SEQUENCE: 336

Leu Val Asp Gln Asn Ile Phe Ser Phe Tyr Leu Ser Arg
1               5                   10

<210> SEQ ID NO 337
<211> LENGTH: 10
<212> TYPE: PRT
<213> ORGANISM: Homo sapiens

<400> SEQUENCE: 337

Val Ser Thr Leu Pro Ala Ile Thr Leu Lys
1               5                   10

<210> SEQ ID NO 338
<211> LENGTH: 8
<212> TYPE: PRT
<213> ORGANISM: Homo sapiens

<400> SEQUENCE: 338

Gln Val Phe Gly Glu Ala Thr Lys
1               5

<210> SEQ ID NO 339
<211> LENGTH: 7
<212> TYPE: PRT
<213> ORGANISM: Homo sapiens

<400> SEQUENCE: 339

Tyr Tyr Thr Val Phe Asp Arg
1               5

<210> SEQ ID NO 340
<211> LENGTH: 10
<212> TYPE: PRT
<213> ORGANISM: Homo sapiens

<400> SEQUENCE: 340

Gln Pro Gly Ile Thr Phe Ile Ala Ala Lys
1               5                   10

<210> SEQ ID NO 341
<211> LENGTH: 9
<212> TYPE: PRT
<213> ORGANISM: Homo sapiens

<400> SEQUENCE: 341

```
Leu Ser Pro Glu Asp Tyr Thr Leu Lys
1               5

<210> SEQ ID NO 342
<211> LENGTH: 9
<212> TYPE: PRT
<213> ORGANISM: Homo sapiens

<400> SEQUENCE: 342

Gln Val Met Asn Gly Phe Gln Asn Arg
1               5

<210> SEQ ID NO 343
<211> LENGTH: 23
<212> TYPE: PRT
<213> ORGANISM: Homo sapiens

<400> SEQUENCE: 343

Ala Val Ala Thr Val Gly Pro Ile Ser Val Ala Ile Asp Ala Gly His
1               5                   10                  15

Glu Ser Phe Leu Phe Tyr Lys
            20

<210> SEQ ID NO 344
<211> LENGTH: 12
<212> TYPE: PRT
<213> ORGANISM: Homo sapiens

<400> SEQUENCE: 344

Val Phe Gln Glu Pro Leu Phe Tyr Glu Ala Pro Arg
1               5                   10

<210> SEQ ID NO 345
<211> LENGTH: 14
<212> TYPE: PRT
<213> ORGANISM: Homo sapiens

<400> SEQUENCE: 345

Tyr Ser Val Ala Asn Asp Thr Gly Phe Val Asp Ile Pro Lys
1               5                   10

<210> SEQ ID NO 346
<211> LENGTH: 14
<212> TYPE: PRT
<213> ORGANISM: Homo sapiens

<400> SEQUENCE: 346

Asn Ser Trp Gly Glu Glu Trp Gly Met Gly Gly Tyr Val Lys
1               5                   10

<210> SEQ ID NO 347
<211> LENGTH: 10
<212> TYPE: PRT
<213> ORGANISM: Homo sapiens

<400> SEQUENCE: 347

Met Ile Glu Leu His Asn Gln Glu Tyr Arg
1               5                   10

<210> SEQ ID NO 348
<211> LENGTH: 11
<212> TYPE: PRT
<213> ORGANISM: Homo sapiens
```

```
<400> SEQUENCE: 348

Leu Tyr Gly Met Asn Glu Glu Gly Trp Arg Arg
1               5                  10

<210> SEQ ID NO 349
<211> LENGTH: 14
<212> TYPE: PRT
<213> ORGANISM: Homo sapiens

<400> SEQUENCE: 349

Asn His Cys Gly Ile Ala Ser Ala Ala Ser Tyr Pro Thr Val
1               5                  10

<210> SEQ ID NO 350
<211> LENGTH: 8
<212> TYPE: PRT
<213> ORGANISM: Homo sapiens

<400> SEQUENCE: 350

Ala Gly Leu Gln Val Tyr Asn Lys
1               5

<210> SEQ ID NO 351
<211> LENGTH: 12
<212> TYPE: PRT
<213> ORGANISM: Homo sapiens

<400> SEQUENCE: 351

Phe Glu His Cys Asn Phe Asn Asp Val Thr Thr Arg
1               5                  10

<210> SEQ ID NO 352
<211> LENGTH: 16
<212> TYPE: PRT
<213> ORGANISM: Homo sapiens

<400> SEQUENCE: 352

Thr Ala Val Asn Cys Ser Ser Asp Phe Asp Ala Cys Leu Ile Thr Lys
1               5                  10                  15

<210> SEQ ID NO 353
<211> LENGTH: 10
<212> TYPE: PRT
<213> ORGANISM: Homo sapiens

<400> SEQUENCE: 353

Glu Asn Glu Leu Thr Tyr Tyr Cys Cys Lys
1               5                  10

<210> SEQ ID NO 354
<211> LENGTH: 18
<212> TYPE: PRT
<213> ORGANISM: Homo sapiens

<400> SEQUENCE: 354

Thr Val Leu Leu Leu Val Thr Pro Phe Leu Ala Ala Ala Trp Ser Leu
1               5                  10                  15

His Pro

<210> SEQ ID NO 355
<211> LENGTH: 18
<212> TYPE: PRT
<213> ORGANISM: Homo sapiens
```

```
<400> SEQUENCE: 355

Gly Ala Asn Gly Ala Pro Gly Ile Ala Gly Ala Pro Gly Phe Pro Gly
1               5                   10                  15

Ala Arg

<210> SEQ ID NO 356
<211> LENGTH: 10
<212> TYPE: PRT
<213> ORGANISM: Homo sapiens

<400> SEQUENCE: 356

Ser Leu Ser Gln Gln Ile Glu Asn Ile Arg
1               5                   10

<210> SEQ ID NO 357
<211> LENGTH: 9
<212> TYPE: PRT
<213> ORGANISM: Homo sapiens

<400> SEQUENCE: 357

Gly Phe Ser Gly Leu Asp Gly Ala Lys
1               5

<210> SEQ ID NO 358
<211> LENGTH: 13
<212> TYPE: PRT
<213> ORGANISM: Homo sapiens

<400> SEQUENCE: 358

Ala Leu Leu Leu Gln Gly Ser Asn Glu Ile Glu Ile Arg
1               5                   10

<210> SEQ ID NO 359
<211> LENGTH: 9
<212> TYPE: PRT
<213> ORGANISM: Homo sapiens

<400> SEQUENCE: 359

Gly Ser Glu Gly Pro Gln Gly Val Arg
1               5

<210> SEQ ID NO 360
<211> LENGTH: 9
<212> TYPE: PRT
<213> ORGANISM: Homo sapiens

<400> SEQUENCE: 360

Gly Glu Ala Gly Pro Gln Gly Pro Arg
1               5

<210> SEQ ID NO 361
<211> LENGTH: 9
<212> TYPE: PRT
<213> ORGANISM: Homo sapiens

<400> SEQUENCE: 361

Gly Val Val Gly Pro Gln Gly Ala Arg
1               5

<210> SEQ ID NO 362
<211> LENGTH: 13
<212> TYPE: PRT
<213> ORGANISM: Homo sapiens
```

```
<400> SEQUENCE: 362

Val Tyr Cys Asp Phe Ser Thr Gly Glu Thr Cys Ile Arg
1               5                   10

<210> SEQ ID NO 363
<211> LENGTH: 10
<212> TYPE: PRT
<213> ORGANISM: Homo sapiens

<400> SEQUENCE: 363

Glu Met Ala Thr Gln Leu Ala Phe Met Arg
1               5                   10

<210> SEQ ID NO 364
<211> LENGTH: 16
<212> TYPE: PRT
<213> ORGANISM: Homo sapiens

<400> SEQUENCE: 364

Ser Leu Asn Asn Gln Ile Glu Thr Leu Leu Thr Pro Glu Gly Ser Arg
1               5                   10                  15

<210> SEQ ID NO 365
<211> LENGTH: 9
<212> TYPE: PRT
<213> ORGANISM: Homo sapiens

<400> SEQUENCE: 365

Thr Gly Leu Gln Glu Val Glu Val Lys
1               5

<210> SEQ ID NO 366
<211> LENGTH: 13
<212> TYPE: PRT
<213> ORGANISM: Homo sapiens

<400> SEQUENCE: 366

Ser Ser Leu Ser Val Pro Tyr Val Ile Val Pro Leu Lys
1               5                   10

<210> SEQ ID NO 367
<211> LENGTH: 14
<212> TYPE: PRT
<213> ORGANISM: Homo sapiens

<400> SEQUENCE: 367

Val Phe Ser Val Ala Ile Thr Pro Asp His Leu Glu Pro Arg
1               5                   10

<210> SEQ ID NO 368
<211> LENGTH: 9
<212> TYPE: PRT
<213> ORGANISM: Homo sapiens

<400> SEQUENCE: 368

Ile Ala Leu Val Ile Thr Asp Gly Arg
1               5

<210> SEQ ID NO 369
<211> LENGTH: 13
<212> TYPE: PRT
<213> ORGANISM: Homo sapiens

<400> SEQUENCE: 369
```

Glu Asn Tyr Ala Glu Leu Leu Glu Asp Ala Phe Leu Lys
1               5                   10

<210> SEQ ID NO 370
<211> LENGTH: 9
<212> TYPE: PRT
<213> ORGANISM: Homo sapiens

<400> SEQUENCE: 370

Val Pro Ser Tyr Gln Ala Leu Leu Arg
1               5

<210> SEQ ID NO 371
<211> LENGTH: 24
<212> TYPE: PRT
<213> ORGANISM: Homo sapiens

<400> SEQUENCE: 371

Thr Thr Met Ala Leu Thr Val Gly Gly Thr Ile Tyr Cys Leu Ile Ala
1               5                   10                  15

Leu Tyr Met Ala Ser Gln Pro Lys
            20

<210> SEQ ID NO 372
<211> LENGTH: 9
<212> TYPE: PRT
<213> ORGANISM: Homo sapiens

<400> SEQUENCE: 372

Ile Glu Pro Asn Leu Pro Ser Tyr Arg
1               5

<210> SEQ ID NO 373
<211> LENGTH: 10
<212> TYPE: PRT
<213> ORGANISM: Homo sapiens

<400> SEQUENCE: 373

Trp Ile Ser Asp His Glu Tyr Leu Tyr Lys
1               5                   10

<210> SEQ ID NO 374
<211> LENGTH: 16
<212> TYPE: PRT
<213> ORGANISM: Homo sapiens

<400> SEQUENCE: 374

Thr Gln Asn Asp Val Asp Ile Ala Asp Val Ala Tyr Tyr Phe Glu Lys
1               5                   10                  15

<210> SEQ ID NO 375
<211> LENGTH: 11
<212> TYPE: PRT
<213> ORGANISM: Homo sapiens

<400> SEQUENCE: 375

Leu Ala Val Asn Cys Phe Val Asn Asn Asn Arg
1               5                   10

<210> SEQ ID NO 376
<211> LENGTH: 9
<212> TYPE: PRT
<213> ORGANISM: Homo sapiens

<400> SEQUENCE: 376

```
Thr Tyr Trp Ile Ile Ile Glu Leu Lys
1               5

<210> SEQ ID NO 377
<211> LENGTH: 8
<212> TYPE: PRT
<213> ORGANISM: Homo sapiens

<400> SEQUENCE: 377

Gly Glu Ser Leu Phe His Ser Lys
1               5

<210> SEQ ID NO 378
<211> LENGTH: 23
<212> TYPE: PRT
<213> ORGANISM: Homo sapiens

<400> SEQUENCE: 378

Phe Ile Thr Ser Ile Leu Tyr Glu Asn Asn Val Ile Thr Ile Asp Leu
1               5                   10                  15

Val Gln Asn Ser Ser Gln Lys
            20

<210> SEQ ID NO 379
<211> LENGTH: 13
<212> TYPE: PRT
<213> ORGANISM: Homo sapiens

<400> SEQUENCE: 379

Val Gly Pro Gln Val Pro Leu Ser Glu Pro Gly Phe Arg
1               5                   10

<210> SEQ ID NO 380
<211> LENGTH: 20
<212> TYPE: PRT
<213> ORGANISM: Homo sapiens

<400> SEQUENCE: 380

Asn Thr Glu Ile Ser Phe Ile Leu Gly Gln Glu Phe Asp Glu Val Thr
1               5                   10                  15

Ala Asp Asp Arg
            20

<210> SEQ ID NO 381
<211> LENGTH: 9
<212> TYPE: PRT
<213> ORGANISM: Homo sapiens

<400> SEQUENCE: 381

Glu Val Gly Val Gly Phe Ala Thr Arg
1               5

<210> SEQ ID NO 382
<211> LENGTH: 15
<212> TYPE: PRT
<213> ORGANISM: Homo sapiens

<400> SEQUENCE: 382

Ser Thr Ile Thr Leu Asp Gly Gly Val Leu Val His Val Gln Lys
1               5                   10                  15

<210> SEQ ID NO 383
<211> LENGTH: 21
```

<212> TYPE: PRT
<213> ORGANISM: Homo sapiens

<400> SEQUENCE: 383

Val Ala Gly Met Ala Lys Pro Asn Met Ile Ile Ser Val Asn Gly Asp
1               5                   10                  15
Val Ile Thr Ile Lys
            20

<210> SEQ ID NO 384
<211> LENGTH: 11
<212> TYPE: PRT
<213> ORGANISM: Homo sapiens

<400> SEQUENCE: 384

Gly Glu Pro Gly Asp Pro Val Asn Leu Leu Arg
1               5                   10

<210> SEQ ID NO 385
<211> LENGTH: 13
<212> TYPE: PRT
<213> ORGANISM: Homo sapiens

<400> SEQUENCE: 385

Tyr Tyr Trp Gly Gly Gln Tyr Thr Trp Asp Met Ala Lys
1               5                   10

<210> SEQ ID NO 386
<211> LENGTH: 15
<212> TYPE: PRT
<213> ORGANISM: Homo sapiens

<400> SEQUENCE: 386

Asn Tyr Cys Gly Leu Pro Gly Glu Tyr Trp Leu Gly Asn Asp Lys
1               5                   10                  15

<210> SEQ ID NO 387
<211> LENGTH: 15
<212> TYPE: PRT
<213> ORGANISM: Homo sapiens

<400> SEQUENCE: 387

Glu Val Gln Gly Phe Glu Ser Ala Thr Phe Leu Gly Tyr Phe Lys
1               5                   10                  15

<210> SEQ ID NO 388
<211> LENGTH: 8
<212> TYPE: PRT
<213> ORGANISM: Homo sapiens

<400> SEQUENCE: 388

Thr Gly Ala Gln Glu Leu Leu Arg
1               5

<210> SEQ ID NO 389
<211> LENGTH: 8
<212> TYPE: PRT
<213> ORGANISM: Homo sapiens

<400> SEQUENCE: 389

Tyr Leu Glu Ser Ala Gly Ala Arg
1               5

<210> SEQ ID NO 390

```
<211> LENGTH: 9
<212> TYPE: PRT
<213> ORGANISM: Homo sapiens

<400> SEQUENCE: 390

Tyr Tyr Ile Ala Ala Ser Tyr Val Lys
1               5

<210> SEQ ID NO 391
<211> LENGTH: 13
<212> TYPE: PRT
<213> ORGANISM: Homo sapiens

<400> SEQUENCE: 391

Asn Leu Asp Gly Ile Ser His Ala Pro Asn Ala Val Lys
1               5                   10

<210> SEQ ID NO 392
<211> LENGTH: 11
<212> TYPE: PRT
<213> ORGANISM: Homo sapiens

<400> SEQUENCE: 392

Ile Glu Phe Ile Ser Thr Met Glu Gly Tyr Lys
1               5                   10

<210> SEQ ID NO 393
<211> LENGTH: 9
<212> TYPE: PRT
<213> ORGANISM: Homo sapiens

<400> SEQUENCE: 393

Met Phe Leu Ser Phe Pro Thr Thr Lys
1               5

<210> SEQ ID NO 394
<211> LENGTH: 16
<212> TYPE: PRT
<213> ORGANISM: Homo sapiens

<400> SEQUENCE: 394

Thr Tyr Phe Pro His Phe Asp Leu Ser His Gly Ser Ala Gln Val Lys
1               5                   10                  15

<210> SEQ ID NO 395
<211> LENGTH: 15
<212> TYPE: PRT
<213> ORGANISM: Homo sapiens

<400> SEQUENCE: 395

Val Gly Ala His Ala Gly Glu Tyr Gly Ala Glu Ala Leu Glu Arg
1               5                   10                  15

<210> SEQ ID NO 396
<211> LENGTH: 12
<212> TYPE: PRT
<213> ORGANISM: Homo sapiens

<400> SEQUENCE: 396

Phe Leu Ala Ser Val Ser Thr Val Leu Thr Ser Lys
1               5                   10

<210> SEQ ID NO 397
<211> LENGTH: 19
<212> TYPE: PRT
```

-continued

<213> ORGANISM: Homo sapiens

<400> SEQUENCE: 397

Phe Phe Glu Ser Phe Gly Asp Leu Ser Thr Pro Asp Ala Val Met Gly
1               5                   10                  15

Asn Pro Lys

<210> SEQ ID NO 398
<211> LENGTH: 9
<212> TYPE: PRT
<213> ORGANISM: Homo sapiens

<400> SEQUENCE: 398

Ser Ala Val Thr Ala Leu Trp Gly Lys
1               5

<210> SEQ ID NO 399
<211> LENGTH: 13
<212> TYPE: PRT
<213> ORGANISM: Homo sapiens

<400> SEQUENCE: 399

Val Asn Val Asp Glu Val Gly Gly Glu Ala Leu Gly Arg
1               5                   10

<210> SEQ ID NO 400
<211> LENGTH: 12
<212> TYPE: PRT
<213> ORGANISM: Homo sapiens

<400> SEQUENCE: 400

Glu Phe Thr Pro Pro Val Gln Ala Ala Tyr Gln Lys
1               5                   10

<210> SEQ ID NO 401
<211> LENGTH: 13
<212> TYPE: PRT
<213> ORGANISM: Homo sapiens

<400> SEQUENCE: 401

Gly Thr Phe Ala Thr Leu Ser Glu Leu His Cys Asp Lys
1               5                   10

<210> SEQ ID NO 402
<211> LENGTH: 9
<212> TYPE: PRT
<213> ORGANISM: Homo sapiens

<400> SEQUENCE: 402

Val Gly Tyr Val Ser Gly Trp Gly Arg
1               5

<210> SEQ ID NO 403
<211> LENGTH: 10
<212> TYPE: PRT
<213> ORGANISM: Homo sapiens

<400> SEQUENCE: 403

Val Thr Ser Ile Gln Asp Trp Val Gln Lys
1               5                   10

<210> SEQ ID NO 404
<211> LENGTH: 16
<212> TYPE: PRT

```
<213> ORGANISM: Homo sapiens

<400> SEQUENCE: 404

Val Val Leu His Pro Asn Tyr Ser Gln Val Asp Ile Gly Leu Ile Lys
1               5                   10                  15

<210> SEQ ID NO 405
<211> LENGTH: 7
<212> TYPE: PRT
<213> ORGANISM: Homo sapiens

<400> SEQUENCE: 405

Asp Tyr Ala Glu Val Gly Arg
1               5

<210> SEQ ID NO 406
<211> LENGTH: 10
<212> TYPE: PRT
<213> ORGANISM: Homo sapiens

<400> SEQUENCE: 406

His Tyr Glu Gly Ser Thr Val Pro Glu Lys
1               5                   10

<210> SEQ ID NO 407
<211> LENGTH: 15
<212> TYPE: PRT
<213> ORGANISM: Homo sapiens

<400> SEQUENCE: 407

Thr His Glu Asp Leu Tyr Ile Ile Pro Ile Pro Asn Cys Asp Arg
1               5                   10                  15

<210> SEQ ID NO 408
<211> LENGTH: 7
<212> TYPE: PRT
<213> ORGANISM: Homo sapiens

<400> SEQUENCE: 408

Leu Ala Ala Ser Gln Ser Arg
1               5

<210> SEQ ID NO 409
<211> LENGTH: 17
<212> TYPE: PRT
<213> ORGANISM: Homo sapiens

<400> SEQUENCE: 409

Glu Asp Ala Arg Pro Val Pro Gln Gly Ser Cys Gln Ser Glu Leu His
1               5                   10                  15

Arg

<210> SEQ ID NO 410
<211> LENGTH: 7
<212> TYPE: PRT
<213> ORGANISM: Homo sapiens

<400> SEQUENCE: 410

Asn Gly Asn Phe His Pro Lys
1               5

<210> SEQ ID NO 411
<211> LENGTH: 10
<212> TYPE: PRT
```

<213> ORGANISM: Homo sapiens

<400> SEQUENCE: 411

Ala Pro Ala Val Ala Glu Glu Asn Pro Lys
1               5                   10

<210> SEQ ID NO 412
<211> LENGTH: 15
<212> TYPE: PRT
<213> ORGANISM: Homo sapiens

<400> SEQUENCE: 412

His Leu Asp Ser Val Leu Gln Gln Leu Gln Thr Glu Val Tyr Arg
1               5                   10                  15

<210> SEQ ID NO 413
<211> LENGTH: 13
<212> TYPE: PRT
<213> ORGANISM: Homo sapiens

<400> SEQUENCE: 413

Gly Ala Gln Thr Leu Tyr Val Pro Asn Cys Asp His Arg
1               5                   10

<210> SEQ ID NO 414
<211> LENGTH: 23
<212> TYPE: PRT
<213> ORGANISM: Homo sapiens

<400> SEQUENCE: 414

Leu Leu Pro Pro Leu Leu Leu Leu Ala Leu Leu Ala Ala Ser
1               5                   10                  15

Pro Gly Gly Ala Leu Ala Arg
            20

<210> SEQ ID NO 415
<211> LENGTH: 7
<212> TYPE: PRT
<213> ORGANISM: Homo sapiens

<400> SEQUENCE: 415

Asp Asp Glu Ala Pro Leu Arg
1               5

<210> SEQ ID NO 416
<211> LENGTH: 16
<212> TYPE: PRT
<213> ORGANISM: Homo sapiens

<400> SEQUENCE: 416

Glu Ser Lys Pro Gln Ala Gly Thr Ala Arg Pro Gln Asp Val Asn Arg
1               5                   10                  15

<210> SEQ ID NO 417
<211> LENGTH: 12
<212> TYPE: PRT
<213> ORGANISM: Homo sapiens

<400> SEQUENCE: 417

Leu Gly Glu Leu Ile Leu Thr Ser Glu Ser Ser Arg
1               5                   10

<210> SEQ ID NO 418
<211> LENGTH: 10

```
<212> TYPE: PRT
<213> ORGANISM: Homo sapiens

<400> SEQUENCE: 418

Gln Ala Asp Ser Asp Ile Pro Leu Asp Arg
1               5                   10

<210> SEQ ID NO 419
<211> LENGTH: 14
<212> TYPE: PRT
<213> ORGANISM: Homo sapiens

<400> SEQUENCE: 419

Phe His Leu Ala Thr Ala Glu Trp Ile Ala Glu Pro Val Arg
1               5                   10

<210> SEQ ID NO 420
<211> LENGTH: 13
<212> TYPE: PRT
<213> ORGANISM: Homo sapiens

<400> SEQUENCE: 420

Leu Tyr Pro Glu Ser Gln Gly Ser Asp Thr Ala Trp Arg
1               5                   10

<210> SEQ ID NO 421
<211> LENGTH: 11
<212> TYPE: PRT
<213> ORGANISM: Homo sapiens

<400> SEQUENCE: 421

Ser Ser Gly Pro Gly Gly Gln Asn Val Asn Lys
1               5                   10

<210> SEQ ID NO 422
<211> LENGTH: 19
<212> TYPE: PRT
<213> ORGANISM: Homo sapiens

<400> SEQUENCE: 422

Thr Pro Glu Val Thr Cys Val Val Val Asp Val Ser His Glu Asp Pro
1               5                   10                  15

Glu Val Lys

<210> SEQ ID NO 423
<211> LENGTH: 12
<212> TYPE: PRT
<213> ORGANISM: Homo sapiens

<400> SEQUENCE: 423

Glu Ala Leu Ala Glu Asn Asn Leu Asn Leu Pro Lys
1               5                   10

<210> SEQ ID NO 424
<211> LENGTH: 8
<212> TYPE: PRT
<213> ORGANISM: Homo sapiens

<400> SEQUENCE: 424

Glu Phe Leu Gln Ser Ser Leu Arg
1               5

<210> SEQ ID NO 425
<211> LENGTH: 9
```

```
<212> TYPE: PRT
<213> ORGANISM: Homo sapiens

<400> SEQUENCE: 425

Phe Glu Ser Ser Glu Glu Gln Ala Arg
1               5

<210> SEQ ID NO 426
<211> LENGTH: 18
<212> TYPE: PRT
<213> ORGANISM: Homo sapiens

<400> SEQUENCE: 426

Ile Ile Thr Gly Leu Leu Glu Phe Glu Val Tyr Leu Glu Tyr Leu Gln
1               5                   10                  15

Asn Arg

<210> SEQ ID NO 427
<211> LENGTH: 18
<212> TYPE: PRT
<213> ORGANISM: Homo sapiens

<400> SEQUENCE: 427

Leu Gln Ala Gln Asn Gln Trp Leu Gln Asp Met Thr Thr His Leu Ile
1               5                   10                  15

Leu Arg

<210> SEQ ID NO 428
<211> LENGTH: 19
<212> TYPE: PRT
<213> ORGANISM: Homo sapiens

<400> SEQUENCE: 428

Asn Leu Asp Ala Ile Thr Thr Pro Asp Pro Thr Thr Asn Ala Ser Leu
1               5                   10                  15

Leu Thr Lys

<210> SEQ ID NO 429
<211> LENGTH: 8
<212> TYPE: PRT
<213> ORGANISM: Homo sapiens

<400> SEQUENCE: 429

Gln Pro Leu Thr Ser Ser Glu Arg
1               5

<210> SEQ ID NO 430
<211> LENGTH: 10
<212> TYPE: PRT
<213> ORGANISM: Homo sapiens

<400> SEQUENCE: 430

Tyr Ile Leu Asp Gly Ile Ser Ala Leu Arg
1               5                   10

<210> SEQ ID NO 431
<211> LENGTH: 16
<212> TYPE: PRT
<213> ORGANISM: Homo sapiens

<400> SEQUENCE: 431

Asp Gly Cys Phe Gln Ser Gly Phe Asn Glu Glu Thr Cys Leu Val Lys
1               5                   10                  15
```

-continued

<210> SEQ ID NO 432
<211> LENGTH: 8
<212> TYPE: PRT
<213> ORGANISM: Homo sapiens

<400> SEQUENCE: 432

Val Leu Ile Gln Phe Leu Gln Lys
1               5

<210> SEQ ID NO 433
<211> LENGTH: 15
<212> TYPE: PRT
<213> ORGANISM: Homo sapiens

<400> SEQUENCE: 433

Leu Leu Gly Ala Ser Glu Leu Pro Ile Val Thr Pro Ala Leu Arg
1               5                   10                  15

<210> SEQ ID NO 434
<211> LENGTH: 9
<212> TYPE: PRT
<213> ORGANISM: Homo sapiens

<400> SEQUENCE: 434

Thr Gly Val Val Pro Gln Leu Val Lys
1               5

<210> SEQ ID NO 435
<211> LENGTH: 18
<212> TYPE: PRT
<213> ORGANISM: Homo sapiens

<400> SEQUENCE: 435

Ile Ile Leu Val Ile Leu Asp Ala Ile Ser Asn Ile Phe Gln Ala Ala
1               5                   10                  15

Glu Lys

<210> SEQ ID NO 436
<211> LENGTH: 8
<212> TYPE: PRT
<213> ORGANISM: Homo sapiens

<400> SEQUENCE: 436

Ala Ser Leu Ser Leu Ile Glu Lys
1               5

<210> SEQ ID NO 437
<211> LENGTH: 15
<212> TYPE: PRT
<213> ORGANISM: Homo sapiens

<400> SEQUENCE: 437

Asn Asn Gln Gly Thr Val Asn Trp Ser Val Asp Asp Ile Val Lys
1               5                   10                  15

<210> SEQ ID NO 438
<211> LENGTH: 11
<212> TYPE: PRT
<213> ORGANISM: Homo sapiens

<400> SEQUENCE: 438

Phe Ser Ile Glu Gly Ser Tyr Gln Leu Glu Lys
1               5                   10

<210> SEQ ID NO 439
<211> LENGTH: 21
<212> TYPE: PRT
<213> ORGANISM: Homo sapiens

<400> SEQUENCE: 439

Val Val Gly Val Pro Tyr Gln Gly Asn Ala Thr Ala Leu Phe Ile Leu
1               5                   10                  15

Pro Ser Glu Gly Lys
            20

<210> SEQ ID NO 440
<211> LENGTH: 13
<212> TYPE: PRT
<213> ORGANISM: Homo sapiens

<400> SEQUENCE: 440

Met Gln Ile Leu Glu Gly Leu Gly Leu Asn Leu Gln Lys
1               5                   10

<210> SEQ ID NO 441
<211> LENGTH: 8
<212> TYPE: PRT
<213> ORGANISM: Homo sapiens

<400> SEQUENCE: 441

Val Gln Ser Thr Ile Thr Ser Arg
1               5

<210> SEQ ID NO 442
<211> LENGTH: 8
<212> TYPE: PRT
<213> ORGANISM: Homo sapiens

<400> SEQUENCE: 442

Asn Asp Leu Ile Ser Ala Thr Lys
1               5

<210> SEQ ID NO 443
<211> LENGTH: 7
<212> TYPE: PRT
<213> ORGANISM: Homo sapiens

<400> SEQUENCE: 443

Thr Ile Leu Asp Asp Leu Arg
1               5

<210> SEQ ID NO 444
<211> LENGTH: 11
<212> TYPE: PRT
<213> ORGANISM: Homo sapiens

<400> SEQUENCE: 444

Val Gln Phe Glu Leu His Tyr Gln Glu Val Lys
1               5                   10

<210> SEQ ID NO 445
<211> LENGTH: 9
<212> TYPE: PRT
<213> ORGANISM: Homo sapiens

<400> SEQUENCE: 445

Ala Phe Asp Ser Asp Gly Asp Gly Arg 1               5

<210> SEQ ID NO 446
<211> LENGTH: 7
<212> TYPE: PRT
<213> ORGANISM: Homo sapiens

<400> SEQUENCE: 446

Tyr Ser Phe Leu Glu Leu Arg
1               5

<210> SEQ ID NO 447
<211> LENGTH: 11
<212> TYPE: PRT
<213> ORGANISM: Homo sapiens

<400> SEQUENCE: 447

Phe Ser Gln Phe Leu Gly Asp Pro Val Glu Lys
1               5                   10

<210> SEQ ID NO 448
<211> LENGTH: 21
<212> TYPE: PRT
<213> ORGANISM: Homo sapiens

<400> SEQUENCE: 448

Leu Thr Tyr Gln Glu Ile Trp Thr Ser Leu Gly Ser Ala Met Pro Glu
1               5                   10                  15

Pro Glu Ser Leu Arg
            20

<210> SEQ ID NO 449
<211> LENGTH: 17
<212> TYPE: PRT
<213> ORGANISM: Homo sapiens

<400> SEQUENCE: 449

Ser Ala Ala Asp Leu Ile Ser Leu Pro Thr Thr Val Glu Gly Leu Gln
1               5                   10                  15

Lys

<210> SEQ ID NO 450
<211> LENGTH: 13
<212> TYPE: PRT
<213> ORGANISM: Homo sapiens

<400> SEQUENCE: 450

Gln Ile Ser Leu Leu Thr Ser Ala Val Asn His Leu Lys
1               5                   10

<210> SEQ ID NO 451
<211> LENGTH: 12
<212> TYPE: PRT
<213> ORGANISM: Homo sapiens

<400> SEQUENCE: 451

Ala Leu Glu Glu Ala Asn Thr Glu Leu Glu Val Lys
1               5                   10

<210> SEQ ID NO 452
<211> LENGTH: 12
<212> TYPE: PRT
<213> ORGANISM: Homo sapiens

```
<400> SEQUENCE: 452

Leu Ser Val Glu Ala Asp Ile Asn Gly Leu Arg Arg
1               5                   10

<210> SEQ ID NO 453
<211> LENGTH: 8
<212> TYPE: PRT
<213> ORGANISM: Homo sapiens

<400> SEQUENCE: 453

Thr Ile Glu Glu Leu Gln Asn Lys
1               5

<210> SEQ ID NO 454
<211> LENGTH: 13
<212> TYPE: PRT
<213> ORGANISM: Homo sapiens

<400> SEQUENCE: 454

Ala Ser Leu Glu Gly Asn Leu Ala Glu Thr Glu Asn Arg
1               5                   10

<210> SEQ ID NO 455
<211> LENGTH: 10
<212> TYPE: PRT
<213> ORGANISM: Homo sapiens

<400> SEQUENCE: 455

Thr Ile Val Glu Glu Val Gln Asp Gly Lys
1               5                   10

<210> SEQ ID NO 456
<211> LENGTH: 8
<212> TYPE: PRT
<213> ORGANISM: Homo sapiens

<400> SEQUENCE: 456

Phe Gly Pro Gly Val Ala Phe Arg
1               5

<210> SEQ ID NO 457
<211> LENGTH: 12
<212> TYPE: PRT
<213> ORGANISM: Homo sapiens

<400> SEQUENCE: 457

Ala Leu Glu Ala Ala Asn Gly Glu Leu Glu Val Lys
1               5                   10

<210> SEQ ID NO 458
<211> LENGTH: 21
<212> TYPE: PRT
<213> ORGANISM: Homo sapiens

<400> SEQUENCE: 458

Ser Ser Gln Ser Leu Leu Asp Ser Gly Asp Gly Asn Thr Tyr Leu Asn
1               5                   10                  15

Trp Tyr Leu Gln Lys
            20

<210> SEQ ID NO 459
<211> LENGTH: 14
<212> TYPE: PRT
<213> ORGANISM: Homo sapiens
```

<400> SEQUENCE: 459

Val Gln Ala Glu Asp Val Gly Val Tyr Tyr Cys Met Gln Arg
1               5                   10

<210> SEQ ID NO 460
<211> LENGTH: 9
<212> TYPE: PRT
<213> ORGANISM: Homo sapiens

<400> SEQUENCE: 460

Thr Val Glu Ser Ile Thr Asp Ile Arg
1               5

<210> SEQ ID NO 461
<211> LENGTH: 8
<212> TYPE: PRT
<213> ORGANISM: Homo sapiens

<400> SEQUENCE: 461

Ala Phe Ser Val Asn Ile Phe Lys
1               5

<210> SEQ ID NO 462
<211> LENGTH: 14
<212> TYPE: PRT
<213> ORGANISM: Homo sapiens

<400> SEQUENCE: 462

Glu Asn Thr Ser Asp Pro Ser Leu Val Ile Ala Phe Gly Arg
1               5                   10

<210> SEQ ID NO 463
<211> LENGTH: 16
<212> TYPE: PRT
<213> ORGANISM: Homo sapiens

<400> SEQUENCE: 463

Asn Met Thr Phe Asp Leu Pro Ser Asp Ala Thr Val Val Leu Asn Arg
1               5                   10                  15

<210> SEQ ID NO 464
<211> LENGTH: 12
<212> TYPE: PRT
<213> ORGANISM: Homo sapiens

<400> SEQUENCE: 464

Val Thr Ser Glu Gly Ala Gly Leu Gln Leu Gln Lys
1               5                   10

<210> SEQ ID NO 465
<211> LENGTH: 17
<212> TYPE: PRT
<213> ORGANISM: Homo sapiens

<400> SEQUENCE: 465

Ser Thr Gly Gly Ile Leu Asp Val Tyr Ile Phe Leu Gly Pro Glu Pro
1               5                   10                  15

Lys

<210> SEQ ID NO 466
<211> LENGTH: 9
<212> TYPE: PRT
<213> ORGANISM: Homo sapiens

```
<400> SEQUENCE: 466

Gly Thr Arg Pro Phe Val Ile Ser Arg
1               5

<210> SEQ ID NO 467
<211> LENGTH: 13
<212> TYPE: PRT
<213> ORGANISM: Homo sapiens

<400> SEQUENCE: 467

Tyr Glu Val Pro Leu Glu Thr Pro His Val His Ser Arg
1               5                   10

<210> SEQ ID NO 468
<211> LENGTH: 15
<212> TYPE: PRT
<213> ORGANISM: Homo sapiens

<400> SEQUENCE: 468

Thr Asp Asp Ile Gly Thr Ala Ser Gly Trp Gly Leu Thr Gln Arg
1               5                   10                  15

<210> SEQ ID NO 469
<211> LENGTH: 8
<212> TYPE: PRT
<213> ORGANISM: Homo sapiens

<400> SEQUENCE: 469

Glu Ser Ala Tyr Leu Tyr Ala Arg
1               5

<210> SEQ ID NO 470
<211> LENGTH: 10
<212> TYPE: PRT
<213> ORGANISM: Homo sapiens

<400> SEQUENCE: 470

Leu Glu Gly Asn Pro Ile Val Leu Gly Lys
1               5                   10

<210> SEQ ID NO 471
<211> LENGTH: 7
<212> TYPE: PRT
<213> ORGANISM: Homo sapiens

<400> SEQUENCE: 471

Leu Thr Leu Phe Asn Ala Lys
1               5

<210> SEQ ID NO 472
<211> LENGTH: 9
<212> TYPE: PRT
<213> ORGANISM: Homo sapiens

<400> SEQUENCE: 472

His Pro Asn Ser Phe Ile Cys Leu Lys
1               5

<210> SEQ ID NO 473
<211> LENGTH: 9
<212> TYPE: PRT
<213> ORGANISM: Homo sapiens

<400> SEQUENCE: 473
```

```
Phe Gln Thr Phe Glu Gly Asp Leu Lys
1               5

<210> SEQ ID NO 474
<211> LENGTH: 15
<212> TYPE: PRT
<213> ORGANISM: Homo sapiens

<400> SEQUENCE: 474

Leu Gly Leu Gly Ala Asp Val Ala Gln Val Thr Gly Ala Leu Arg
1               5                   10                  15

<210> SEQ ID NO 475
<211> LENGTH: 16
<212> TYPE: PRT
<213> ORGANISM: Homo sapiens

<400> SEQUENCE: 475

Gln Leu Ser Leu Pro Glu Thr Gly Glu Leu Asp Ser Ala Thr Leu Lys
1               5                   10                  15

<210> SEQ ID NO 476
<211> LENGTH: 12
<212> TYPE: PRT
<213> ORGANISM: Homo sapiens

<400> SEQUENCE: 476

Gln Ser Thr Leu Val Leu Phe Pro Gly Asp Leu Arg
1               5                   10

<210> SEQ ID NO 477
<211> LENGTH: 10
<212> TYPE: PRT
<213> ORGANISM: Homo sapiens

<400> SEQUENCE: 477

Ser Tyr Ser Ala Cys Thr Thr Asp Gly Arg
1               5                   10

<210> SEQ ID NO 478
<211> LENGTH: 15
<212> TYPE: PRT
<213> ORGANISM: Homo sapiens

<400> SEQUENCE: 478

Asp Ile Ser Ser Ser Leu Asn Ser Leu Ala Asp Ser Asn Ala Arg
1               5                   10                  15

<210> SEQ ID NO 479
<211> LENGTH: 9
<212> TYPE: PRT
<213> ORGANISM: Homo sapiens

<400> SEQUENCE: 479

Leu Val Glu Gly Glu Ser Asp Asn Arg
1               5

<210> SEQ ID NO 480
<211> LENGTH: 10
<212> TYPE: PRT
<213> ORGANISM: Homo sapiens

<400> SEQUENCE: 480

Thr Leu Leu Ala Asp Gln Gly Glu Ile Arg
```

```
1               5                  10

<210> SEQ ID NO 481
<211> LENGTH: 11
<212> TYPE: PRT
<213> ORGANISM: Homo sapiens

<400> SEQUENCE: 481

Gln Phe Glu Ser Leu Pro Ala Thr His Ile Arg
1               5                  10

<210> SEQ ID NO 482
<211> LENGTH: 18
<212> TYPE: PRT
<213> ORGANISM: Homo sapiens

<400> SEQUENCE: 482

Val Gly Asp Tyr Val Tyr Phe Glu Asn Ser Ser Asn Pro Tyr Leu
1               5                  10                  15

Val Arg

<210> SEQ ID NO 483
<211> LENGTH: 16
<212> TYPE: PRT
<213> ORGANISM: Homo sapiens

<400> SEQUENCE: 483

Glu Phe Glu Glu Glu Ser Lys Gln Pro Gly Val Ser Glu Gln Gln Arg
1               5                  10                  15

<210> SEQ ID NO 484
<211> LENGTH: 11
<212> TYPE: PRT
<213> ORGANISM: Homo sapiens

<400> SEQUENCE: 484

Leu Thr Pro Leu Gln Phe Gly Asn Leu Gln Lys
1               5                  10

<210> SEQ ID NO 485
<211> LENGTH: 13
<212> TYPE: PRT
<213> ORGANISM: Homo sapiens

<400> SEQUENCE: 485

Thr Gly Leu Leu Val Glu Gln Ser Gly Asp Tyr Ile Lys
1               5                  10

<210> SEQ ID NO 486
<211> LENGTH: 16
<212> TYPE: PRT
<213> ORGANISM: Homo sapiens

<400> SEQUENCE: 486

Leu Phe Val Glu Ser Tyr Glu Leu Ile Leu Gln Glu Gly Thr Phe Lys
1               5                  10                  15

<210> SEQ ID NO 487
<211> LENGTH: 14
<212> TYPE: PRT
<213> ORGANISM: Homo sapiens

<400> SEQUENCE: 487

Ser Val Val Gly Asp Ala Leu Glu Phe Gly Asn Ser Trp Lys
```

```
1               5                   10
```

<210> SEQ ID NO 488
<211> LENGTH: 12
<212> TYPE: PRT
<213> ORGANISM: Homo sapiens

<400> SEQUENCE: 488

```
Glu Leu Leu Asn Glu Thr Glu Glu Ile Asn Lys
1               5                   10
```

<210> SEQ ID NO 489
<211> LENGTH: 8
<212> TYPE: PRT
<213> ORGANISM: Homo sapiens

<400> SEQUENCE: 489

```
Leu Phe Leu Asp Tyr Thr Ile Lys
1               5
```

<210> SEQ ID NO 490
<211> LENGTH: 9
<212> TYPE: PRT
<213> ORGANISM: Homo sapiens

<400> SEQUENCE: 490

```
Leu Gln Asn Ile Ile Asp Asn Gln Lys
1               5
```

<210> SEQ ID NO 491
<211> LENGTH: 9
<212> TYPE: PRT
<213> ORGANISM: Homo sapiens

<400> SEQUENCE: 491

```
Asn Glu Leu Gln Gln Thr Ile Asn Lys
1               5
```

<210> SEQ ID NO 492
<211> LENGTH: 12
<212> TYPE: PRT
<213> ORGANISM: Homo sapiens

<400> SEQUENCE: 492

```
Asn Ser Gln Leu Gly Ile Phe Ser Ser Ser Glu Lys
1               5                   10
```

<210> SEQ ID NO 493
<211> LENGTH: 10
<212> TYPE: PRT
<213> ORGANISM: Homo sapiens

<400> SEQUENCE: 493

```
Gln His Gly Asp Val Val Ser Ala Ile Arg
1               5                   10
```

<210> SEQ ID NO 494
<211> LENGTH: 14
<212> TYPE: PRT
<213> ORGANISM: Homo sapiens

<400> SEQUENCE: 494

```
Ser Val Asp Pro Asp Ser Pro Ala Glu Ala Ser Gly Leu Arg
1               5                   10
```

<210> SEQ ID NO 495
<211> LENGTH: 13
<212> TYPE: PRT
<213> ORGANISM: Homo sapiens

<400> SEQUENCE: 495

Gly Pro Asn Gly Tyr Gly Phe His Leu His Gly Glu Lys
1               5                   10

<210> SEQ ID NO 496
<211> LENGTH: 10
<212> TYPE: PRT
<213> ORGANISM: Homo sapiens

<400> SEQUENCE: 496

Leu Val Glu Pro Gly Ser Pro Ala Glu Lys
1               5                   10

<210> SEQ ID NO 497
<211> LENGTH: 17
<212> TYPE: PRT
<213> ORGANISM: Homo sapiens

<400> SEQUENCE: 497

Glu Ala Leu Ala Glu Ala Ala Leu Glu Ser Pro Arg Pro Ala Leu Val
1               5                   10                  15

Arg

<210> SEQ ID NO 498
<211> LENGTH: 12
<212> TYPE: PRT
<213> ORGANISM: Homo sapiens

<400> SEQUENCE: 498

Ile Val Glu Val Asn Gly Val Cys Met Glu Gly Lys
1               5                   10

<210> SEQ ID NO 499
<211> LENGTH: 8
<212> TYPE: PRT
<213> ORGANISM: Homo sapiens

<400> SEQUENCE: 499

Glu Glu Asp Thr Gly Arg Pro Arg
1               5

<210> SEQ ID NO 500
<211> LENGTH: 8
<212> TYPE: PRT
<213> ORGANISM: Homo sapiens

<400> SEQUENCE: 500

Ser Asp His Pro Ala Ile Leu Arg
1               5

<210> SEQ ID NO 501
<211> LENGTH: 9
<212> TYPE: PRT
<213> ORGANISM: Homo sapiens

<400> SEQUENCE: 501

Gly Phe Ser Gly Ile Phe Glu Asp Arg
1               5

<210> SEQ ID NO 502
<211> LENGTH: 15
<212> TYPE: PRT
<213> ORGANISM: Homo sapiens

<400> SEQUENCE: 502

Leu Leu Gly Glu Val Gly Thr Leu Gln Phe Ala Glu Leu His Arg
1               5                   10                  15

<210> SEQ ID NO 503
<211> LENGTH: 11
<212> TYPE: PRT
<213> ORGANISM: Homo sapiens

<400> SEQUENCE: 503

Glu Val Asp Ser Asp Ala Tyr Tyr Val Tyr Arg
1               5                   10

<210> SEQ ID NO 504
<211> LENGTH: 17
<212> TYPE: PRT
<213> ORGANISM: Homo sapiens

<400> SEQUENCE: 504

Leu Val Glu Pro Val Thr Asp Phe Leu Leu Asp Met Pro Tyr His Ile
1               5                   10                  15

Arg

<210> SEQ ID NO 505
<211> LENGTH: 15
<212> TYPE: PRT
<213> ORGANISM: Homo sapiens

<400> SEQUENCE: 505

Asp Leu Pro Glu Thr Leu Asn Glu Leu His Leu Asp His Asn Lys
1               5                   10                  15

<210> SEQ ID NO 506
<211> LENGTH: 14
<212> TYPE: PRT
<213> ORGANISM: Homo sapiens

<400> SEQUENCE: 506

Gly Leu Gln His Leu Tyr Ala Leu Val Leu Val Asn Asn Lys
1               5                   10

<210> SEQ ID NO 507
<211> LENGTH: 10
<212> TYPE: PRT
<213> ORGANISM: Homo sapiens

<400> SEQUENCE: 507

Val Val Gln Cys Ser Asp Leu Gly Leu Lys
1               5                   10

<210> SEQ ID NO 508
<211> LENGTH: 9
<212> TYPE: PRT
<213> ORGANISM: Homo sapiens

<400> SEQUENCE: 508

Val Pro Ser Gly Leu Pro Asp Leu Lys
1               5

<210> SEQ ID NO 509
<211> LENGTH: 12
<212> TYPE: PRT
<213> ORGANISM: Homo sapiens

<400> SEQUENCE: 509

His Ile Asn Pro Val Ala Ala Ser Leu Ile Gln Lys
1               5                   10

<210> SEQ ID NO 510
<211> LENGTH: 13
<212> TYPE: PRT
<213> ORGANISM: Homo sapiens

<400> SEQUENCE: 510

Leu Gly Asn Leu Phe Leu Asn Glu Asp Leu Glu Val Lys
1               5                   10

<210> SEQ ID NO 511
<211> LENGTH: 15
<212> TYPE: PRT
<213> ORGANISM: Homo sapiens

<400> SEQUENCE: 511

Leu Ile Leu Tyr Asn Asp Gly Asp Ser Leu Gln Tyr Ile Glu Arg
1               5                   10                  15

<210> SEQ ID NO 512
<211> LENGTH: 13
<212> TYPE: PRT
<213> ORGANISM: Homo sapiens

<400> SEQUENCE: 512

Phe Ser Ile Ala Pro Ser Ser Leu Asp Pro Ser Asn Arg
1               5                   10

<210> SEQ ID NO 513
<211> LENGTH: 9
<212> TYPE: PRT
<213> ORGANISM: Homo sapiens

<400> SEQUENCE: 513

Ile Gly Asp Phe Gly Leu Ala Thr Lys
1               5

<210> SEQ ID NO 514
<211> LENGTH: 8
<212> TYPE: PRT
<213> ORGANISM: Homo sapiens

<400> SEQUENCE: 514

Ala Gly Ala Asn Ile Thr Pro Arg
1               5

<210> SEQ ID NO 515
<211> LENGTH: 11
<212> TYPE: PRT
<213> ORGANISM: Homo sapiens

<400> SEQUENCE: 515

Gly Leu Glu Asn Pro Leu Pro Glu Arg Pro Arg
1               5                   10

<210> SEQ ID NO 516

```
<211> LENGTH: 10
<212> TYPE: PRT
<213> ORGANISM: Homo sapiens

<400> SEQUENCE: 516

Met His Ala Ala Phe Gly Gly Thr Phe Lys
1               5                   10

<210> SEQ ID NO 517
<211> LENGTH: 8
<212> TYPE: PRT
<213> ORGANISM: Homo sapiens

<400> SEQUENCE: 517

Asp Ile Ser Leu Ser Asp Tyr Lys
1               5

<210> SEQ ID NO 518
<211> LENGTH: 8
<212> TYPE: PRT
<213> ORGANISM: Homo sapiens

<400> SEQUENCE: 518

Ala Asp Glu Gly Ile Ser Phe Arg
1               5

<210> SEQ ID NO 519
<211> LENGTH: 11
<212> TYPE: PRT
<213> ORGANISM: Homo sapiens

<400> SEQUENCE: 519

Ala Thr Ala Val Met Pro Asp Gly Gln Phe Lys
1               5                   10

<210> SEQ ID NO 520
<211> LENGTH: 16
<212> TYPE: PRT
<213> ORGANISM: Homo sapiens

<400> SEQUENCE: 520

Gln Gly Gly Leu Gly Pro Met Asn Ile Pro Leu Val Ser Asp Pro Lys
1               5                   10                  15

<210> SEQ ID NO 521
<211> LENGTH: 10
<212> TYPE: PRT
<213> ORGANISM: Homo sapiens

<400> SEQUENCE: 521

Thr Ile Ala Gln Asp Tyr Gly Val Leu Lys
1               5                   10

<210> SEQ ID NO 522
<211> LENGTH: 9
<212> TYPE: PRT
<213> ORGANISM: Homo sapiens

<400> SEQUENCE: 522

Ile Gly His Pro Ala Pro Asn Phe Lys
1               5

<210> SEQ ID NO 523
<211> LENGTH: 10
<212> TYPE: PRT
```

<213> ORGANISM: Homo sapiens

<400> SEQUENCE: 523

Leu Val Gln Ala Phe Gln Phe Thr Asp Lys
1               5                   10

<210> SEQ ID NO 524
<211> LENGTH: 14
<212> TYPE: PRT
<213> ORGANISM: Homo sapiens

<400> SEQUENCE: 524

Asp Tyr Gly Val Tyr Leu Glu Asp Ser Gly His Thr Leu Arg
1               5                   10

<210> SEQ ID NO 525
<211> LENGTH: 13
<212> TYPE: PRT
<213> ORGANISM: Homo sapiens

<400> SEQUENCE: 525

Ile Pro Leu Leu Ser Asp Leu Thr His Gln Ile Ser Lys
1               5                   10

<210> SEQ ID NO 526
<211> LENGTH: 12
<212> TYPE: PRT
<213> ORGANISM: Homo sapiens

<400> SEQUENCE: 526

Val Ser Val Ala Asp His Ser Leu His Leu Ser Lys
1               5                   10

<210> SEQ ID NO 527
<211> LENGTH: 10
<212> TYPE: PRT
<213> ORGANISM: Homo sapiens

<400> SEQUENCE: 527

Leu Val Gln Ala Phe Gln Tyr Thr Asp Lys
1               5                   10

<210> SEQ ID NO 528
<211> LENGTH: 11
<212> TYPE: PRT
<213> ORGANISM: Homo sapiens

<400> SEQUENCE: 528

Gln Ile Thr Leu Asn Asp Leu Pro Val Gly Arg
1               5                   10

<210> SEQ ID NO 529
<211> LENGTH: 19
<212> TYPE: PRT
<213> ORGANISM: Homo sapiens

<400> SEQUENCE: 529

Ile Ser Lys Pro Ala Pro Tyr Trp Glu Gly Thr Ala Val Ile Asp Gly
1               5                   10                  15

Glu Phe Lys

<210> SEQ ID NO 530
<211> LENGTH: 8
<212> TYPE: PRT

<213> ORGANISM: Homo sapiens

<400> SEQUENCE: 530

Gln Gly Gly Leu Gly Pro Ile Arg
1               5

<210> SEQ ID NO 531
<211> LENGTH: 14
<212> TYPE: PRT
<213> ORGANISM: Homo sapiens

<400> SEQUENCE: 531

Ser Thr Gly Gly Ala Pro Thr Phe Asn Val Thr Val Thr Lys
1               5                   10

<210> SEQ ID NO 532
<211> LENGTH: 8
<212> TYPE: PRT
<213> ORGANISM: Homo sapiens

<400> SEQUENCE: 532

Thr Leu Val Leu Leu Met Gly Lys
1               5

<210> SEQ ID NO 533
<211> LENGTH: 12
<212> TYPE: PRT
<213> ORGANISM: Homo sapiens

<400> SEQUENCE: 533

Asp Ser Pro Ser Val Trp Ala Ala Val Pro Gly Lys
1               5                   10

<210> SEQ ID NO 534
<211> LENGTH: 16
<212> TYPE: PRT
<213> ORGANISM: Homo sapiens

<400> SEQUENCE: 534

Thr Phe Val Asn Ile Thr Pro Ala Glu Val Gly Val Leu Val Gly Lys
1               5                   10                  15

<210> SEQ ID NO 535
<211> LENGTH: 14
<212> TYPE: PRT
<213> ORGANISM: Homo sapiens

<400> SEQUENCE: 535

Ser Ser Phe Tyr Val Asn Gly Leu Thr Leu Gly Gly Gln Lys
1               5                   10

<210> SEQ ID NO 536
<211> LENGTH: 14
<212> TYPE: PRT
<213> ORGANISM: Homo sapiens

<400> SEQUENCE: 536

Asp Ser Leu Leu Gln Asp Gly Glu Phe Ser Met Asp Leu Arg
1               5                   10

<210> SEQ ID NO 537
<211> LENGTH: 17
<212> TYPE: PRT
<213> ORGANISM: Homo sapiens

```
<400> SEQUENCE: 537

Ala Gln Gly Phe Thr Glu Asp Thr Ile Val Phe Leu Pro Gln Thr Asp
1               5                   10                  15
Lys

<210> SEQ ID NO 538
<211> LENGTH: 19
<212> TYPE: PRT
<213> ORGANISM: Homo sapiens

<400> SEQUENCE: 538

Ser Val Val Ala Pro Ala Thr Asp Gly Gly Leu Asn Leu Thr Ser Thr
1               5                   10                  15
Phe Leu Arg

<210> SEQ ID NO 539
<211> LENGTH: 14
<212> TYPE: PRT
<213> ORGANISM: Homo sapiens

<400> SEQUENCE: 539

Trp Phe Ser Ala Gly Leu Ala Ser Asn Ser Ser Trp Leu Arg
1               5                   10

<210> SEQ ID NO 540
<211> LENGTH: 16
<212> TYPE: PRT
<213> ORGANISM: Homo sapiens

<400> SEQUENCE: 540

Thr Met Leu Leu Gln Pro Ala Gly Ser Leu Gly Ser Tyr Ser Tyr Arg
1               5                   10                  15

<210> SEQ ID NO 541
<211> LENGTH: 10
<212> TYPE: PRT
<213> ORGANISM: Homo sapiens

<400> SEQUENCE: 541

Ala Leu Ala Ala Val Leu Glu Glu Leu Arg
1               5                   10

<210> SEQ ID NO 542
<211> LENGTH: 13
<212> TYPE: PRT
<213> ORGANISM: Homo sapiens

<400> SEQUENCE: 542

Leu Thr Ser Ala Leu Asp Glu Leu Leu Gln Ala Thr Arg
1               5                   10

<210> SEQ ID NO 543
<211> LENGTH: 11
<212> TYPE: PRT
<213> ORGANISM: Homo sapiens

<400> SEQUENCE: 543

Glu Thr Gly Gly Ala Glu Ser Cys His Ile Arg
1               5                   10

<210> SEQ ID NO 544
<211> LENGTH: 9
<212> TYPE: PRT
```

```
<213> ORGANISM: Homo sapiens

<400> SEQUENCE: 544

Thr Ile Leu Phe Ser Tyr Gly Thr Lys
1               5

<210> SEQ ID NO 545
<211> LENGTH: 9
<212> TYPE: PRT
<213> ORGANISM: Homo sapiens

<400> SEQUENCE: 545

Ala His Ala Trp Pro Ser Pro Tyr Lys
1               5

<210> SEQ ID NO 546
<211> LENGTH: 13
<212> TYPE: PRT
<213> ORGANISM: Homo sapiens

<400> SEQUENCE: 546

Thr Asn Val Asn Val Phe Ser Glu Leu Ser Ala Pro Arg
1               5                   10

<210> SEQ ID NO 547
<211> LENGTH: 7
<212> TYPE: PRT
<213> ORGANISM: Homo sapiens

<400> SEQUENCE: 547

Ser Tyr Gly Val Glu Asn Arg
1               5

<210> SEQ ID NO 548
<211> LENGTH: 35
<212> TYPE: PRT
<213> ORGANISM: Homo sapiens

<400> SEQUENCE: 548

Ala Tyr Ser Gln Glu Glu Ile Thr Gln Gly Phe Glu Glu Thr Gly Asp
1               5                   10                  15

Thr Leu Tyr Ala Pro Tyr Ser Thr His Phe Gln Leu Gln Asn Gln Pro
            20                  25                  30

Pro Gln Lys
        35

<210> SEQ ID NO 549
<211> LENGTH: 10
<212> TYPE: PRT
<213> ORGANISM: Homo sapiens

<400> SEQUENCE: 549

Met Ala Thr Thr Val Pro Asp Gly Cys Arg
1               5                   10

<210> SEQ ID NO 550
<211> LENGTH: 24
<212> TYPE: PRT
<213> ORGANISM: Homo sapiens

<400> SEQUENCE: 550

Phe Phe Leu Phe Gly Ile Leu Phe Ser Ile Cys Phe Ser Cys Leu Leu
1               5                   10                  15
```

Ala His Ala Val Ser Leu Thr Lys
            20

<210> SEQ ID NO 551
<211> LENGTH: 8
<212> TYPE: PRT
<213> ORGANISM: Homo sapiens

<400> SEQUENCE: 551

Gln Val Ser Val Glu Glu Ala Lys
1               5

<210> SEQ ID NO 552
<211> LENGTH: 7
<212> TYPE: PRT
<213> ORGANISM: Homo sapiens

<400> SEQUENCE: 552

Ser Asp Leu Glu Asp Lys Arg
1               5

<210> SEQ ID NO 553
<211> LENGTH: 9
<212> TYPE: PRT
<213> ORGANISM: Homo sapiens

<400> SEQUENCE: 553

Val Pro Val Ile Leu Val Gly Asn Lys
1               5

<210> SEQ ID NO 554
<211> LENGTH: 7
<212> TYPE: PRT
<213> ORGANISM: Homo sapiens

<400> SEQUENCE: 554

Val Asp Leu Glu Ser Glu Arg
1               5

<210> SEQ ID NO 555
<211> LENGTH: 12
<212> TYPE: PRT
<213> ORGANISM: Homo sapiens

<400> SEQUENCE: 555

Tyr Glu Lys Val Pro Val Ile Leu Val Gly Asn Lys
1               5                   10

<210> SEQ ID NO 556
<211> LENGTH: 12
<212> TYPE: PRT
<213> ORGANISM: Homo sapiens

<400> SEQUENCE: 556

Ala Ser Val Asp Glu Leu Phe Ala Glu Ile Val Arg
1               5                   10

<210> SEQ ID NO 557
<211> LENGTH: 15
<212> TYPE: PRT
<213> ORGANISM: Homo sapiens

<400> SEQUENCE: 557

Ser Ala Leu Thr Val Gln Phe Val Thr Gly Ser Phe Ile Glu Lys
1               5                   10                  15

<210> SEQ ID NO 558
<211> LENGTH: 8
<212> TYPE: PRT
<213> ORGANISM: Homo sapiens

<400> SEQUENCE: 558

Glu Val Ser Tyr Gly Glu Gly Lys
1               5

<210> SEQ ID NO 559
<211> LENGTH: 7
<212> TYPE: PRT
<213> ORGANISM: Homo sapiens

<400> SEQUENCE: 559

Gln Ala His Glu Leu Ala Lys
1               5

<210> SEQ ID NO 560
<211> LENGTH: 15
<212> TYPE: PRT
<213> ORGANISM: Homo sapiens

<400> SEQUENCE: 560

Thr Gly Glu Gly Phe Leu Cys Val Phe Ala Ile Asn Asn Ser Lys
1               5                   10                  15

<210> SEQ ID NO 561
<211> LENGTH: 15
<212> TYPE: PRT
<213> ORGANISM: Homo sapiens

<400> SEQUENCE: 561

Ala Ile Ser Ser Ile Gly Leu Glu Cys Gln Ser Val Thr Ser Arg
1               5                   10                  15

<210> SEQ ID NO 562
<211> LENGTH: 8
<212> TYPE: PRT
<213> ORGANISM: Homo sapiens

<400> SEQUENCE: 562

Gly Asp Leu Ala Thr Cys Pro Arg
1               5

<210> SEQ ID NO 563
<211> LENGTH: 12
<212> TYPE: PRT
<213> ORGANISM: Homo sapiens

<400> SEQUENCE: 563

Thr Leu Cys Ser Met Glu Glu Ala Ile Asn Glu Arg
1               5                   10

<210> SEQ ID NO 564
<211> LENGTH: 18
<212> TYPE: PRT
<213> ORGANISM: Homo sapiens

<400> SEQUENCE: 564

Ala Glu Thr Thr Cys His Cys Gln Cys Ala Gly Met Asp Trp Thr Gly
1               5                   10                  15

Ala Arg

-continued

<210> SEQ ID NO 565
<211> LENGTH: 7
<212> TYPE: PRT
<213> ORGANISM: Homo sapiens

<400> SEQUENCE: 565

Glu Leu Thr Ile Gly Ser Lys
1               5

<210> SEQ ID NO 566
<211> LENGTH: 18
<212> TYPE: PRT
<213> ORGANISM: Homo sapiens

<400> SEQUENCE: 566

Met Ala Cys Pro Leu Asp Gln Ala Ile Gly Leu Leu Val Ala Ile Phe
1               5                   10                  15

His Lys

<210> SEQ ID NO 567
<211> LENGTH: 15
<212> TYPE: PRT
<213> ORGANISM: Homo sapiens

<400> SEQUENCE: 567

Val Ile Glu His Ile Met Glu Asp Leu Asp Thr Asn Ala Asp Lys
1               5                   10                  15

<210> SEQ ID NO 568
<211> LENGTH: 8
<212> TYPE: PRT
<213> ORGANISM: Homo sapiens

<400> SEQUENCE: 568

Leu Thr Trp Ala Ser His Glu Lys
1               5

<210> SEQ ID NO 569
<211> LENGTH: 13
<212> TYPE: PRT
<213> ORGANISM: Homo sapiens

<400> SEQUENCE: 569

Gln Leu Ser Phe Glu Glu Phe Ile Met Leu Met Ala Arg
1               5                   10

<210> SEQ ID NO 570
<211> LENGTH: 15
<212> TYPE: PRT
<213> ORGANISM: Homo sapiens

<400> SEQUENCE: 570

Asn Ile Glu Thr Ile Ile Asn Thr Phe His Gln Tyr Ser Val Lys
1               5                   10                  15

<210> SEQ ID NO 571
<211> LENGTH: 14
<212> TYPE: PRT
<213> ORGANISM: Homo sapiens

<400> SEQUENCE: 571

Gly Asp Gly Pro Val Gln Gly Ile Ile Asn Phe Glu Gln Lys
1               5                   10

<210> SEQ ID NO 572
<211> LENGTH: 12
<212> TYPE: PRT
<213> ORGANISM: Homo sapiens

<400> SEQUENCE: 572

His Val Gly Asp Leu Gly Asn Val Thr Ala Asp Lys
1               5                   10

<210> SEQ ID NO 573
<211> LENGTH: 10
<212> TYPE: PRT
<213> ORGANISM: Homo sapiens

<400> SEQUENCE: 573

Leu Ala Cys Gly Val Ile Gly Ile Ala Gln
1               5                   10

<210> SEQ ID NO 574
<211> LENGTH: 24
<212> TYPE: PRT
<213> ORGANISM: Homo sapiens

<400> SEQUENCE: 574

Asp Gly Val Ala Asp Val Ser Ile Glu Asp Ser Val Ile Ser Leu Ser
1               5                   10                  15

Gly Asp His Cys Ile Ile Gly Arg
            20

<210> SEQ ID NO 575
<211> LENGTH: 10
<212> TYPE: PRT
<213> ORGANISM: Homo sapiens

<400> SEQUENCE: 575

Ala Ser Asn Leu Leu Leu Gly Phe Asp Arg
1               5                   10

<210> SEQ ID NO 576
<211> LENGTH: 11
<212> TYPE: PRT
<213> ORGANISM: Homo sapiens

<400> SEQUENCE: 576

Asn Leu Leu Val Asn Thr Leu Tyr Thr Val Arg
1               5                   10

<210> SEQ ID NO 577
<211> LENGTH: 10
<212> TYPE: PRT
<213> ORGANISM: Homo sapiens

<400> SEQUENCE: 577

Tyr Ser Thr Asn Glu Gly Glu Thr Trp Lys
1               5                   10

<210> SEQ ID NO 578
<211> LENGTH: 8
<212> TYPE: PRT
<213> ORGANISM: Homo sapiens

<400> SEQUENCE: 578

Asn Leu Gln Leu Ser Leu Pro Arg

<210> SEQ ID NO 579
<211> LENGTH: 9
<212> TYPE: PRT
<213> ORGANISM: Homo sapiens

<400> SEQUENCE: 579

Asn Val Leu Val Thr Leu Tyr Glu Arg
1               5

<210> SEQ ID NO 580
<211> LENGTH: 16
<212> TYPE: PRT
<213> ORGANISM: Homo sapiens

<400> SEQUENCE: 580

Tyr Ile Pro Pro Cys Leu Asp Ser Glu Leu Thr Glu Phe Pro Leu Arg
1               5                   10                  15

<210> SEQ ID NO 581
<211> LENGTH: 13
<212> TYPE: PRT
<213> ORGANISM: Homo sapiens

<400> SEQUENCE: 581

Leu Glu Ala Gly Asp His Pro Val Glu Leu Leu Ala Arg
1               5                   10

<210> SEQ ID NO 582
<211> LENGTH: 10
<212> TYPE: PRT
<213> ORGANISM: Homo sapiens

<400> SEQUENCE: 582

Leu His Leu Asp Tyr Ile Gly Pro Cys Lys
1               5                   10

<210> SEQ ID NO 583
<211> LENGTH: 20
<212> TYPE: PRT
<213> ORGANISM: Homo sapiens

<400> SEQUENCE: 583

Glu Gln Ala Asn Ala Val Ser Glu Ala Val Val Ser Ser Val Asn Thr
1               5                   10                  15

Val Ala Thr Lys
            20

<210> SEQ ID NO 584
<211> LENGTH: 16
<212> TYPE: PRT
<213> ORGANISM: Homo sapiens

<400> SEQUENCE: 584

Thr Val Glu Glu Ala Glu Asn Ile Ala Val Thr Ser Gly Val Val Arg
1               5                   10                  15

<210> SEQ ID NO 585
<211> LENGTH: 13
<212> TYPE: PRT
<213> ORGANISM: Homo sapiens

<400> SEQUENCE: 585

```
Glu Asn Val Val Gln Ser Val Thr Ser Val Ala Glu Lys
1               5                   10
```

<210> SEQ ID NO 586
<211> LENGTH: 9
<212> TYPE: PRT
<213> ORGANISM: Homo sapiens

<400> SEQUENCE: 586

```
Glu Gly Val Val Gly Ala Val Glu Lys
1               5
```

<210> SEQ ID NO 587
<211> LENGTH: 12
<212> TYPE: PRT
<213> ORGANISM: Homo sapiens

<400> SEQUENCE: 587

```
Glu Glu Val Ala Glu Glu Ala Gln Ser Gly Gly Asp
1               5                   10
```

<210> SEQ ID NO 588
<211> LENGTH: 9
<212> TYPE: PRT
<213> ORGANISM: Homo sapiens

<400> SEQUENCE: 588

```
Asp Val Asp Leu Glu Phe Leu Ala Lys
1               5
```

<210> SEQ ID NO 589
<211> LENGTH: 12
<212> TYPE: PRT
<213> ORGANISM: Homo sapiens

<400> SEQUENCE: 589

```
Glu Val Asp Ile Gly Ile Pro Asp Ala Thr Gly Arg
1               5                   10
```

<210> SEQ ID NO 590
<211> LENGTH: 13
<212> TYPE: PRT
<213> ORGANISM: Homo sapiens

<400> SEQUENCE: 590

```
Leu Asp Gln Leu Ile Tyr Ile Pro Leu Pro Asp Glu Lys
1               5                   10
```

<210> SEQ ID NO 591
<211> LENGTH: 9
<212> TYPE: PRT
<213> ORGANISM: Homo sapiens

<400> SEQUENCE: 591

```
Leu Glu Ile Leu Gln Ile His Thr Lys
1               5
```

<210> SEQ ID NO 592
<211> LENGTH: 15
<212> TYPE: PRT
<213> ORGANISM: Homo sapiens

<400> SEQUENCE: 592

```
Asp Asn Thr Leu Gln Val Asp Ile Asn Gly Phe Thr Thr Gly Arg
1               5                   10                  15
```

```
<210> SEQ ID NO 593
<211> LENGTH: 10
<212> TYPE: PRT
<213> ORGANISM: Homo sapiens

<400> SEQUENCE: 593

Val Glu Gln His Val Glu Leu Tyr Gln Lys
1               5                   10

<210> SEQ ID NO 594
<211> LENGTH: 8
<212> TYPE: PRT
<213> ORGANISM: Homo sapiens

<400> SEQUENCE: 594

Gly Gly Glu Ile Glu Gly Phe Arg
1               5

<210> SEQ ID NO 595
<211> LENGTH: 19
<212> TYPE: PRT
<213> ORGANISM: Homo sapiens

<400> SEQUENCE: 595

Val Ala Gly Glu Ser Ala Glu Pro Glu Pro Glu Pro Glu Ala Asp Tyr
1               5                   10                  15

Tyr Ala Lys

<210> SEQ ID NO 596
<211> LENGTH: 11
<212> TYPE: PRT
<213> ORGANISM: Homo sapiens

<400> SEQUENCE: 596

Glu Ala Val Pro Glu Pro Val Leu Leu Ser Arg
1               5                   10

<210> SEQ ID NO 597
<211> LENGTH: 8
<212> TYPE: PRT
<213> ORGANISM: Homo sapiens

<400> SEQUENCE: 597

Ile Glu Leu Pro Thr Thr Val Lys
1               5

<210> SEQ ID NO 598
<211> LENGTH: 13
<212> TYPE: PRT
<213> ORGANISM: Homo sapiens

<400> SEQUENCE: 598

Asp Leu Ser Leu Ile Ser Pro Leu Ala Gln Ala Val Arg
1               5                   10

<210> SEQ ID NO 599
<211> LENGTH: 8
<212> TYPE: PRT
<213> ORGANISM: Homo sapiens

<400> SEQUENCE: 599

Ile Ala Val Ser Tyr Gln Thr Lys
1               5
```

<210> SEQ ID NO 600
<211> LENGTH: 12
<212> TYPE: PRT
<213> ORGANISM: Homo sapiens

<400> SEQUENCE: 600

Ala Asn Ala Leu Leu Ala Asn Gly Val Glu Leu Arg
1               5                   10

<210> SEQ ID NO 601
<211> LENGTH: 21
<212> TYPE: PRT
<213> ORGANISM: Homo sapiens

<400> SEQUENCE: 601

Asp Asn Gln Leu Val Val Pro Ser Glu Gly Leu Tyr Leu Ile Tyr Ser
1               5                   10                  15

Gln Val Leu Phe Lys
            20

<210> SEQ ID NO 602
<211> LENGTH: 8
<212> TYPE: PRT
<213> ORGANISM: Homo sapiens

<400> SEQUENCE: 602

Glu Val Val Leu Gln His Val Arg
1               5

<210> SEQ ID NO 603
<211> LENGTH: 20
<212> TYPE: PRT
<213> ORGANISM: Homo sapiens

<400> SEQUENCE: 603

Ser Ser Val Ala Ala Asp Val Ile Ser Leu Leu Leu Asn Gly Asp Gly
1               5                   10                  15

Gly Val Gly Arg
            20

<210> SEQ ID NO 604
<211> LENGTH: 14
<212> TYPE: PRT
<213> ORGANISM: Homo sapiens

<400> SEQUENCE: 604

Cys Gln Cys Pro Ala Gly Ala Ala Leu Gln Ala Asp Gly Arg
1               5                   10

<210> SEQ ID NO 605
<211> LENGTH: 7
<212> TYPE: PRT
<213> ORGANISM: Homo sapiens

<400> SEQUENCE: 605

Gly His Leu Met Thr Val Arg
1               5

<210> SEQ ID NO 606
<211> LENGTH: 15
<212> TYPE: PRT
<213> ORGANISM: Homo sapiens

```
<400> SEQUENCE: 606

Leu Trp Ile Gly Leu Gln Leu Pro Pro Gly Cys Gly Asp Pro Lys
1               5                   10                  15

<210> SEQ ID NO 607
<211> LENGTH: 15
<212> TYPE: PRT
<213> ORGANISM: Homo sapiens

<400> SEQUENCE: 607

Gly Phe Gln Trp Val Thr Gly Asp Asn Asn Thr Ser Tyr Ser Arg
1               5                   10                  15

<210> SEQ ID NO 608
<211> LENGTH: 8
<212> TYPE: PRT
<213> ORGANISM: Homo sapiens

<400> SEQUENCE: 608

Tyr Leu Gly Glu Glu Tyr Val Lys
1               5

<210> SEQ ID NO 609
<211> LENGTH: 8
<212> TYPE: PRT
<213> ORGANISM: Homo sapiens

<400> SEQUENCE: 609

Asp Ser Ala His Gly Phe Leu Lys
1               5

<210> SEQ ID NO 610
<211> LENGTH: 12
<212> TYPE: PRT
<213> ORGANISM: Homo sapiens

<400> SEQUENCE: 610

Phe Val Phe Gly Thr Thr Pro Glu Asp Ile Leu Arg
1               5                   10

<210> SEQ ID NO 611
<211> LENGTH: 17
<212> TYPE: PRT
<213> ORGANISM: Homo sapiens

<400> SEQUENCE: 611

Gln His Val Val Ser Val Glu Glu Ala Leu Leu Ala Thr Gly Gln Trp
1               5                   10                  15

Lys

<210> SEQ ID NO 612
<211> LENGTH: 12
<212> TYPE: PRT
<213> ORGANISM: Homo sapiens

<400> SEQUENCE: 612

Gly Thr Ser Gln Asn Asp Pro Asn Trp Val Val Arg
1               5                   10

<210> SEQ ID NO 613
<211> LENGTH: 10
<212> TYPE: PRT
<213> ORGANISM: Homo sapiens
```

```
<400> SEQUENCE: 613

Ser Ile Thr Leu Phe Val Gln Glu Asp Arg
1               5                  10

<210> SEQ ID NO 614
<211> LENGTH: 13
<212> TYPE: PRT
<213> ORGANISM: Homo sapiens

<400> SEQUENCE: 614

Leu Thr Phe Asp Ser Ser Phe Ser Pro Asn Thr Gly Lys
1               5                  10

<210> SEQ ID NO 615
<211> LENGTH: 20
<212> TYPE: PRT
<213> ORGANISM: Homo sapiens

<400> SEQUENCE: 615

Val Asn Asn Ser Ser Leu Ile Gly Leu Gly Tyr Thr Gln Thr Leu Lys
1               5                  10                  15

Pro Gly Ile Lys
            20

<210> SEQ ID NO 616
<211> LENGTH: 10
<212> TYPE: PRT
<213> ORGANISM: Homo sapiens

<400> SEQUENCE: 616

Leu Thr Leu Ser Ala Leu Leu Asp Gly Lys
1               5                  10

<210> SEQ ID NO 617
<211> LENGTH: 11
<212> TYPE: PRT
<213> ORGANISM: Homo sapiens

<400> SEQUENCE: 617

Val Thr Gln Ser Asn Phe Ala Val Gly Tyr Lys
1               5                  10

<210> SEQ ID NO 618
<211> LENGTH: 12
<212> TYPE: PRT
<213> ORGANISM: Homo sapiens

<400> SEQUENCE: 618

Tyr Gln Ile Asp Pro Asp Ala Cys Phe Ser Ala Lys
1               5                  10

<210> SEQ ID NO 619
<211> LENGTH: 8
<212> TYPE: PRT
<213> ORGANISM: Homo sapiens

<400> SEQUENCE: 619

Glu Asp Ile Phe Tyr Thr Ser Lys
1               5

<210> SEQ ID NO 620
<211> LENGTH: 8
<212> TYPE: PRT
<213> ORGANISM: Homo sapiens
```

```
<400> SEQUENCE: 620

Leu Ala Ile Glu Ala Gly Phe Arg
1               5

<210> SEQ ID NO 621
<211> LENGTH: 6
<212> TYPE: PRT
<213> ORGANISM: Homo sapiens

<400> SEQUENCE: 621

Asn Phe Asp Ile Pro Lys
1               5

<210> SEQ ID NO 622
<211> LENGTH: 20
<212> TYPE: PRT
<213> ORGANISM: Homo sapiens

<400> SEQUENCE: 622

Ser Ala Leu Thr Leu Gln Phe Met Tyr Asp Glu Phe Val Glu Asp Tyr
1               5                   10                  15

Glu Pro Thr Lys
            20

<210> SEQ ID NO 623
<211> LENGTH: 11
<212> TYPE: PRT
<213> ORGANISM: Homo sapiens

<400> SEQUENCE: 623

Val Ile Met Val Gly Ser Gly Gly Val Gly Lys
1               5                   10

<210> SEQ ID NO 624
<211> LENGTH: 15
<212> TYPE: PRT
<213> ORGANISM: Homo sapiens

<400> SEQUENCE: 624

Ser Ala Leu Thr Val Gln Phe Val Thr Gly Thr Phe Ile Glu Lys
1               5                   10                  15

<210> SEQ ID NO 625
<211> LENGTH: 12
<212> TYPE: PRT
<213> ORGANISM: Homo sapiens

<400> SEQUENCE: 625

Gln Gly Val Glu Asp Ala Phe Tyr Thr Leu Val Arg
1               5                   10

<210> SEQ ID NO 626
<211> LENGTH: 10
<212> TYPE: PRT
<213> ORGANISM: Homo sapiens

<400> SEQUENCE: 626

Ala Gly Glu Val Gln Glu Pro Glu Leu Arg
1               5                   10

<210> SEQ ID NO 627
<211> LENGTH: 7
<212> TYPE: PRT
```

<213> ORGANISM: Homo sapiens

<400> SEQUENCE: 627

Ile Asp Val His Trp Thr Arg
1               5

<210> SEQ ID NO 628
<211> LENGTH: 12
<212> TYPE: PRT
<213> ORGANISM: Homo sapiens

<400> SEQUENCE: 628

Gly Lys Val Glu Glu Val Glu Leu Pro Val Glu Lys
1               5                   10

<210> SEQ ID NO 629
<211> LENGTH: 13
<212> TYPE: PRT
<213> ORGANISM: Homo sapiens

<400> SEQUENCE: 629

Phe Ser Gly Ser Gly Ser Gly Thr Asp Phe Thr Leu Lys
1               5                   10

<210> SEQ ID NO 630
<211> LENGTH: 9
<212> TYPE: PRT
<213> ORGANISM: Homo sapiens

<400> SEQUENCE: 630

Gly Asp Phe Cys Ile Gln Val Gly Arg
1               5

<210> SEQ ID NO 631
<211> LENGTH: 12
<212> TYPE: PRT
<213> ORGANISM: Homo sapiens

<400> SEQUENCE: 631

Thr Phe Ile Ala Ile Lys Pro Asp Gly Val Gln Arg
1               5                   10

<210> SEQ ID NO 632
<211> LENGTH: 17
<212> TYPE: PRT
<213> ORGANISM: Homo sapiens

<400> SEQUENCE: 632

Val Met Leu Gly Glu Thr Asn Pro Ala Asp Ser Lys Pro Gly Thr Ile
1               5                   10                  15

Arg

<210> SEQ ID NO 633
<211> LENGTH: 11
<212> TYPE: PRT
<213> ORGANISM: Homo sapiens

<400> SEQUENCE: 633

Leu Val Val Val Gly Ala Gly Gly Val Gly Lys
1               5                   10

<210> SEQ ID NO 634
<211> LENGTH: 7
<212> TYPE: PRT

```
<213> ORGANISM: Homo sapiens

<400> SEQUENCE: 634

Gln Ala Gln Asp Leu Ala Arg
1               5

<210> SEQ ID NO 635
<211> LENGTH: 12
<212> TYPE: PRT
<213> ORGANISM: Homo sapiens

<400> SEQUENCE: 635

Ser Tyr Gly Ile Pro Phe Ile Glu Thr Ser Ala Lys
1               5                   10

<210> SEQ ID NO 636
<211> LENGTH: 15
<212> TYPE: PRT
<213> ORGANISM: Homo sapiens

<400> SEQUENCE: 636

Thr Gly Glu Gly Phe Leu Cys Val Phe Ala Ile Asn Asn Thr Lys
1               5                   10                  15

<210> SEQ ID NO 637
<211> LENGTH: 14
<212> TYPE: PRT
<213> ORGANISM: Homo sapiens

<400> SEQUENCE: 637

Ile Thr Pro Asn Leu Ala Glu Phe Ala Phe Ser Leu Tyr Arg
1               5                   10

<210> SEQ ID NO 638
<211> LENGTH: 15
<212> TYPE: PRT
<213> ORGANISM: Homo sapiens

<400> SEQUENCE: 638

Leu Gln His Leu Glu Asn Glu Leu Thr His Asp Ile Ile Thr Lys
1               5                   10                  15

<210> SEQ ID NO 639
<211> LENGTH: 10
<212> TYPE: PRT
<213> ORGANISM: Homo sapiens

<400> SEQUENCE: 639

Leu Ser Ile Thr Gly Thr Tyr Asp Leu Lys
1               5                   10

<210> SEQ ID NO 640
<211> LENGTH: 18
<212> TYPE: PRT
<213> ORGANISM: Homo sapiens

<400> SEQUENCE: 640

Leu Tyr His Ser Glu Ala Phe Thr Val Asn Phe Gly Asp Thr Glu Glu
1               5                   10                  15

Ala Lys

<210> SEQ ID NO 641
<211> LENGTH: 10
<212> TYPE: PRT
```

<213> ORGANISM: Homo sapiens

<400> SEQUENCE: 641

Ser Val Leu Gly Gln Leu Gly Ile Thr Lys
1               5                   10

<210> SEQ ID NO 642
<211> LENGTH: 11
<212> TYPE: PRT
<213> ORGANISM: Homo sapiens

<400> SEQUENCE: 642

Ala Thr Trp Ser Gly Ala Val Leu Ala Gly Arg
1               5                   10

<210> SEQ ID NO 643
<211> LENGTH: 20
<212> TYPE: PRT
<213> ORGANISM: Homo sapiens

<400> SEQUENCE: 643

Asp Gly Val Ser Glu Gly Gln Phe Gln Gln Val Leu His His Glu Leu
1               5                   10                  15

Leu Ala Ile Arg
            20

<210> SEQ ID NO 644
<211> LENGTH: 13
<212> TYPE: PRT
<213> ORGANISM: Homo sapiens

<400> SEQUENCE: 644

Asp Tyr Gln Pro Gly Ile Thr Phe Ile Val Val Gln Lys
1               5                   10

<210> SEQ ID NO 645
<211> LENGTH: 11
<212> TYPE: PRT
<213> ORGANISM: Homo sapiens

<400> SEQUENCE: 645

Ser Ala Ser Phe Asn Thr Asp Pro Tyr Val Arg
1               5                   10

<210> SEQ ID NO 646
<211> LENGTH: 7
<212> TYPE: PRT
<213> ORGANISM: Homo sapiens

<400> SEQUENCE: 646

Ser Phe Thr Glu Gln Leu Arg
1               5

<210> SEQ ID NO 647
<211> LENGTH: 12
<212> TYPE: PRT
<213> ORGANISM: Homo sapiens

<400> SEQUENCE: 647

Val Glu Leu Glu Val Thr Leu Pro Gly Glu Gly Lys
1               5                   10

<210> SEQ ID NO 648
<211> LENGTH: 12

```
<212> TYPE: PRT
<213> ORGANISM: Homo sapiens

<400> SEQUENCE: 648

Val Leu Gln Pro Pro Ser Ile Leu Tyr Gly Gly Arg
1               5                   10

<210> SEQ ID NO 649
<211> LENGTH: 11
<212> TYPE: PRT
<213> ORGANISM: Homo sapiens

<400> SEQUENCE: 649

Ala Gly Leu Ile Leu Phe Gly Asn Asp Asp Lys
1               5                   10

<210> SEQ ID NO 650
<211> LENGTH: 15
<212> TYPE: PRT
<213> ORGANISM: Homo sapiens

<400> SEQUENCE: 650

Ala Asn Ala Thr Glu Phe Gly Leu Ala Ser Gly Val Phe Thr Arg
1               5                   10                  15

<210> SEQ ID NO 651
<211> LENGTH: 12
<212> TYPE: PRT
<213> ORGANISM: Homo sapiens

<400> SEQUENCE: 651

Asp Leu Gly Glu Ala Ala Leu Asn Glu Tyr Leu Arg
1               5                   10

<210> SEQ ID NO 652
<211> LENGTH: 12
<212> TYPE: PRT
<213> ORGANISM: Homo sapiens

<400> SEQUENCE: 652

Phe Ala Asp Gly Asp Leu Asp Ala Val Leu Ser Arg
1               5                   10

<210> SEQ ID NO 653
<211> LENGTH: 21
<212> TYPE: PRT
<213> ORGANISM: Homo sapiens

<400> SEQUENCE: 653

Gly Ala Ala Ser Ser Val Leu Glu Leu Thr Glu Ala Glu Leu Val Thr
1               5                   10                  15

Ala Glu Ala Val Arg
            20

<210> SEQ ID NO 654
<211> LENGTH: 16
<212> TYPE: PRT
<213> ORGANISM: Homo sapiens

<400> SEQUENCE: 654

Gly Val Val Asn Val Leu Pro Gly Ser Gly Ser Leu Val Gly Gln Arg
1               5                   10                  15

<210> SEQ ID NO 655
```

```
<211> LENGTH: 12
<212> TYPE: PRT
<213> ORGANISM: Homo sapiens

<400> SEQUENCE: 655

Val Leu Glu Val Glu Asp Ser Thr Asp Phe Phe Lys
1               5                   10

<210> SEQ ID NO 656
<211> LENGTH: 12
<212> TYPE: PRT
<213> ORGANISM: Homo sapiens

<400> SEQUENCE: 656

Ala Asp Asp Gly Arg Pro Phe Pro Gln Val Ile Lys
1               5                   10

<210> SEQ ID NO 657
<211> LENGTH: 8
<212> TYPE: PRT
<213> ORGANISM: Homo sapiens

<400> SEQUENCE: 657

Ala Leu Gln Ala Ser Ala Leu Lys
1               5

<210> SEQ ID NO 658
<211> LENGTH: 8
<212> TYPE: PRT
<213> ORGANISM: Homo sapiens

<400> SEQUENCE: 658

Glu Leu Ser Asp Ile Ala His Arg
1               5

<210> SEQ ID NO 659
<211> LENGTH: 14
<212> TYPE: PRT
<213> ORGANISM: Homo sapiens

<400> SEQUENCE: 659

Gly Ile Leu Ala Ala Asp Glu Ser Thr Gly Ser Ile Ala Lys
1               5                   10

<210> SEQ ID NO 660
<211> LENGTH: 20
<212> TYPE: PRT
<213> ORGANISM: Homo sapiens

<400> SEQUENCE: 660

Ile Gly Glu His Thr Pro Ser Ala Leu Ala Ile Met Glu Asn Ala Asn
1               5                   10                  15

Val Leu Ala Arg
            20

<210> SEQ ID NO 661
<211> LENGTH: 9
<212> TYPE: PRT
<213> ORGANISM: Homo sapiens

<400> SEQUENCE: 661

Gln Leu Leu Leu Thr Ala Asp Asp Arg
1               5
```

<210> SEQ ID NO 662
<211> LENGTH: 12
<212> TYPE: PRT
<213> ORGANISM: Homo sapiens

<400> SEQUENCE: 662

Asp Ala Pro Leu Glu Tyr Asp Asp Ser Val Gln Arg
1               5                   10

<210> SEQ ID NO 663
<211> LENGTH: 9
<212> TYPE: PRT
<213> ORGANISM: Homo sapiens

<400> SEQUENCE: 663

His Ile Ile Gln Leu Gln Ser Ile Lys
1               5

<210> SEQ ID NO 664
<211> LENGTH: 13
<212> TYPE: PRT
<213> ORGANISM: Homo sapiens

<400> SEQUENCE: 664

Ile Val Thr Ala Thr Val Asn Asn Ser Val Leu Gln Lys
1               5                   10

<210> SEQ ID NO 665
<211> LENGTH: 11
<212> TYPE: PRT
<213> ORGANISM: Homo sapiens

<400> SEQUENCE: 665

Gln Ile Leu Asp Gln Thr Ser Glu Ile Asn Lys
1               5                   10

<210> SEQ ID NO 666
<211> LENGTH: 10
<212> TYPE: PRT
<213> ORGANISM: Homo sapiens

<400> SEQUENCE: 666

Gln Asn Ser Ile Ile Glu Glu Leu Glu Lys
1               5                   10

<210> SEQ ID NO 667
<211> LENGTH: 21
<212> TYPE: PRT
<213> ORGANISM: Homo sapiens

<400> SEQUENCE: 667

Ser Gly His Thr Thr Asn Gly Ile Tyr Thr Leu Thr Phe Pro Asn Ser
1               5                   10                  15

Thr Glu Glu Ile Lys
            20

<210> SEQ ID NO 668
<211> LENGTH: 11
<212> TYPE: PRT
<213> ORGANISM: Homo sapiens

<400> SEQUENCE: 668

Ala Thr Leu Tyr Val Thr Ala Ile Glu Asp Arg
1               5                   10

<210> SEQ ID NO 669
<211> LENGTH: 14
<212> TYPE: PRT
<213> ORGANISM: Homo sapiens

<400> SEQUENCE: 669

Asp Lys Trp Leu Ala Pro Asp Gly Leu Ile Phe Pro Asp Arg
1               5                   10

<210> SEQ ID NO 670
<211> LENGTH: 10
<212> TYPE: PRT
<213> ORGANISM: Homo sapiens

<400> SEQUENCE: 670

Glu Pro Leu Val Asp Val Val Asp Pro Lys
1               5                   10

<210> SEQ ID NO 671
<211> LENGTH: 9
<212> TYPE: PRT
<213> ORGANISM: Homo sapiens

<400> SEQUENCE: 671

Leu Asp His Val Val Thr Ile Ile Lys
1               5

<210> SEQ ID NO 672
<211> LENGTH: 17
<212> TYPE: PRT
<213> ORGANISM: Homo sapiens

<400> SEQUENCE: 672

Asn Asp Tyr Val His Ala Leu Val Ala Tyr Phe Asn Ile Glu Phe Thr
1               5                   10                  15
Arg

<210> SEQ ID NO 673
<211> LENGTH: 15
<212> TYPE: PRT
<213> ORGANISM: Homo sapiens

<400> SEQUENCE: 673

Thr Gly Phe Ser Thr Ser Pro Glu Ser Pro Tyr Thr His Trp Lys
1               5                   10                  15

<210> SEQ ID NO 674
<211> LENGTH: 9
<212> TYPE: PRT
<213> ORGANISM: Homo sapiens

<400> SEQUENCE: 674

Ala Leu Tyr Val His Gly Gly Tyr Lys
1               5

<210> SEQ ID NO 675
<211> LENGTH: 16
<212> TYPE: PRT
<213> ORGANISM: Homo sapiens

<400> SEQUENCE: 675

Glu Gln Tyr Ala Val Val Gly His Ser Ala His Ile Val Thr Leu Lys
1               5                   10                  15

<210> SEQ ID NO 676
<211> LENGTH: 12
<212> TYPE: PRT
<213> ORGANISM: Homo sapiens

<400> SEQUENCE: 676

Ile Asp Ser Thr Gly Asn Val Thr Asn Glu Leu Arg
1               5                   10

<210> SEQ ID NO 677
<211> LENGTH: 7
<212> TYPE: PRT
<213> ORGANISM: Homo sapiens

<400> SEQUENCE: 677

Leu Ala Asp Asp Leu Tyr Arg
1               5

<210> SEQ ID NO 678
<211> LENGTH: 10
<212> TYPE: PRT
<213> ORGANISM: Homo sapiens

<400> SEQUENCE: 678

Leu Thr Leu Thr Pro Trp Val Gly Leu Arg
1               5                   10

<210> SEQ ID NO 679
<211> LENGTH: 8
<212> TYPE: PRT
<213> ORGANISM: Homo sapiens

<400> SEQUENCE: 679

Ser Val Asn Asn Val Val Val Arg
1               5

<210> SEQ ID NO 680
<211> LENGTH: 9
<212> TYPE: PRT
<213> ORGANISM: Homo sapiens

<400> SEQUENCE: 680

Tyr Gly His Ser Leu Ala Leu Tyr Lys
1               5

<210> SEQ ID NO 681
<211> LENGTH: 7
<212> TYPE: PRT
<213> ORGANISM: Homo sapiens

<400> SEQUENCE: 681

Glu Phe Glu Glu Thr Ala Lys
1               5

<210> SEQ ID NO 682
<211> LENGTH: 16
<212> TYPE: PRT
<213> ORGANISM: Homo sapiens

<400> SEQUENCE: 682

Glu Leu Glu Gly Trp Glu Pro Asp Asp Pro Ile Glu Glu His Lys
1               5                   10                  15

<210> SEQ ID NO 683

```
<211> LENGTH: 15
<212> TYPE: PRT
<213> ORGANISM: Homo sapiens

<400> SEQUENCE: 683

Met Gly Ala Pro Thr Leu Pro Pro Ala Trp Gln Pro Phe Leu Lys
1               5                   10                  15

<210> SEQ ID NO 684
<211> LENGTH: 14
<212> TYPE: PRT
<213> ORGANISM: Homo sapiens

<400> SEQUENCE: 684

Asn Trp Pro Phe Leu Glu Gly Cys Ala Cys Thr Pro Glu Arg
1               5                   10

<210> SEQ ID NO 685
<211> LENGTH: 12
<212> TYPE: PRT
<213> ORGANISM: Homo sapiens

<400> SEQUENCE: 685

Gln Phe Glu Glu Leu Thr Leu Gly Glu Phe Leu Lys
1               5                   10

<210> SEQ ID NO 686
<211> LENGTH: 11
<212> TYPE: PRT
<213> ORGANISM: Homo sapiens

<400> SEQUENCE: 686

Asp Ile Gln Gly Ser Leu Gln Asp Ile Phe Lys
1               5                   10

<210> SEQ ID NO 687
<211> LENGTH: 12
<212> TYPE: PRT
<213> ORGANISM: Homo sapiens

<400> SEQUENCE: 687

Ile Asn Glu Asn Thr Gly Ser Val Ser Val Thr Arg
1               5                   10

<210> SEQ ID NO 688
<211> LENGTH: 7
<212> TYPE: PRT
<213> ORGANISM: Homo sapiens

<400> SEQUENCE: 688

Thr Leu Phe Val His Ala Arg
1               5

<210> SEQ ID NO 689
<211> LENGTH: 11
<212> TYPE: PRT
<213> ORGANISM: Homo sapiens

<400> SEQUENCE: 689

Val Asn Ser Asp Gly Gly Leu Val Ala Leu Arg
1               5                   10

<210> SEQ ID NO 690
<211> LENGTH: 9
<212> TYPE: PRT
```

<213> ORGANISM: Homo sapiens

<400> SEQUENCE: 690

Tyr Glu Val Ser Ser Pro Tyr Phe Lys
1               5

<210> SEQ ID NO 691
<211> LENGTH: 7
<212> TYPE: PRT
<213> ORGANISM: Homo sapiens

<400> SEQUENCE: 691

Phe Thr Gln Asp Thr Phe Arg
1               5

<210> SEQ ID NO 692
<211> LENGTH: 22
<212> TYPE: PRT
<213> ORGANISM: Homo sapiens

<400> SEQUENCE: 692

Ile Phe Tyr Ser Ile Thr Gly Pro Gly Ala Asp Ser Pro Pro Glu Gly
1               5                   10                  15

Val Phe Ala Val Glu Lys
            20

<210> SEQ ID NO 693
<211> LENGTH: 15
<212> TYPE: PRT
<213> ORGANISM: Homo sapiens

<400> SEQUENCE: 693

Leu Thr Val Thr Asp Leu Asp Ala Pro Asn Ser Pro Ala Trp Arg
1               5                   10                  15

<210> SEQ ID NO 694
<211> LENGTH: 14
<212> TYPE: PRT
<213> ORGANISM: Homo sapiens

<400> SEQUENCE: 694

Ser Thr Gly Thr Ile Ser Val Ile Ser Ser Gly Leu Asp Arg
1               5                   10

<210> SEQ ID NO 695
<211> LENGTH: 16
<212> TYPE: PRT
<213> ORGANISM: Homo sapiens

<400> SEQUENCE: 695

Tyr Glu Ala His Val Pro Glu Asn Ala Val Gly His Glu Val Gln Arg
1               5                   10                  15

<210> SEQ ID NO 696
<211> LENGTH: 9
<212> TYPE: PRT
<213> ORGANISM: Homo sapiens

<400> SEQUENCE: 696

Ala Ala Ser Gln Pro Gly Glu Leu Lys
1               5

<210> SEQ ID NO 697
<211> LENGTH: 8

```
<212> TYPE: PRT
<213> ORGANISM: Homo sapiens

<400> SEQUENCE: 697

Leu Leu Ile Pro Gly Asn Tyr Lys
1               5

<210> SEQ ID NO 698
<211> LENGTH: 13
<212> TYPE: PRT
<213> ORGANISM: Homo sapiens

<400> SEQUENCE: 698

Leu Gln Gln Glu Asp Gly Ile Ser Phe Glu Tyr His Arg
1               5                   10

<210> SEQ ID NO 699
<211> LENGTH: 7
<212> TYPE: PRT
<213> ORGANISM: Homo sapiens

<400> SEQUENCE: 699

Asn Phe Pro Asp Leu Asp Arg
1               5

<210> SEQ ID NO 700
<211> LENGTH: 12
<212> TYPE: PRT
<213> ORGANISM: Homo sapiens

<400> SEQUENCE: 700

Asn Ser Leu Ile Ser Tyr Leu Glu Gln Ile His Arg
1               5                   10

<210> SEQ ID NO 701
<211> LENGTH: 10
<212> TYPE: PRT
<213> ORGANISM: Homo sapiens

<400> SEQUENCE: 701

Ser Asn Ala Gln Gly Ile Asp Leu Asn Arg
1               5                   10

<210> SEQ ID NO 702
<211> LENGTH: 13
<212> TYPE: PRT
<213> ORGANISM: Homo sapiens

<400> SEQUENCE: 702

Tyr Ile Gly Asn Met His Gly Asn Glu Ala Val Gly Arg
1               5                   10

<210> SEQ ID NO 703
<211> LENGTH: 10
<212> TYPE: PRT
<213> ORGANISM: Homo sapiens

<400> SEQUENCE: 703

Ala Leu Ser Ile Gly Phe Glu Thr Cys Arg
1               5                   10

<210> SEQ ID NO 704
<211> LENGTH: 7
<212> TYPE: PRT
<213> ORGANISM: Homo sapiens
```

<400> SEQUENCE: 704

Glu Gln Trp Phe Gly Asn Arg
1               5

<210> SEQ ID NO 705
<211> LENGTH: 9
<212> TYPE: PRT
<213> ORGANISM: Homo sapiens

<400> SEQUENCE: 705

Phe Ala Gly Val Phe His Val Glu Lys
1               5

<210> SEQ ID NO 706
<211> LENGTH: 8
<212> TYPE: PRT
<213> ORGANISM: Homo sapiens

<400> SEQUENCE: 706

Asn Leu Gln Asn Val Asp Met Lys
1               5

<210> SEQ ID NO 707
<211> LENGTH: 8
<212> TYPE: PRT
<213> ORGANISM: Homo sapiens

<400> SEQUENCE: 707

Thr Glu Ala Ala Asp Leu Cys Lys
1               5

<210> SEQ ID NO 708
<211> LENGTH: 12
<212> TYPE: PRT
<213> ORGANISM: Homo sapiens

<400> SEQUENCE: 708

Tyr Gly Phe Ile Glu Gly His Val Val Ile Pro Arg
1               5                   10

<210> SEQ ID NO 709
<211> LENGTH: 12
<212> TYPE: PRT
<213> ORGANISM: Homo sapiens

<400> SEQUENCE: 709

Ala Ser Ser Ile Ile Asp Glu Leu Phe Gln Asp Arg
1               5                   10

<210> SEQ ID NO 710
<211> LENGTH: 11
<212> TYPE: PRT
<213> ORGANISM: Homo sapiens

<400> SEQUENCE: 710

Glu Leu Asp Glu Ser Leu Gln Val Ala Glu Arg
1               5                   10

<210> SEQ ID NO 711
<211> LENGTH: 9
<212> TYPE: PRT
<213> ORGANISM: Homo sapiens

<400> SEQUENCE: 711

```
Ile Asp Ser Leu Leu Glu Asn Asp Arg
1               5

<210> SEQ ID NO 712
<211> LENGTH: 17
<212> TYPE: PRT
<213> ORGANISM: Homo sapiens

<400> SEQUENCE: 712

Leu Phe Asp Ser Asp Pro Ile Thr Val Thr Val Pro Val Glu Val Ser
1               5                   10                  15

Arg

<210> SEQ ID NO 713
<211> LENGTH: 11
<212> TYPE: PRT
<213> ORGANISM: Homo sapiens

<400> SEQUENCE: 713

Ala Gln Cys Gly Gly Gly Leu Leu Gly Val Arg
1               5                   10

<210> SEQ ID NO 714
<211> LENGTH: 8
<212> TYPE: PRT
<213> ORGANISM: Homo sapiens

<400> SEQUENCE: 714

Ile Thr Glu Glu Phe Leu Gly Lys
1               5

<210> SEQ ID NO 715
<211> LENGTH: 10
<212> TYPE: PRT
<213> ORGANISM: Homo sapiens

<400> SEQUENCE: 715

Leu Leu Ala Ser Asp Ala Gly Leu Tyr Arg
1               5                   10

<210> SEQ ID NO 716
<211> LENGTH: 19
<212> TYPE: PRT
<213> ORGANISM: Homo sapiens

<400> SEQUENCE: 716

Val Ser Val Pro Thr His Pro Glu Ala Val Gly Asp Ala Ser Leu Thr
1               5                   10                  15

Val Val Lys

<210> SEQ ID NO 717
<211> LENGTH: 10
<212> TYPE: PRT
<213> ORGANISM: Homo sapiens

<400> SEQUENCE: 717

Tyr Thr Leu Asn Phe Glu Ala Ala Gln Lys
1               5                   10

<210> SEQ ID NO 718
<211> LENGTH: 19
<212> TYPE: PRT
<213> ORGANISM: Homo sapiens
```

<400> SEQUENCE: 718

Glu Ile Tyr Cys Pro Ala Pro Pro Gln Ile Asp Asn Gly Ile Ile Gln
1               5                   10                  15

Gly Glu Arg

<210> SEQ ID NO 719
<211> LENGTH: 13
<212> TYPE: PRT
<213> ORGANISM: Homo sapiens

<400> SEQUENCE: 719

Gly Ser Gln Trp Ser Asp Ile Glu Glu Phe Cys Asn Arg
1               5                   10

<210> SEQ ID NO 720
<211> LENGTH: 8
<212> TYPE: PRT
<213> ORGANISM: Homo sapiens

<400> SEQUENCE: 720

Leu Thr Cys Leu Gln Asn Leu Lys
1               5

<210> SEQ ID NO 721
<211> LENGTH: 9
<212> TYPE: PRT
<213> ORGANISM: Homo sapiens

<400> SEQUENCE: 721

Ser Cys Pro Asn Pro Gly Glu Ile Arg
1               5

<210> SEQ ID NO 722
<211> LENGTH: 12
<212> TYPE: PRT
<213> ORGANISM: Homo sapiens

<400> SEQUENCE: 722

Thr Ser Phe Pro Glu Asp Thr Val Ile Thr Tyr Lys
1               5                   10

<210> SEQ ID NO 723
<211> LENGTH: 10
<212> TYPE: PRT
<213> ORGANISM: Homo sapiens

<400> SEQUENCE: 723

Thr Thr Thr Pro Asn Ala Gln Ala Thr Arg
1               5                   10

<210> SEQ ID NO 724
<211> LENGTH: 24
<212> TYPE: PRT
<213> ORGANISM: Homo sapiens

<400> SEQUENCE: 724

Val Pro Pro Thr Val Gln Lys Pro Thr Thr Val Asn Val Pro Thr Thr
1               5                   10                  15

Glu Val Ser Pro Thr Ser Gln Lys
            20

<210> SEQ ID NO 725

```
<211> LENGTH: 11
<212> TYPE: PRT
<213> ORGANISM: Homo sapiens

<400> SEQUENCE: 725

Ile Glu Ser Ser Ser Leu Gln Gly Leu Gly Arg
1               5                   10

<210> SEQ ID NO 726
<211> LENGTH: 8
<212> TYPE: PRT
<213> ORGANISM: Homo sapiens

<400> SEQUENCE: 726

Ile Tyr Trp Val Asp Leu Glu Arg
1               5

<210> SEQ ID NO 727
<211> LENGTH: 8
<212> TYPE: PRT
<213> ORGANISM: Homo sapiens

<400> SEQUENCE: 727

Leu Phe Trp Ile Gln Tyr Asn Arg
1               5

<210> SEQ ID NO 728
<211> LENGTH: 11
<212> TYPE: PRT
<213> ORGANISM: Homo sapiens

<400> SEQUENCE: 728

Asn Gln Val Thr Pro Leu Asp Ile Leu Ser Lys
1               5                   10

<210> SEQ ID NO 729
<211> LENGTH: 14
<212> TYPE: PRT
<213> ORGANISM: Homo sapiens

<400> SEQUENCE: 729

Phe Ser Phe Leu Leu His Phe Tyr Thr Val Pro Ile Pro Lys
1               5                   10

<210> SEQ ID NO 730
<211> LENGTH: 12
<212> TYPE: PRT
<213> ORGANISM: Homo sapiens

<400> SEQUENCE: 730

Gly Glu Val Thr Tyr Thr Thr Ser Gln Val Ser Lys
1               5                   10

<210> SEQ ID NO 731
<211> LENGTH: 18
<212> TYPE: PRT
<213> ORGANISM: Homo sapiens

<400> SEQUENCE: 731

Gly Pro Ile Thr Ser Ala Ala Glu Leu Asn Asp Pro Gln Ser Ile Leu
1               5                   10                  15

Leu Arg

<210> SEQ ID NO 732
```

-continued

```
<211> LENGTH: 13
<212> TYPE: PRT
<213> ORGANISM: Homo sapiens

<400> SEQUENCE: 732

Leu Pro Asp Thr Pro Gln Gly Leu Leu Gly Glu Ala Arg
1               5                   10

<210> SEQ ID NO 733
<211> LENGTH: 10
<212> TYPE: PRT
<213> ORGANISM: Homo sapiens

<400> SEQUENCE: 733

Thr Gly Ser Gln Asp Gln Glu Val His Arg
1               5                   10

<210> SEQ ID NO 734
<211> LENGTH: 10
<212> TYPE: PRT
<213> ORGANISM: Homo sapiens

<400> SEQUENCE: 734

Thr Gln Ile Leu Glu Trp Ala Ala Glu Arg
1               5                   10

<210> SEQ ID NO 735
<211> LENGTH: 10
<212> TYPE: PRT
<213> ORGANISM: Homo sapiens

<400> SEQUENCE: 735

Val Leu Pro Gly His Ser Ala Gly Pro Arg
1               5                   10

<210> SEQ ID NO 736
<211> LENGTH: 10
<212> TYPE: PRT
<213> ORGANISM: Homo sapiens

<400> SEQUENCE: 736

Ala Ala Gly Glu Gly Leu Leu Thr Leu Arg
1               5                   10

<210> SEQ ID NO 737
<211> LENGTH: 16
<212> TYPE: PRT
<213> ORGANISM: Homo sapiens

<400> SEQUENCE: 737

Ala Pro Glu Pro Gln Leu Ser Pro Gly Ser Asp Ala Ser Glu Val Arg
1               5                   10                  15

<210> SEQ ID NO 738
<211> LENGTH: 14
<212> TYPE: PRT
<213> ORGANISM: Homo sapiens

<400> SEQUENCE: 738

Val Ser Pro Asp His Val Thr Leu Leu Asp Pro Ala Ser Lys
1               5                   10

<210> SEQ ID NO 739
<211> LENGTH: 9
<212> TYPE: PRT
```

<213> ORGANISM: Homo sapiens

<400> SEQUENCE: 739

Val Tyr Ser Gln Val Thr Val Gln Arg
1               5

<210> SEQ ID NO 740
<211> LENGTH: 8
<212> TYPE: PRT
<213> ORGANISM: Homo sapiens

<400> SEQUENCE: 740

Tyr Ala Phe Ser Leu Leu Ala Arg
1               5

<210> SEQ ID NO 741
<211> LENGTH: 8
<212> TYPE: PRT
<213> ORGANISM: Homo sapiens

<400> SEQUENCE: 741

Ile Leu Tyr Asp Phe Thr Ala Arg
1               5

<210> SEQ ID NO 742
<211> LENGTH: 18
<212> TYPE: PRT
<213> ORGANISM: Homo sapiens

<400> SEQUENCE: 742

Ser Gln Pro Val Ser Gln Pro Leu Thr Tyr Glu Ser Gly Pro Asp Glu
1               5                   10                  15

Val Arg

<210> SEQ ID NO 743
<211> LENGTH: 14
<212> TYPE: PRT
<213> ORGANISM: Homo sapiens

<400> SEQUENCE: 743

Leu Leu Gly Glu Val Asp His Tyr Gln Leu Ala Leu Gly Lys
1               5                   10

<210> SEQ ID NO 744
<211> LENGTH: 9
<212> TYPE: PRT
<213> ORGANISM: Homo sapiens

<400> SEQUENCE: 744

Gln Asp Gly Ser Val Asp Phe Phe Arg
1               5

<210> SEQ ID NO 745
<211> LENGTH: 9
<212> TYPE: PRT
<213> ORGANISM: Homo sapiens

<400> SEQUENCE: 745

Thr Phe Ala His Tyr Ala Thr Phe Arg
1               5

<210> SEQ ID NO 746
<211> LENGTH: 10
<212> TYPE: PRT

```
<213> ORGANISM: Homo sapiens

<400> SEQUENCE: 746

Tyr Ala Val Ser Glu Ala Ala Ala His Lys
1               5                   10

<210> SEQ ID NO 747
<211> LENGTH: 9
<212> TYPE: PRT
<213> ORGANISM: Homo sapiens

<400> SEQUENCE: 747

Tyr Gly Ile Asp Trp Ala Ser Gly Arg
1               5

<210> SEQ ID NO 748
<211> LENGTH: 17
<212> TYPE: PRT
<213> ORGANISM: Homo sapiens

<400> SEQUENCE: 748

Ala Ser Thr Pro Asn Gly Tyr Asp Asn Gly Ile Ile Trp Ala Thr Trp
1               5                   10                  15

Lys

<210> SEQ ID NO 749
<211> LENGTH: 15
<212> TYPE: PRT
<213> ORGANISM: Homo sapiens

<400> SEQUENCE: 749

Ile His Leu Ile Ser Thr Gln Ser Ala Ile Pro Tyr Ala Leu Arg
1               5                   10                  15

<210> SEQ ID NO 750
<211> LENGTH: 11
<212> TYPE: PRT
<213> ORGANISM: Homo sapiens

<400> SEQUENCE: 750

Gln Ser Gly Leu Tyr Phe Ile Lys Pro Leu Lys
1               5                   10

<210> SEQ ID NO 751
<211> LENGTH: 10
<212> TYPE: PRT
<213> ORGANISM: Homo sapiens

<400> SEQUENCE: 751

Thr Ser Thr Ala Asp Tyr Ala Met Phe Lys
1               5                   10

<210> SEQ ID NO 752
<211> LENGTH: 13
<212> TYPE: PRT
<213> ORGANISM: Homo sapiens

<400> SEQUENCE: 752

Tyr Glu Ala Ser Ile Leu Thr His Asp Ser Ser Ile Arg
1               5                   10

<210> SEQ ID NO 753
<211> LENGTH: 13
<212> TYPE: PRT
```

<213> ORGANISM: Homo sapiens

<400> SEQUENCE: 753

Ala Gly Ala Leu Asn Ser Asn Asp Ala Phe Val Leu Lys
1               5                   10

<210> SEQ ID NO 754
<211> LENGTH: 15
<212> TYPE: PRT
<213> ORGANISM: Homo sapiens

<400> SEQUENCE: 754

Glu Val Gln Gly Phe Glu Ser Ala Thr Phe Leu Gly Tyr Phe Lys
1               5                   10                  15

<210> SEQ ID NO 755
<211> LENGTH: 17
<212> TYPE: PRT
<213> ORGANISM: Homo sapiens

<400> SEQUENCE: 755

Gln Thr Gln Val Ser Val Leu Pro Glu Gly Gly Glu Thr Pro Leu Phe
1               5                   10                  15

Lys

<210> SEQ ID NO 756
<211> LENGTH: 8
<212> TYPE: PRT
<213> ORGANISM: Homo sapiens

<400> SEQUENCE: 756

Thr Gly Ala Gln Glu Leu Leu Arg
1               5

<210> SEQ ID NO 757
<211> LENGTH: 9
<212> TYPE: PRT
<213> ORGANISM: Homo sapiens

<400> SEQUENCE: 757

Tyr Ile Glu Thr Asp Pro Ala Asn Arg
1               5

<210> SEQ ID NO 758
<211> LENGTH: 13
<212> TYPE: PRT
<213> ORGANISM: Homo sapiens

<400> SEQUENCE: 758

Gly Glu Gly Glu Pro Cys Gly Gly Gly Ala Gly Arg
1               5                   10

<210> SEQ ID NO 759
<211> LENGTH: 14
<212> TYPE: PRT
<213> ORGANISM: Homo sapiens

<400> SEQUENCE: 759

Gly Thr Cys Glu Gln Gly Pro Ser Ile Val Thr Pro Pro Lys
1               5                   10

<210> SEQ ID NO 760
<211> LENGTH: 8
<212> TYPE: PRT

```
<213> ORGANISM: Homo sapiens

<400> SEQUENCE: 760

Thr Glu Leu Leu Pro Gly Asp Arg
1               5

<210> SEQ ID NO 761
<211> LENGTH: 15
<212> TYPE: PRT
<213> ORGANISM: Homo sapiens

<400> SEQUENCE: 761

Asp Val Ser Thr Pro Pro Thr Val Leu Pro Asp Asn Phe Pro Arg
1               5                   10                  15

<210> SEQ ID NO 762
<211> LENGTH: 8
<212> TYPE: PRT
<213> ORGANISM: Homo sapiens

<400> SEQUENCE: 762

Phe Phe Gln Tyr Asp Thr Trp Lys
1               5

<210> SEQ ID NO 763
<211> LENGTH: 10
<212> TYPE: PRT
<213> ORGANISM: Homo sapiens

<400> SEQUENCE: 763

Gly Phe Tyr Phe Ser Arg Pro Ala Ser Arg
1               5                   10

<210> SEQ ID NO 764
<211> LENGTH: 9
<212> TYPE: PRT
<213> ORGANISM: Homo sapiens

<400> SEQUENCE: 764

Gly Ile Val Glu Glu Cys Cys Phe Arg
1               5

<210> SEQ ID NO 765
<211> LENGTH: 16
<212> TYPE: PRT
<213> ORGANISM: Homo sapiens

<400> SEQUENCE: 765

Ser Cys Asp Leu Ala Leu Leu Glu Thr Tyr Cys Ala Thr Pro Ala Lys
1               5                   10                  15

<210> SEQ ID NO 766
<211> LENGTH: 9
<212> TYPE: PRT
<213> ORGANISM: Homo sapiens

<400> SEQUENCE: 766

Asp Phe Trp Leu His Ala Asn Asn Lys
1               5

<210> SEQ ID NO 767
<211> LENGTH: 8
<212> TYPE: PRT
<213> ORGANISM: Homo sapiens
```

<400> SEQUENCE: 767

Asp Asn His Leu Ala Leu Ile Lys
1               5

<210> SEQ ID NO 768
<211> LENGTH: 8
<212> TYPE: PRT
<213> ORGANISM: Homo sapiens

<400> SEQUENCE: 768

Glu His Ser Val Glu Leu His Lys
1               5

<210> SEQ ID NO 769
<211> LENGTH: 10
<212> TYPE: PRT
<213> ORGANISM: Homo sapiens

<400> SEQUENCE: 769

Thr Asp Pro Gly Val Phe Ile Gly Val Lys
1               5                   10

<210> SEQ ID NO 770
<211> LENGTH: 22
<212> TYPE: PRT
<213> ORGANISM: Homo sapiens

<400> SEQUENCE: 770

Val Leu Leu Ser Tyr Tyr Glu Ser Gln His Pro Ser Asn Glu Ser Gly
1               5                   10                  15

Asp Gly Val Asp Gly Lys
            20

<210> SEQ ID NO 771
<211> LENGTH: 17
<212> TYPE: PRT
<213> ORGANISM: Homo sapiens

<400> SEQUENCE: 771

Leu Lys Pro Glu Asp Ile Thr Gln Ile Gln Pro Gln Gln Leu Val Leu
1               5                   10                  15

Arg

<210> SEQ ID NO 772
<211> LENGTH: 11
<212> TYPE: PRT
<213> ORGANISM: Homo sapiens

<400> SEQUENCE: 772

Phe Cys Glu Cys Asp Asn Phe Asn Cys Asp Arg
1               5                   10

<210> SEQ ID NO 773
<211> LENGTH: 17
<212> TYPE: PRT
<213> ORGANISM: Homo sapiens

<400> SEQUENCE: 773

Leu Leu Val Phe Ser Thr Asp Ala Gly Phe His Phe Ala Gly Asp Gly
1               5                   10                  15

Lys

```
<210> SEQ ID NO 774
<211> LENGTH: 10
<212> TYPE: PRT
<213> ORGANISM: Homo sapiens

<400> SEQUENCE: 774

Leu Ser Glu Gly Val Thr Ile Ser Tyr Lys
1               5                   10

<210> SEQ ID NO 775
<211> LENGTH: 21
<212> TYPE: PRT
<213> ORGANISM: Homo sapiens

<400> SEQUENCE: 775

Leu Ser Glu Asn Asn Ile Gln Thr Ile Phe Ala Val Thr Glu Glu Phe
1               5                   10                  15

Gln Pro Val Tyr Lys
            20

<210> SEQ ID NO 776
<211> LENGTH: 9
<212> TYPE: PRT
<213> ORGANISM: Homo sapiens

<400> SEQUENCE: 776

Phe Ala His Thr Val Val Thr Ser Arg
1               5

<210> SEQ ID NO 777
<211> LENGTH: 12
<212> TYPE: PRT
<213> ORGANISM: Homo sapiens

<400> SEQUENCE: 777

Gly Pro Asp Val Leu Thr Ala Thr Val Ser Gly Lys
1               5                   10

<210> SEQ ID NO 778
<211> LENGTH: 9
<212> TYPE: PRT
<213> ORGANISM: Homo sapiens

<400> SEQUENCE: 778

Leu Gly Val Tyr Glu Leu Leu Leu Lys
1               5

<210> SEQ ID NO 779
<211> LENGTH: 16
<212> TYPE: PRT
<213> ORGANISM: Homo sapiens

<400> SEQUENCE: 779

Ser Pro Glu Gln Gln Glu Thr Val Leu Asp Gly Asn Leu Ile Ile Arg
1               5                   10                  15

<210> SEQ ID NO 780
<211> LENGTH: 21
<212> TYPE: PRT
<213> ORGANISM: Homo sapiens

<400> SEQUENCE: 780

Ala Val Cys Gly Gly Val Leu Val His Pro Gln Trp Val Leu Thr Ala
1               5                   10                  15
```

Ala His Cys Ile Arg
            20

<210> SEQ ID NO 781
<211> LENGTH: 16
<212> TYPE: PRT
<213> ORGANISM: Homo sapiens

<400> SEQUENCE: 781

Phe Leu Arg Pro Gly Asp Asp Ser Ser His Asp Leu Met Leu Leu Arg
1               5                   10                  15

<210> SEQ ID NO 782
<211> LENGTH: 12
<212> TYPE: PRT
<213> ORGANISM: Homo sapiens

<400> SEQUENCE: 782

His Ser Gln Pro Trp Gln Val Leu Val Ala Ser Arg
1               5                   10

<210> SEQ ID NO 783
<211> LENGTH: 12
<212> TYPE: PRT
<213> ORGANISM: Homo sapiens

<400> SEQUENCE: 783

Leu Ser Glu Pro Ala Glu Leu Thr Asp Ala Val Lys
1               5                   10

<210> SEQ ID NO 784
<211> LENGTH: 7
<212> TYPE: PRT
<213> ORGANISM: Homo sapiens

<400> SEQUENCE: 784

Ser Val Ile Leu Leu Gly Arg
1               5

<210> SEQ ID NO 785
<211> LENGTH: 19
<212> TYPE: PRT
<213> ORGANISM: Homo sapiens

<400> SEQUENCE: 785

Asp Ile Pro Thr Asn Ser Pro Glu Leu Glu Glu Thr Leu Thr His Thr
1               5                   10                  15

Ile Thr Lys

<210> SEQ ID NO 786
<211> LENGTH: 12
<212> TYPE: PRT
<213> ORGANISM: Homo sapiens

<400> SEQUENCE: 786

Leu Asn Ala Glu Asn Asn Ala Thr Phe Tyr Phe Lys
1               5                   10

<210> SEQ ID NO 787
<211> LENGTH: 9
<212> TYPE: PRT
<213> ORGANISM: Homo sapiens

<400> SEQUENCE: 787

Gln Val Val Ala Gly Leu Asn Phe Arg
1               5

<210> SEQ ID NO 788
<211> LENGTH: 11
<212> TYPE: PRT
<213> ORGANISM: Homo sapiens

<400> SEQUENCE: 788

Thr Val Gly Ser Asp Thr Phe Tyr Ser Phe Lys
1               5                   10

<210> SEQ ID NO 789
<211> LENGTH: 8
<212> TYPE: PRT
<213> ORGANISM: Homo sapiens

<400> SEQUENCE: 789

Tyr Phe Ile Asp Phe Val Ala Arg
1               5

<210> SEQ ID NO 790
<211> LENGTH: 15
<212> TYPE: PRT
<213> ORGANISM: Homo sapiens

<400> SEQUENCE: 790

Tyr Asn Ser Gln Asn Gln Ser Asn Asn Gln Phe Val Leu Tyr Arg
1               5                   10                  15

<210> SEQ ID NO 791
<211> LENGTH: 11
<212> TYPE: PRT
<213> ORGANISM: Homo sapiens

<400> SEQUENCE: 791

Cys Cys Ser Gly Ala Ile Ile Val Leu Thr Lys
1               5                   10

<210> SEQ ID NO 792
<211> LENGTH: 18
<212> TYPE: PRT
<213> ORGANISM: Homo sapiens

<400> SEQUENCE: 792

Gly Ala Asp Phe Leu Val Thr Glu Val Glu Asn Gly Gly Ser Leu Gly
1               5                   10                  15

Ser Lys

<210> SEQ ID NO 793
<211> LENGTH: 13
<212> TYPE: PRT
<213> ORGANISM: Homo sapiens

<400> SEQUENCE: 793

Ile Tyr Val Asp Asp Gly Leu Ile Ser Leu Gln Val Lys
1               5                   10

<210> SEQ ID NO 794
<211> LENGTH: 22
<212> TYPE: PRT
<213> ORGANISM: Homo sapiens

<400> SEQUENCE: 794

```
Leu Ala Pro Ile Thr Ser Asp Pro Thr Glu Ala Thr Ala Val Gly Ala
1               5                   10                  15

Val Glu Ala Ser Phe Lys
            20

<210> SEQ ID NO 795
<211> LENGTH: 11
<212> TYPE: PRT
<213> ORGANISM: Homo sapiens

<400> SEQUENCE: 795

Leu Asp Ile Asp Ser Pro Pro Ile Thr Ala Arg
1               5                   10

<210> SEQ ID NO 796
<211> LENGTH: 11
<212> TYPE: PRT
<213> ORGANISM: Homo sapiens

<400> SEQUENCE: 796

Asp Ala Pro Ser Trp Asp Pro Val Ala Leu Lys
1               5                   10

<210> SEQ ID NO 797
<211> LENGTH: 13
<212> TYPE: PRT
<213> ORGANISM: Homo sapiens

<400> SEQUENCE: 797

His Phe Val Ile Asp Gly His Pro Val Ser Phe Ser Lys
1               5                   10

<210> SEQ ID NO 798
<211> LENGTH: 10
<212> TYPE: PRT
<213> ORGANISM: Homo sapiens

<400> SEQUENCE: 798

Leu Ala Ala Leu Ser Ile Glu Glu Gly Lys
1               5                   10

<210> SEQ ID NO 799
<211> LENGTH: 8
<212> TYPE: PRT
<213> ORGANISM: Homo sapiens

<400> SEQUENCE: 799

Leu Ile Thr Glu Glu Ala Asn Arg
1               5

<210> SEQ ID NO 800
<211> LENGTH: 14
<212> TYPE: PRT
<213> ORGANISM: Homo sapiens

<400> SEQUENCE: 800

Ser Gly Val Leu Ser Val Ser Ser Gly Ala Ala Ala His Arg
1               5                   10

<210> SEQ ID NO 801
<211> LENGTH: 12
<212> TYPE: PRT
<213> ORGANISM: Homo sapiens

<400> SEQUENCE: 801
```

Ser Leu Leu Ser Asp Val Glu Glu Leu Val Glu Lys
1               5                   10

<210> SEQ ID NO 802
<211> LENGTH: 15
<212> TYPE: PRT
<213> ORGANISM: Homo sapiens

<400> SEQUENCE: 802

Val Phe Leu Thr Val Pro Ser Leu Ser Ser Thr Ala Glu Glu Lys
1               5                   10                  15

<210> SEQ ID NO 803
<211> LENGTH: 18
<212> TYPE: PRT
<213> ORGANISM: Homo sapiens

<400> SEQUENCE: 803

Glu Gln Thr Val Ser Val Ser Gly Ala Phe Gln Ile Asn Thr Phe Asp
1               5                   10                  15

Leu Arg

<210> SEQ ID NO 804
<211> LENGTH: 12
<212> TYPE: PRT
<213> ORGANISM: Homo sapiens

<400> SEQUENCE: 804

Gly Ile Leu Thr Val Asp Glu Leu Leu Ala Ile Arg
1               5                   10

<210> SEQ ID NO 805
<211> LENGTH: 8
<212> TYPE: PRT
<213> ORGANISM: Homo sapiens

<400> SEQUENCE: 805

Ile Pro Leu Asn Asp Leu Phe Arg
1               5

<210> SEQ ID NO 806
<211> LENGTH: 7
<212> TYPE: PRT
<213> ORGANISM: Homo sapiens

<400> SEQUENCE: 806

Ser His Thr Ala Leu Leu Arg
1               5

<210> SEQ ID NO 807
<211> LENGTH: 10
<212> TYPE: PRT
<213> ORGANISM: Homo sapiens

<400> SEQUENCE: 807

Val Gln Pro Phe Asn Val Thr Gln Gly Lys
1               5                   10

<210> SEQ ID NO 808
<211> LENGTH: 9
<212> TYPE: PRT
<213> ORGANISM: Homo sapiens

<400> SEQUENCE: 808

```
Tyr Leu Asp Phe Val Phe Ala Val Lys
1               5
```

<210> SEQ ID NO 809
<211> LENGTH: 15
<212> TYPE: PRT
<213> ORGANISM: Homo sapiens

<400> SEQUENCE: 809

```
Asp Leu Ala Asp Glu Leu Ala Leu Val Asp Val Ile Glu Asp Lys
1               5                   10                  15
```

<210> SEQ ID NO 810
<211> LENGTH: 8
<212> TYPE: PRT
<213> ORGANISM: Homo sapiens

<400> SEQUENCE: 810

```
Phe Ile Ile Pro Asn Val Val Lys
1               5
```

<210> SEQ ID NO 811
<211> LENGTH: 9
<212> TYPE: PRT
<213> ORGANISM: Homo sapiens

<400> SEQUENCE: 811

```
Leu Val Ile Ile Thr Ala Gly Ala Arg
1               5
```

<210> SEQ ID NO 812
<211> LENGTH: 10
<212> TYPE: PRT
<213> ORGANISM: Homo sapiens

<400> SEQUENCE: 812

```
Ser Ala Asp Thr Leu Trp Gly Ile Gln Lys
1               5                   10
```

<210> SEQ ID NO 813
<211> LENGTH: 10
<212> TYPE: PRT
<213> ORGANISM: Homo sapiens

<400> SEQUENCE: 813

```
Val Thr Leu Thr Ser Glu Glu Glu Ala Arg
1               5                   10
```

<210> SEQ ID NO 814
<211> LENGTH: 10
<212> TYPE: PRT
<213> ORGANISM: Homo sapiens

<400> SEQUENCE: 814

```
Glu Leu Ala Pro Leu Phe Glu Glu Leu Arg
1               5                   10
```

<210> SEQ ID NO 815
<211> LENGTH: 23
<212> TYPE: PRT
<213> ORGANISM: Homo sapiens

<400> SEQUENCE: 815

```
Leu Pro Leu Val Val Ser Phe Ile Ala Ser Ser Ser Ala Asn Thr Gly
```

```
1               5                   10                  15
Leu Ile Val Ser Leu Glu Lys
            20

<210> SEQ ID NO 816
<211> LENGTH: 15
<212> TYPE: PRT
<213> ORGANISM: Homo sapiens

<400> SEQUENCE: 816

Leu Pro Ser Val Glu Gly Leu His Ala Ile Val Val Ser Asp Arg
1               5                   10                  15

<210> SEQ ID NO 817
<211> LENGTH: 16
<212> TYPE: PRT
<213> ORGANISM: Homo sapiens

<400> SEQUENCE: 817

Ser Ile Ile Cys Tyr Tyr Asn Thr Tyr Gln Val Val Gln Phe Asn Arg
1               5                   10                  15

<210> SEQ ID NO 818
<211> LENGTH: 7
<212> TYPE: PRT
<213> ORGANISM: Homo sapiens

<400> SEQUENCE: 818

Ala Gly Tyr Val Leu His Arg
1               5

<210> SEQ ID NO 819
<211> LENGTH: 15
<212> TYPE: PRT
<213> ORGANISM: Homo sapiens

<400> SEQUENCE: 819

Asp Thr Phe Tyr Ser Leu Gly Ser Ser Leu Asp Ile Thr Phe Arg
1               5                   10                  15

<210> SEQ ID NO 820
<211> LENGTH: 8
<212> TYPE: PRT
<213> ORGANISM: Homo sapiens

<400> SEQUENCE: 820

Trp Pro Glu Pro Val Phe Gly Arg
1               5

<210> SEQ ID NO 821
<211> LENGTH: 10
<212> TYPE: PRT
<213> ORGANISM: Homo sapiens

<400> SEQUENCE: 821

Trp Thr Leu Thr Ala Pro Pro Gly Tyr Arg
1               5                   10

<210> SEQ ID NO 822
<211> LENGTH: 15
<212> TYPE: PRT
<213> ORGANISM: Homo sapiens

<400> SEQUENCE: 822
```

Phe Leu Asn Ser Asn Ser Gly Leu Gln Gly Leu Gln Phe Tyr Arg
1               5                   10                  15

<210> SEQ ID NO 823
<211> LENGTH: 10
<212> TYPE: PRT
<213> ORGANISM: Homo sapiens

<400> SEQUENCE: 823

Ile Gly Leu Ala Ser Ala Leu Gln Pro Arg
1               5                   10

<210> SEQ ID NO 824
<211> LENGTH: 14
<212> TYPE: PRT
<213> ORGANISM: Homo sapiens

<400> SEQUENCE: 824

Asn Asp Val Val Phe Gln Pro Ile Ser Gly Glu Asp Val Arg
1               5                   10

<210> SEQ ID NO 825
<211> LENGTH: 12
<212> TYPE: PRT
<213> ORGANISM: Homo sapiens

<400> SEQUENCE: 825

Ser Leu Glu Pro Phe Thr Leu Glu Ile Leu Ala Arg
1               5                   10

<210> SEQ ID NO 826
<211> LENGTH: 22
<212> TYPE: PRT
<213> ORGANISM: Homo sapiens

<400> SEQUENCE: 826

Thr Val Asp Phe Thr Ser Pro Leu Phe Lys Pro Ala Thr Gly Phe Pro
1               5                   10                  15

Leu Gly Ser Ser Leu Arg
            20

<210> SEQ ID NO 827
<211> LENGTH: 14
<212> TYPE: PRT
<213> ORGANISM: Homo sapiens

<400> SEQUENCE: 827

Trp Asn Asp Lys Pro Tyr Leu Cys Ala Leu Tyr Gln Gln Arg
1               5                   10

<210> SEQ ID NO 828
<211> LENGTH: 14
<212> TYPE: PRT
<213> ORGANISM: Homo sapiens

<400> SEQUENCE: 828

Asn Ile Ile His Gly Ser Asp Ser Val Glu Ser Ala Glu Lys
1               5                   10

<210> SEQ ID NO 829
<211> LENGTH: 10
<212> TYPE: PRT
<213> ORGANISM: Homo sapiens

<400> SEQUENCE: 829

```
Ala Leu His Ile Pro Phe Pro Val Glu Lys
1               5                   10
```

<210> SEQ ID NO 830
<211> LENGTH: 18
<212> TYPE: PRT
<213> ORGANISM: Homo sapiens

<400> SEQUENCE: 830

```
Asp Glu Asp Gly Lys Pro Tyr Ser Pro Ser Glu Tyr Ser Leu Gln Gln
1               5                   10                  15

Thr Arg
```

<210> SEQ ID NO 831
<211> LENGTH: 9
<212> TYPE: PRT
<213> ORGANISM: Homo sapiens

<400> SEQUENCE: 831

```
Asp Gly Asn Val Phe Leu Val Pro Lys
1               5
```

<210> SEQ ID NO 832
<211> LENGTH: 12
<212> TYPE: PRT
<213> ORGANISM: Homo sapiens

<400> SEQUENCE: 832

```
Glu Gln Phe Asn Glu Ala Gln Leu Ala Leu Ile Arg
1               5                   10
```

<210> SEQ ID NO 833
<211> LENGTH: 15
<212> TYPE: PRT
<213> ORGANISM: Homo sapiens

<400> SEQUENCE: 833

```
Ile Ile Asn Leu Pro Val Val Asp Phe Asn Glu Met Met Ser Lys
1               5                   10                  15
```

<210> SEQ ID NO 834
<211> LENGTH: 15
<212> TYPE: PRT
<213> ORGANISM: Homo sapiens

<400> SEQUENCE: 834

```
Leu Glu Asn Ile Val Glu Leu Glu Gln Asp Leu Asp His Leu Lys
1               5                   10                  15
```

<210> SEQ ID NO 835
<211> LENGTH: 8
<212> TYPE: PRT
<213> ORGANISM: Homo sapiens

<400> SEQUENCE: 835

```
Ala Ile Ala Val Asp Pro Ile Arg
1               5
```

<210> SEQ ID NO 836
<211> LENGTH: 8
<212> TYPE: PRT
<213> ORGANISM: Homo sapiens

<400> SEQUENCE: 836

```
Asp Gly Val Val Ser Val Asn Lys
1               5

<210> SEQ ID NO 837
<211> LENGTH: 14
<212> TYPE: PRT
<213> ORGANISM: Homo sapiens

<400> SEQUENCE: 837

Glu Gly Thr Ser Leu Gly Glu Val Gly Gly Pro Asp Leu Lys
1               5                   10

<210> SEQ ID NO 838
<211> LENGTH: 12
<212> TYPE: PRT
<213> ORGANISM: Homo sapiens

<400> SEQUENCE: 838

Glu Ser Tyr Asn Val Gln Leu Gln Leu Pro Ala Arg
1               5                   10

<210> SEQ ID NO 839
<211> LENGTH: 12
<212> TYPE: PRT
<213> ORGANISM: Homo sapiens

<400> SEQUENCE: 839

His Ala Gln Ala Gln Tyr Ala Tyr Pro Gly Ala Arg
1               5                   10

<210> SEQ ID NO 840
<211> LENGTH: 17
<212> TYPE: PRT
<213> ORGANISM: Homo sapiens

<400> SEQUENCE: 840

Ile Thr Gln Thr Ala Glu Gly Leu Asp Pro Glu Asn Tyr Leu Ser Ile
1               5                   10                  15
Lys

<210> SEQ ID NO 841
<211> LENGTH: 11
<212> TYPE: PRT
<213> ORGANISM: Homo sapiens

<400> SEQUENCE: 841

Leu Ala Asn Pro Leu His Phe Tyr Glu Ala Arg
1               5                   10

<210> SEQ ID NO 842
<211> LENGTH: 17
<212> TYPE: PRT
<213> ORGANISM: Homo sapiens

<400> SEQUENCE: 842

Ala Ile Pro Val Ala Gln Asp Leu Asn Ala Pro Ser Asp Trp Asp Ser
1               5                   10                  15
Arg

<210> SEQ ID NO 843
<211> LENGTH: 19
<212> TYPE: PRT
<213> ORGANISM: Homo sapiens
```

<400> SEQUENCE: 843

Ala Asn Asp Glu Ser Asn Glu His Ser Asp Val Ile Asp Ser Gln Glu
1               5                   10                  15

Leu Ser Lys

<210> SEQ ID NO 844
<211> LENGTH: 9
<212> TYPE: PRT
<213> ORGANISM: Homo sapiens

<400> SEQUENCE: 844

Gly Asp Ser Val Val Tyr Gly Leu Arg
1               5

<210> SEQ ID NO 845
<211> LENGTH: 19
<212> TYPE: PRT
<213> ORGANISM: Homo sapiens

<400> SEQUENCE: 845

Gln Asn Leu Leu Ala Pro Gln Asn Ala Val Ser Ser Glu Glu Thr Asn
1               5                   10                  15

Asp Phe Lys

<210> SEQ ID NO 846
<211> LENGTH: 16
<212> TYPE: PRT
<213> ORGANISM: Homo sapiens

<400> SEQUENCE: 846

Tyr Pro Asp Ala Val Ala Thr Trp Leu Asn Pro Asp Pro Ser Gln Lys
1               5                   10                  15

<210> SEQ ID NO 847
<211> LENGTH: 9
<212> TYPE: PRT
<213> ORGANISM: Homo sapiens

<400> SEQUENCE: 847

Glu Leu Asn Glu Ala Leu Glu Leu Lys
1               5

<210> SEQ ID NO 848
<211> LENGTH: 10
<212> TYPE: PRT
<213> ORGANISM: Homo sapiens

<400> SEQUENCE: 848

Leu Gly Phe Leu His Ser Gly Thr Ala Lys
1               5                   10

<210> SEQ ID NO 849
<211> LENGTH: 19
<212> TYPE: PRT
<213> ORGANISM: Homo sapiens

<400> SEQUENCE: 849

Arg Pro Ile Leu Thr Ile Ile Thr Leu Glu Asp Ser Ser Gly Asn Leu
1               5                   10                  15

Leu Gly Arg

<210> SEQ ID NO 850
<211> LENGTH: 9
<212> TYPE: PRT
<213> ORGANISM: Homo sapiens

<400> SEQUENCE: 850

Thr Tyr Gln Gly Ser Tyr Gly Phe Arg
1               5

<210> SEQ ID NO 851
<211> LENGTH: 7
<212> TYPE: PRT
<213> ORGANISM: Homo sapiens

<400> SEQUENCE: 851

Val Glu Tyr Leu Asp Asp Arg
1               5

<210> SEQ ID NO 852
<211> LENGTH: 8
<212> TYPE: PRT
<213> ORGANISM: Homo sapiens

<400> SEQUENCE: 852

Ala His Gly Val His Ala Thr Lys
1               5

<210> SEQ ID NO 853
<211> LENGTH: 19
<212> TYPE: PRT
<213> ORGANISM: Homo sapiens

<400> SEQUENCE: 853

Leu Glu Glu His Leu Glu Cys Ala Cys Ala Thr Thr Ser Leu Asn Pro
1               5                   10                  15

Asp Tyr Arg

<210> SEQ ID NO 854
<211> LENGTH: 18
<212> TYPE: PRT
<213> ORGANISM: Homo sapiens

<400> SEQUENCE: 854

Leu Leu Glu Ile Asp Ser Val Gly Ser Glu Asp Ser Leu Asp Thr Ser
1               5                   10                  15

Leu Arg

<210> SEQ ID NO 855
<211> LENGTH: 7
<212> TYPE: PRT
<213> ORGANISM: Homo sapiens

<400> SEQUENCE: 855

Ser Gln Ile His Ser Ile Arg
1               5

<210> SEQ ID NO 856
<211> LENGTH: 8
<212> TYPE: PRT
<213> ORGANISM: Homo sapiens

<400> SEQUENCE: 856

Thr Val Ile Tyr Glu Ile Pro Arg
1               5

<210> SEQ ID NO 857
<211> LENGTH: 12
<212> TYPE: PRT
<213> ORGANISM: Homo sapiens

<400> SEQUENCE: 857

Ala Gly Ala Leu Gln Leu Leu Leu Val Gly Asp Lys
1               5                   10

<210> SEQ ID NO 858
<211> LENGTH: 20
<212> TYPE: PRT
<213> ORGANISM: Homo sapiens

<400> SEQUENCE: 858

Ala Thr Tyr Phe Gly Ser Ile Val Leu Leu Ser Pro Ala Val Ile Asp
1               5                   10                  15

Ser Pro Leu Lys
            20

<210> SEQ ID NO 859
<211> LENGTH: 11
<212> TYPE: PRT
<213> ORGANISM: Homo sapiens

<400> SEQUENCE: 859

Ala Val Glu Pro Gln Leu Gln Glu Glu Glu Arg
1               5                   10

<210> SEQ ID NO 860
<211> LENGTH: 12
<212> TYPE: PRT
<213> ORGANISM: Homo sapiens

<400> SEQUENCE: 860

Glu Gly His Phe Tyr Tyr Asn Ile Ser Glu Val Lys
1               5                   10

<210> SEQ ID NO 861
<211> LENGTH: 15
<212> TYPE: PRT
<213> ORGANISM: Homo sapiens

<400> SEQUENCE: 861

Phe Leu Glu Gln Glu Leu Glu Thr Ile Thr Ile Pro Asp Leu Arg
1               5                   10                  15

<210> SEQ ID NO 862
<211> LENGTH: 14
<212> TYPE: PRT
<213> ORGANISM: Homo sapiens

<400> SEQUENCE: 862

Val Tyr Asp Phe Leu Ser Thr Phe Ile Thr Ser Gly Met Arg
1               5                   10

<210> SEQ ID NO 863
<211> LENGTH: 8
<212> TYPE: PRT
<213> ORGANISM: Homo sapiens

<400> SEQUENCE: 863

Asp Phe Ile Ala Thr Leu Gly Lys

```
<210> SEQ ID NO 864
<211> LENGTH: 15
<212> TYPE: PRT
<213> ORGANISM: Homo sapiens

<400> SEQUENCE: 864

Glu Leu Ser Glu Leu Ser Leu Leu Ser Leu Tyr Gly Ile His Lys
1               5                   10                  15

<210> SEQ ID NO 865
<211> LENGTH: 10
<212> TYPE: PRT
<213> ORGANISM: Homo sapiens

<400> SEQUENCE: 865

Phe Gln Glu Leu Glu Ser Glu Thr Leu Lys
1               5                   10

<210> SEQ ID NO 866
<211> LENGTH: 7
<212> TYPE: PRT
<213> ORGANISM: Homo sapiens

<400> SEQUENCE: 866

Phe Val Thr Leu Val Phe Arg
1               5

<210> SEQ ID NO 867
<211> LENGTH: 12
<212> TYPE: PRT
<213> ORGANISM: Homo sapiens

<400> SEQUENCE: 867

Ser Pro Ile Asp Thr Phe Pro Thr Asp Pro Ile Lys
1               5                   10

<210> SEQ ID NO 868
<211> LENGTH: 9
<212> TYPE: PRT
<213> ORGANISM: Homo sapiens

<400> SEQUENCE: 868

Ser Phe Glu Asp Ile His His Tyr Arg
1               5

<210> SEQ ID NO 869
<211> LENGTH: 8
<212> TYPE: PRT
<213> ORGANISM: Homo sapiens

<400> SEQUENCE: 869

Glu Ile Leu Asp Ala Phe Asp Lys
1               5

<210> SEQ ID NO 870
<211> LENGTH: 15
<212> TYPE: PRT
<213> ORGANISM: Homo sapiens

<400> SEQUENCE: 870

Glu Ile Val Asp Ser Tyr Leu Pro Val Ile Leu Asp Ile Ile Lys
1               5                   10                  15
```

<210> SEQ ID NO 871
<211> LENGTH: 10
<212> TYPE: PRT
<213> ORGANISM: Homo sapiens

<400> SEQUENCE: 871

Gly Ser Ala Val Trp Cys Gln Asn Val Lys
1               5                   10

<210> SEQ ID NO 872
<211> LENGTH: 7
<212> TYPE: PRT
<213> ORGANISM: Homo sapiens

<400> SEQUENCE: 872

Leu Val Gly Tyr Leu Asp Arg
1               5

<210> SEQ ID NO 873
<211> LENGTH: 9
<212> TYPE: PRT
<213> ORGANISM: Homo sapiens

<400> SEQUENCE: 873

Gln Glu Ile Leu Ala Ala Leu Glu Lys
1               5

<210> SEQ ID NO 874
<211> LENGTH: 9
<212> TYPE: PRT
<213> ORGANISM: Homo sapiens

<400> SEQUENCE: 874

Asp Gly Leu Ile Pro Leu Glu Ile Arg
1               5

<210> SEQ ID NO 875
<211> LENGTH: 14
<212> TYPE: PRT
<213> ORGANISM: Homo sapiens

<400> SEQUENCE: 875

Gly Gly Phe Val Leu Leu Asp Gly Glu Thr Phe Glu Val Lys
1               5                   10

<210> SEQ ID NO 876
<211> LENGTH: 13
<212> TYPE: PRT
<213> ORGANISM: Homo sapiens

<400> SEQUENCE: 876

Leu Thr Gly Gln Leu Phe Leu Gly Gly Ser Ile Val Lys
1               5                   10

<210> SEQ ID NO 877
<211> LENGTH: 10
<212> TYPE: PRT
<213> ORGANISM: Homo sapiens

<400> SEQUENCE: 877

Leu Val Leu Pro Ser Leu Ile Ser Ser Arg
1               5                   10

<210> SEQ ID NO 878

```
<211> LENGTH: 10
<212> TYPE: PRT
<213> ORGANISM: Homo sapiens

<400> SEQUENCE: 878

Asn Glu Gly Gly Thr Trp Ser Val Glu Lys
1               5                   10

<210> SEQ ID NO 879
<211> LENGTH: 8
<212> TYPE: PRT
<213> ORGANISM: Homo sapiens

<400> SEQUENCE: 879

Phe Phe Glu Ser His Val Ala Arg
1               5

<210> SEQ ID NO 880
<211> LENGTH: 14
<212> TYPE: PRT
<213> ORGANISM: Homo sapiens

<400> SEQUENCE: 880

Ile Leu Asn Thr Pro Asn Cys Ala Leu Gln Ile Val Ala Arg
1               5                   10

<210> SEQ ID NO 881
<211> LENGTH: 8
<212> TYPE: PRT
<213> ORGANISM: Homo sapiens

<400> SEQUENCE: 881

Trp Ile Gln Glu Tyr Leu Glu Lys
1               5

<210> SEQ ID NO 882
<211> LENGTH: 11
<212> TYPE: PRT
<213> ORGANISM: Homo sapiens

<400> SEQUENCE: 882

Asp Arg Pro Phe Val Cys Ala Pro Ser Ser Lys
1               5                   10

<210> SEQ ID NO 883
<211> LENGTH: 15
<212> TYPE: PRT
<213> ORGANISM: Homo sapiens

<400> SEQUENCE: 883

His Asp Ser Ala Thr Asp Thr Ile Asp Ile Ala Pro Asn His Arg
1               5                   10                  15

<210> SEQ ID NO 884
<211> LENGTH: 10
<212> TYPE: PRT
<213> ORGANISM: Homo sapiens

<400> SEQUENCE: 884

Thr Ile Val Leu Gln Glu Ser Ile Gly Lys
1               5                   10

<210> SEQ ID NO 885
<211> LENGTH: 12
<212> TYPE: PRT
```

<213> ORGANISM: Homo sapiens

<400> SEQUENCE: 885

Thr Leu Ser Gln Leu Ser Gln Gln Glu Gly Ile Lys
1               5                   10

<210> SEQ ID NO 886
<211> LENGTH: 16
<212> TYPE: PRT
<213> ORGANISM: Homo sapiens

<400> SEQUENCE: 886

Val Ile His Asn Ser Met Cys Ile Ala Glu Ile Asp Leu Ile Pro Arg
1               5                   10                  15

<210> SEQ ID NO 887
<211> LENGTH: 21
<212> TYPE: PRT
<213> ORGANISM: Homo sapiens

<400> SEQUENCE: 887

Val Pro Asn Glu Glu Asp Pro Ser Leu Asp Arg Pro Phe Ile Ser Glu
1               5                   10                  15

Gly Thr Thr Leu Lys
            20

<210> SEQ ID NO 888
<211> LENGTH: 16
<212> TYPE: PRT
<213> ORGANISM: Homo sapiens

<400> SEQUENCE: 888

Asp Ser Thr Ile Gln Val Val Glu Asn Gly Glu Ser Ser Gln Gly Arg
1               5                   10                  15

<210> SEQ ID NO 889
<211> LENGTH: 10
<212> TYPE: PRT
<213> ORGANISM: Homo sapiens

<400> SEQUENCE: 889

Asp Trp Val Ser Val Val Thr Pro Ala Arg
1               5                   10

<210> SEQ ID NO 890
<211> LENGTH: 8
<212> TYPE: PRT
<213> ORGANISM: Homo sapiens

<400> SEQUENCE: 890

Phe Val Gly Gln Gly Gly Ala Arg
1               5

<210> SEQ ID NO 891
<211> LENGTH: 9
<212> TYPE: PRT
<213> ORGANISM: Homo sapiens

<400> SEQUENCE: 891

Ser Gly Ser Val Ile Asp Gln Ser Arg
1               5

<210> SEQ ID NO 892
<211> LENGTH: 7

-continued

```
<212> TYPE: PRT
<213> ORGANISM: Homo sapiens

<400> SEQUENCE: 892

Thr Leu Asp Glu Tyr Trp Arg
1               5

<210> SEQ ID NO 893
<211> LENGTH: 9
<212> TYPE: PRT
<213> ORGANISM: Homo sapiens

<400> SEQUENCE: 893

Val Leu Asn Leu Gly Pro Ile Thr Arg
1               5

<210> SEQ ID NO 894
<211> LENGTH: 9
<212> TYPE: PRT
<213> ORGANISM: Homo sapiens

<400> SEQUENCE: 894

Glu Leu Gln Val Tyr Ile Ser Pro Lys
1               5

<210> SEQ ID NO 895
<211> LENGTH: 11
<212> TYPE: PRT
<213> ORGANISM: Homo sapiens

<400> SEQUENCE: 895

Gly Ile Gln Val Glu Ile Tyr Ser Phe Pro Lys
1               5                   10

<210> SEQ ID NO 896
<211> LENGTH: 13
<212> TYPE: PRT
<213> ORGANISM: Homo sapiens

<400> SEQUENCE: 896

Leu His Ile Asp Glu Met Asp Ser Val Pro Thr Val Arg
1               5                   10

<210> SEQ ID NO 897
<211> LENGTH: 11
<212> TYPE: PRT
<213> ORGANISM: Homo sapiens

<400> SEQUENCE: 897

Asn Thr Val Ile Ser Val Asn Pro Ser Thr Lys
1               5                   10

<210> SEQ ID NO 898
<211> LENGTH: 15
<212> TYPE: PRT
<213> ORGANISM: Homo sapiens

<400> SEQUENCE: 898

Ser Leu Glu Val Thr Phe Thr Pro Val Ile Glu Asp Ile Gly Lys
1               5                   10                  15

<210> SEQ ID NO 899
<211> LENGTH: 10
<212> TYPE: PRT
<213> ORGANISM: Homo sapiens
```

<400> SEQUENCE: 899

Thr Gln Ile Asp Ser Pro Leu Asn Gly Lys
1               5                   10

<210> SEQ ID NO 900
<211> LENGTH: 13
<212> TYPE: PRT
<213> ORGANISM: Homo sapiens

<400> SEQUENCE: 900

Glu Asp Phe Thr Ser Leu Ser Leu Val Leu Tyr Ser Arg
1               5                   10

<210> SEQ ID NO 901
<211> LENGTH: 8
<212> TYPE: PRT
<213> ORGANISM: Homo sapiens

<400> SEQUENCE: 901

Glu Leu Pro Glu His Thr Val Lys
1               5

<210> SEQ ID NO 902
<211> LENGTH: 11
<212> TYPE: PRT
<213> ORGANISM: Homo sapiens

<400> SEQUENCE: 902

His Leu Ser Leu Leu Thr Thr Leu Ser Asn Arg
1               5                   10

<210> SEQ ID NO 903
<211> LENGTH: 10
<212> TYPE: PRT
<213> ORGANISM: Homo sapiens

<400> SEQUENCE: 903

Thr His Leu Pro Glu Val Phe Leu Ser Lys
1               5                   10

<210> SEQ ID NO 904
<211> LENGTH: 7
<212> TYPE: PRT
<213> ORGANISM: Homo sapiens

<400> SEQUENCE: 904

Tyr Thr Phe Glu Leu Ser Arg
1               5

<210> SEQ ID NO 905
<211> LENGTH: 13
<212> TYPE: PRT
<213> ORGANISM: Homo sapiens

<400> SEQUENCE: 905

Ala Leu Gly Phe Glu Asp Ala Thr Gln Ala Leu Gly Arg
1               5                   10

<210> SEQ ID NO 906
<211> LENGTH: 12
<212> TYPE: PRT
<213> ORGANISM: Homo sapiens

<400> SEQUENCE: 906

Gly Leu Asp Leu Thr Glu Asp Thr Tyr Lys Pro Arg
1               5                   10

<210> SEQ ID NO 907
<211> LENGTH: 21
<212> TYPE: PRT
<213> ORGANISM: Homo sapiens

<400> SEQUENCE: 907

Gln Gln Gln His Leu Phe Gly Ser Asp Val Thr Asp Cys Ser Gly Asn
1               5                   10                  15

Phe Cys Leu Phe Arg
            20

<210> SEQ ID NO 908
<211> LENGTH: 14
<212> TYPE: PRT
<213> ORGANISM: Homo sapiens

<400> SEQUENCE: 908

Gln Asp Phe Asp Ile Thr Asp Ile Ser Leu Leu Glu His Arg
1               5                   10

<210> SEQ ID NO 909
<211> LENGTH: 20
<212> TYPE: PRT
<213> ORGANISM: Homo sapiens

<400> SEQUENCE: 909

Asp Glu Thr His Ala Thr Tyr Ser Asn Thr Leu Tyr Leu Ala Asp Glu
1               5                   10                  15

Ile Ile Ile Arg
            20

<210> SEQ ID NO 910
<211> LENGTH: 10
<212> TYPE: PRT
<213> ORGANISM: Homo sapiens

<400> SEQUENCE: 910

Asp Arg Pro Phe Phe Ala Gly Leu Val Lys
1               5                   10

<210> SEQ ID NO 911
<211> LENGTH: 13
<212> TYPE: PRT
<213> ORGANISM: Homo sapiens

<400> SEQUENCE: 911

Ala Ala Ile Pro Ser Ala Leu Asp Thr Asp Ser Ser Lys
1               5                   10

<210> SEQ ID NO 912
<211> LENGTH: 23
<212> TYPE: PRT
<213> ORGANISM: Homo sapiens

<400> SEQUENCE: 912

Asp Pro Asp His Ser Glu Gly Ser Thr Thr Leu Leu Glu Gly Tyr Thr
1               5                   10                  15

Ser His Tyr Pro His Thr Lys
            20

<210> SEQ ID NO 913
<211> LENGTH: 22
<212> TYPE: PRT
<213> ORGANISM: Homo sapiens

<400> SEQUENCE: 913

Ile Ser His Glu Leu Asp Ser Ala Ser Ser Glu Val Asn Ser Ala Val
1               5                   10                  15

Thr Ala Leu Trp Gly Lys
            20

<210> SEQ ID NO 914
<211> LENGTH: 5
<212> TYPE: PRT
<213> ORGANISM: Homo sapiens

<400> SEQUENCE: 914

Ala Asp Asp Gly Arg
1               5

<210> SEQ ID NO 915
<211> LENGTH: 7
<212> TYPE: PRT
<213> ORGANISM: Homo sapiens

<400> SEQUENCE: 915

Pro Phe Pro Gln Val Ile Lys
1               5

<210> SEQ ID NO 916
<211> LENGTH: 23
<212> TYPE: PRT
<213> ORGANISM: Homo sapiens

<400> SEQUENCE: 916

Ile Arg Pro Phe Phe Pro Gln Gln Ile His Leu Ile Ser Thr Gln Ser
1               5                   10                  15

Ala Ile Pro Tyr Ala Leu Arg
            20

<210> SEQ ID NO 917
<211> LENGTH: 16
<212> TYPE: PRT
<213> ORGANISM: Homo sapiens

<400> SEQUENCE: 917

Leu Leu Gly Asn Val Leu Val Cys Val Leu Ala His His Phe Gly Lys
1               5                   10                  15

<210> SEQ ID NO 918
<211> LENGTH: 10
<212> TYPE: PRT
<213> ORGANISM: Homo sapiens

<400> SEQUENCE: 918

Ala Gln Gly Tyr Ser Gly Leu Ser Val Lys
1               5                   10

<210> SEQ ID NO 919
<211> LENGTH: 9
<212> TYPE: PRT
<213> ORGANISM: Homo sapiens

<400> SEQUENCE: 919

```
Ser Val Ser Cys Pro Leu Leu Ser Arg
1               5

<210> SEQ ID NO 920
<211> LENGTH: 8
<212> TYPE: PRT
<213> ORGANISM: Homo sapiens

<400> SEQUENCE: 920

Phe Gly Ser Asp Asp Glu Gly Arg
1               5

<210> SEQ ID NO 921
<211> LENGTH: 8
<212> TYPE: PRT
<213> ORGANISM: Homo sapiens

<400> SEQUENCE: 921

Ile Pro Phe Thr Phe Trp Ala Arg
1               5

<210> SEQ ID NO 922
<211> LENGTH: 7
<212> TYPE: PRT
<213> ORGANISM: Homo sapiens

<400> SEQUENCE: 922

Gln Leu Tyr Leu Gln His Arg
1               5

<210> SEQ ID NO 923
<211> LENGTH: 13
<212> TYPE: PRT
<213> ORGANISM: Homo sapiens

<400> SEQUENCE: 923

Asn Val Phe Gln Leu Glu Gln Ala Phe Val Leu Ser Lys
1               5                   10

<210> SEQ ID NO 924
<211> LENGTH: 18
<212> TYPE: PRT
<213> ORGANISM: Homo sapiens

<400> SEQUENCE: 924

Asn Gln His Thr Leu Tyr Val Glu Val Thr Asn Glu Ala Pro Phe Val
1               5                   10                  15

Leu Lys

<210> SEQ ID NO 925
<211> LENGTH: 11
<212> TYPE: PRT
<213> ORGANISM: Homo sapiens

<400> SEQUENCE: 925

Gly Leu Glu Ala Arg Pro Glu Val Val Leu Arg
1               5                   10

<210> SEQ ID NO 926
<211> LENGTH: 12
<212> TYPE: PRT
<213> ORGANISM: Homo sapiens

<400> SEQUENCE: 926
```

Ala Gln Pro Asp Val His Phe Phe Gln Gly Leu Arg
1               5                   10

<210> SEQ ID NO 927
<211> LENGTH: 16
<212> TYPE: PRT
<213> ORGANISM: Homo sapiens

<400> SEQUENCE: 927

Leu Ser Leu Leu Glu Glu Leu Ser Leu Ala Glu Asn Gln Leu Leu Lys
1               5                   10                  15

<210> SEQ ID NO 928
<211> LENGTH: 8
<212> TYPE: PRT
<213> ORGANISM: Homo sapiens

<400> SEQUENCE: 928

Tyr Ser Val Ala Asp Ile Glu Arg
1               5

<210> SEQ ID NO 929
<211> LENGTH: 11
<212> TYPE: PRT
<213> ORGANISM: Homo sapiens

<400> SEQUENCE: 929

Val Val Val Leu Gly Ser Gly Val Gly Lys
1               5                   10

<210> SEQ ID NO 930
<211> LENGTH: 10
<212> TYPE: PRT
<213> ORGANISM: Homo sapiens

<400> SEQUENCE: 930

Tyr Gly Asp Leu Val Asp Tyr Leu His Arg
1               5                   10

<210> SEQ ID NO 931
<211> LENGTH: 13
<212> TYPE: PRT
<213> ORGANISM: Homo sapiens

<400> SEQUENCE: 931

Gly Gly Pro Val Gln Val Leu Glu Asp Glu Glu Leu Lys
1               5                   10

<210> SEQ ID NO 932
<211> LENGTH: 7
<212> TYPE: PRT
<213> ORGANISM: Homo sapiens

<400> SEQUENCE: 932

Thr Leu Val Val His Glu Lys
1               5

<210> SEQ ID NO 933
<211> LENGTH: 12
<212> TYPE: PRT
<213> ORGANISM: Homo sapiens

<400> SEQUENCE: 933

Thr Phe Asp Ser Ser Cys His Phe Phe Ala Thr Lys

```
1               5                   10

<210> SEQ ID NO 934
<211> LENGTH: 7
<212> TYPE: PRT
<213> ORGANISM: Homo sapiens

<400> SEQUENCE: 934

Tyr Ser Asn Asn Ser Trp Arg
1               5

<210> SEQ ID NO 935
<211> LENGTH: 4
<212> TYPE: PRT
<213> ORGANISM: Artificial Sequence
<220> FEATURE:
<223> OTHER INFORMATION: Start peptide

<400> SEQUENCE: 935

Met Ala Gly Arg
1

<210> SEQ ID NO 936
<211> LENGTH: 8
<212> TYPE: PRT
<213> ORGANISM: Artificial Sequence
<220> FEATURE:
<223> OTHER INFORMATION: Tag peptide

<400> SEQUENCE: 936

Trp Ser His Pro Gln Phe Glu Lys
1               5

<210> SEQ ID NO 937
<211> LENGTH: 14
<212> TYPE: PRT
<213> ORGANISM: Artificial Sequence
<220> FEATURE:
<223> OTHER INFORMATION: GluFib peptide

<400> SEQUENCE: 937

Glu Gly Val Asn Asp Asn Glu Glu Gly Phe Phe Ser Ala Arg
1               5                   10

<210> SEQ ID NO 938
<211> LENGTH: 13
<212> TYPE: PRT
<213> ORGANISM: Artificial Sequence
<220> FEATURE:
<223> OTHER INFORMATION: GluFib 2 peptide

<400> SEQUENCE: 938

Gly Val Asn Asp Asn Glu Glu Gly Phe Phe Ser Ala Arg
1               5                   10

<210> SEQ ID NO 939
<211> LENGTH: 12
<212> TYPE: PRT
<213> ORGANISM: Artificial Sequence
<220> FEATURE:
<223> OTHER INFORMATION: Tag 2 peptide

<400> SEQUENCE: 939

Leu Ala Ala Ala Leu Glu His His His His His His
1               5                   10
```

-continued

```
<210> SEQ ID NO 940
<211> LENGTH: 9
<212> TYPE: PRT
<213> ORGANISM: Artificial Sequence
<220> FEATURE:
<223> OTHER INFORMATION: Start/Tag peptide

<400> SEQUENCE: 940

Met Trp Ser His Pro Gln Phe Glu Lys
1               5

<210> SEQ ID NO 941
<211> LENGTH: 629
<212> TYPE: PRT
<213> ORGANISM: Artificial Sequence
<220> FEATURE:
<223> OTHER INFORMATION: QconCAT no. 1

<400> SEQUENCE: 941

Met Ala Gly Arg Trp Ser His Pro Gln Phe Glu Lys Glu Gly Val Asn
1               5                   10                  15

Asp Asn Glu Glu Gly Phe Phe Ser Ala Arg Asp Ile Val Leu Val Ala
                20                  25                  30

His Ser Ala Leu Gly Thr Gln Arg His Ile Asp Ser Ala Tyr Leu Tyr
            35                  40                  45

Asn Asn Glu Glu Gln Val Gly Leu Ala Ile Arg Glu Leu Gly Trp
        50                  55                  60

Glu Pro Asp Asp Pro Ile Glu Glu His Lys Gln Phe Glu Glu Leu
65                  70                  75                  80

Thr Leu Gly Glu Phe Leu Lys Leu Val Asp Gln Asn Ile Phe Ser Phe
                85                  90                  95

Tyr Leu Ser Arg Val Ser Thr Leu Pro Ala Ile Thr Leu Lys Tyr Ser
            100                 105                 110

Gln Ala Val Pro Ala Val Thr Glu Gly Pro Ile Pro Glu Val Leu Lys
        115                 120                 125

Val Phe Gln Glu Pro Leu Phe Tyr Glu Ala Pro Arg Ala Val Ala Thr
130                 135                 140

Val Gly Pro Ile Ser Val Ala Ile Asp Ala Gly His Glu Ser Phe Leu
145                 150                 155                 160

Phe Tyr Lys Tyr Ser Val Ala Asn Asp Thr Gly Phe Val Asp Ile Pro
                165                 170                 175

Lys Ala Gly Leu Gln Val Tyr Asn Lys Phe Glu His Cys Asn Phe Asn
            180                 185                 190

Asp Val Thr Thr Arg Thr Ser Phe Pro Glu Asp Thr Val Ile Thr Tyr
        195                 200                 205

Lys Thr Thr Thr Pro Asn Ala Gln Ala Thr Arg Val Pro Pro Thr Val
210                 215                 220

Gln Lys Pro Thr Thr Val Asn Val Pro Thr Thr Glu Val Ser Pro Thr
225                 230                 235                 240

Ser Gln Lys Leu Leu Asp Ile Glu Ser Gln Glu Leu Glu Asp Phe
                245                 250                 255

Pro Leu Pro Thr Val Gln Arg Leu Ala Ile Asn Leu Leu Ala Lys Ser
            260                 265                 270

Gln Pro Val Ser Gln Pro Leu Thr Tyr Glu Ser Gly Pro Asp Glu Val
        275                 280                 285

Arg Glu Val Gly Val Gly Phe Ala Thr Arg Asn Thr Glu Ile Ser Phe
        290                 295                 300
```

```
Ile Leu Gly Gln Glu Phe Asp Glu Val Thr Ala Asp Asp Arg Ser Thr
305                 310                 315                 320

Ile Thr Leu Asp Gly Gly Val Leu Val His Val Gln Lys Thr Ala Phe
                325                 330                 335

Tyr Leu Ala Glu Phe Phe Val Asn Glu Ala Arg Tyr Pro Val Tyr Gly
                340                 345                 350

Val Gln Trp His Pro Glu Lys Ala Pro Ala Val Ala Glu Glu Asn Pro
            355                 360                 365

Lys His Leu Asp Ser Val Leu Gln Gln Leu Gln Thr Glu Val Tyr Arg
        370                 375                 380

His Glu Val Thr Gly Trp Val Leu Val Ser Pro Leu Ser Lys Ile Thr
385                 390                 395                 400

Val Val Asp Ala Leu His Glu Ile Pro Val Lys Leu Lys Pro Glu Asp
                405                 410                 415

Ile Thr Gln Ile Gln Pro Gln Leu Val Leu Arg Leu Leu Val Phe
                420                 425                 430

Ser Thr Asp Ala Gly Phe His Phe Ala Gly Asp Gly Lys Leu Gly Val
            435                 440                 445

Tyr Glu Leu Leu Leu Lys Ser Pro Glu Gln Gln Glu Thr Val Leu Asp
        450                 455                 460

Gly Asn Leu Ile Ile Arg Leu Asn Ala Glu Asn Asn Ala Thr Phe Tyr
465                 470                 475                 480

Phe Lys Thr Val Gly Ser Asp Thr Phe Tyr Ser Phe Lys Ala Leu Gly
                485                 490                 495

Phe Glu Asp Ala Thr Gln Ala Leu Gly Arg Gly Leu Asp Leu Thr Glu
            500                 505                 510

Asp Thr Tyr Lys Pro Arg Leu Ala Asp Gly Gly Ala Thr Asn Gln Gly
        515                 520                 525

Arg Gln Gln Gln His Leu Phe Gly Ser Asp Val Thr Asp Cys Ser Gly
            530                 535                 540

Asn Phe Cys Leu Phe Arg Asp Gly Ala Gly Asp Val Ala Phe Val Lys
545                 550                 555                 560

Gln Asp Phe Asp Ile Thr Asp Ile Ser Leu Leu Glu His Arg Asp Glu
                565                 570                 575

Thr His Ala Thr Tyr Ser Asn Thr Leu Tyr Leu Ala Asp Glu Ile Ile
            580                 585                 590

Ile Arg Asp Trp Val Ser Val Val Thr Pro Ala Arg Gly Val Asn Asp
        595                 600                 605

Asn Glu Glu Gly Phe Pro Ser Ala Arg Leu Ala Ala Ala Leu Glu His
    610                 615                 620

His His His His His
625

<210> SEQ ID NO 942
<211> LENGTH: 689
<212> TYPE: PRT
<213> ORGANISM: Artificial Sequence
<220> FEATURE:
<223> OTHER INFORMATION: QconCAT no. 2

<400> SEQUENCE: 942

Met Ala Gly Arg Trp Ser His Pro Gln Phe Glu Lys Glu Gly Val Asn
1               5                   10                  15

Asp Asn Glu Glu Gly Phe Phe Ser Ala Arg Tyr Phe Ile Asp Phe Val
                20                  25                  30
```

```
Ala Arg Tyr Asn Ser Gln Asn Gln Ser Asn Asn Gln Phe Val Leu Tyr
             35                  40                  45

Arg Ala Gly Gln Ser Pro Gln Leu Leu Ile Tyr Thr Leu Ser Tyr Arg
 50                  55                  60

Leu Glu Ile Pro Tyr Thr Phe Gly Gln Gly Thr Lys Gly His Thr Leu
 65                  70                  75                  80

Thr Leu Asn Phe Thr Arg Ala Leu Gln Ala Thr Val Gly Asn Ser Tyr
                 85                  90                  95

Lys Phe Phe Leu Gln Gly Ile Gln Leu Asn Thr Ile Leu Pro Asp Ala
                100                 105                 110

Arg Gly Glu Leu Phe Trp Asp Asp Gly Glu Ser Leu Glu Val Leu Glu
            115                 120                 125

Arg Trp Gly Tyr Ser Ser Thr Ala Ile Thr Arg Ser Leu Glu Pro Phe
    130                 135                 140

Thr Leu Glu Ile Leu Ala Arg Ile Gly Leu Ala Ser Ala Leu Gln Pro
145                 150                 155                 160

Arg Asp Arg Pro Phe Phe Ala Gly Leu Val Lys Asn Ile Ile His Gly
                165                 170                 175

Ser Asp Ser Val Glu Ser Ala Glu Lys Ala Ile Pro Val Ala Gln Asp
            180                 185                 190

Leu Asn Ala Pro Ser Asp Trp Asp Ser Arg Ala Asn Asp Glu Ser Asn
    195                 200                 205

Glu His Ser Asp Val Ile Asp Ser Gln Glu Leu Ser Lys Tyr Pro Asp
210                 215                 220

Ala Val Ala Thr Trp Leu Asn Pro Asp Pro Ser Gln Lys Ile Pro Leu
225                 230                 235                 240

Leu Ser Asp Leu Thr His Gln Ile Ser Lys Val Ser Val Ala Asp His
                245                 250                 255

Ser Leu His Leu Ser Lys Ala Gln Gly Phe Thr Glu Asp Thr Ile Val
            260                 265                 270

Phe Leu Pro Gln Thr Asp Lys Trp Phe Ser Ala Gly Leu Ala Ser Asn
    275                 280                 285

Ser Ser Trp Leu Arg Ala His Ala Trp Pro Ser Pro Tyr Lys Thr Asn
290                 295                 300

Val Asn Val Phe Ser Glu Leu Ser Ala Pro Arg Ala Glu Gln Trp Asn
305                 310                 315                 320

Val Asn Tyr Val Glu Thr Ser Ala Lys Glu Asp Glu Asn Val Pro Phe
                325                 330                 335

Leu Leu Val Gly Asn Lys Ile Gln Glu Val Ala Gly Ser Leu Ile Phe
            340                 345                 350

Arg Glu Ile Val Asp Ser Tyr Leu Pro Val Ile Leu Asp Ile Ile Lys
    355                 360                 365

Gln Glu Ile Leu Ala Ala Leu Glu Lys Phe Phe Glu Ser His Val Ala
370                 375                 380

Arg Trp Ile Gln Glu Tyr Leu Glu Lys Thr Val Glu Glu Ala Glu Asn
385                 390                 395                 400

Ile Ala Val Thr Ser Gly Val Val Arg Glu Gln Ala Asn Ala Val Ser
                405                 410                 415

Glu Ala Val Val Ser Ser Val Asn Thr Val Ala Thr Lys Glu Leu Gln
            420                 425                 430

Glu Leu Val Gln Tyr Pro Val Glu His Pro Asp Lys Leu Ile Val Asp
    435                 440                 445

Glu Ala Ile Asn Glu Asp Asn Ser Val Val Ser Leu Ser Gln Pro Lys
```

```
                  450                 455                 460
Ile Glu Leu Pro Thr Thr Val Lys Thr Ile Val Leu Gln Glu Ser Ile
465                 470                 475                 480

Gly Lys Glu Val Val Leu Gln His Val Arg Ser Ser Val Ala Ala Asp
                  485                 490                 495

Val Ile Ser Leu Leu Leu Asn Gly Asp Gly Val Gly Arg Thr Ile
                  500                 505                 510

Val Thr Thr Leu Gln Asp Ser Ile Arg Gly Gly Val Asn Asp Asn Phe
                  515                 520                 525

Gln Gly Val Leu Gln Asn Val Arg Leu Thr Phe Asp Ser Ser Phe Ser
                  530                 535                 540

Pro Asn Thr Gly Lys Val Asn Asn Ser Ser Leu Ile Gly Leu Gly Tyr
545                 550                 555                 560

Thr Gln Thr Leu Lys Pro Gly Ile Lys Ala Ala Ile Pro Ser Ala Leu
                  565                 570                 575

Asp Thr Asp Ser Ser Lys Ser Asp Leu Ala Val Pro Ser Glu Leu Ala
                  580                 585                 590

Leu Leu Lys Phe Ala Gly Val Phe His Val Glu Lys Asp Pro Asp His
                  595                 600                 605

Ser Glu Gly Ser Thr Thr Leu Leu Glu Gly Tyr Thr Ser His Tyr Pro
610                 615                 620

His Thr Lys Tyr Gly Phe Ile Glu Gly His Val Val Ile Pro Arg Leu
625                 630                 635                 640

Leu Gln Val Val Tyr Leu His Ser Asn Asn Ile Thr Lys Ile Gln Ala
                  645                 650                 655

Ile Glu Leu Glu Asp Leu Leu Arg Gly Val Asn Asp Asn Glu Glu Gly
                  660                 665                 670

Phe Phe Ser Ala Arg Leu Ala Ala Ala Leu Glu His His His His
                  675                 680                 685

His

<210> SEQ ID NO 943
<211> LENGTH: 799
<212> TYPE: PRT
<213> ORGANISM: Artificial Sequence
<220> FEATURE:
<223> OTHER INFORMATION: QconCAT no. 3

<400> SEQUENCE: 943

Met Ala Gly Arg Trp Ser His Pro Gln Phe Glu Lys Glu Gly Val Asn
1               5                   10                  15

Asp Asn Glu Glu Gly Phe Phe Ser Ala Arg Phe Asn Trp Tyr Val Asp
                20                  25                  30

Gly Val Glu Val His Asn Ala Lys Gly Pro Ser Val Phe Pro Leu Ala
                35                  40                  45

Pro Ser Ser Lys Thr Thr Pro Pro Val Leu Asp Ser Asp Gly Ser Phe
                50                  55                  60

Phe Leu Tyr Ser Lys Gln Leu Ser Phe Glu Glu Phe Ile Met Leu Met
65                  70                  75                  80

Ala Arg Leu Thr Trp Ala Ser His Glu Lys Val Ile Glu His Ile Met
                85                  90                  95

Glu Asp Leu Asp Thr Asn Ala Asp Lys Leu Val Leu Pro Ser Leu Ile
                100                 105                 110

Ser Ser Arg Ala Ala Asp Leu Leu Leu His Ser Lys Thr Asn Val Tyr
                115                 120                 125
```

-continued

```
Ile Ser Ser Ser Ala Gly Ala Arg Ile Thr Thr Val Ser Leu Ser Ala
    130                 135                 140
Pro Asp Ala Leu Lys Glu Asp Phe Thr Ser Leu Ser Leu Val Leu Tyr
145                 150                 155                 160
Ser Arg Tyr Thr Phe Glu Leu Ser Arg Thr His Leu Pro Glu Val Phe
                165                 170                 175
Leu Ser Lys Glu Ala Thr Asp Val Ile Ile His Ser Lys Ser Ile
            180                 185                 190
Gln Leu Pro Thr Thr Val Arg Phe Ser Thr Glu Tyr Glu Leu Gln Gln
        195                 200                 205
Leu Glu Gln Phe Lys Ala Leu Tyr Leu Gln Tyr Thr Asp Glu Thr Phe
    210                 215                 220
Arg Gly Ala Tyr Pro Leu Ser Ile Glu Pro Ile Gly Val Arg Asn Asn
225                 230                 235                 240
Glu Gly Thr Tyr Tyr Ser Pro Asn Tyr Asn Pro Gln Ser Arg Gly Ile
                245                 250                 255
Pro Gly Pro Val Gly Ala Ala Gly Ala Thr Gly Ala Arg Gly Glu Pro
            260                 265                 270
Gly Asn Ile Gly Phe Pro Gly Pro Lys Val Leu Glu Asp Asn Ser Ala
        275                 280                 285
Leu Asp Lys Leu Gly Thr Phe Glu Val Glu Asp Gln Ile Glu Ala Ala
    290                 295                 300
Arg Trp Glu Tyr Tyr Asp Ser Val Tyr Thr Glu Arg Thr Leu Val Leu
305                 310                 315                 320
Leu Met Gly Lys Ser Thr Gly Gly Ala Pro Thr Phe Asn Val Thr Val
                325                 330                 335
Thr Lys Val Ala Ala Gly Ala Phe Gln Gly Leu Arg Gly Gln Thr Leu
            340                 345                 350
Leu Ala Val Ala Lys Asp Leu Leu Pro Gln Pro Asp Leu Arg Ile
        355                 360                 365
Asp Ser Leu Leu Glu Asn Asp Arg Glu Leu Asp Glu Ser Leu Gln Val
    370                 375                 380
Ala Glu Arg Ala Ser Ser Ile Ile Asp Glu Leu Phe Gln Asp Arg Ser
385                 390                 395                 400
Leu Ser Gln Gln Ile Glu Asn Ile Arg Gly Ala Asn Gly Ala Pro Gly
                405                 410                 415
Ile Ala Gly Ala Pro Gly Phe Pro Gly Ala Arg Phe Val Thr Asp Gly
            420                 425                 430
Ser Val Thr Ala Ser Gly Phe Arg Glu Gln Leu Ala Asn Pro Ile Val
        435                 440                 445
Ser Ser Gly Asn Ser Leu Phe Leu Arg Asp Phe Val Glu Ile Leu Asp
    450                 455                 460
Gly Gly His Glu Asp Ala Pro Leu Arg Ile Glu Ser Ser Leu Gln
465                 470                 475                 480
Gly Leu Gly Arg Asn Gln Val Thr Pro Leu Asp Ile Leu Ser Lys Ile
                485                 490                 495
Tyr Trp Val Asp Leu Glu Arg Gln Asp Gly Ser Val Asp Phe Phe Arg
            500                 505                 510
Tyr Gly Ile Asp Trp Ala Ser Gly Arg Phe Ala Asp Gly Asp Leu Asp
        515                 520                 525
Ala Val Leu Ser Arg Ala Gly Leu Ile Leu Phe Gly Asn Asp Asp Lys
530                 535                 540
```

Asp Leu Gly Glu Ala Ala Leu Asn Glu Tyr Leu Arg Leu Gly Val Tyr
545                 550                 555                 560

Glu Leu Leu Leu Lys Ser Pro Glu Gln Gln Glu Thr Val Leu Asp Gly
            565                 570                 575

Asn Leu Ile Ile Arg Phe Ala His Thr Val Val Thr Ser Arg Tyr Ser
            580                 585                 590

Ser Asp Tyr Phe Gln Ala Pro Ser Asp Tyr Arg Ile Asp Ile Thr Leu
        595                 600                 605

Ser Ser Val Lys Glu Leu Ser Glu Ala Leu Gly Gln Ile Phe Asp Ser
        610                 615                 620

Gln Arg Phe Gln Thr Phe Glu Gly Asp Leu Lys Gln Ser Thr Leu Val
625                 630                 635                 640

Leu Phe Pro Gly Asp Leu Arg Leu Gly Leu Gly Ala Asp Val Ala Gln
            645                 650                 655

Val Thr Gly Ala Leu Arg Ala Ala Tyr Glu Asp Phe Asn Val Gln Leu
            660                 665                 670

Arg Ala Val Thr Leu Ser Leu Asp Gly Gly Asp Thr Ala Ile Arg Tyr
        675                 680                 685

Pro Asp Ala Val Ala Thr Trp Leu Asn Pro Asp Pro Ser Gln Lys Ala
690                 695                 700

Ile Pro Val Ala Gln Asp Leu Asn Ala Pro Ser Asp Trp Asp Ser Arg
705                 710                 715                 720

Ile Ser His Glu Leu Asp Ser Ala Ser Ser Glu Val Asn Ser Ala Val
            725                 730                 735

Thr Ala Leu Trp Gly Lys Val Asn Val Asp Glu Val Gly Gly Glu Ala
            740                 745                 750

Leu Gly Arg Phe Phe Glu Ser Phe Gly Asp Leu Ser Thr Pro Asp Ala
        755                 760                 765

Val Met Gly Asn Pro Lys Gly Val Asn Asp Asn Glu Glu Gly Phe Phe
770                 775                 780

Ser Ala Arg Leu Ala Ala Ala Leu Glu His His His His His His
785                 790                 795

<210> SEQ ID NO 944
<211> LENGTH: 792
<212> TYPE: PRT
<213> ORGANISM: Artificial Sequence
<220> FEATURE:
<223> OTHER INFORMATION: QconCAT no. 4

<400> SEQUENCE: 944

Met Ala Gly Arg Trp Ser His Pro Gln Phe Glu Lys Glu Gly Val Asn
1               5                   10                  15

Asp Asn Glu Glu Gly Phe Phe Ser Ala Arg Ser Asp Val Met Tyr Thr
            20                  25                  30

Asp Trp Lys Asn Trp Gly Leu Ser Phe Tyr Ala Asp Lys Pro Glu Thr
        35                  40                  45

Thr Lys Glu His Val Ala His Leu Leu Phe Leu Arg Leu Gln His Leu
    50                  55                  60

Glu Asn Glu Leu Thr His Asp Ile Ile Thr Lys Ser Val Leu Gly Gln
65                  70                  75                  80

Leu Gly Ile Thr Lys Ile Thr Pro Asn Leu Ala Glu Phe Ala Phe Ser
            85                  90                  95

Leu Tyr Arg Gln Gly Ile Pro Phe Phe Gly Gln Val Arg Asn Glu Asp
            100                 105                 110

-continued

Ser Leu Val Phe Val Gln Thr Asp Lys Leu Val His Val Glu Glu Pro
            115                 120                 125

His Thr Glu Thr Val Arg Asp Ala Asp Pro Asp Thr Phe Phe Ala Lys
130                 135                 140

Phe Thr Phe Glu Tyr Ser Arg Ile Ala Pro Gln Leu Ser Thr Glu Glu
145                 150                 155                 160

Leu Val Ser Leu Gly Glu Lys Gly Ile Leu Ala Ala Asp Glu Ser Thr
                165                 170                 175

Gly Ser Ile Ala Lys Ala Asp Asp Gly Arg Pro Phe Pro Gln Val Ile
            180                 185                 190

Lys Val Ser Phe Leu Ser Ala Leu Glu Glu Tyr Thr Lys Ala Thr Glu
            195                 200                 205

His Leu Ser Thr Leu Ser Glu Lys Val Gln Pro Tyr Leu Asp Asp Phe
210                 215                 220

Gln Lys Leu Gly Glu Val Asn Thr Tyr Ala Gly Asp Leu Gln Lys Ser
225                 230                 235                 240

Leu Ala Pro Tyr Ala Gln Asp Thr Gln Glu Lys Ser Glu Leu Thr Gln
                245                 250                 255

Gln Leu Asn Ala Leu Phe Gln Asp Lys Leu Gly Pro Leu Val Glu Gln
            260                 265                 270

Gly Arg Ser Glu Leu Glu Glu Gln Leu Thr Pro Val Ala Glu Glu Thr
            275                 280                 285

Arg Ala Phe Asp Ser Asp Gly Asp Gly Arg Tyr Ser Phe Leu Glu Leu
            290                 295                 300

Arg His Asp Leu Gly His Phe Met Leu Arg Ser Asn Leu Asp Glu Asp
305                 310                 315                 320

Ile Ile Ala Glu Glu Asn Ile Val Ser Arg Ile His Trp Glu Ser Ala
                325                 330                 335

Ser Leu Leu Arg Thr Ile Tyr Thr Pro Gly Ser Thr Val Leu Tyr Arg
            340                 345                 350

Thr Tyr Phe Pro His Phe Asp Leu Ser His Gly Ser Ala Gln Val Lys
            355                 360                 365

Val Gly Ala His Ala Gly Glu Tyr Gly Ala Glu Ala Leu Glu Arg Met
370                 375                 380

Phe Leu Ser Phe Pro Thr Thr Lys Gly Asp Gly Pro Val Gln Gly Ile
385                 390                 395                 400

Ile Asn Phe Glu Gln Lys Leu Met Glu Asp Leu Asp Arg Leu Gln Asp
                405                 410                 415

Ala Glu Ile Ala Arg Asp Asn Glu Asn Val Val Asn Glu Tyr Ser Ser
            420                 425                 430

Glu Leu Glu Lys His Gln Leu Tyr Ile Asp Glu Thr Val Asn Ser Asn
            435                 440                 445

Ile Pro Thr Asn Leu Arg Ile Arg Pro Phe Phe Pro Gln Gln Ile His
450                 455                 460

Leu Ile Ser Thr Gln Ser Ala Ile Pro Tyr Ala Leu Arg Tyr Glu Ala
465                 470                 475                 480

Ser Ile Leu Thr His Asp Ser Ser Ile Arg Gln Ser Gly Leu Tyr Phe
                485                 490                 495

Ile Lys Pro Leu Lys Thr Glu Val Asn Val Leu Pro Gly Ala Lys Ile
            500                 505                 510

Gln Pro Ser Gly Gly Thr Asn Ile Asn Glu Ala Leu Leu Arg Phe Tyr
            515                 520                 525

Asn Gln Val Ser Thr Pro Leu Leu Arg Ile Tyr Val Asp Asp Gly Leu

```
                    530                 535                 540
Ile Ser Leu Gln Val Lys Leu Asp Ile Asp Ser Pro Pro Ile Thr Ala
545                 550                 555                 560

Arg Gly Ala Asp Phe Leu Val Thr Glu Val Glu Asn Gly Gly Ser Leu
                    565                 570                 575

Gly Ser Lys Ser Ala Asp Thr Leu Trp Gly Ile Gln Lys Val Thr Leu
                    580                 585                 590

Thr Ser Glu Glu Glu Ala Arg Asp Leu Ala Asp Glu Leu Ala Leu Val
                    595                 600                 605

Asp Val Ile Glu Asp Lys Ser Val Asp Pro Asp Ser Pro Ala Glu Ala
                    610                 615                 620

Ser Gly Leu Arg Gln Gly Gly Leu Gly Pro Met Asn Ile Pro Leu Val
625                 630                 635                 640

Ser Asp Pro Lys Ala Thr Ala Val Met Pro Asp Gly Gln Phe Lys Asp
                    645                 650                 655

Ile Ser Leu Ser Asp Tyr Lys Ser Leu Glu Val Thr Phe Thr Pro Val
                    660                 665                 670

Ile Glu Asp Ile Gly Lys Glu Leu Gln Val Tyr Ile Ser Pro Lys Ala
                    675                 680                 685

Gly Ala Leu Asn Ser Asn Asp Ala Phe Val Leu Lys Gln Thr Gln Val
                    690                 695                 700

Ser Val Leu Pro Glu Gly Gly Glu Thr Pro Leu Phe Lys Tyr Ile Glu
705                 710                 715                 720

Thr Asp Pro Ala Asn Arg Asp Phe Ala Asp Ile Pro Asn Leu Arg Leu
                    725                 730                 735

Ser Leu Glu Ile Glu Gln Leu Glu Leu Gln Arg Glu Asp Val Tyr Val
                    740                 745                 750

Val Gly Thr Val Leu Arg Gly Tyr Ile Leu Val Gly Gln Ala Lys Gly
                    755                 760                 765

Val Asn Asp Asn Glu Glu Gly Phe Phe Ser Ala Arg Leu Ala Ala Ala
                    770                 775                 780

Leu Glu His His His His His His
785                 790

<210> SEQ ID NO 945
<211> LENGTH: 833
<212> TYPE: PRT
<213> ORGANISM: Artificial Sequence
<220> FEATURE:
<223> OTHER INFORMATION: QconCAT no. 5

<400> SEQUENCE: 945

Met Trp Ser His Pro Gln Phe Glu Lys Glu Gly Val Asn Asp Asn Glu
1                   5                   10                  15

Glu Gly Phe Phe Ser Ala Arg Ser Ala Ser Asp Leu Thr Trp Asp Asn
                    20                  25                  30

Leu Lys Leu Leu Gly Asn Val Leu Val Cys Val Leu Ala His His Phe
                    35                  40                  45

Gly Lys Gly Glu Val Thr Tyr Thr Thr Ser Gln Val Ser Lys Tyr Ser
                    50                  55                  60

Leu Thr Tyr Ile Tyr Thr Gly Leu Ser Lys His Ile Asn Pro Val Ala
65                  70                  75                  80

Ala Ser Leu Ile Gln Lys Leu Ser Ile Thr Gly Thr Tyr Asp Leu Lys
                    85                  90                  95

Ser Ser Gly Pro Gly Gly Gln Asn Val Asn Lys Glu Gly His Phe Tyr
```

```
                100             105             110
Tyr Asn Ile Ser Glu Val Lys Ile Leu Gly Ala Thr Ile Glu Asn Ser
            115             120             125

Arg Glu Ile Pro Ala Trp Val Pro Phe Asp Pro Ala Ala Gln Ile Thr
        130             135             140

Lys Ser Phe Glu Asp Ile His His Tyr Arg Ala Gln Gly Tyr Ser Gly
145             150             155             160

Leu Ser Val Lys Gly Leu Gln Thr Ser Gln Asp Ala Arg Gln Ile Asp
                165             170             175

Asn Pro Asp Tyr Lys Ile Val Thr Ala Thr Val Asn Asn Ser Val Leu
            180             185             190

Gln Lys Asp Tyr Gln Pro Gly Ile Thr Phe Ile Val Gln Lys His
        195             200             205

Ala Gln Ala Gln Tyr Ala Tyr Pro Gly Ala Arg Asn His Leu Val Glu
210             215             220

Ile Pro Pro Asn Leu Pro Ser Ser Leu Val Glu Leu Arg Leu Asp His
225             230             235             240

Val Val Thr Ile Ile Lys Ala Thr Trp Ser Gly Ala Val Leu Ala Gly
                245             250             255

Arg Thr Gly Phe Ser Thr Ser Pro Glu Ser Pro Tyr Thr His Trp Lys
            260             265             270

Gly Thr Phe Ala Thr Leu Ser Glu Leu His Cys Asp Lys Leu Pro Asp
        275             280             285

Thr Pro Gln Gly Leu Leu Gly Glu Ala Arg Asp Ala Pro Ser Trp Asp
    290             295             300

Pro Val Ala Leu Lys Leu Gly Glu Leu Ile Leu Thr Ser Glu Ser Ser
305             310             315             320

Arg Gly Pro Asp Val Leu Thr Ala Thr Val Ser Gly Lys Glu Ala Leu
                325             330             335

Ala Glu Asn Asn Leu Asn Leu Pro Lys Gly Asp Asp Leu Ser Thr Ala
            340             345             350

Ile Leu Lys Leu Ile Leu Tyr Asn Asp Gly Asp Ser Leu Gln Tyr Ile
        355             360             365

Glu Arg Ser Val Val Ala Pro Ala Thr Asp Gly Gly Leu Asn Leu Thr
    370             375             380

Ser Thr Phe Leu Arg Val Glu Leu Glu Val Thr Leu Pro Gly Glu Gly
385             390             395             400

Lys Glu Gln Tyr Ala Val Val Gly His Ser Ala His Ile Val Thr Leu
                405             410             415

Lys Asp Val Ser Thr Pro Pro Thr Val Leu Pro Asp Asn Phe Pro Arg
            420             425             430

Ser Val Ser Cys Pro Leu Leu Ser Arg Asp Gly Val Val Ser Val Asn
        435             440             445

Lys Ala Asp Gly Val Pro Val Tyr Leu Lys Val Glu Asp Ala Phe Tyr
    450             455             460

Thr Leu Val Arg Glu Phe Thr Pro Val Gln Ala Ala Tyr Gln Lys
465             470             475             480

Val Pro Val Ile Leu Val Gly Asn Lys Phe Gly Ser Asp Glu Gly
                485             490             495

Arg Thr Gln Ile Leu Glu Trp Ala Ala Glu Arg Ala Thr Tyr Phe Gly
            500             505             510

Ser Ile Val Leu Leu Ser Pro Ala Val Ile Asp Ser Pro Leu Lys Ile
        515             520             525
```

```
Pro Phe Thr Phe Trp Ala Arg Thr Glu Leu Leu Pro Gly Asp Arg Phe
        530                 535                 540

Phe Asn Val Leu Thr Thr Asn Thr Asp Gly Lys Ala Gly Ala Leu Gln
545                 550                 555                 560

Leu Leu Leu Val Gly Asp Lys Gly Ala Tyr Thr Gln Val Ile Phe Leu
                565                 570                 575

Ala Arg Gly Leu Pro Asp Gln Met Leu Tyr Arg Glu Phe Leu Gln Ser
            580                 585                 590

Ser Leu Arg His Asp Ser Ala Thr Asp Thr Ile Asp Ile Ala Pro Asn
        595                 600                 605

His Arg Leu Tyr His Ser Glu Ala Phe Thr Val Asn Phe Gly Asp Thr
        610                 615                 620

Glu Glu Ala Lys Gln Ile Leu Asp Gln Thr Ser Glu Ile Asn Lys Leu
625                 630                 635                 640

Gly Asn Leu Phe Leu Asn Glu Asp Leu Glu Val Lys Asp Ser Thr Ile
                645                 650                 655

Gln Val Val Glu Asn Gly Glu Ser Ser Gln Gly Arg Asp Tyr Gly Val
            660                 665                 670

Tyr Leu Glu Asp Ser Gly His Thr Leu Arg Gln Val Met Asn Gly Phe
        675                 680                 685

Gln Asn Arg Leu Thr Ser Asp Ser Thr Val Tyr Asp Tyr Ala Gly Lys
690                 695                 700

Thr His Leu Ala Pro Tyr Ser Asp Glu Leu Arg Leu Ile Thr Glu Glu
705                 710                 715                 720

Ala Asn Arg Glu Gly Tyr Tyr Gly Tyr Thr Gly Ala Phe Arg Asp Tyr
                725                 730                 735

Val Ser Gln Phe Glu Gly Ser Ala Leu Gly Lys Ala Thr Leu Tyr Val
            740                 745                 750

Thr Ala Ile Glu Asp Arg Gly Gln Asn Ser Leu Ala Leu His Lys Glu
        755                 760                 765

Ser Tyr Asn Val Gln Leu Gln Leu Pro Ala Arg Trp Glu Ala Glu Pro
770                 775                 780

Val Tyr Val Gln Arg Phe Glu Ser Ser Glu Glu Gln Ala Arg Ala Lys
785                 790                 795                 800

Pro Ala Leu Glu Asp Leu Arg Ser Gly Val Leu Ser Val Ser Ser Gly
                805                 810                 815

Ala Ala Ala His Arg Leu Ala Ala Ala Leu Glu His His His His His
            820                 825                 830

His
```

BLADDER CANCER BIOMARKER PROTEINS

CROSS-REFERENCE TO RELATED APPLICATION(S)

This application is a National Stage application under 35 U.S.C. § 371 of PCT/EP2016/082558, filed Dec. 23, 2016, which claims priority to European Application No. 15 202 453.5, filed Dec. 23, 2015.

SEQUENCE LISTING

The instant application contains a Sequence Listing which has been submitted in ASCII format via EFS-Web. Said ASCII copy, created on Dec. 23, 2016, is named 18050_015US1_SL and is 192,512 bytes in size.

FIELD OF THE INVENTION

The invention relates to a collection of signature peptides representing at least 10 proteins for use in cancer diagnosis and/or prognosis, to an artificial protein comprising signature peptides representing at least 10 proteins and to a nucleic acid construct encoding for such an artificial protein. The invention further relates to a collection of at least 10 proteins for use in cancer diagnosis and/or prognosis. Additionally, the invention relates to a method for cancer diagnosis and/or prognosis comprising the step of analyzing at least 10 proteins in a urine sample of a subject. Finally, the invention relates to an immunoassay product comprising antibodies for detecting at least 10 proteins.

BACKGROUND OF THE INVENTION

Urothelial bladder cancer, which arises from the epithelium of the bladder, is one of the most common malignancies of the urinary tract and the most frequently occurring cancer associated with smoking. Diagnosis of bladder cancer is usually done by cystoscopy and subsequent analysis of biopsies collected during the procedure. Although cytology from urine was previously discussed for cancer diagnosis, reliable results have not yet been achieved. In consequence, cystoscopy and biopsies are yet unavoidable to obtain unambiguous diagnostic and/or prognostic results. Both are, however, invasive procedures, which are not only particularly unpleasant for the patient, but also highly expensive. Moreover, within the first five years after surgical resection of a primary bladder tumor, patients have a high risk to relapse and therefore need to be closely monitored by periodical examinations. To do this by cystoscopy is not only expensive and elaborate, but patients may tend to neglect the necessary aftercare due to the physical and psychological stress of the procedure.

Therefore, means and methods for a fast and reliable diagnosis as well as prognosis of bladder cancer avoiding invasive interventions are needed.

SUMMARY OF THE INVENTION

In a first aspect, the invention relates to a collection of signature peptides representing at least 10 proteins selected from group 1 consisting of

| | | |
|---|---|---|
| A1AG2_HUMAN | DPP4_HUMAN | LYAG_HUMAN |
| A1AT_HUMAN | EGF_HUMAN | MIME_HUMAN |
| A1BG_HUMAN | ES8L2_HUMAN | MUC5B_HUMAN |
| A2GL_HUMAN | FCN3_HUMAN | NF2L2_HUMAN |
| A2MG_HUMAN | FIBB_HUMAN | NID2_HUMAN |
| AFAM_HUMAN | FIBG_HUMAN | OSTP_HUMAN |
| AK1C4_HUMAN | GDF15_HUMAN | P53_HUMAN |
| ALDOA_HUMAN | GELS_HUMAN | PDGFA_HUMAN |
| AMPN_HUMAN | GGH_HUMAN | PGS1_HUMAN |
| ANAG_HUMAN | HEPC_HUMAN | PIP_HUMAN |
| ANGP2_HUMAN | IBP4_HUMAN | PLTP_HUMAN |
| APOA1_HUMAN | IBP7_HUMAN | PPAP_HUMAN |
| APOA4_HUMAN | IGF2_HUMAN | PTX3_HUMAN |
| BIRC5_HUMAN | IGHG1_HUMAN | RALA_HUMAN |
| C4BPA_HUMAN | IPSP_HUMAN | RASK_HUMAN |
| CALR_HUMAN | ITIH2_HUMAN | RET4_HUMAN |
| CATB_HUMAN | ITIH4_HUMAN | RETN_HUMAN |
| CBPE_HUMAN | K1C19_HUMAN | S100P_HUMAN |
| CD44_HUMAN | KLK3_HUMAN | S10A6_HUMAN |
| CERU_HUMAN | KNG1_HUMAN | SORL_HUMAN |
| CLUS_HUMAN | KV201_HUMAN | TERA_HUMAN |
| CO1A2_HUMAN | LAMA4_HUMAN | TNFA_HUMAN |
| CO3_HUMAN | LAMP1_HUMAN | TRFE_HUMAN |
| CO6A1_HUMAN | LAMP2_HUMAN | TSP1_HUMAN |
| COX7R_HUMAN | LDHA_HUMAN | UROM_HUMAN |
| CUBN_HUMAN | LG3BP_HUMAN | VTDB_HUMAN |
| CYTM_HUMAN | LTOR3_HUMAN | ZA2G_HUMAN |
| APOE_HUMAN | IL6_HUMAN | PTGDS_HUMAN |
| BLVRB_HUMAN | IMA2_HUMAN | RAI3_HUMAN |
| CADH1_HUMAN | EFC14_HUMAN | RAP2A_HUMAN |
| CATD_HUMAN | K1C17_HUMAN | RAP2B_HUMAN |
| CATL1_HUMAN | MASP2_HUMAN | RASN_HUMAN |
| CD59_HUMAN | MMP9_HUMAN | S10A9_HUMAN |
| CO1A1_HUMAN | MTA2_HUMAN | SODC_HUMAN |
| EPCAM_HUMAN | NDC80_HUMAN | SPRC_HUMAN |
| FABP4_HUMAN | NHRF1_HUMAN | SYUG_HUMAN |
| HBA_HUMAN | PGFRB_HUMAN | TGFB1_HUMAN |
| HBB_HUMAN | PLK1_HUMAN | TGFR1_HUMAN |
| HPT_HUMAN | PRDX1_HUMAN | TRBM_HUMAN |
| IBP6_HUMAN | PRDX4_HUMAN | VDAC1_HUMAN |
| ICT1_HUMAN | PROF1_HUMAN | | for use in cancer diagnosis and/or prognosis, wherein the cancer is of a urinary tract or organ and each signature peptide represents a single protein.

In a further aspect, the invention relates to an artificial protein comprising signature peptides representing at least 10 proteins selected from the group 1, wherein each signature peptide represents a single protein and consecutive signature peptides are separated by a cleavage sequence.

In a further aspect, the invention relates to a nucleic acid construct encoding the artificial protein of the invention.

In a further aspect, the invention relates to a collection of at least 10 proteins selected from the group 1 for use in cancer diagnosis and/or prognosis, wherein the cancer is of a urinary tract or organ.

In a further aspect, the invention relates to a method for cancer diagnosis and/or prognosis comprising the step of analyzing at least 10 proteins in a urine sample of a subject, wherein the cancer is of a urinary tract or organ and the proteins are selected from the group 1.

In a further aspect, the invention relates to an immunoassay product comprising antibodies for detecting at least 10 proteins selected from the group 1.

DESCRIPTION OF DRAWINGS

FIG. 1 depicts the contingency table showing the frequency distribution of the patient population of the Selected Reaction Monitoring (SRM) screening.

DETAILED DESCRIPTION OF THE INVENTION

In a first aspect, the invention relates to a collection of signature peptides representing at least 10 proteins selected from group 1 consisting of

| | | |
|---|---|---|
| A1AG2_HUMAN | DPP4_HUMAN | LYAG_HUMAN |
| A1AT_HUMAN | EGF_HUMAN | MIME_HUMAN |
| A1BG_HUMAN | ES8L2_HUMAN | MUC5B_HUMAN |
| A2GL_HUMAN | FCN3_HUMAN | NF2L2_HUMAN |
| A2MG_HUMAN | FIBB_HUMAN | NID2_HUMAN |
| AFAM_HUMAN | FIBG_HUMAN | OSTP_HUMAN |
| AK1C4_HUMAN | GDF15_HUMAN | P53_HUMAN |
| ALDOA_HUMAN | GELS_HUMAN | PDGFA_HUMAN |
| AMPN_HUMAN | GGH_HUMAN | PGS1_HUMAN |
| ANAG_HUMAN | HEPC_HUMAN | PIP_HUMAN |
| ANGP2_HUMAN | IBP4_HUMAN | PLTP_HUMAN |
| APOA1_HUMAN | IBP7_HUMAN | PPAP_HUMAN |
| APOA4_HUMAN | IGF2_HUMAN | PTX3_HUMAN |
| BIRC5_HUMAN | IGHG1_HUMAN | RALA_HUMAN |
| C4BPA_HUMAN | IPSP_HUMAN | RASK_HUMAN |
| CALR_HUMAN | ITIH2_HUMAN | RET4_HUMAN |
| CATB_HUMAN | ITIH4_HUMAN | RETN_HUMAN |
| CBPE_HUMAN | K1C19_HUMAN | S100P_HUMAN |
| CD44_HUMAN | KLK3_HUMAN | S10A6_HUMAN |
| CERU_HUMAN | KNG1_HUMAN | SORL_HUMAN |
| CLUS_HUMAN | KV201_HUMAN | TERA_HUMAN |
| CO1A2_HUMAN | LAMA4_HUMAN | TNFA_HUMAN |
| CO3_HUMAN | LAMP1_HUMAN | TRFE_HUMAN |
| CO6A1_HUMAN | LAMP2_HUMAN | TSP1_HUMAN |
| COX7R_HUMAN | LDHA_HUMAN | UROM_HUMAN |
| CUBN_HUMAN | LG3BP_HUMAN | VTDB_HUMAN |
| CYTM_HUMAN | LTOR3_HUMAN | ZA2G_HUMAN |
| APOE_HUMAN | IL6_HUMAN | PTGDS_HUMAN |
| BLVRB_HUMAN | IMA2_HUMAN | RAI3_HUMAN |
| CADH1_HUMAN | EFC14_HUMAN | RAP2A_HUMAN |
| CATD_HUMAN | K1C17_HUMAN | RAP2B_HUMAN |
| CATL1_HUMAN | MASP2_HUMAN | RASN_HUMAN |
| CD59_HUMAN | MMP9_HUMAN | S10A9_HUMAN |
| CO1A1_HUMAN | MTA2_HUMAN | SODC_HUMAN |
| EPCAM_HUMAN | NDC80_HUMAN | SPRC_HUMAN |
| FABP4_HUMAN | NHRF1_HUMAN | SYUG_HUMAN |
| HBA_HUMAN | PGFRB_HUMAN | TGFB1_HUMAN |
| HBB_HUMAN | PLK1_HUMAN | TGFR1_HUMAN |
| HPT_HUMAN | PRDX1_HUMAN | TRBM_HUMAN |
| IBP6_HUMAN | PRDX4_HUMAN | VDAC1_HUMAN |
| ICT1_HUMAN | PROF1_HUMAN | | for use in cancer diagnosis and/or prognosis, wherein the cancer is of a urinary tract or organ and each signature peptide represents a single protein.

The analysis of a large scale Selected Reaction Monitoring (SRM) screening of 134 potential bladder cancer biomarker proteins and a preceding analysis allowed the identification of a total of 81 proteins (table 1A), which were found to be present in deviating amounts in the urine of patients having bladder cancer or with an elevated risk of cancer progression and recurrence. For each protein, the Uniprot entry name, the Uniprot accession number and the Uniprot entry version are given in table 1A. The information is taken from the Uniprot (Universal Protein Resource) database.

TABLE 1A

| Uniprot entry-name | Uniprot accession number | Uniprot entry version | Protein name |
|---|---|---|---|
| A1AG2_HUMAN | P19652 | 162 | Alpha-1-acid glycoprotein 2 |
| A1AT_HUMAN | P01009 | 222 | Alpha-1-antitrypsin |
| A1BG_HUMAN | P04217 | 152 | Alpha-1B-glycoprotein |
| A2GL_HUMAN | P02750 | 149 | Leucine-rich alpha-2-glycoprotein |
| A2MG_HUMAN | P01023 | 186 | Alpha-2-macroglobulin |
| AFAM_HUMAN | P43652 | 135 | Afamin |
| AK1C4_HUMAN | P17516 | 176 | Aldo-keto reductase family 1 member C4 |
| ALDOA_HUMAN | P04075 | 192 | Fructose-bisphosphate aldolase A |
| AMPN_HUMAN | P15144 | 186 | Aminopeptidase N |
| ANAG_HUMAN | P54802 | 151 | Alpha-N-acetylglucosaminidase |
| ANGP2_HUMAN | O15123 | 138 | Angiopoietin-2 |
| APOA1_HUMAN | P02647 | 209 | Apolipoprotein A-I |
| APOA4_HUMAN | P06727 | 176 | Apolipoprotein A-IV |
| BIRC5_HUMAN | O15392 | 184 | Baculoviral IAP repeat-containing protein 5 |
| C4BPA_HUMAN | P04003 | 158 | C4b-binding protein alpha chain |
| CALR_HUMAN | P27797 | 191 | Calreticulin |
| CATB_HUMAN | P07858 | 189 | Cathepsin B |
| CBPE_HUMAN | P16870 | 166 | Carboxypeptidase E |
| CD44_HUMAN | P16070 | 195 | CD44 antigen |
| CERU_HUMAN | P00450 | 185 | Ceruloplasmin |
| CLUS_HUMAN | P10909 | 183 | Clusterin |
| CO1A2_HUMAN | P08123 | 186 | Collagen alpha-2(I) chain |
| CO3_HUMAN | P01024 | 200 | Complement C3 |
| CO6A1_HUMAN | P12109 | 170 | Collagen alpha-1(VI) chain |
| COX7R_HUMAN | O14548 | 138 | Cytochrome c oxidase subunit 7A-related protein, mitochondrial |
| CUBN_HUMAN | O60494 | 144 | Cubilin |
| CYTM_HUMAN | Q15828 | 133 | Cystatin-M |
| DPP4_HUMAN | P27487 | 183 | Dipeptidyl peptidase 4 |
| EGF_HUMAN | P01133 | 183 | Pro-epidermal growth factor |
| ES8L2_HUMAN | Q9H6S3 | 117 | Epidermal growth factor receptor kinase substrate 8-like protein 2 |
| FCN3_HUMAN | O75636 | 164 | Ficolin-3 |
| FIBB_HUMAN | P02675 | 192 | Fibrinogen beta chain |
| FIBG_HUMAN | P02679 | 203 | Fibrinogen gamma chain |
| GDF15_HUMAN | Q99988 | 137 | Growth/differentiation factor 15 |
| GELS_HUMAN | P06396 | 192 | Gelsolin |
| GGH_HUMAN | Q92820 | 143 | Gamma-glutamyl hydrolase |
| HEPC_HUMAN | P81172 | 149 | Hepcidin |
| IBP4_HUMAN | P22692 | 162 | Insulin-like growth factor-binding protein 4 |
| IBP7_HUMAN | Q16270 | 151 | Insulin-like growth factor-binding protein 7 |
| IGF2_HUMAN | P01344 | 202 | Insulin-like growth factor II |
| IGHG1_HUMAN | P01857 | 170 | Ig gamma-1 chain C region |
| IPSP_HUMAN | P05154 | 181 | Plasma serine protease inhibitor |
| ITIH2_HUMAN | P19823 | 154 | Inter-alpha-trypsin inhibitor heavy chain H2 |
| ITIH4_HUMAN | Q14624 | 147 | Inter-alpha-trypsin inhibitor heavy chain H4 |
| K1C19_HUMAN | P08727 | 167 | Keratin, type I cytoskeletal 19 |
| KLK3_HUMAN | P07288 | 182 | Prostate-specific antigen |
| KNG1_HUMAN | P01042 | 184 | Kininogen-1 |
| KV201_HUMAN | P01614 | 97 | Ig kappa chain V-II region Cum |
| LAMA4_HUMAN | Q16363 | 164 | Laminin subunit alpha-4 |
| LAMP1_HUMAN | P11279 | 154 | Lysosome-associated membrane glycoprotein 1 |
| LAMP2_HUMAN | P13473 | 174 | Lysosome-associated membrane glycoprotein 2 |
| LDHA_HUMAN | P00338 | 194 | L-lactate dehydrogenase A chain |
| LG3BP_HUMAN | Q08380 | 145 | Galectin-3-binding protein |
| LTOR3_HUMAN | Q9UHA4 | 126 | Ragulator complex protein LAMTOR3 |

TABLE 1A-continued

| Uniprot entry-name | Uniprot accession number | Uniprot entry version | Protein name |
|---|---|---|---|
| LYAG_HUMAN | P10253 | 186 | Lysosomal alpha-glucosidase |
| MIME_HUMAN | P20774 | 156 | Mimecan |
| MUC5B_HUMAN | Q9HC84 | 140 | Mucin-5B |
| NF2L2_HUMAN | Q16236 | 158 | Nuclear factor erythroid 2-related factor 2 |
| NID2_HUMAN | Q14112 | 156 | Nidogen-2 |
| OSTP_HUMAN | P10451 | 181 | Osteopontin |
| P53_HUMAN | P04637 | 237 | Cellular tumor antigen p53 |
| PDGFA_HUMAN | P04085 | 168 | Platelet-derived growth factor subunit A |
| PGS1_HUMAN | P21810 | 162 | Biglycan |
| PIP_HUMAN | P12273 | 150 | Prolactin-inducible protein |
| PLTP_HUMAN | P55058 | 152 | Phospholipid transfer protein |
| PPAP_HUMAN | P15309 | 155 | Prostatic acid phosphatase |
| PTX3_HUMAN | P26022 | 132 | Pentraxin-related protein PTX3 |
| RALA_HUMAN | P11233 | 170 | Ras-related protein Ral-A |
| RASK_HUMAN | P01116 | 193 | GTPase Kras |
| RET4_HUMAN | P02753 | 188 | Retinol-binding protein 4 |
| RETN_HUMAN | Q9HD89 | 117 | Resistin |
| S100P_HUMAN | P25815 | 147 | Protein S100-P |
| S10A6_HUMAN | P06703 | 163 | Protein S100-A6 |
| SORL_HUMAN | Q92673 | 161 | Sortilin-related receptor |
| TERA_HUMAN | P55072 | 173 | Transitional endoplasmic reticulum ATPase |
| TNFA_HUMAN | P01375 | 210 | Tumor necrosis factor |
| TRFE_HUMAN | P02787 | 200 | Serotransferrin |
| TSP1_HUMAN | P07996 | 200 | Thrombospondin-1 |
| UROM_HUMAN | P07911 | 160 | Uromodulin |
| VTDB_HUMAN | P02774 | 179 | Vitamin D-binding protein |
| ZA2G_HUMAN | P25311 | 166 | Zinc-alpha-2-glycoprotein |

The analysis was conducted using urine samples from a large patient cohort (n=121) representing the actual population to be tested for bladder cancer detection, including incident and recurrent cases, and controls. The identification of the 81 biomarker proteins resulted from the evaluation of 134 candidate proteins and from a preceding analysis. The 134 candidate proteins have been identified in an independent discovery study or had previously been described in the literature. Determining the presence and the amount of these proteins in urine samples of a large cohort of patients representing different stages of cancer development allowed a strikingly reliable analysis and precise interpretation of the results. In detail, the cohort comprised patients suffering from initially occurred bladder cancer as well as patients that had the initial tumor resected but experienced a cancer relapse. Moreover, the analyzed urine samples were obtained from patients that were suspected of suffering from bladder cancer, but before respective biopsies of the patients were analysed. Therefore, the cohort comprised patients having bladder cancer (initial occurrence or recurrence) as confirmed by biopsy, but also patients which had been wrongly suspected of bladder cancer. This and the extended surveillance of patents allowed the identification of biomarker proteins specifically indicating the risk of progression and recurrence of bladder cancer. In consequence, the obtained data provide the basis for bladder cancer diagnosis and prognosis with a not yet achieved accuracy and reliability. Moreover, they provide a practicable approach for diagnosis as well as prognosis of a cancer of a urinary tract or organ by examination of urine samples avoiding the need of cystoscopy and collection of biopsies. This is particularly advantageous for monitoring patients during aftercare, which requires regular re-examination. Additionally, it also reduces the necessity of cystoscopy and the collection of biopsies upon first suspicion of bladder cancer. This will have a significant impact on bladder cancer diagnosis, since about 40% of biopsies upon first suspicion turned out to be negative in the present study. Thus, an accurate and reliable diagnosis and/or prognosis by examination of urine samples will greatly reduce the strain on patients and create significant savings for the health care system.

In a second study, the analysis of a Parallel Reaction Monitoring (PRM) screening of potential bladder cancer biomarker proteins allowed the identification of 41 further proteins (table 1B), which were found to be present in deviating amounts in the urine of patients having bladder cancer. For each protein, the Uniprot entry name, the Uniprot accession number and the Uniprot entry version are given in table 1B. The information is taken from the Uniprot (Universal Protein Resource) database.

TABLE 1B

| Uniprot entry-name | Uniprot accession number | Uniprot entry version | Protein name |
|---|---|---|---|
| APOE_HUMAN | P02649 | 216 | Apolipoprotein E |
| BLVRB_HUMAN | P30043 | 168 | Flavin reductase (NADPH) |
| CADH1_HUMAN | P12830 | 211 | Cadherin-1 |
| CATD_HUMAN | P07339 | 199 | Cathepsin D |
| CATL1_HUMAN | P07711 | 191 | Cathepsin L1 |
| CD59_HUMAN | P13987 | 191 | CD59 glycoprotein |
| CO1A1_HUMAN | P02452 | 212 | Collagen alpha-1(I) chain |
| EPCAM_HUMAN | P16422 | 165 | Epithelial cell adhesion molecule |
| FABP4_HUMAN | P15090 | 171 | Fatty acid-binding protein, adipocyte |
| HBA_HUMAN | P69905 | 156 | Hemoglobin subunit alpha |
| HBB_HUMAN | P68871 | 157 | Hemoglobin subunit beta |
| HPT_HUMAN | P00738 | 189 | Haptoglobin |
| IBP6_HUMAN | P24592 | 171 | Insulin-like growth factor-binding protein 6 |
| ICT1_HUMAN | Q14197 | 140 | Peptidyl-tRNA hydrolase ICT1, mitochondrial |
| IL6_HUMAN | P05231 | 200 | Interleukin-6 |
| IMA2_HUMAN | P52292 | 196 | Importin subunit alpha-1 |
| EFC14_HUMAN | O75071 | 129 | EF-hand calcium-binding domain-containing protein 14 |
| K1C17_HUMAN | Q04695 | 174 | Keratin, type I cytoskeletal 17 |
| MASP2_HUMAN | O00187 | 187 | Mannan-binding lectin serine protease 2 |
| MMP9_HUMAN | P14780 | 215 | Matrix metalloproteinase-9 |
| MTA2_HUMAN | O94776 | 155 | Metastasis-associated protein MTA2 |
| NDC80_HUMAN | O14777 | 142 | Kinetochore protein NDC80 homolog |
| NHRF1_HUMAN | O14745 | 178 | Na(+)/H(+) exchange regulatory cofactor NHE-RF1 |
| PGFRB_HUMAN | P09619 | 209 | Platelet-derived growth factor receptor beta |
| PLK1_HUMAN | P53350 | 192 | Serine/threonine-protein kinase PLK1 |
| PRDX1_HUMAN | Q06830 | 189 | Peroxiredoxin-1 |
| PRDX4_HUMAN | Q13162 | 168 | Peroxiredoxin-4 |
| PROF1_HUMAN | P07737 | 188 | Profilin-1 |
| PTGDS_HUMAN | P41222 | 169 | Prostaglandin-H2 D-isomerase |
| RAI3_HUMAN | Q8NFJ5 | 131 | Retinoic acid-induced protein 3 |
| RAP2A_HUMAN | P10114 | 184 | Ras-related protein Rap-2a |
| RAP2B_HUMAN | P61225 | 136 | Ras-related protein Rap-2b |
| RASN_HUMAN | P01111 | 197 | GTPase NRas |
| S10A9_HUMAN | P06702 | 192 | Protein S100-A9 |
| SODC_HUMAN | P00441 | 218 | Superoxide dismutase [Cu—Zn] |
| SPRC_HUMAN | P09486 | 184 | SPARC |
| SYUG_HUMAN | O76070 | 155 | Gamma-synuclein |
| TGFB1_HUMAN | P01137 | 223 | Transforming growth factor beta-1 |

TABLE 1B-continued

| Uniprot entry-name | Uniprot accession number | Uniprot entry version | Protein name |
|---|---|---|---|
| TGFR1_HUMAN | P36897 | 197 | TGF-beta receptor type-1 |
| TRBM_HUMAN | P07204 | 211 | Thrombomodulin |
| VDAC1_HUMAN | P21796 | 190 | Voltage-dependent anion-selective channel protein 1 |

The term "signature peptide" refers to a proteotypic peptide, which represents a protein of interest. Accordingly, the amino acid sequence of the signature peptide corresponds to a part of the protein of interest, wherein the sequence is selected to be unique for the protein of interest. Thus, a single protein of interest, i.e. biomarker protein, may be represented by several signature peptides, but each signature peptide is unique to one biomarker protein. The signature peptides can be used as isolated peptides and are preferably used for determining the presence and the amount of proteins by mass spectrometry methods, for example Selected Reaction Monitoring (SRM), time-scheduled SRM or Parallel Reaction Monitoring (PRM). They may be selected by standard methods depending on the mass spectroscopy technique used. In general, signature peptides are chosen according to their MS response, which e.g. can be by calculated from extracted ion chromatograms of the monoisotopic peak of each peptide. Alternatively, signature peptides may be selected by using the information provided by publicly accessible databases. For example, peptides with high observation numbers, i.e. frequently reported, can be expected to have high MS response. Additionally, an increasing number of computational approaches have become available, which can be even combined to achieve best results (Zhao and Brasier, 2013).

Since the signature peptides are identical to a part of the amino acid sequence of the protein of interest, i.e. the biomarker protein, the signature peptide and the respective native peptide derived from the protein of interest have the same physicochemical properties, e.g. chromatographic co-elution, ionization efficiency and relative patterns of fragment ions. Thus, the signature peptides can be used as internal standards when labelled, for example by introducing stable isotopes. In that case, a known amount of each signature peptide is spiked into the sample to be examined and both are analyzed together, e.g. by liquid chromatography-SRM mass spectroscopy. The signature peptides allow the identification of the native peptide derived from the protein of interest due to the identical physicochemical properties but distinguished from them by their different mass. Thus, by comparing the mass spectrometry (MS) response of the signature peptide and the corresponding native peptide, the amount of the native peptide and, therefore, the protein of interest can be quantified.

Additionally, the collection of signature peptides may be used as an external standard for optimizing fragmentation conditions and determine best precursorproduct ion transitions. To do so, the collection is directly introduced into an analysis device, e.g. a triple quadrupole (QqQ-MS), without a sample.

Taken together, the collection of signature peptides allows the analysis and quantification of distinct proteins that have been found to provide a reliable and accurate diagnosis and prognosis for bladder cancer from urine samples.

The term "biomarker", or biological marker, refers to an indicator of a biological state or condition, in particular a medical state or condition. The biomarkers of the present invention are proteins that have been found to be suited for the diagnosis and/or prognosis of a cancer of the urinary tract or organ.

In a preferred embodiment, the signature peptides represent at least 15, preferably at least 20, more preferred at least 30 proteins. Since the biomarker proteins were identified by evaluation using highly stringent SRM technique, significant and reliable information for diagnosis and/or prognosis can be achieved with analyzing as few as 10 proteins. However, increasing the number of detected proteins will improve the significance and reliability of the diagnosis.

In a preferred embodiment, the signature peptides represent at least 10 proteins selected from group 1A consisting of

| | | |
|---|---|---|
| A1AG2_HUMAN | DPP4_HUMAN | LYAG_HUMAN |
| A1AT_HUMAN | EGF_HUMAN | MIME_HUMAN |
| A1BG_HUMAN | ES8L2_HUMAN | MUC5B_HUMAN |
| A2GL_HUMAN | FCN3_HUMAN | NF2L2_HUMAN |
| A2MG_HUMAN | FIBB_HUMAN | NID2_HUMAN |
| AFAM_HUMAN | FIBG_HUMAN | OSTP_HUMAN |
| AK1C4_HUMAN | GELS_HUMAN | P53_HUMAN |
| ALDOA_HUMAN | GGH_HUMAN | PDGFA_HUMAN |
| AMPN_HUMAN | IBP4_HUMAN | PGS1_HUMAN |
| ANAG_HUMAN | IBP7_HUMAN | PLTP_HUMAN |
| ANGP2_HUMAN | IGF2_HUMAN | PPAP_HUMAN |
| APOA1_HUMAN | IGHG1_HUMAN | PTX3_HUMAN |
| APOA4_HUMAN | ITIH2_HUMAN | RALA_HUMAN |
| BIRC5_HUMAN | ITIH4_HUMAN | RASK_HUMAN |
| C4BPA_HUMAN | K1C19_HUMAN | RETN_HUMAN |
| CALR_HUMAN | KLK3_HUMAN | S10A6_HUMAN |
| CBPE_HUMAN | KNG1_HUMAN | SORL_HUMAN |
| CD44_HUMAN | KV201_HUMAN | TERA_HUMAN |
| CERU_HUMAN | LAMA4_HUMAN | TNFA_HUMAN |
| CLUS_HUMAN | LAMP1_HUMAN | TRFE_HUMAN |
| CO1A2_HUMAN | LAMP2_HUMAN | TSP1_HUMAN |
| CO3_HUMAN | LDHA_HUMAN | UROM_HUMAN |
| CO6A1_HUMAN | LG3BP_HUMAN | VTDB_HUMAN |
| | LTOR3_HUMAN | ZA2G_HUMAN |

In a preferred embodiment, the signature peptides represent at least 3 proteins selected from group 2 consisting of

| |
|---|
| CLUS_HUMAN, |
| K1C19_HUMAN |
| S10A6_HUMAN |
| TSP1_HUMAN |
| UROM_HUMAN | at least 3 proteins selected from group 3 consisting of

| | | |
|---|---|---|
| A2MG_HUMAN | IGHG1_HUMAN | IGF2_HUMAN |
| AFAM_HUMAN | PGS1_HUMAN | EGF_HUMAN |
| APOA1_HUMAN | A1BG_HUMAN | NF2L2_HUMAN |
| BIRC5_HUMAN | P53_HUMAN | LDHA_HUMAN |
| C4BPA_HUMAN | OSTP_HUMAN | KV201_HUMAN |
| CALR_HUMAN | SORL_HUMAN | A2GL_HUMAN |
| CO3_HUMAN | RETN_HUMAN | PTX3_HUMAN |
| ES8L2_HUMAN | VTDB_HUMAN | MIME_HUMAN |
| FCN3_HUMAN | APOA4_HUMAN | AK1C4_HUMAN |
| FIBB_HUMAN | CO1A2_HUMAN | GELS_HUMAN |
| FIBG_HUMAN | CERU_HUMAN | NID2_HUMAN |
| ITIH2_HUMAN | IBP4_HUMAN | A1AG2_HUMAN |
| ITIH4_HUMAN | TERA_HUMAN | TSP1_HUMAN |
| K1C19_HUMAN | PDGFA_HUMAN | PPAP_HUMAN |
| PLTP_HUMAN | ALDOA_HUMAN | MUC5B_HUMAN |
| RASK_HUMAN | A1AT_HUMAN | ANGP2_HUMAN |
| TRFE_HUMAN | UROM_HUMAN | | at least 3 proteins selected from the group 4 consisting of

| |
|---|
| AMPN_HUMAN |
| CD44_HUMAN |
| DPP4_HUMAN |
| LAMA4_HUMAN |
| LAMP1_HUMAN |
| LAMP2_HUMAN |
| LYAG_HUMAN |
| RALA_HUMAN |
| TNFA_HUMAN |
| ZA2G_HUMAN | and at least 3 proteins selected from the group 5 consisting of

| | |
|---|---|
| AMPN_HUMAN | CO6A1_HUMAN |
| DPP4_HUMAN | GGH_HUMAN |
| EGF_HUMAN | IBP7_HUMAN |
| LAMA4_HUMAN | KNG1_HUMAN |
| LAMP1_HUMAN | KLK3_HUMAN |
| LAMP2_HUMAN | LG3BP_HUMAN |
| LYAG_HUMAN | LTOR3_HUMAN |
| OSTP_HUMAN | ANAG_HUMAN |
| RALA_HUMAN | CBPE_HUMAN |
| TNFA_HUMAN | |

The evaluation, with which the significant biomarker proteins for bladder cancer were identified, was performed on samples derived from different groups of patients, including patients suffering from an initial occurrence of bladder cancer as well as such suffering from a relapse after primary tumor resection. Since the analysis was done on urine samples before cancer incidence, progression or relapse was confirmed by biopsy, the evaluation was done on blind samples including important negative controls. For example, samples of patients were included that were suspected but not found to have developed an initial bladder cancer or relapse. This allowed the identification of specific proteins indicating incidences of initial occurrence and recurrence of bladder cancer but also the risk for progression and recurrence of existing bladder cancer. "Initial bladder cancer" or "initial occurrence of bladder cancer" refers to the first incident of bladder cancer in a patient. "Recurrence" of bladder cancer refers to the relapse of bladder cancer after the initial tumor had been removed. In detail, the proteins as shown in groups 2 and 4 were found in significantly different amounts in the urine of patients with initiate occurrence or recurrence of bladder cancer relative to the corresponding controls, respectively. Additionally, proteins depicted in groups 3 and 5 were found in significantly different amounts in the urine of patients with higher risk of progression and recurrence of an initial or a relapsed bladder cancer, respectively. By representing proteins of all described groups, the collection of signature peptides provides information on the initial and recurrence of bladder cancer as well as the risk of progression and recurrence of existing bladder cancer, both initial and relapsed. This cannot be achieved by diagnostic tools of the prior art. Moreover, by covering biomarker proteins of all groups, a comprehensive test can be provided allowing the examination of all patients by standard methods, which makes the application of the test convenient and economically efficient.

In a preferred embodiment, the collection comprises about 10 to 100, preferably about 20 to 70, more preferred about 30 to 50 signature peptides. In general, one signature peptide for each biomarker protein is sufficient for detecting the respective protein, in particular if the signature peptide is suitable to produce high and reproducible MS response. However, depending on the biomarker protein and the MS response of the available signature peptides, it may be advantageous to use more than one, preferably 2 to 5 signature peptides for a protein. According to the number of biomarker proteins represented in the collection, the number of signature peptides may thus vary. Moreover, depending on the way the collection is provided (e.g. as a mixture of peptides in one composition, or as single compositions, each comprising multiple copies of one signature peptide), different numbers of signature peptides may be covered by the collection.

In a preferred embodiment, the cancer is a bladder cancer, preferably an urothelial bladder cancer. The urinary system comprises various organs including bladder, prostate gland, ureter and urethra, which are of common developmental origin, namely the endoderm. Moreover, the tracts and organs of the urinary system all comprise a transitional epithelium lining their lumen. The uroepithelium, from which tumor cells of urothelial bladder cancer are known to be derived, is a subspecies of the transitional epithelium lining the urinary tract including the renal pelvis, the ureters, the bladder, and parts of the urethra. Thus, the proteins identified in the present study as differentially present in the urine of patients suffering from urothelial bladder cancer, may likewise be used to gain information regarding possible cancer incidence or risk of progression or recurrence regarding other organs of the urothelial system. However, for urothelial bladder cancer, the proteins have been found to allow for reliably distinguishing various stages of urothelial bladder cancer, such as initial occurrence, recurrence and the risk of progression and recurrence of initial and relapsed bladder cancer.

In a preferred embodiment, the collection of signature peptides is used as an internal reference standard. Because the signature peptides represent proteotypic peptides of the proteins of interest, they can be used as an internal reference standard for protein quantification. To do so, a known amount of each signature peptide is added to the sample to be analyzed and the amount of the represented protein calculated by comparing the MS response of the corresponding exogenous labelled and the endogenous unlabelled peptides. Employing multiplexed MS techniques such as scheduled SRM or PRM, it is possible to analyze several hundreds of signature peptides and represented proteins simultaneously.

In a preferred embodiment, the collection of signature peptides is used to quantify proteins of a urine sample. The urine is a collection of secretions derived from the kidney, urethra and bladder. Besides urine production, cells within these organs, in particular cells lining the lumen, are likely to release proteins into the urine. Thus, the urine is by nature preferred for collecting and subsequently analyzing proteins derived from the urinary tracts and organs. Moreover, any lesions or pathological changes within the urinary tracts or organs are likely to influence the composition of the urine. Since the urine is retained most of the time within the bladder, proteins released by cells of the bladder will be collected in rather high concentrations and, thus, have a high probability for being detected within a urine sample. This is particularly so for urothelial cells, which line the lumen of the bladder such that extensively proliferating, i.e. carcinogenic, urothelial cells will secrete proteins or release entire cell cytoplasms into the urine. In addition, exosomes may be present in the urine, containing or releasing proteins well suited for detection in urine samples. Exosomes are cell-derived vesicles that are e.g. released from cells when multivesicular bodies fuse with the plasma membrane or they are released directly from the plasma membrane. There is growing evidence that exosomes have specialized functions and play a key role in, for example, coagulation, intercellular signalling, and waste management. Thus, exosomes might be used for prognosis, therapy, and biomarkers for health and disease. Thus, analysis of a urine sample is particularly preferred for the diagnosis of urothelial bladder cancer. In addition, urine samples are also particularly suitable for diagnostic purposes from a technical point of view, because they are easy to obtain and handle. Invasive procedures such as biopsy can therefore be omitted, and the collection and storage of urine samples is even more practicable than that of blood samples.

In a preferred embodiment, each signature peptide is labelled by a stable isotope, preferably $^{13}$C, $^{15}$N or a combination of both. This allows distinguishing the signature peptide from the native peptide of the biomarker protein by different mass, e.g. in MS analysis methods. The isotope may be included by using isotope labelled amino acids, preferably Lysine or Arginine, for generating the signature peptides. Alternatively, all amino acids used for peptide generation may comprise a stable isotope. In a preferred embodiment, each signature peptide consists of 5 to 30, preferably 7 to 25, more preferred 10 to 15 amino acids. As each signature peptide corresponds to a native peptide derived from the protein of interest by proteolysis, it may vary in length. However, for applications such as MS techniques, peptides of a certain length are preferred. For example, for SRM and PRM signature peptides of 5 to 25 amino acids are particularly preferred.

In a preferred embodiment, each signature peptide is selected according to table 2A and/or table 2B.

TABLE 2A

| Protein | signature peptide | SEQ ID NO. |
|---|---|---|
| A1AG2_HUMAN | EHVAHLLFLR | 1 |
| A1AG2_HUMAN | NWGLSFYADKPETTK | 2 |
| A1AG2_HUMAN | SDVMYTDWK | 3 |
| A1AT_HUMAN | ITPNLAEFAFSLYR | 4 |
| A1AT_HUMAN | LQHLENELTHDIITK | 5 |
| A1AT_HUMAN | LSITGTYDLK | 6 |
| A1AT_HUMAN | LYHSEAFTVNFGDTEEAK | 7 |
| A1AT_HUMAN | SVLGQLGITK | 8 |
| A1BG_HUMAN | ATWSGAVLAGR | 9 |
| A1BG_HUMAN | HQFLLTGDTQGR | 10 |
| A2GL_HUMAN | DLLLPQPDLR | 11 |
| A2GL_HUMAN | GQTLLAVAK | 12 |
| A2GL_HUMAN | VAAGAFQGLR | 13 |
| A2MG_HUMAN | LVHVEEPHTETVR | 14 |
| A2MG_HUMAN | NEDSLVFVQTDK | 15 |
| A2MG_HUMAN | QGIPFFGQVR | 16 |
| AFAM_HUMAN | DADPDTFFAK | 17 |
| AFAM_HUMAN | FTFEYSR | 18 |
| AFAM_HUMAN | IAPQLSTEELVSLGEK | 19 |
| AK1C4_HUMAN | DIVLVAHSALGTQR | 20 |
| AK1C4_HUMAN | HIDSAYLYNNEEQVGLAIR | 21 |
| ALDOA_HUMAN | ADDGRPFPQVIK | 22 |
| ALDOA_HUMAN | GILAADESTGSIAK | 23 |
| AMPN_HUMAN | EATDVIIHSK | 24 |
| AMPN_HUMAN | FSTEYELQQLEQFK | 25 |
| AMPN_HUMAN | SIQLPTTVR | 26 |
| ANAG_HUMAN | LLLTSAPSLATSPAFR | 27 |
| ANGP2_HUMAN | IVTATVNNSVLQK | 28 |
| ANGP2_HUMAN | QILDQTSEINK | 29 |
| APOA1_HUMAN | AKPALEDLR | 30 |
| APOA1_HUMAN | ATEHLSTLSEK | 31 |
| APOA1_HUMAN | DYVSQFEGSALGK | 32 |
| APOA1_HUMAN | EQLGPVTQEFWDNLEK | 33 |
| APOA1_HUMAN | QGLLPVLESFK | 34 |
| APOA1_HUMAN | THLAPYSDELR | 35 |
| APOA1_HUMAN | VQPYLDDFQK | 36 |
| APOA1_HUMAN | VSFLSALEEYTK | 37 |
| APOA4_HUMAN | LGEVNTYAGDLQK | 38 |
| APOA4_HUMAN | SELTQQLNALFQDK | 39 |
| APOA4_HUMAN | SLAPYAQDTQEK | 40 |
| BIRC5_HUMAN | ELEGWEPDDDPIEEHK | 41 |
| BIRC5_HUMAN | QFEELTLGEFLK | 42 |
| C4BPA_HUMAN | EDVYVVGTVLR | 43 |
| C4BPA_HUMAN | GYILVGQAK | 44 |
| C4BPA_HUMAN | LSLEIEQLELQR | 45 |
| CALR_HUMAN | GLQTSQDAR | 46 |
| CALR_HUMAN | QIDNPDYK | 47 |
| CALR_HUMAN | VHVIFNYK | 48 |
| CATB_HUMAN | EQWPQCPTIK | 49 |
| CATB_HUMAN | LPASFDAR | 50 |
| CATB_HUMAN | NGPVEGAFSVYSDFLLYK | 51 |
| CATB_HUMAN | SGVYQHVTGEMMGGHAIR | 52 |
| CATB_HUMAN | TDQYWEK | 53 |
| CATB_HUMAN | GQDHCGIESEWAGIPR | 54 |
| CATB_HUMAN | DQGSCGSCWAFGAVEAISDR | 55 |
| CATB_HUMAN | HYGYNSYSVSNSEK | 56 |

TABLE 2A-continued

| Protein | signature peptide | SEQ ID NO. |
|---|---|---|
| CATB_HUMAN | GLVSGGLYESHVGCR | 57 |
| CATB_HUMAN | HYGYNSYSVSNSEKDIMAEIYK | 58 |
| CATB_HUMAN | ICEPGYSPTYKQDK | 59 |
| CATB_HUMAN | QDKHYGYNSYSVSNSEKDIMAEIYK | 60 |
| CATB_HUMAN | ICEPGYSPTYK | 61 |
| CATB_HUMAN | QDKHYGYNSYSVSNSEK | 62 |
| CATB_HUMAN | DIMAEIYK | 63 |
| CBPE_HUMAN | AASQPGELK | 64 |
| CBPE_HUMAN | NSLISYLEQIHR | 65 |
| CBPE_HUMAN | SNAQGIDLNR | 66 |
| CD44_HUMAN | FAGVFHVEK | 67 |
| CD44_HUMAN | YGFIEGHVVIPR | 68 |
| CERU_HUMAN | AEEEHLGILGPQLHADVGDK | 69 |
| CERU_HUMAN | ALYLQYTDETFR | 70 |
| CERU_HUMAN | GAYPLSIEPIGVR | 71 |
| CERU_HUMAN | NNEGTYYSPNYNPQSR | 72 |
| CLUS_HUMAN | ASSIIDELFQDR | 73 |
| CLUS_HUMAN | ELDESLQVAER | 74 |
| CLUS_HUMAN | IDSLLENDR | 75 |
| CLUS_HUMAN | LFDSDPITVTVPVEVSR | 76 |
| CO1A2_HUMAN | GEPGNIGFPGPK | 77 |
| CO1A2_HUMAN | GIPGPVGAAGATGAR | 78 |
| CO3_HUMAN | IHWESASLLR | 79 |
| CO3_HUMAN | SNLDEDIIAEENIVSR | 80 |
| CO3_HUMAN | TIYTPGSTVLYR | 81 |
| CO6A1_HUMAN | LSIIATDHTYR | 82 |
| COX7R_HUMAN | ADGVPVYLK | 83 |
| COX7R_HUMAN | GLPDQMLYR | 84 |
| COX7R_HUMAN | LTSDSTVYDYAGK | 85 |
| CUBN_HUMAN | DFVEILDGGHEDAPLR | 86 |
| CUBN_HUMAN | EQLANPIVSSGNSLFLR | 87 |
| CUBN_HUMAN | FVTDGSVTASGFR | 88 |
| CUBN_HUMAN | SDNSPTHVGFK | 89 |
| CYTM_HUMAN | AAQAAVASYNMGSNSIYYFR | 90 |
| CYTM_HUMAN | AQSQLVAGIK | 91 |
| CYTM_HUMAN | ARPQER | 92 |
| CYTM_HUMAN | CDFEVLVVPWQNSSQLLK | 93 |
| CYTM_HUMAN | DLSPDDPQVQK | 94 |
| CYTM_HUMAN | DTHIIK | 95 |
| CYTM_HUMAN | LRCDFEVLVVPWQNSSQLLK | 96 |
| CYTM_HUMAN | SNLPLALGLALVAFCLLALPR | 97 |
| CYTM_HUMAN | TRVTGDHVDLTTCPLAAGAQQEK | 98 |
| CYTM_HUMAN | VTGDHVDLTTCPLAAGAQQEK | 99 |
| CYTM_HUMAN | YFLTMEMGSTDCR | 100 |
| CYTM_HUMAN | YFLTMEMGSTDCRK | 101 |
| DPP4_HUMAN | LGTFEVEDQIEAAR | 102 |
| DPP4_HUMAN | VLEDNSALDK | 103 |
| DPP4_HUMAN | WEYYDSVYTER | 104 |
| EGF_HUMAN | IESSSLQGLGR | 105 |
| EGF_HUMAN | IYWVDLER | 106 |
| EGF_HUMAN | LFWIQYNR | 107 |
| EGF_HUMAN | NQVTPLDILSK | 108 |
| ES8L2_HUMAN | LAINLLAK | 109 |
| ES8L2_HUMAN | LLDIESQEELEDFPLPTVQR | 110 |
| ES8L2_HUMAN | SQPVSQPLTYESGPDEVR | 111 |
| FCN3_HUMAN | QDGSVDFFR | 112 |
| FCN3_HUMAN | YGIDWASGR | 113 |
| FIBB_HUMAN | DNENVVNEYSSELEK | 114 |
| FIBB_HUMAN | HQLYIDETVNSNIPTNLR | 115 |
| FIBB_HUMAN | IRPFFPQQ | 116 |
| FIBG_HUMAN | IHLISTQSAIPYALR | 117 |
| FIBG_HUMAN | QSGLYFIKPLK | 118 |
| FIBG_HUMAN | YEASILTHDSSIR | 119 |
| GDF15_HUMAN | AALPEGLPEASR | 120 |
| GDF15_HUMAN | AANMHAQIK | 121 |
| GDF15_HUMAN | ANQSWEDSNTDLVPAPAVR | 122 |
| GDF15_HUMAN | ASLEDLGWADWVLSPR | 123 |
| GDF15_HUMAN | EVQVTMCIGACPSQFR | 124 |
| GDF15_HUMAN | ILTPEVR | 125 |
| GDF15_HUMAN | LGSGGHLHLR | 126 |
| GDF15_HUMAN | LKPDTVPAPCCVPASYNPMVLIQK | 127 |
| GDF15_HUMAN | LSPTASR | 128 |
| GDF15_HUMAN | NGDHCPLGPGR | 129 |
| GDF15_HUMAN | QLSLARPQAPALHLR | 130 |
| GDF15_HUMAN | SWDVTRPLR | 131 |
| GDF15_HUMAN | TDTGVSLQTYDDLLAK | 132 |
| GDF15_HUMAN | TDTGVSLQTYDDLLAKDCHCI | 133 |

TABLE 2A-continued

| Protein | signature peptide | SEQ ID NO. |
|---|---|---|
| GDF15_HUMAN | YEDLLTR | 134 |
| GELS_HUMAN | AGALNSNDAFVLK | 135 |
| GELS_HUMAN | QTQVSVLPEGGETPLFK | 136 |
| GELS_HUMAN | YIETDPANR | 137 |
| GGH_HUMAN | FFNVLTTNTDGK | 138 |
| GGH_HUMAN | TAFYLAEFFVNEAR | 139 |
| GGH_HUMAN | YPVYGVQWHPEK | 140 |
| HEPC_HUMAN | ASWMPMFQR | 141 |
| HEPC_HUMAN | CGMCCKT | 142 |
| HEPC_HUMAN | DTHFPICIFCCGCCHR | 143 |
| HEPC_HUMAN | SKCGMCCKT | 144 |
| IBP4_HUMAN | LPGGLEPK | 145 |
| IBP7_HUMAN | HEVTGWVLVSPLSK | 146 |
| IBP7_HUMAN | ITVVDALHEIPVK | 147 |
| IBP7_HUMAN | TELLPGDR | 148 |
| IGF2_HUMAN | DVSTPPTVLPDNFPR | 149 |
| IGHG1_HUMAN | FNWYVDGVEVHNAK | 150 |
| IGHG1_HUMAN | GPSVFPLAPSSK | 151 |
| IGHG1_HUMAN | TTPPVLDSDGSFFLYSK | 152 |
| IPSP_HUMAN | AVVEVDESGTR | 153 |
| IPSP_HUMAN | EDQYHYLLDR | 154 |
| IPSP_HUMAN | VEDLHVGATVAPSSR | 155 |
| ITIH2_HUMAN | FYNQVSTPLLR | 156 |
| ITIH2_HUMAN | IQPSGGTNINEALLR | 157 |
| ITIH2_HUMAN | TEVNVLPGAK | 158 |
| ITIH4_HUMAN | FAHTVVTSR | 159 |
| ITIH4_HUMAN | GPDVLTATVSGK | 160 |
| ITIH4_HUMAN | LGVYELLLK | 161 |
| ITIH4_HUMAN | SPEQQETVLDGNLIIR | 162 |
| K1C19_HUMAN | AALEDTLAETEAR | 163 |
| K1C19_HUMAN | ILGATIENSR | 164 |
| K1C19_HUMAN | SLLEGQEDHYNNLSASK | 165 |
| KLK3_HUMAN | LSEPAELTDAVK | 166 |
| KNG1_HUMAN | LNAENNATFYFK | 167 |
| KNG1_HUMAN | TVGSDTFYSFK | 168 |
| KNG1_HUMAN | YFIDFVAR | 169 |
| KNG1_HUMAN | YNSQNQSNNQFVLYR | 170 |
| KV201_HUMAN | AGQSPQLLIYTLSYR | 171 |
| KV201_HUMAN | LEIPYTFGQGTK | 172 |
| LAMA4_HUMAN | DAPSWDPVALK | 173 |
| LAMA4_HUMAN | LITEEANR | 174 |
| LAMA4_HUMAN | SGVLSVSSGAAAHR | 175 |
| LAMP1_HUMAN | ALQATVGNSYK | 176 |
| LAMP1_HUMAN | FFLQGIQLNTILPDAR | 177 |
| LAMP1_HUMAN | GHTLTLNFTR | 178 |
| LAMP2_HUMAN | GILTVDELLAIR | 179 |
| LAMP2_HUMAN | YLDFVFAVK | 180 |
| LDHA_HUMAN | DLADELALVDVIEDK | 181 |
| LDHA_HUMAN | SADTLWGIQK | 182 |
| LDHA_HUMAN | VTLTSEEEAR | 183 |
| LG3BP_HUMAN | ELSEALGQIFDSQR | 184 |
| LG3BP_HUMAN | IDITLSSVK | 185 |
| LG3BP_HUMAN | LADGGATNQGR | 186 |
| LG3BP_HUMAN | SDLAVPSELALLK | 187 |
| LG3BP_HUMAN | YSSDYFQAPSDYR | 188 |
| LTOR3_HUMAN | ELAPLFEELR | 189 |
| LTOR3_HUMAN | LPSVEGLHAIVVSDR | 190 |
| LYAG_HUMAN | GAYTQVIFLAR | 191 |
| LYAG_HUMAN | GELFWDDGESLEVLER | 192 |
| LYAG_HUMAN | WGYSSTAITR | 193 |
| MIME_HUMAN | DFADIPNLR | 194 |
| MUC5B_HUMAN | AAYEDFNVQLR | 195 |
| MUC5B_HUMAN | AVTLSLDGGDTAIR | 196 |
| NF2L2_HUMAN | DGNVFLVPK | 197 |
| NF2L2_HUMAN | EQFNEAQLALIR | 198 |
| NID2_HUMAN | DGVVSVNK | 199 |
| NID2_HUMAN | ESYNVQLQLPAR | 200 |
| NID2_HUMAN | HAQAQYAYPGAR | 201 |
| OSTP_HUMAN | AIPVAQDLNAPSDWDSR | 202 |
| OSTP_HUMAN | ANDESNEHSDVIDSQELSK | 203 |
| OSTP_HUMAN | YPDAVATWLNPDPSQK | 204 |
| P53_HUMAN | LGFLHSGTAK | 205 |
| PDGFA_HUMAN | LLEIDSVGSEDSLDTSLR | 206 |
| PDGFA_HUMAN | TVIYEIPR | 207 |
| PGS1_HUMAN | IQAIELEDLLR | 208 |
| PGS1_HUMAN | LLQVVYLHSNNITK | 209 |
| PGS1_HUMAN | NHLVEIPPNLPSSLVELR | 210 |

TABLE 2A-continued

| Protein | signature peptide | SEQ ID NO. |
|---|---|---|
| PIP_HUMAN | ASPATLLLVLCLQLGANK | 211 |
| PIP_HUMAN | ELGICPDDAAVIPIK | 212 |
| PIP_HUMAN | ELGICPDDAAVIPIKNNR | 213 |
| PIP_HUMAN | FYTIEILK | 214 |
| PIP_HUMAN | FYTIEILKVE | 215 |
| PIP_HUMAN | LLQLLFR | 216 |
| PIP_HUMAN | NFDIPK | 217 |
| PIP_HUMAN | SVRPNDEVTAVLAVQTELK | 218 |
| PIP_HUMAN | SVRPNDEVTAVLAVQTELKECMVVK | 219 |
| PIP_HUMAN | TFYWDFYTNR | 220 |
| PIP_HUMAN | TVQIAAVVDVIR | 221 |
| PIP_HUMAN | TYLISSIPLQGAFNYK | 222 |
| PIP_HUMAN | YTACLCDDNPK | 223 |
| PLTP_HUMAN | AGALQLLLVGDK | 224 |
| PLTP_HUMAN | ATYFGSIVLLSPAVIDSPLK | 225 |
| PLTP_HUMAN | EGHFYYNISEVK | 226 |
| PPAP_HUMAN | ELSELSLLSLYGIHK | 227 |
| PPAP_HUMAN | FQELESETLK | 228 |
| PPAP_HUMAN | SPIDTFPTDPIK | 229 |
| PTX3_HUMAN | ADLHAVQGWAAR | 230 |
| PTX3_HUMAN | MLLQATDDVLR | 231 |
| PTX3_HUMAN | SWLPAGCETAILFPMR | 232 |
| RALA_HUMAN | AEQWNVNYVETSAK | 233 |
| RALA_HUMAN | EDENVPFLLVGNK | 234 |
| RALA_HUMAN | GQNSLALHK | 235 |
| RASK_HUMAN | SFEDIHHYR | 236 |
| RASK_HUMAN | VEDAFYTLVR | 237 |
| RASN_HUMAN | SFADINLYR | 238 |
| RET4_HUMAN | DPNGLPPEAQK | 239 |
| RET4_HUMAN | DPNGLPPEAQKIVR | 240 |
| RET4_HUMAN | FSGTWYAMAK | 241 |
| RET4_HUMAN | GNDDHWIVDTDYDTYAVQYSCR | 242 |
| RET4_HUMAN | KDPEGLFLQDNIVAEFSVDETGQMSATAK | 243 |
| RET4_HUMAN | LIVHNGYCDGR | 244 |
| RET4_HUMAN | LIVHNGYCDGRSER | 245 |
| RET4_HUMAN | LLNLDGTCADSYSFVFSR | 246 |
| RET4_HUMAN | LLNNWDVCADMVGTFTDTEDPAK | 247 |
| RET4_HUMAN | LLNNWDVCADMVGTFTDTEDPAKFK | 248 |
| RET4_HUMAN | MKYWGVASFLQK | 249 |
| RET4_HUMAN | QEELCLAR | 250 |
| RET4_HUMAN | QRQEELCLAR | 251 |
| RET4_HUMAN | VKENFDKAR | 252 |
| RET4_HUMAN | WVWALLLLAALGSGR | 253 |
| RET4_HUMAN | YWGVASFLQK | 254 |
| REIN_HUMAN | IQEVAGSLIFR | 255 |
| S100P_HUMAN | DKDAVDKLLK | 256 |
| S100P_HUMAN | DLDANGDAQVDFSEFIVFVAAITSACHK | 257 |
| S100P_HUMAN | ELPGFLQSGK | 258 |
| S100P_HUMAN | ELPGFLQSGKDKDAVDK | 259 |
| S100P_HUMAN | MTELETAMGMIIDVFSR | 260 |
| S100P_HUMAN | TELETAMGMIIDVFSR | 261 |
| S100P_HUMAN | YSGSEGSTQTLTK | 262 |
| S100P_HUMAN | YSGSEGSTQTLTKGELK | 263 |
| S10A6_HUMAN | LMEDLDR | 264 |
| S10A6_HUMAN | LQDAEIAR | 265 |
| SORL_HUMAN | AADLLLHSK | 266 |
| SORL_HUMAN | ITTVSLSAPDALK | 267 |
| SORL_HUMAN | TNVY1SSSAGAR | 268 |
| TERA_HUMAN | ELQELVQYPVEHPDK | 269 |
| TERA_HUMAN | GDDLSTAILK | 270 |
| TERA_HUMAN | LIVDEAINEDNSVVSLSQPK | 271 |
| TNFA_HUMAN | GQGCPSTHVLLTHTISR | 272 |
| TNFA_HUMAN | VNLLSAIK | 273 |
| TREE_HUMAN | DGAGDVAFVK | 274 |
| TRFE_HUMAN | EGYYGYTGAFR | 275 |
| TRFE_HUMAN | SASDLTWDNLK | 276 |
| TSP1_HUMAN | GGVNDNFQGVLQNVR | 277 |
| TSP1_HUMAN | TIVTTLQDSIR | 278 |
| UROM_HUMAN | DSTIQVVENGESSQGR | 279 |
| UROM_HUMAN | DWVSVVTPAR | 280 |
| VTDB_HUMAN | EDFTSLSLVLYSR | 281 |
| VTDB_HUMAN | THLPEVFLSK | 282 |
| VTDB_HUMAN | YTFELSR | 283 |
| ZA2G_HUMAN | EIPAWVPFDPAAQITK | 284 |
| ZA2G_HUMAN | WEAEPVYVQR | 285 |
| ZA2G_HUMAN | YSLTYIYTGLSK | 286 |

The signature peptides of table 2A have been found to give consistent MS responses based in SRM transition patterns (i.e. SRM traces) of the individual peptides, and, thus, are suitable to provide best detection sensitivity. However, other peptides may provide suitable MS responses, in particular dependent on the MS techniques (e.g. acquisition mode/method) and devices used.

The signature peptides of table 2B have been found to give consistent MS responses in PRM and thus also provide suitable MS responses.

TABLE 2B

| Protein | signature peptide | SEQ ID NO. |
|---|---|---|
| A1AG2_HUMAN | TLMFGSYLDDEK | 287 |
| A1AG2_HUMAN | EQLGEFYEALDCLCIPR | 288 |
| A1AG2_HUMAN | QNQCFYNSSYLNVQR | 289 |
| A1BG_HUMAN | LLELTGPK | 290 |
| A1BG_HUMAN | NGVAQEPVHLDSPAIK | 291 |
| A1BG_HUMAN | SGLSTGWTQLSK | 292 |
| A2GL_HUMAN | ENQLEVLEVSWLHGLK | 293 |
| A2GL_HUMAN | GPLQLER | 294 |
| A2MG_HUMAN | GHFSISIPVK | 295 |
| A2MG_HUMAN | HYDGSYSTFGER | 296 |
| AFAM_HUMAN | AIPVTQYLK | 297 |
| AFAM_HUMAN | LPNNVLQEK | 298 |
| AK1C4_HUMAN | VLDGLNR | 299 |
| AK1C4_HUMAN | VIFDTVDLSATWEVMEK | 300 |
| AMPN_HUMAN | DHSAIPVINR | 301 |
| AMPN_HUMAN | ELWILNR | 302 |
| AMPN_HUMAN | AQIINDAFNLASAHK | 303 |
| AMPN_HUMAN | IQTQLQR | 304 |
| ANAG_HUMAN | LLGPGPAADFSVSVER | 305 |
| ANAG_HUMAN | FLLGSWLEQAR | 306 |
| ANAG_HUMAN | YDLLDLTR | 307 |
| ANAG_HUMAN | SDVFEAWR | 308 |
| APOA4_HUMAN | VNSFFSTFK | 309 |
| APOA4_HUMAN | ALVQQMEQLR | 310 |
| APOE_HUMAN | LGPLVEQGR | 311 |
| APOE_HUMAN | SELEEQLTPVAEETR | 312 |
| APOE_HUMAN | QQTEWQSGQR | 313 |
| APOE_HUMAN | WELALGR | 314 |
| APOE_HUMAN | LEEQAQQIR | 315 |
| APOE_HUMAN | LAVYQAGAR | 316 |
| BLVRB_HUMAN | HDLGHFMLR | 317 |

TABLE 2B-continued

| Protein | signature peptide | SEQ ID NO. |
|---|---|---|
| BLVRB_HUMAN | LQAVTDDHIR | 318 |
| BLVRB_HUMAN | TVAGQDAVIVLLGTR | 319 |
| BLVRB_HUMAN | NDLSPTTVMSEGAR | 320 |
| BLVRB_HUMAN | VVACTSAFLLWDPTK | 321 |
| C4BPA_HUMAN | GVGWSHPLPQCEIVK | 322 |
| C4BPA_HUMAN | LNNGEITQHR | 323 |
| C4BPA_HUMAN | EEIIYECDK | 324 |
| C4BPA_HUMAN | GSSVIHCDADSK | 325 |
| CADH1_HUMAN | DTANWLEINPDTGAISTR | 326 |
| CADH1_HUMAN | GQVPENEANVVITTLK | 327 |
| CADH1_HUMAN | NTGVISVVTTGLDR | 328 |
| CADH1_HUMAN | VGTDGVITVK | 329 |
| CADH1_HUMAN | VTEPLDR | 330 |
| CALR_HUMAN | EQFLDGDGWTSR | 331 |
| CALR_HUMAN | GQTLVVQFTVK | 332 |
| CALR_HUMAN | FYALSASFEPFSNK | 333 |
| CALR_HUMAN | HEQNIDCGGGYVK | 334 |
| CATD_HUMAN | YSQAVPAVTEGPIPEVLK | 335 |
| CATD_HUMAN | LVDQNIFSFYLSR | 336 |
| CATD_HUMAN | VSTLPAITLK | 337 |
| CATD_HUMAN | QVFGEATK | 338 |
| CATD_HUMAN | YYTVFDR | 339 |
| CATD_HUMAN | QPGITFIAAK | 340 |
| CATD_HUMAN | LSPEDYTLK | 341 |
| CATL1_HUMAN | QVMNGFQNR | 342 |
| CATL1_HUMAN | AVATVGPISVAIDAGHESFLFYK | 343 |
| CATL1_HUMAN | VFQEPLFYEAPR | 344 |
| CATL1_HUMAN | YSVANDTGFVDIPK | 345 |
| CATL1_HUMAN | NSWGEEWGMGGYVK | 346 |
| CATL1_HUMAN | MIELHNQEYR | 347 |
| CATL1_HUMAN | LYGMNEEGWRR | 348 |
| CATL1_HUMAN | NHCGIASAASYPTV | 349 |
| CD59_HUMAN | AGLQVYNK | 350 |
| CD59_HUMAN | FEHCNFNDVTTR | 351 |
| CD59_HUMAN | TAVNCSSDFDACLITK | 352 |
| CD59_HUMAN | ENELTYYCCK | 353 |
| CD59_HUMAN | TVLLLVTPFLAAAWSLHP | 354 |
| CO1A1_HUMAN | GANGAPGIAGAPGFPGAR | 355 |

TABLE 2B-continued

| Protein | signature peptide | SEQ ID NO. |
|---|---|---|
| CO1A1_HUMAN | SLSQQIENIR | 356 |
| CO1A1_HUMAN | GFSGLDGAK | 357 |
| CO1A1_HUMAN | ALLLQGSNEIEIR | 358 |
| CO1A1_HUMAN | GSEGPQGVR | 359 |
| CO1A1_HUMAN | GEAGPQGPR | 360 |
| CO1A2_HUMAN | GVVGPQGAR | 361 |
| CO1A2_HUMAN | VYCDFSTGETCIR | 362 |
| CO1A2_HUMAN | EMATQLAFMR | 363 |
| CO1A2_HUMAN | SLNNQIETLLTPEGSR | 364 |
| CO3_HUMAN | TGLQEVEVK | 365 |
| CO3_HUMAN | SSLSVPYVIVPLK | 366 |
| CO6A1_HUMAN | VFSVAITPDHLEPR | 367 |
| CO6A1_HUMAN | IALVITDGR | 368 |
| CO6A1_HUMAN | ENYAELLEDAFLK | 369 |
| CO6A1_HUMAN | VPSYQALLR | 370 |
| COX7R_HUMAN | TTMALTVGGTIYCLIALYMASQPK | 371 |
| DPP4_HUMAN | IEPNLPSYR | 372 |
| DPP4_HUMAN | WISDHEYLYK | 373 |
| EPCAM_HUMAN | TQNDVDIADVAYYFEK | 374 |
| EPCAM_HUMAN | LAVNCFVNNNR | 375 |
| EPCAM_HUMAN | TYWIIIELK | 376 |
| EPCAM_HUMAN | GESLFHSK | 377 |
| EPCAM_HUMAN | FITSILYENNVITIDLVQNSSQK | 378 |
| ES8L2_HUMAN | VGPQVPLSEPGFR | 379 |
| FABP4_HUMAN | NTEISFILGQEFDEVTADDR | 380 |
| FABP4_HUMAN | EVGVGFATR | 381 |
| FABP4_HUMAN | STITLDGGVLVHVQK | 382 |
| FABP4_HUMAN | VAGMAKPNMIISVNGDVITIK | 383 |
| FCN3_HUMAN | GEPGDPVNLLR | 384 |
| FIBB_HUMAN | YYWGGQYTWDMAK | 385 |
| FIBB_HUMAN | NYCGLPGEYWLGNDK | 386 |
| GELS_HUMAN | EVQGFESATFLGYFK | 387 |
| GELS_HUMAN | TGAQELLR | 388 |
| GGH_HUMAN | YLESAGAR | 389 |
| GGH_HUMAN | YYIAASYVK | 390 |
| GGH_HUMAN | NLDGISHAPNAVK | 391 |
| GGH_HUMAN | IEFISTMEGYK | 392 |
| HBA_HUMAN | MFLSFPTTK | 393 |
| HBA_HUMAN | TYFPHFDLSHGSAQVK | 394 |
| HBA_HUMAN | VGAHAGEYGAEALER | 395 |
| HBA_HUMAN | FLASVSTVLTSK | 396 |
| HBB_HUMAN | FFESFGDLSTPDAVMGNPK | 397 |
| HBB_HUMAN | SAVTALWGK | 398 |
| HBB_HUMAN | VNVDEVGGEALGR | 399 |
| HBB_HUMAN | EFTPPVQAAYQK | 400 |
| HBB_HUMAN | GTFATLSELHCDK | 401 |
| HPT_HUMAN | VGYVSGWGR | 402 |
| HPT_HUMAN | VTSIQDWVQK | 403 |
| HPT_HUMAN | VVLHPNYSQVDIGLIK | 404 |
| HPT_HUMAN | DYAEVGR | 405 |
| HPT_HUMAN | HYEGSTVPEK | 406 |
| IBP4_HUMAN | THEDLYIIPIPNCDR | 407 |
| IBP4_HUMAN | LAASQSR | 408 |
| IBP4_HUMAN | EDARPVPQGSCQSELHR | 409 |
| IBP4_HUMAN | NGNFHPK | 410 |
| IBP6_HUMAN | APAVAEENPK | 411 |
| IBP6_HUMAN | HLDSVLQQLQTEVYR | 412 |
| IBP6_HUMAN | GAQTLYVPNCDHR | 413 |
| IBP6_HUMAN | LLPPLLLLLALLLAASPGGALAR | 414 |
| IBP6_HUMAN | DDEAPLR | 415 |
| IBP6_HUMAN | ESKPQAGTARPQDVNR | 416 |
| ICT1_HUMAN | LGELILTSESSR | 417 |
| ICT1_HUMAN | QADSDIPLDR | 418 |
| ICT1_HUMAN | FHLATAEWIAEPVR | 419 |
| ICT1_HUMAN | LYPESQGSDTAWR | 420 |
| ICT1_HUMAN | SSGPGGQNVNK | 421 |
| IGHG1_HUMAN | TPEVTCVVVDVSHEDPEVK | 422 |
| IL6_HUMAN | EALAENNLNLPK | 423 |
| IL6_HUMAN | EFLQSSLR | 424 |
| IL6_HUMAN | FESSEEQAR | 425 |
| IL6_HUMAN | IITGLLEFEVYLEYLQNR | 426 |
| IL6_HUMAN | LQAQNQWLQDMTTHLILR | 427 |
| IL6_HUMAN | NLDAITTPDPTTNASLLTK | 428 |
| IL6_HUMAN | QPLTSSER | 429 |
| IL6_HUMAN | YILDGISALR | 430 |
| IL6_HUMAN | DGCFQSGFNEETCLVK | 431 |

TABLE 2B-continued

| Protein | signature peptide | SEQ ID NO. |
|---|---|---|
| IL6_HUMAN | VLIQFLQK | 432 |
| IMA2_HUMAN | LLGASELPIVTPALR | 433 |
| IMA2_HUMAN | TGVVPQLVK | 434 |
| IMA2_HUMAN | IILVILDAISNIFQAAEK | 435 |
| IMA2_HUMAN | ASLSLIEK | 436 |
| IMA2_HUMAN | NNQGTVNWSVDDIVK | 437 |
| IPSP_HUMAN | FSIEGSYQLEK | 438 |
| IPSP_HUMAN | VVGVPYQGNATALFILPSEGK | 439 |
| IPSP_HUMAN | MQILEGLGLNLQK | 440 |
| ITIH2_HUMAN | VQSTITSR | 441 |
| ITIH2_HUMAN | NDLISATK | 442 |
| ITIH2_HUMAN | TILDDLR | 443 |
| ITIH2_HUMAN | VQFELHYQEVK | 444 |
| EFC14_HUMAN | AFDSDGDGR | 445 |
| EFC14_HUMAN | YSFLELR | 446 |
| EFC14_HUMAN | FSQFLGDPVEK | 447 |
| EFC14_HUMAN | LTYQEIWTSLGSAMPEPESLR | 448 |
| EFC14_HUMAN | SAADLISLPTTVEGLQK | 449 |
| EFC14_HUMAN | QISLLTSAVNHLK | 450 |
| K1C17_HUMAN | ALEEANTELEVK | 451 |
| K1C17_HUMAN | LSVEADINGLRR | 452 |
| K1C17_HUMAN | TIEELQNK | 453 |
| K1C17_HUMAN | ASLEGNLAETENR | 454 |
| K1C17_HUMAN | TIVEEVQDGK | 455 |
| K1C19_HUMAN | FGPGVAFR | 456 |
| K1C19_HUMAN | ALEAANGELEVK | 457 |
| KV201_HUMAN | SSQSLLDSGDGNTYLNWYLQK | 458 |
| KV201_HUMAN | VQAEDVGVYYCMQR | 459 |
| LAMP1_HUMAN | TVESITDIR | 460 |
| LAMP1_HUMAN | AFSVNIFK | 461 |
| LAMP1_HUMAN | ENTSDPSLVIAFGR | 462 |
| LAMP1_HUMAN | NMTFDLPSDATVVLNR | 463 |
| LYAG_HUMAN | VTSEGAGLQLQK | 464 |
| LYAG_HUMAN | STGGILDVYIFLGPEPK | 465 |
| LYAG_HUMAN | GTRPFVISR | 466 |
| LYAG_HUMAN | YEVPLETPHVHSR | 467 |
| MASP2_HUMAN | TDDIGTASGWGLTQR | 468 |
| MIME_HUMAN | ESAYLYAR | 469 |
| MIME_HUMAN | LEGNPIVLGK | 470 |
| MIME_HUMAN | LTLFNAK | 471 |
| MIME_HUMAN | HPNSFICLK | 472 |
| MMP9_HUMAN | FQTFEGDLK | 473 |
| MMP9_HUMAN | LGLGADVAQVTGALR | 474 |
| MMP9_HUMAN | QLSLPETGELDSATLK | 475 |
| MMP9_HUMAN | QSTLVLFPGDLR | 476 |
| MMP9_HUMAN | SYSACTTDGR | 477 |
| MTA2_HUMAN | DISSSLNSLADSNAR | 478 |
| MTA2_HUMAN | LVEGESDNR | 479 |
| MTA2_HUMAN | TLLADQGEIR | 480 |
| MTA2_HUMAN | QFESLPATHIR | 481 |
| MTA2_HUMAN | VGDYVYFENSSSNPYLVR | 482 |
| MTA2_HUMAN | EFEEESKQPGVSEQQR | 483 |
| MUC5B_HUMAN | LTPLQFGNLQK | 484 |
| MUC5B_HUMAN | TGLLVEQSGDYIK | 485 |
| MUC5B_HUMAN | LFVESYELILQEGTFK | 486 |
| MUC5B_HUMAN | SVVGDALEFGNSWK | 487 |
| NDC80_HUMAN | ELLNETEEEINK | 488 |
| NDC80_HUMAN | LFLDYTIK | 489 |
| NDC80_HUMAN | LQNIIDNQK | 490 |
| NDC80_HUMAN | NELQQTINK | 491 |
| NDC80_HUMAN | NSQLGIFSSSEK | 492 |
| NHRF1_HUMAN | QHGDVVSAIR | 493 |
| NHRF1_HUMAN | SVDPDSPAEASGLR | 494 |
| NHRF1_HUMAN | GPNGYGFHLHGEK | 495 |
| NHRF1_HUMAN | LVEPGSPAEK | 496 |
| NHRF1_HUMAN | EALAEAALESPRPALVR | 497 |
| NHRF1_HUMAN | IVEVNGVCMEGK | 498 |
| PDGFA_HUMAN | EEDTGRPR | 499 |
| PGFRB_HUMAN | SDHPAILR | 500 |
| PGFRB_HUMAN | GFSGIFEDR | 501 |
| PGFRB_HUMAN | LLGEVGTLQFAELHR | 502 |
| PGFRB_HUMAN | EVDSDAYYVYR | 503 |
| PGFRB_HUMAN | LVEPVTDFLLDMPYHIR | 504 |
| PGS1_HUMAN | DLPETLNELHLDHNK | 505 |
| PGS1_HUMAN | GLQHLYALVLVNNK | 506 |
| PGS1_HUMAN | WQCSDLGLK | 507 |

TABLE 2B-continued

| Protein | signature peptide | SEQ ID NO. |
|---|---|---|
| PGS1_HUMAN | VPSGLPDLK | 508 |
| PLK1_HUMAN | HINPVAASLIQK | 509 |
| PLK1_HUMAN | LGNLFLNEDLEVK | 510 |
| PLK1_HUMAN | LILYNDGDSLQYIER | 511 |
| PLK1_HUMAN | FSIAPSSLDPSNR | 512 |
| PLK1_HUMAN | IGDFGLATK | 513 |
| PLK1_HUMAN | AGANITPR | 514 |
| PLK1_HUMAN | GLENPLPERPR | 515 |
| PLTP_HUMAN | MHAAFGGTFK | 516 |
| PRDX1_HUMAN | DISLSDYK | 517 |
| PRDX1_HUMAN | ADEGISFR | 518 |
| PRDX1_HUMAN | ATAVMPDGQFK | 519 |
| PRDX1_HUMAN | QGGLGPMNIPLVSDPK | 520 |
| PRDX1_HUMAN | TIAQDYGVLK | 521 |
| PRDX1_HUMAN | IGHPAPNFK | 522 |
| PRDX1_HUMAN | LVQAFQFTDK | 523 |
| PRDX4_HUMAN | DYGVYLEDSGHTLR | 524 |
| PRDX4_HUMAN | IPLLSDLTHQISK | 525 |
| PRDX4_HUMAN | VSVADHSLHLSK | 526 |
| PRDX4_HUMAN | LVQAFQYTDK | 527 |
| PRDX4_HUMAN | QITLNDLPVGR | 528 |
| PRDX4_HUMAN | ISKPAPYWEGTAVIDGEFK | 529 |
| PRDX4_HUMAN | QGGLGPIR | 530 |
| PROF1_HUMAN | STGGAPTFNVTVTK | 531 |
| PROF1_HUMAN | TLVLLMGK | 532 |
| PROF1_HUMAN | DSPSVWAAVPGK | 533 |
| PROF1_HUMAN | TFVNITPAEVGVLGK | 534 |
| PROF1_HUMAN | SSFYVNGLTLGGQK | 535 |
| PROF1_HUMAN | DSLLQDGEFSMDLR | 536 |
| PTGDS_HUMAN | AQGFTEDTIVFLPQTDK | 537 |
| PTGDS_HUMAN | SVVAPATDGGLNLTSTFLR | 538 |
| PTGDS_HUMAN | WFSAGLASNSSWLR | 539 |
| PTGDS_HUMAN | TMLLQPAGSLGSYSYR | 540 |
| PTX3_HUMAN | ALAAVLEELR | 541 |
| PTX3_HUMAN | LTSALDELLQATR | 542 |
| PTX3_HUMAN | ETGGAESCHIR | 543 |
| PTX3_HUMAN | TILFSYGTK | 544 |
| RAI3_HUMAN | AHAWPSPYK | 545 |
| RAI3_HUMAN | TNVNVFSELSAPR | 546 |
| RAI3_HUMAN | SYGVENR | 547 |
| RAI3_HUMAN | AYSQEEITQGFEETGDTLYAPYSTHFQLQNQPPQK | 548 |
| RAI3_HUMAN | MATTVPDGCR | 549 |
| RAI3_HUMAN | FFLFGILFSICFSCLLAHAVSLTK | 550 |
| RALA_HUMAN | QVSVEEAK | 551 |
| RALA_HUMAN | SDLEDKR | 552 |
| RAP2A_HUMAN | VPVILVGNK | 553 |
| RAP2A_HUMAN | VDLESER | 554 |
| RAP2A_HUMAN | YEKVPVILVGNK | 555 |
| RAP2B_HUMAN | ASVDELFAEIVR | 556 |
| RAP2B_HUMAN | SALTVQFVTGSFIEK | 557 |
| RAP2B_HUMAN | EVSYGEGK | 558 |
| RASN_HUMAN | QAHELAK | 559 |
| RASN_HUMAN | TGEGFLCVFAINNSK | 560 |
| RETN_HUMAN | AISSIGLECQSVTSR | 561 |
| RETN_HUMAN | GDLATCPR | 562 |
| RETN_HUMAN | TLCSMEEAINER | 563 |
| RETN_HUMAN | AETTCHCQCAGMDWTGAR | 564 |
| S10A6_HUMAN | ELTIGSK | 565 |
| S10A6_HUMAN | MACPLDQAIGLLVAIFHK | 566 |
| S10A9_HUMAN | VIEHIMEDLDTNADK | 567 |
| S10A9_HUMAN | LTWASHEK | 568 |
| S10A9_HUMAN | QLSFEEFIMLMAR | 569 |
| S10A9_HUMAN | NIETIIINTFHQYSVK | 570 |
| SODC_HUMAN | GDGPVQGIINFEQK | 571 |
| SODC_HUMAN | HVGDLGNVTADK | 572 |
| SODC_HUMAN | LACGVIGIAQ | 573 |
| SODC_HUMAN | DGVADVSIEDSVISLSGDHCIIGR | 574 |
| SORL_HUMAN | ASNLLLGFDR | 575 |
| SORL_HUMAN | NLLVNTLYTVR | 576 |
| SORL_HUMAN | YSTNEGETWK | 577 |
| SORL_HUMAN | NLQLSLPR | 578 |
| SPRC_HUMAN | NVLVTLYER | 579 |
| SPRC_HUMAN | YIPPCLDSELTEFPLR | 580 |
| SPRC_HUMAN | LEAGDHPVELLAR | 581 |
| SPRC_HUMAN | LHLDYIGPCK | 582 |
| SYUG_HUMAN | EQANAVSEAVVSSVNTVATK | 583 |

TABLE 2B-continued

| Protein | signature peptide | SEQ ID NO. |
|---|---|---|
| SYUG_HUMAN | TVEEAENIAVTSGVVR | 584 |
| SYUG_HUMAN | ENVVQSVTSVAEK | 585 |
| SYUG_HUMAN | EGVVGAVEK | 586 |
| SYUG_HUMAN | EEVAEEAQSGGD | 587 |
| TERA_HUMAN | DVDLEFLAK | 588 |
| TERA_HUMAN | EVDIGIPDATGR | 589 |
| TERA_HUMAN | LDQLIYIPLPDEK | 590 |
| TERA_HUMAN | LEILQIHTK | 591 |
| TGFB1_HUMAN | DNTLQVDINGFTTGR | 592 |
| TGFB1_HUMAN | VEQHVELYQK | 593 |
| TGFB1_HUMAN | GGEIEGFR | 594 |
| TGFB1_HUMAN | VAGESAEPEPEPEADYYAK | 595 |
| TGFB1_HUMAN | EAVPEPVLLSR | 596 |
| TGFR1_HUMAN | IELPTTVK | 597 |
| TNFA_HUMAN | DLSLISPLAQAVR | 598 |
| TNFA_HUMAN | IAVSYQTK | 599 |
| TNFA_HUMAN | ANALLANGVELR | 600 |
| TNFA_HUMAN | DNQLVVPSEGLYLIYSQVLFK | 601 |
| TRBM_HUMAN | EVVLQHVR | 602 |
| TRBM_HUMAN | SSVAADVISLLLNGDGGVGR | 603 |
| TRBM_HUMAN | CQCPAGAALQADGR | 604 |
| TRBM_HUMAN | GHLMTVR | 605 |
| TRBM_HUMAN | LWIGLQLPPGCGDPK | 606 |
| TRBM_HUMAN | GFQWVTGDNNTSYSR | 607 |
| TRFE_HUMAN | YLGEEYVK | 608 |
| TRFE_HUMAN | DSAHGFLK | 609 |
| TSP1_HUMAN | FVFGTTPEDILR | 610 |
| TSP1_HUMAN | QHWSVEEALLATGQWK | 611 |
| TSP1_HUMAN | GTSQNDPNWVVR | 612 |
| TSP1_HUMAN | SITLFVQEDR | 613 |
| VDAC1_HUMAN | LTFDSSFSPNTGK | 614 |
| VDAC1_HUMAN | VNNSSLIGLGYTQTLKPGIK | 615 |
| VDAC1_HUMAN | LTLSALLDGK | 616 |
| VDAC1_HUMAN | VTQSNFAVGYK | 617 |
| VDAC1_HUMAN | YQIDPDACFSAK | 618 |

Further signature peptides are listed in table 2C.

TABLE 2C

| Protein | signature peptide | SEQ ID NO. |
|---|---|---|
| LG3BP_HUMAN | ALGFEDATQALGR | 905 |
| LG3BP_HUMAN | GLDLTEDTYKPR | 906 |
| TRFE_HUMAN | QQQHLFGSDVTDCSGNFCLFR | 907 |
| UROM_HUMAN | QDFDITDISLLEHR | 908 |
| UROM_HUMAN | DETHATYSNTLYLADEIIIR | 909 |
| NDKA_HUMAN | DRPFFAGLVK | 910 |
| LG3BP_HUMAN | AAIPSALDTDSSK | 911 |
| CD44_HUMAN | DPDHSEGSTTLLEGYTSHYPHTK | 912 |
| HBB_HUMAN | ISHELDSASSEVNSAVTALWGK | 913 |
| ALDOA_HUMAN | ADDGR | 914 |
| ALDOA_HUMAN | PFPQVIK | 915 |
| FIBG_HUMAN | IRPFFPQQIHLISTQSAIPYALR | 916 |
| HBB_HUMAN | LLGNVLVCVLAHHFGK | 917 |
| TSP1_HUMAN | AQGYSGLSVK | 918 |
| ES8L2_HUMAN | SVSCPLLSR | 919 |
| PTHR_HUMAN | FGSDDEGR | 920 |
| MAGD1_HUMAN | IPFTFWAR | 921 |
| ANAG_HUMAN | QLYLQHR | 922 |
| ANAG_HUMAN | NVFQLEQAFVLSK | 923 |
| CADH3_HUMAN | NQHTLYVEVTNEAPFVLK | 924 |
| CADH3_HUMAN | GLEARPEVVLR | 925 |
| ES8L1_HUMAN | AQPDVHFFQGLR | 926 |
| MIME_HUMAN | LSLLEELSLAENQLLK | 927 |
| NDC80_HUMAN | YSVADIER | 928 |
| RAP2B_HUMAN | VVVLGSGGVGK | 929 |
| PGFRB_HUMAN | YGDLVDYLHR | 930 |
| SBP1_HUMAN | GGPVQVLEDEELK | 931 |
| SODC_HUMAN | TLVVHEK | 932 |
| SPRC_HUMAN | TFDSSCHFFATK | 933 |
| TGFB1_HUMAN | YSNNSWR | 934 |

In a preferred embodiment, the signature peptides are selected not to display miscleavage, to be devoid of methionine and preferably to be detectable by MS/MS.

It is particularly preferred to select signature peptides which have been previously detected and identified by MS/MS.

In a preferred embodiment, the signature peptides are selected from the group consisting of SEQ ID NO.: 290, 291, 295, 296, 297, 298, 301, 302, 305, 306, 307, 308, 311, 312, 313, 314, 326, 327, 328, 331, 332, 336, 337, 343, 345, 350, 351, 365, 367, 368, 369, 370, 372, 373, 381, 382, 387, 388, 389, 390, 391, 393, 394, 395, 397, 398, 399, 400, 402, 403, 404, 411, 412, 414, 418, 433, 434, 435, 436, 438, 439, 441, 447, 450, 453, 454, 455, 456, 461, 462, 464, 468, 473, 474, 475, 476, 477, 481, 484, 485, 489, 490, 494, 495, 496, 501, 502, 505, 513, 518, 519, 522, 523, 527, 531, 533, 534, 537, 538, 539, 557, 568, 569, 570, 571, 575, 576, 577, 578, 584, 586, 588, 594, 598, 599, 602, 603, 607, 608, 609, 610, 611, 615, 616, 287, 288, 289, 292, 293, 294, 300, 303, 304, 309, 310, 315, 316, 318, 319, 320, 321, 322, 323, 324, 325, 329, 330, 333, 334, 338, 339, 340, 341, 346, 347, 352, 354, 357, 358, 361, 362, 363, 364, 366, 375, 376, 377, 378, 379, 384, 385, 386, 392, 396, 401, 405, 406, 407, 409, 413, 415, 416, 419, 420, 421, 422, 429, 430, 431, 437, 440, 442, 443, 444, 448, 452, 457, 458, 460, 463, 465, 466, 467, 469, 470, 471, 472, 486, 487, 491, 492, 497, 499, 503, 504, 506, 507, 508, 529, 535, 536, 540, 541, 542, 543, 544, 551, 554, 558, 560, 561, 562, 563, 565, 566, 572, 573, 580, 581, 585, 587, 589, 590, 591, 593, 595, 596, 600, 604, 605, 612, 613, 617 and 618.

These signature peptides are particularly suited for detection by mass spectrometry.

In a further preferred embodiment, the signature peptides are selected from the group consisting of SEQ ID NO.: 290, 291, 295, 296, 297, 298, 301, 302, 305, 306, 307, 308, 311, 312, 313, 314, 326, 327, 328, 331, 332, 336, 337, 343, 345, 350, 351, 365, 367, 368, 369, 370, 372, 373, 381, 382, 387, 388, 389, 390, 391, 393, 394, 395, 397, 398, 399, 400, 402, 403, 404, 411, 412, 414, 418, 433, 434, 435, 436, 438, 439, 441, 447, 450, 453, 454, 455, 456, 461, 462, 464, 468, 473, 474, 475, 476, 477, 481, 484, 485, 489, 490, 494, 495, 496, 501, 502, 505, 513, 518, 519, 522, 523, 527, 531, 533, 534, 537, 538, 539, 557, 568, 569, 570, 571, 575, 576, 577, 578, 584, 586, 588, 594, 598, 599, 602, 603, 607, 608, 609, 610, 611, 615 and 616.

These signature peptides are best suited for detection by mass spectrometry.

In a preferred embodiment, the signature peptides are concatenated into an artificial protein. To do so, the signature peptides are consecutively joined into a polypeptide e.g. by use of the QconCAT technology (Pratt et al., 2006). The order of the joined signature peptides within the artificial protein may vary to improve the expression yield of the artificial protein.

In a further aspect, the invention relates to an artificial protein comprising signature peptides representing at least 10 proteins selected from group 1, wherein each signature peptide represents a single protein, and consecutive signature peptides are separated by a cleavage sequence. Using the QconCAT technology, individual signature peptides are combined into a polypeptide, wherein each signature peptide is separated from the subsequent signature peptide by a cleavage site for a protease. For use, e.g. as an internal reference standard, the polypeptide is digested into the single signature peptides. In case the standard is used together with a sample, the polypeptide may be digested beforehand and the digest added to the sample, or the polypeptide may be added to the sample such that the sample and the polypeptide are digested together. The latter is particularly preferred as the digest condition will be identical for both, the standard and the sample, such that the signature peptides and the peptides derived from the proteins of interest are expected to be digested with a similar efficiency. For example, the signature peptides may be selected to terminate with a lysine residue, such that enzymatic digest by the two most common enzymes, i.e. endoprotease Lys-C and trypsin, is possible. An artificial protein comprising signature peptides comprises about 10 to 70 signature peptides, preferably about 30-70 signature peptides, further preferred about 30 to 50 signature peptides, but may include as much as 100 signature peptides. For covering even more signature peptides, e.g. for analyzing a sample for the entire panel of biomarker proteins, two or three or even more different artificial proteins may be used in combination.

In a preferred embodiment, the artificial protein comprises each signature peptide in a stoichiometry of 1:1. In case loss of protein occurs during storage, the signature peptides will still remain in the 1:1 stoichiometry prior to digestion, such that all signature peptides will be comprised in the same amount.

In a preferred embodiment, the artificial protein further comprises a peptide located at the N-terminus, which comprises a methionine initiator residue. Thereby, the polypeptide may be prepared by heterologous expression in E. coli.

In a preferred embodiment, the artificial protein further comprises a peptide located at the C-terminus, which comprises a His tag. This allows for high purity preparations of the polypeptide and subsequent quantification by amino acid analysis.

In a preferred embodiment, the cleavage sequence is cleaved by a protease, preferably by trypsin. When provided as a polypeptide (artificial protein), the signature peptides are preferably separated by the cleavage site of a single proteolytic enzyme. Moreover, since the signature peptides correspond to native proteolytic peptides, the proteolytic enzyme is preferably a prevalent one recognizing a protease cleavage site comprised in most proteins such as trypsin or lysine-C.

In a further aspect, the invention relates to a nucleic acid construct encoding the artificial protein of the invention. The construct is suitable to be introduced into a cell such that the cell expresses the artificial protein. To achieve this, the construct may be included into a plasmid, which is then introduced into a cell, e.g. by transformation. The cell then expresses the polypeptide, which can be purified from the cell's lysate.

In a further aspect, the invention relates to a cell, preferably a bacterial cell, comprising a nucleic acid construct of the invention. Such cells may be cultured in industrial scale to produce the artificial protein comprising the signature peptides.

In a further aspect, the invention relates to a collection of signature peptides representing at least 3, preferably 5, proteins selected from group 2 for use in determining an initial occurrence of bladder cancer, wherein each signature peptide represents a single protein.

In a further aspect, the invention relates to a collection of signature peptides representing at least 10, preferably at least 15, proteins selected from group 3 consisting for use in determining the risk of progression and recurrence of an initial occurrence of bladder cancer, wherein each signature peptide represents a single protein.

In a further aspect, the invention relates to a collection of signature peptides representing at least 3, preferably at least 5, proteins selected from group 4 for use in determining a recurrence of bladder cancer, wherein each signature peptide represents a single protein.

In a further aspect, the invention relates to a collection of signature peptides representing at least 3, preferably at least 5, proteins selected from group 5 for use in determining the risk of progression and recurrence of a relapsed bladder cancer, wherein each signature peptide represents a single protein.

The study underlying the invention revealed distinct proteins which are differentially present in the urine of patients facing an initial occurrence of bladder cancer (group 2) or a recurrence of bladder cancer after resection of the primary tumor (group 3) as well as proteins differentially present in the urine of patients having an increased risk of progression and recurrence of an initial bladder cancer (group 4) or a bladder cancer relapse (group 5). Thus, detection and quantification of the respective proteins derived from a urine sample of a patient, e.g. by mass spectrometric methods using signature peptides as internal standards, is not only suitable for diagnosing bladder cancer but also for evaluating the risk of a bladder cancer to progress or re-occur.

In a preferred embodiment, the bladder cancer is an urothelial bladder cancer.

In a preferred embodiment, the collection of signature peptides is used as an internal reference standard as described above.

In a preferred embodiment, the collection of signature peptides is used to quantify the proteins in a urine sample as described above.

In a further aspect, the invention relates to a collection of at least 10 proteins selected from group 1 for use in cancer diagnosis and/or prognosis, wherein the cancer is of a urinary tract or organ.

In a further aspect, the invention relates to an in vitro method for cancer diagnosis and/or prognosis comprising the step of analyzing at least 10 proteins in a urine sample of a subject, wherein the cancer is of a urinary tract or organ and the proteins are selected from group 1. From the comprehensive study evaluating 134 proteins, which were suggested to be associated with bladder cancer, and from a preceding analysis, 81 proteins were identified as significantly differentially present in the urine of patients and healthy persons (Table 1A). In a second study, 41 further proteins were identified which are also significantly differentially present in the urine of bladder cancer patients and healthy persons (Table 1B). Accordingly, detection and quantification of these proteins are distinctly suitable for diagnosis of cancer of a tissue or organ of the urinary tract, which are likely to release proteins into the urine. Moreover, different amounts of the identified proteins of Table 1A could be specifically related with distinct stages of the development of bladder cancer, namely an initial occurrence of bladder cancer, a recurrence of bladder cancer as well as the risk of bladder cancer progression and relapse after primary tumor resection. Thus, by analyzing the presence and/or amount of the identified proteins within a urine sample provides a fast and easy method for bladder cancer diagnosis and prognosis. The term "analyzing" as used herein refers to detecting the presence as well as determining the quantity of one or several proteins within a sample. The detection or quantification of the diverse proteins can be carried out by the use of various techniques. For example, antibodies binding to the proteins can be used to specifically detect each protein and, given a respective labelling of the antibody, quantify them by standard techniques (e.g. enzyme-linked immunosorbent assay—ELISA). More recently, however, mass spectrometry techniques gain increasing importance in diagnostic procedures. Due to modern devices allowing fast and reliable results, as well as software programs for immediate interpretation, mass spectrometry has become available for standard procedures, e.g. as capillary electrophoreses coupled with mass spectrometry. Preferred mass spectrometry techniques include SRM, time-scheduled SRM and PRM. Likewise, methods based on peptide arrays or data independent acquisition (DIA) mass spectrometry-based proteomics may be employed.

In a preferred embodiment, at least 15, preferably at least 20, more preferred at least 30 proteins are analyzed.

In a preferred embodiment, the cancer of the urinary tract or organ is a bladder cancer, preferably an urothelial bladder cancer.

In a further aspect, the invention relates to a method for determining the initial occurrence of bladder cancer, comprising the step of analyzing at least 3, preferably 5, proteins in a urine sample, wherein the proteins are selected from group 2.

In a further aspect, the invention relates to a method for determining the risk of progression and recurrence of an initial occurrence of bladder cancer, comprising the step of analyzing at least 10, preferably at least 15, proteins in a urine sample, wherein the proteins are selected from group 3.

In a further aspect, the invention relates to a method for determining the recurrence of bladder cancer, comprising the step of analyzing at least 3, preferably at least 5, proteins in a urine sample, wherein the proteins are selected from group 4.

In a further aspect, the invention relates to a method for determining the risk of progression and recurrence of a relapsed bladder cancer, comprising the step of analyzing at least 3, preferably at least 5, proteins in a urine sample, wherein the proteins are selected from group 5.

In a preferred embodiment, analyzing the proteins comprises quantifying the level of each protein in the urine sample and comparing the level of each protein with a reference value. With the exception of Ras-related protein Ral-A (RalA), all proteins were present in the urine of healthy persons, patients with the risk of developing cancer and patients experiencing initial or recurrence of bladder cancer. This may be explained by the fact that urothelial bladder cancer mainly involves cell types, which are already physiologically located in the bladder and not infiltrating from other origins. Thus, for the interpretation of test results and obtaining a diagnosis, the quantities of biomarker proteins detected within the urine sample of a patient are preferably compared to standardized reference values. Due to certain variability of the concentrations of the biomarker proteins beyond the healthy population, the reference value is preferably determined by a comprehensive survey of the healthy population.

Accordingly, in a preferred embodiment, the reference value is the level of protein expected to be contained in a urine sample of a healthy subject.

In a preferred embodiment, the reference value is the level of protein contained in a previous urine sample of the subject. Alternatively or in addition to the standardized reference value, the amount of biomarker protein detected in the sample of a patient may be compared to the amount of biomarker protein detected in a previous sample of the same patient. This could be of particular interest for patients with high risk of developing bladder cancer such as hard smokers or patients monitored for a relapse after primary tumor resection. As the risk of relapse is rather high for bladder cancer, close monitoring is needed after surgery. This could be facilitated by comparing the values of biomarker proteins contained in urine sampies collected throughout the monitoring, which would reveal continued alterations in the composition of the urine. Such data could provide additional information on changes of the health status of the patient.

In a preferred embodiment, an increased level of one or more proteins selected from the group consisting of

CLUS_HUMAN
K1C19_HUMAN
S10A6_HUMAN
TSP1_HUMAN
UROM_HUMAN indicates an initial occurrence of bladder cancer.

In a preferred embodiment, an increased level of one or more proteins selected from the group consisting of

| | |
|---|---|
| A1AT_HUMAN | IGF2_HUMAN |
| A2MG_HUMAN | IGHG1_HUMAN |
| AK1C4_HUMAN | ITIH2_HUMAN |
| ALDOA_HUMAN | ITIH4_HUMAN |
| APOA1_HUMAN | K1C19_HUMAN |
| APOA4_HUMAN | LDHA_HUMAN |
| BIRC5_HUMAN | MUC5B_HUMAN |
| C4BPA_HUMAN | NF2L2_HUMAN |
| CERU_HUMAN | NID2_HUMAN |
| CO3_HUMAN | PLTP_HUMAN |
| FCN3_HUMAN | PTX3_HUMAN |
| FIBB_HUMAN | SORL_HUMAN |
| FIBG_HUMAN | TERA_HUMAN |
| IBP4_HUMAN | TSP1_HUMAN |
| | VTDB_HUMAN | and/or a reduced level of one or more proteins selected from the group consisting of

| |
|---|
| MIME_HUMAN |
| PPAP_HUMAN |
| RETN_HUMAN | indicates an increased risk for progression and recurrence of an initial bladder cancer.

In a preferred embodiment, an increased level of one or more proteins selected from the group consisting of

| |
|---|
| RALA_HUMAN |
| TNFA_HUMAN | and/or a reduced level of one or more proteins selected from the group consisting of

| |
|---|
| AMPN_HUMAN |
| CD44_HUMAN |
| DPP4_HUMAN |
| LAMA4_HUMAN |
| LAMP1_HUMAN |
| LAMP2_HUMAN |
| LYAG_HUMAN |
| ZA2G_HUMAN | indicates a recurrence of bladder cancer.

In a preferred embodiment, an increased level of one or more proteins selected from the group consisting of

| |
|---|
| LTOR3_HUMAN |
| TNFA_HUMAN | and/or a reduced level of one or more proteins selected from the group consisting of

| | |
|---|---|
| ANAG_HUMAN | IBP7_HUMAN |
| CBPE_HUMAN | KLK3_HUMAN |
| CO6A1_HUMAN | KNG1_HUMAN |
| EGF_HUMAN | LG3BP_HUMAN |
| GGH_HUMAN | OSTP_HUMAN | indicates an increased risk of progression and/or recurrence of a relapsed bladder cancer.

In a preferred embodiment, each protein is analyzed using mass spectrometry, preferably Selected Reaction Monitoring (SRM), more preferred time-scheduled SRM, or Parallel Reaction Monitoring (PRM). For analyzing, in particular for quantifying, proteins in a urine sample, mass spectrometry techniques such as SRM, time-scheduled SRM or PRM are particularly suited. SRM, also refer to as "Multiple Reaction Monitoring" (MRM), provides a targeted mass spectrometric approach using tandem quadrupole mass spectrometers (QqQ). For analyses, the first quadrupole mass analyzer admits a single m/z value, namely that of the ionized target peptide (precursor) to the collision cell. In the collision cell, the precursor ion is fragmented by (low energy) collision-induced dissociation (CID) to generate specific product ions. The second quadrupole mass analyzer is then also fixed on one or more m/z value(s), namely the m/z value of the product ion(s), such that only the specific product ion(s) derived from the predefined precursor ion will have a stable trajectory to the detector. The two levels of m/z selection result in a high selectivity, a low background signal and a high duty cycle, which together provide the significant advantages of SRM. Since a peptide to be detected needs to satisfy the m/z value of the first quadrupole and the generated product must correspond to the m/z value of the second quadrupole, even co-eluting peptides may be distinguished, because they will be recognized by their different product ions (Holman et al., 2012). PRM provides a further developed MS technique using quadrupole-equipped high resolution and accurate mass instruments. In PRM instruments, the third quadrupole of the triple quadrupole is substituted with a high resolution and accurate mass analyzer. This enables the parallel detection of all target product ions in one single analysis. Therefore, PRM provides quantitative data over an even wider dynamic range than SRM. Moreover, multiplexed PRM additionally allows the detection of product ions of several targeted peptides in one single scan (Peterson et al., 2012).

In a further aspect, the invention relates to an immunoassay product comprising antibodies for detecting at least 10 proteins selected from group 1. Alternatively to mass spectrometric analysis, the biomarker proteins may be detected and quantified using antibody based techniques. The antibodies are selected such that each antibody is directed against one of the at least 10 proteins of group 1. They may be compiled in an immunoassay product such as an ELISA assay product or a microarray. For example, the antibodies may be immobilized onto solid surface, for example a chip, a multi-well plate or beads, where they can be easily contacted with the sample to be tested and the non-bound remnants of the sample removed by washing if necessary. Such immunoassay products allow a fast and specific detection suitable to be implemented in standard diagnostic processes.

In a preferred embodiment, the immunoassay product is a microarray, a beadbased assay product, an ELISA plate or a lateral flow test. Microarrays and beadbased assay products are particularly preferred for detecting the presence of a multitude of different proteins, because they allow the simultaneous use and specific readout of many antibodies directed against different proteins. Likewise, ELISA plates, usually multi-well or microtiter plates, allow a simultaneous testing of a substantial number of different antibodies. Lateral flow tests, in contrast, provide a particular fast readout, however, usually cover only one or few different antibodies. Depending on the number of proteins to be detected and the time available, different immunoassay products may be advantageous. All of these assays are fully established standard methods allowing a sensitive and fast readout of antibody-antigen interaction. Moreover, readout systems have been developed, in particular for microarrays and ELISA, which allow a fast and fully automated analysis.

In a further aspect, the invention relates to a second collection of signature peptides and/or reference peptides representing at least 10 proteins selected from the group 1 for use in cancer diagnosis and/or prognosis, wherein the cancer is of a urinary tract or organ, each signature peptide represents a single protein and each reference peptide represents two or more isoforms and/or homologs of a protein.

Each signature peptide is unique to one biomarker protein. In contrast, a reference peptide represents two or more isoforms and/or homologs of a given biomarker protein. Accordingly, the amino acid sequence of the reference peptide corresponds to a part of the protein of interest, wherein the sequence is also present in at least one isoform or homolog of the protein of interest. Like the signature peptides, the reference peptides can be used as isolated peptides and are preferably used for determining the presence and the amount of proteins by mass spectrometry methods, for example Selected Reaction Monitoring (SRM), time-scheduled SRM or Parallel Reaction Monitoring (PRM). For the selection of reference peptides, the same methods and criteria as for signature peptides may be applied.

The collection of signature peptides and/or reference peptides allows the analysis and quantification of distinct proteins that have been found to provide a reliable and accurate diagnosis and prognosis for bladder cancer from urine samples.

Reference peptides which represents two or more homologs of a protein are shown in table 3A. Reference peptides which represents two or more isoforms and homologs of a protein are shown in table 3B. Reference peptides which represents two or more isoforms of a protein are shown in table 3C.

TABLE 3A

| Protein | reference peptide | SEQ ID NO. |
|---|---|---|
| AK1C4_HUMAN | EDIFYTSK | 619 |
| AK1C4_HUMAN | LAIEAGFR | 620 |
| PIP_HUMAN | NFDIPK | 621 |
| RALA_HUMAN | SALTLQFMYDEFVEDYEPTK | 622 |
| RALA_HUMAN | VIMVGSGGVGK | 623 |
| RAP2A_HUMAN | SALTVQFVTGTFIEK | 624 |
| RASN_HUMAN | QGVEDAFYTLVR | 625 |
| ZA2G_HUMAN | AGEVQEPELR | 626 |
| ZA2G_HUMAN | IDVHWTR | 627 |

TABLE 3B

| Protein | reference peptide | SEQ ID NO. |
|---|---|---|
| ANM1_HUMAN | GKVEEVELPVEK | 628 |
| KV201_HUMAN | FSGSGSGTDFTLK | 629 |
| NDKA_HUMAN | GDFCIQVGR | 630 |
| NDKA_HUMAN | TFIAIKPDGVQR | 631 |
| NDKA_HUMAN | VMLGETNPADSKPGTIR | 632 |
| RASK_HUMAN | LVVVGAGGVGK | 633 |
| RASK_HUMAN | QAQDLAR | 634 |
| RASK_HUMAN | SYGIPFIETSAK | 635 |
| RASK_HUMAN | TGEGFLCVFAINNTK | 636 |

TABLE 3C

| Protein | reference peptide | SEQ ID NO. |
|---|---|---|
| A1AT_HUMAN | ITPNLAEFAFSLYR | 637 |
| A1AT_HUMAN | LQHLENELTHDIITK | 638 |
| A1AT_HUMAN | LSITGTYDLK | 639 |
| A1AT_HUMAN | LYHSEAFTVNFGDTEEAK | 640 |
| A1AT_HUMAN | SVLGQLGITK | 641 |
| A1BG_HUMAN | ATWSGAVLAGR | 642 |
| AGO2_HUMAN | DGVSEGQFQQVLHHELLAIR | 643 |
| AGO2_HUMAN | DYQPGITFIVVQK | 644 |
| AGO2_HUMAN | SASFNTDPYVR | 645 |
| AGO2_HUMAN | SFTEQLR | 646 |
| AGO2_HUMAN | VELEVTLPGEGK | 647 |
| AGO2_HUMAN | VLQPPSILYGGR | 648 |
| AL1L1_HUMAN | AGLILFGNDDK | 649 |
| AL1L1_HUMAN | ANATEFGLASGVFTR | 650 |
| AL1L1_HUMAN | DLGEAALNEYLR | 651 |
| AL1L1_HUMAN | FADGDLDAVLSR | 652 |
| AL1L1_HUMAN | GAASSVLELTEAELVTAEAVR | 653 |
| AL1L1_HUMAN | GVVNVLPGSGSLVGQR | 654 |
| AL1L1_HUMAN | VLEVEDSTDFFK | 655 |
| ALDOA_HUMAN | ADDGRPFPQVIK | 656 |
| ALDOA_HUMAN | ALQASALK | 657 |
| ALDOA_HUMAN | ELSDIAHR | 658 |
| ALDOA_HUMAN | GILAADESTGSIAK | 659 |
| ALDOA_HUMAN | IGEHTPSALAIMENANVLAR | 660 |
| ALDOA_HUMAN | QLLLTADDR | 661 |
| ANGP2_HUMAN | DAPLEYDDSVQR | 662 |
| ANGP2_HUMAN | HIIQLQSIK | 663 |
| ANGP2_HUMAN | IVTATVNNSVLQK | 664 |
| ANGP2_HUMAN | QILDQTSEINK | 665 |
| ANGP2_HUMAN | QNSIIEELEK | 666 |

TABLE 3C-continued

| Protein | reference peptide | SEQ ID NO. |
|---|---|---|
| ANGP2_HUMAN | SGHTTNGIYTLTFPNSTEEIK | 667 |
| ANM1_HUMAN | ATLYVTAIEDR | 668 |
| ANM1_HUMAN | DKWLAPDGLIFPDR | 669 |
| ANM1_HUMAN | EPLVDVVDPK | 670 |
| ANM1_HUMAN | LDHVVTIIK | 671 |
| ANM1_HUMAN | NDYVHALVAYFNIEFTR | 672 |
| ANM1_HUMAN | TGFSTSPESPYTHWK | 673 |
| ATRN_HUMAN | ALYVHGGYK | 674 |
| ATRN_HUMAN | EQYAVVGHSAHIVTLK | 675 |
| ATRN_HUMAN | IDSTGNVTNELR | 676 |
| ATRN_HUMAN | LADDLYR | 677 |
| ATRN_HUMAN | LTLTPWVGLR | 678 |
| ATRN_HUMAN | SVNNVVR | 679 |
| ATRN_HUMAN | YGHSLALYK | 680 |
| BIRC5_HUMAN | EFEETAK | 681 |
| BIRC5_HUMAN | ELEGWEPDDDPIEEHK | 682 |
| BIRC5_HUMAN | MGAPTLPPAWQPFLK | 683 |
| BIRC5_HUMAN | NWPFLEGCACTPER | 684 |
| BIRC5_HUMAN | QFEELTLGEFLK | 685 |
| CAD13_HUMAN | DIQGSLQDIFK | 686 |
| CAD13_HUMAN | INENTGSVSVTR | 687 |
| CAD13_HUMAN | TLFVHAR | 688 |
| CAD13_HUMAN | VNSDGGLVALR | 689 |
| CAD13_HUMAN | YEVSSPYFK | 690 |
| CADH3_HUMAN | FTQDTFR | 691 |
| CADH3_HUMAN | IFYSITGPGADSPPEGVFAVEK | 692 |
| CADH3_HUMAN | LTVTDLDAPNSPAWR | 693 |
| CADH3_HUMAN | STGTISVISSGLDR | 694 |
| CADH3_HUMAN | YEAHVPENAVGHEVQR | 695 |
| CBPE_HUMAN | AASQPGELK | 696 |
| CBPE_HUMAN | LLIPGNYK | 697 |
| CBPE_HUMAN | LQQEDGISFEYHR | 698 |
| CBPE_HUMAN | NFPDLDR | 699 |
| CBPE_HUMAN | NSLISYLEQIHR | 700 |
| CBPE_HUMAN | SNAQGIDLNR | 701 |
| CBPE_HUMAN | YIGNMHGNEAVGR | 702 |
| CD44_HUMAN | ALSIGFETCR | 703 |
| CD44_HUMAN | EQWFGNR | 704 |
| CD44_HUMAN | FAGVFHVEK | 705 |
| CD44_HUMAN | NLQNVDMK | 706 |
| CD44_HUMAN | TEAADLCK | 707 |
| CD44_HUMAN | YGFIEGHVVIPR | 708 |
| CLUS_HUMAN | ASSIIDELFQDR | 709 |
| CLUS_HUMAN | ELDESLQVAER | 710 |
| CLUS_HUMAN | IDSLLENDR | 711 |
| CLUS_HUMAN | LFDSDPITVTVPVEVSR | 712 |
| CSPG2_HUMAN | AQCGGGLLGVR | 713 |
| CSPG2_HUMAN | ITEEFLGK | 714 |
| CSPG2_HUMAN | LLASDAGLYR | 715 |
| CSPG2_HUMAN | VSVPTHPEAVGDASLTVVK | 716 |
| CSPG2_HUMAN | YTLNFEAAQK | 717 |
| DAF_HUMAN | EIYCPAPPQIDNGIIQGER | 718 |
| DAF_HUMAN | GSQWSDIEEFCNR | 719 |
| DAF_HUMAN | LTCLQNLK | 720 |
| DAF_HUMAN | SCPNPGEIR | 721 |
| DAF_HUMAN | TSFPEDTVITYK | 722 |
| DAF_HUMAN | TTTPNAQATR | 723 |
| DAF_HUMAN | VPPTVQKPTTVNVPTTEVSPTSQK | 724 |
| EGF_HUMAN | IESSSLQGLGR | 725 |
| EGF_HUMAN | IYWVDLER | 726 |
| EGF_HUMAN | LFWIQYNR | 727 |
| EGF_HUMAN | NQVTPLDILSK | 728 |
| EGLN_HUMAN | FSFLLHFYTVPIPK | 729 |
| EGLN_HUMAN | GEVTYTTSQVSK | 730 |
| EGLN_HUMAN | GPITSAAELNDPQSILLR | 731 |
| EGLN_HUMAN | LPDTPQGLLGEAR | 732 |
| EGLN_HUMAN | TGSQDQEVHR | 733 |
| EGLN_HUMAN | TQILEWAAER | 734 |
| EGLN_HUMAN | VLPGHSAGPR | 735 |
| ES8L1_HUMAN | AAGEGLLTLR | 736 |
| ES8L1_HUMAN | APEPQLSPGSDASEVR | 737 |
| ES8L1_HUMAN | VSPDHVTLLDPASK | 738 |
| ES8L1_HUMAN | VYSQVTVQR | 739 |
| ES8L1_HUMAN | YAFSLLAR | 740 |
| ES8L2_HUMAN | ILYDFTAR | 741 |
| ES8L2_HUMAN | SQPVSQPLTYESGPDEVR | 742 |
| FCN3_HUMAN | LLGEVDHYQLALGK | 743 |
| FCN3_HUMAN | QDGSVDFFR | 744 |

TABLE 3C-continued

| Protein | reference peptide | SEQ ID NO. |
|---|---|---|
| FCN3_HUMAN | TFAHYATFR | 745 |
| FCN3_HUMAN | YAVSEAAAHK | 746 |
| FCN3_HUMAN | YGIDWASGR | 747 |
| FIBG_HUMAN | ASTPNGYDNGIIWATWK | 748 |
| FIBG_HUMAN | IHLISTQSAIPYALR | 749 |
| FIBG_HUMAN | QSGLYFIKPLK | 750 |
| FIBG_HUMAN | TSTADYAMFK | 751 |
| FIBG_HUMAN | YEASILTHDSSIR | 752 |
| GELS_HUMAN | AGALNSNDAFVLK | 753 |
| GELS_HUMAN | EVQGFESATFLGYFK | 754 |
| GELS_HUMAN | QTQVSVLPEGGETPLFK | 755 |
| GELS_HUMAN | TGAQELLR | 756 |
| GELS_HUMAN | YIETDPANR | 757 |
| IBP7_HUMAN | GEGEPCGGGGAGR | 758 |
| IBP7_HUMAN | GTCEQGPSIVTPPK | 759 |
| IBP7_HUMAN | TELLPGDR | 760 |
| IGF2_HUMAN | DVSTPPTVLPDNFPR | 761 |
| IGF2_HUMAN | FFQYDTWK | 762 |
| IGF2_HUMAN | GFYFSRPASR | 763 |
| IGF2_HUMAN | GIVEECCFR | 764 |
| IGF2_HUMAN | SCDLALLETYCATPAK | 765 |
| IL33_HUMAN | DFWLHANNK | 766 |
| IL33_HUMAN | DNHLALIK | 767 |
| IL33_HUMAN | EHSVELHK | 768 |
| IL33_HUMAN | TDPGVFIGVK | 769 |
| IL33_HUMAN | VLLSYYESQHPSNESGDGVDGK | 770 |
| ITB1_HUMAN | LKPEDITQIQPQQLVLR | 771 |
| ITB1_HUMAN | FCECDNFNCDR | 772 |
| ITB1_HUMAN | LLVFSTDAGFHFAGDGK | 773 |
| ITB1_HUMAN | LSEGVTISYK | 774 |
| ITB1_HUMAN | LSENNIQTIFAVTEEFQPVYK | 775 |
| ITIH4_HUMAN | FAHTVVTSR | 776 |
| ITIH4_HUMAN | IGPDVLTATVSGK | 777 |
| ITIH4_HUMAN | LGVYELLLK | 778 |
| ITIH4_HUMAN | SPEQQETVLDGNLIIR | 779 |
| KLK3_HUMAN | AVCGGVLVHPQWVLTAAHCIR | 780 |
| KLK3_HUMAN | FLRPGDDSSHDLMLLR | 781 |
| KLK3_HUMAN | HSQPWQVLVASR | 782 |
| KLK3_HUMAN | LSEPAELTDAVK | 783 |
| KLK3_HUMAN | SVILLGR | 784 |
| KNG1_HUMAN | DIPTNSPELEETLTHTITK | 785 |
| KNG1_HUMAN | LNAENNATFYFK | 786 |
| KNG1_HUMAN | QVVAGLNFR | 787 |
| KNG1_HUMAN | TVGSDTFYSFK | 788 |
| KNG1_HUMAN | YFIDFVAR | 789 |
| KNG1_HUMAN | YNSQNQSNNQFVLYR | 790 |
| KPYM_HUMAN | CCSGAIIVLTK | 791 |
| KPYM_HUMAN | GADFLVTEVENGGSLGSK | 792 |
| KPYM_HUMAN | IYVDDGLISLQVK | 793 |
| KPYM_HUMAN | LAPITSDPTEATAVGAVEASFK | 794 |
| KPYM_HUMAN | LDIDSPPITAR | 795 |
| LAMA4_HUMAN | DAPSWDPVALK | 796 |
| LAMA4_HUMAN | HFVIDGHPVSFSK | 797 |
| LAMA4_HUMAN | LAALSIEEGK | 798 |
| LAMA4_HUMAN | LITEEANR | 799 |
| LAMA4_HUMAN | SGVLSVSSGAAAHR | 800 |
| LAMA4_HUMAN | SLLSDVEELVEK | 801 |
| LAMA4_HUMAN | VFLTVPSLSSTAEEK | 802 |
| LAMP2_HUMAN | EQTVSVSGAFQINTFDLR | 803 |
| LAMP2_HUMAN | GILTVDELLAIR | 804 |
| LAMP2_HUMAN | IPLNDLFR | 805 |
| LAMP2_HUMAN | SHTALLR | 806 |
| LAMP2_HUMAN | VQPFNVTQGK | 807 |
| LAMP2_HUMAN | YLDFVFAVK | 808 |
| LDHA_HUMAN | DLADELALVDVIEDK | 809 |
| LDHA_HUMAN | FIIPNVVK | 810 |
| LDHA_HUMAN | LVIITAGAR | 811 |
| LDHA_HUMAN | SADTLWGIQK | 812 |
| LDHA_HUMAN | VTLTSEEEAR | 813 |
| LTOR3_HUMAN | ELAPLFEELR | 814 |
| LTOR3_HUMAN | LPLVVSFIASSSANTGLIVSLEK | 815 |
| LTOR3_HUMAN | LPSVEGLHAIVVSDR | 816 |
| LTOR3_HUMAN | SIICYYNTYQVVQFNR | 817 |
| MASP2_HUMAN | AGYVLHR | 818 |
| MASP2_HUMAN | DTFYSLGSSLDITFR | 819 |
| MASP2_HUMAN | WPEPVFGR | 820 |
| MASP2_HUMAN | WTLTAPPGYR | 821 |
| MUC4_HUMAN | FLNSNSGLQGLQFYR | 822 |

TABLE 3C-continued

| Protein | reference peptide | SEQ ID NO. |
|---|---|---|
| MUC4_HUMAN | IGLASALQPR | 823 |
| MUC4_HUMAN | NDVVFQPISGEDVR | 824 |
| MUC4_HUMAN | SLEPFTLEILAR | 825 |
| MUC4_HUMAN | TVDFTSPLFKPATGFPLGSSLR | 826 |
| MUC4_HUMAN | WNDKPYLCALYQQR | 827 |
| NDKA_HUMAN | NIIHGSDSVESAEK | 828 |
| NF2L2_HUMAN | ALHIPFPVEK | 829 |
| NF2L2_HUMAN | DEDGKPYSPSEYSLQQTR | 830 |
| NF2L2_HUMAN | DGNVFLVPK | 831 |
| NF2L2_HUMAN | EQFNEAQLALIR | 832 |
| NF2L2_HUMAN | IINLPVVDFNEMMSK | 833 |
| NF2L2_HUMAN | LENIVELEQDLDHLK | 834 |
| NID2_HUMAN | AIAVDPIR | 835 |
| NID2_HUMAN | DGVVSVNK | 836 |
| NID2_HUMAN | EGTSLGEVGGPDLK | 837 |
| NID2_HUMAN | ESYNVQLQLPAR | 838 |
| NID2_HUMAN | HAQAQYAYPGAR | 839 |
| NID2_HUMAN | ITQTAEGLDPENYLSIK | 840 |
| NID2_HUMAN | LANPLHFYEAR | 841 |
| OSTP_HUMAN | AIPVAQDLNAPSDWDSR | 842 |
| OSTP_HUMAN | ANDESNEHSDVIDSQELSK | 843 |
| OSTP_HUMAN | GDSVVYGLR | 844 |
| OSTP_HUMAN | QNLLAPQNAVSSEETNDFK | 845 |
| OSTP_HUMAN | YPDAVATWLNPDPSQK | 846 |
| P53_HUMAN | ELNEALELK | 847 |
| P53_HUMAN | LGFLHSGTAK | 848 |
| P53_HUMAN | RPILTIITLEDSSGNLLGR | 849 |
| P53_HUMAN | TYQGSYGFR | 850 |
| P53_HUMAN | VEYLDDR | 851 |
| PDGFA_HUMAN | AHGVHATK | 852 |
| PDGFA_HUMAN | LEEHLECACATTSLNPDYR | 853 |
| PDGFA_HUMAN | LLEIDSVGSEDSLDTSLR | 854 |
| PDGFA_HUMAN | SQIHSIR | 855 |
| PDGFA_HUMAN | TVIYEIPR | 856 |
| PLTP_HUMAN | AGALQLLLVGDK | 857 |
| PLTP_HUMAN | ATYFGSIVLLSPAVIDSPLK | 858 |
| PLTP_HUMAN | AVEPQLQEEER | 859 |
| PLTP_HUMAN | EGHFYYNISEVK | 860 |
| PLTP_HUMAN | FLEQELETITIPDLR | 861 |
| PLTP_HUMAN | VYDFLSTFITSGMR | 862 |
| PPAP_HUMAN | DFIATLGK | 863 |
| PPAP_HUMAN | ELSELSLLSLYGIHK | 864 |
| PPAP_HUMAN | FQELESETLK | 865 |
| PPAP_HUMAN | FVTLVFR | 866 |
| PPAP_HUMAN | SPIDTFPTDPIK | 867 |
| RASK_HUMAN | SFEDIHHYR | 868 |
| SAP_HUMAN | EILDAFDK | 869 |
| SAP_HUMAN | EIVDSYLPVILDIIK | 870 |
| SAP_HUMAN | GSAVWCQNVK | 871 |
| SAP_HUMAN | LVGYLDR | 872 |
| SAP_HUMAN | QEILAALEK | 873 |
| SBP1_HUMAN | DGLIPLEIR | 874 |
| SBP1_HUMAN | GGFVLLDGETFEVK | 875 |
| SBP1_HUMAN | LTGQLFLGGSIVK | 876 |
| SBP1_HUMAN | LVLPSLISSR | 877 |
| SBP1_HUMAN | NEGGTWSVEK | 878 |
| SDF1_HUMAN | FFESHVAR | 879 |
| SDF1_HUMAN | ILNTPNCALQIVAR | 880 |
| SDF1_HUMAN | WIQEYLEK | 881 |
| TGFR1_HUMAN | DRPFVCAPSSK | 882 |
| TGFR1_HUMAN | HDSATDTIDIAPNHR | 883 |
| TGFR1_HUMAN | TIVLQESIGK | 884 |
| TGFR1_HUMAN | TLSQLSQQEGIK | 885 |
| TGFR1_HUMAN | VIHNSMCIAEIDLIPR | 886 |
| TGFR1_HUMAN | VPNEEDPSLDRPFISEGTTLK | 887 |
| UROM_HUMAN | DSTIQVVENGESSQGR | 888 |
| UROM_HUMAN | DWVSVVTPAR | 889 |
| UROM_HUMAN | FVGQGGAR | 890 |
| UROM_HUMAN | SGSVIDQSR | 891 |
| UROM_HUMAN | TLDEYWR | 892 |
| UROM_HUMAN | VLNLGPITR | 893 |
| VCAM1_HUMAN | ELQVYISPK | 894 |
| VCAM1_HUMAN | GIQVEIYSFPK | 895 |
| VCAM1_HUMAN | LHIDEMDSVPTVR | 896 |
| VCAM1_HUMAN | NTVISVNPSTK | 897 |
| VCAM1_HUMAN | SLEVTFTPVIEDIGK | 898 |
| VCAM1_HUMAN | TQIDSPLNGK | 899 |
| VTDB_HUMAN | EDFTSLSLVLYSR | 900 |

TABLE 3C-continued

| Protein | reference peptide | SEQ ID NO. |
|---|---|---|
| VTDB_HUMAN | ELPEHTVK | 901 |
| VTDB_HUMAN | HLSLLTTLSNR | 902 |
| VTDB_HUMAN | THLPEVFLSK | 903 |
| VTDB_HUMAN | YTFELSR | 904 |

In a preferred embodiment, each reference peptide is selected according to table 3A, 3B and/or 3C.

In a preferred embodiment, the signature peptides and/or reference peptides are selected from the group consisting of SEQ ID NO.: 290, 291, 295, 296, 297, 298, 301, 302, 305, 306, 307, 308, 311, 312, 313, 314, 326, 327, 328, 331, 332, 336, 337, 343, 345, 350, 351, 365, 367, 368, 369, 370, 372, 373, 381, 382, 387, 388, 389, 390, 391, 393, 394, 395, 397, 398, 399, 400, 402, 403, 404, 411, 412, 414, 418, 433, 434, 435, 436, 438, 439, 441, 447, 450, 453, 454, 455, 456, 461, 462, 464, 468, 473, 474, 475, 476, 477, 481, 484, 485, 489, 490, 494, 495, 496, 501, 502, 505, 513, 518, 519, 522, 523, 527, 531, 533, 534, 537, 538, 539, 557, 568, 569, 570, 571, 575, 576, 577, 578, 584, 586, 588, 594, 598, 599, 602, 603, 607, 608, 609, 610, 611, 615, 616, 620, 626, 627, 631, 633, 635, 643, 644, 648, 649, 653, 654, 655, 662, 671, 678, 679, 686, 688, 689, 693, 697, 699, 704, 714, 715, 717, 722, 733, 739, 741, 743, 746, 748, 763, 767, 771, 773, 774, 775, 782, 792, 793, 795, 797, 798, 805, 807, 811, 820, 821, 823, 828, 829, 835, 837, 840, 841, 850, 859, 870, 872, 873, 874, 875, 877, 879, 887, 892, 894, 897, 898, 899, 901, 902, 287, 288, 289, 292, 293, 294, 300, 303, 304, 309, 310, 315, 316, 318, 319, 320, 321, 322, 323, 324, 325, 329, 330, 333, 334, 338, 339, 340, 341, 346, 347, 352, 354, 357, 358, 361, 362, 363, 364, 366, 375, 376, 377, 378, 379, 384, 385, 386, 392, 396, 401, 405, 406, 407, 409, 413, 415, 416, 419, 420, 421, 422, 429, 430, 431, 437, 440, 442, 443, 444, 448, 452, 457, 458, 460, 463, 465, 466, 467, 469, 470, 471, 472, 486, 487, 491, 492, 497, 499, 503, 504, 506, 507, 508, 529, 535, 536, 540, 541, 542, 543, 544, 551, 554, 558, 560, 561, 562, 563, 565, 566, 572, 573, 580, 581, 585, 587, 589, 590, 591, 593, 595, 596, 600, 604, 605, 612, 613, 617, 618, 619, 622, 623, 624, 625, 628, 629, 630, 632, 634, 636, 650, 657, 658, 660, 661, 663, 667, 669, 670, 674, 677, 680, 683, 684, 687, 690, 691, 692, 694, 698, 702, 703, 706, 707, 713, 718, 719, 720, 731, 736, 737, 740, 745, 751, 758, 759, 762, 764, 765, 766, 768, 770, 772, 780, 781, 784, 785, 787, 791, 803, 810, 815, 817, 818, 819, 827, 830, 833, 844, 845, 847, 849, 851, 852, 853, 855, 861, 863, 866, 869, 871, 876, 878, 880, 882, 890, 891, 893, 895 and 896.

These signature peptides and reference peptides are particularly suited for detection by mass spectrometry.

In a further preferred embodiment, the signature peptides and/or reference peptides are selected from the group consisting of SEQ ID NO.: 290, 291, 295, 296, 297, 298, 301, 302, 305, 306, 307, 308, 311, 312, 313, 314, 326, 327, 328, 331, 332, 336, 337, 343, 345, 350, 351, 365, 367, 368, 369, 370, 372, 373, 381, 382, 387, 388, 389, 390, 391, 393, 394, 395, 397, 398, 399, 400, 402, 403, 404, 411, 412, 414, 418, 433, 434, 435, 436, 438, 439, 441, 447, 450, 453, 454, 455, 456, 461, 462, 464, 468, 473, 474, 475, 476, 477, 481, 484, 485, 489, 490, 494, 495, 496, 501, 502, 505, 513, 518, 519, 522, 523, 527, 531, 533, 534, 537, 538, 539, 557, 568, 569, 570, 571, 575, 576, 577, 578, 584, 586, 588, 594, 598, 599, 602, 603, 607, 608, 609, 610, 611, 615, 616, 620, 626, 627, 631, 633, 635, 643, 644, 648, 649, 653, 654, 655, 662, 671, 678, 679, 686, 688, 689, 693, 697, 699, 704, 714, 715, 717, 722, 733, 739, 741, 743, 746, 748, 763, 767, 771, 773, 774, 775, 782, 792, 793, 795, 797, 798, 805, 807, 811, 820, 821, 823, 828, 829, 835, 837, 840, 841, 850, 859, 870, 872, 873, 874, 875, 877, 879, 887, 892, 894, 897, 898, 899, 901 and 902.

These signature peptides and reference peptides are best suited for detection by mass spectrometry.

In a preferred embodiment, a protein which is represented by a reference peptide is additionally represented by at least one signature peptide. Since the signature peptide is unique for a given protein, it can be used to confirm the presence of the protein detected by the reference peptide and to determine which isoform or homolog of the protein is present.

In a preferred embodiment, the signature peptides and/or reference peptides represent at least 15, preferably at least 20, more preferred at least 30 proteins.

In a preferred embodiment, the collection comprises about 10 to 100, preferably about 20 to 70, more preferred about 30 to 50 signature peptides and/or reference peptides.

In a preferred embodiment, the cancer is a bladder cancer, preferably an urothelial bladder cancer.

In a preferred embodiment, the signature peptides and/or reference peptides are concatenated into an artificial protein, e.g. by use of the QconCAT technology (Pratt et al., 2006).

In a further aspect, the invention relates to a second artificial protein comprising signature peptides and/or reference peptides representing at least 10 proteins selected from the group 1, wherein each signature peptide represents a single protein, each reference peptide represents two or more isoforms and/or homologs of a protein and consecutive signature peptides are separated by a cleavage sequence.

The second artificial protein may comprise about 10 to 70 signature peptides and/or reference peptides, preferably about 30-70 signature peptides and/or reference peptides, further preferred about 30 to 50 signature peptides and/or reference peptides, but may include as much as 100 signature peptides and/or reference peptides. For covering even more signature peptides and/or reference peptides, e.g. for analyzing a sample for the entire panel of biomarker proteins, two or three or even more different second artificial proteins may be used in combination.

In a further aspect, the invention relates to a nucleic acid construct encoding the second artificial protein of the invention.

Examples

First Study
Material and Methods
Cohort

Urine samples were obtained from patients with a suspicion of urinary bladder cancer (UBC) that were subsequently confirmed (cases) or refuted (urological controls) and from donors with no urological pathology at the Henri Mondor hospital in Créteil (France) and at the hospital del Mar in Barcelona (Spain). The present study protocol received the institutional review board (IRB) approval from both hospitals. Inform consent forms have been designed and used at both hospitals. A Standard Operating Procedure taking into account clinical as well as analytical constraints was developed and strictly applied by technicians in charge of urine collection at both centers involved in the study. A list of recommendation was presented to the patients prior to urine collection. Information on the conditions urine was obtained was gathered with a questionnaire designed ad hoc.

These recommendations included avoiding strenuous activities, diuretics or excess fluids. Blood, proteins, leucocytes, nitrites, ketones, pH, bilirubin, and glucose levels were determined in all collected samples. Cases recruited in this study were non-muscle invasive UBC with both incident and prevalent (i.e. recurrent) tumors. They were subsequently classified in three risk levels—low, intermediate and high risksaccording to the EORTC criteria (Babjuk et al., 2008). Patient classification was not shared with the proteomics laboratory until statistical analysis of the data. Since the urine collection was performed prior to cystoscopy and clinical diagnostic, the study was performed in a double blind manner. A urine sample tracking form recapitulated all pertinent data required for sample and statistical analysis, including sample processing information (e.g., volume collected, storage temperature and duration, urinalysis at bedside) and patient related data specific to the day of collection (blood pressure, medical treatment, drink type and volume in the hours preceding collection).

Sample Collection

Second morning or random mid-stream urine was collected from each patient prior to cystoscopy, when applicable. Forty milliliters of urine were immediately transferred to a prepared Falcon tube containing one pill of proteases inhibitor cocktail (Roche EDTA free). Tubes were stored for less than 4 h at room temperature before low-speed centrifugation (10 min, 2000 g at room temperature) for cellular debris removal. Supernatants were collected and transferred into clean tubes before freezing and storage at −80° C. Samples were transferred to the analytical laboratory under dry ice.

Sample Preparation

Protein precipitation of urine samples corresponding to 250 µg of total protein amount was achieved by adding trichloroacetic acid (TCA, Sigma-Aldrich) to a final concentration of 6%. The sample was mixed prior to incubation at 4° C. for 2 h followed by centrifugation at 14 000 g for 15 min. The supernatant was removed and the pellet washed twice with 100% ice-cold acetone (Sigma-Aldrich) to remove interfering compounds. The supernatant was removed and the pellet airdried, and re-suspended in 300 mL of denaturing buffer containing 8 M urea (Sigma-Aldrich) and 0.1M ammonium bicarbonate (Sigma-Aldrich). The protein concentration was assessed with Bradford protein assay (Bio-Rad), employing BSA as a standard.

Protein extracts were reduced with dithiothreitol (DTT), alkylated with iodoacetamide and digested in solution with sequencing grade porcine trypsin (Promega) as reported in Court et al. (Court et al., 2011). Briefly, urinary protein extracts were reduced with 12 mM DTT (Sigma-Aldrich) for 30 min at 37° C. and alkylated with 40 mM iodoacetamide (Sigma-Aldrich) for 30 min in the dark before diluting the sample with 0.1 M ammonium bicarbonate (Sigma-Aldrich) to a final urea concentration below 2 M. Proteins were digested overnight by incubation with trypsin (Promega) to a final enzyme:substrate ratio of 1:100. Digestion was stopped by addition of formic acid to a final concentration of 1%. Peptides were cleaned up using Sep-Pak tC18 cartridges 100 mg (Waters) according to the manufacturer's instructions, and eluted with 50% ACN (Sigma-Aldrich) containing 0.1% formic acid (Sigma-Aldrich). The resulting peptide samples were evaporated to dryness on a vacuum centrifuge (SpeedVac, Thermo Fisher Scientific), and stored at −80° C. in low-absorption tubes (Mµlti; Dutscher) until further use.

Targeted Quantitative Analysis Using SRM

Standards

Synthetic stable isotope-labelled peptides of "crude" quality, with C-terminal $^{15}N$ and $^{13}C$-labeled arginine or lysine residue were purchased from Thermo Fisher Scientific. They were spiked in urine digests at a nominal concentration of 57 or 571 fmol/µL (depending on their purity and their analytical response in the biological matrix of interest, as assessed using a pooled urine sample prior to the large scale study) before targeted quantification by LC-SRM. By spiking standards at these concentrations, the signal intensities of the synthetic peptides were close to those of the corresponding endogenous peptides in the urine digest.

LC-SRM Measurements

SRM analysis were performed using a TSQ Vantage extended mass range triple quadrupole mass spectrometer (Thermo Fischer Scientific) coupled to an Ultimate 3000 RSLC nano system (Thermo Fisher Scientific) through a nano-electrospray ionization interface. The selectivity for both Q1 and Q3 was set to 0.7 u (FWHM). The collision gas pressure of Q2 was set at 1.5 mTorr argon. For each peptide, the two fragment ions presenting the higher response were selected, based on preliminary experiments using SIL standards. The collision energy was calculated using the formula $CE=0.033\times$(precursor ion m/z)$+1.8$ and $CE=0.038\times$(precursor ion m/z)$+2.3$ for doubly and triply charged precursor ions, respectively. The time-scheduled SRM method targeted pairs of isotopically labelled peptides/native peptides in +/−2.5 min retention time windows.

For each analysis, 1 µL of digested urine extract (corresponding to ~500 ng of total protein amount) was injected into a trap column (Acclaim PepMap 2 cm×75 µm i.d., C18, 3 µm, 100 Å, Thermo Fischer Scientific) at 5 µL/min with aqueous solution containing 0.05% (v/v) trifluoroacetic acid and 1% acetonitrile. After three minutes, the trap column was switched on-line with the analytical column (Acclaim PepMap RSLC 15 cm×75 µm i.d., C18, 2 µm, 100 Å, Thermo Fisher Scientific). Peptide elution was performed by applying a gradient mixture of solvent A/B at 300 nL/min. Solvent A was HPLC grade water with 0.1% (v/v) formic acid, and solvent B was HPLC grade acetonitrile with 0.1% (v/v) formic acid. A linear gradient from 2 to 35% solvent B over 48 min was first applied, followed by a washing step (5 min at 90% solvent B) and an equilibration step (10 min at 2% solvent B). Samples were analyzed multiple times (2 to 3) to control for analytical variability.

Quality control (QC) samples (Pierce Retention Time Calibration Mixture, Thermo Fisher Scientific) were analyzed at the beginning of the series, between patient samples, and at the end of the analytical campaign to monitor instrument performances. In addition, this calibration mixture was also spiked in individual samples for retention time realignment, which in turn permitted the use of scheduling windows (±2.5 min) for transitions monitoring.

Data Processing: Signal Extraction

A software was developed to automate the processing of large SRM datasets. The software extracts the individual chromatographic traces from raw files and performs peak detection and integration of the area under the curve. In this study, the entire dataset comprised 1,168 raw files, corresponding to 121 samples analyzed repeatedly (2 to 3 times) with four injections per sample. Traces were smoothed using a Gaussian filter, and peak detection was performed for each peptide using a multiple step heuristic approach: (i) intensity-based picking of candidate peaks from a trace corresponding to the product of the transition chromatograms, (ii) selection of peaks presenting the highest signal-to-noise ratio, and co-elution of fragment ions to collect correct ion ratios between the native peptides and the corresponding SIL standard. When either no signal was detected for the native peptide, the SIL peptide, or both peptide forms, or when transitions failed to co-elute, a non-numerical value was reported by the software. Therefore, missing values were obtained (3-12% per sample), which mostly originate from native peptides going undetected due to their low abundance in urine samples. In only few cases, no signal for SIL peptides were detected (e.g., ionization suppression). SRM peak areas were calculated by numerical integration using the boundaries of the first derivatives. A two-steps correction procedure relying on the SIL peptide transition measurements were also implemented to correct for assay variability: First, interLC-run variability and overall fluctuations of the sensitivity of the mass spectrometers (caused by e.g. contamination) was corrected though median adjustment at the individual LC-MS run level: (i) median value of all SIL peptides was determined for each raw file, and adjusted to correct for the injected peptide amount, then (ii) native and SIL peptide areas were uniformly corrected for each raw file by adjusting its median to a reference (i.e. the overall median of the individual injection median population). Furthermore, the inter-run variability (arising from e.g., ion suppression effect) was corrected at the peptide level though a similar process: (i) for a given peptide, the median area of the SIL peptide population across all the samples was determined and chosen as a reference, and (ii) native and SIL peptide areas were corrected by adjusting SIL peptide area in each raw files to the reference. During both steps of the latter process, outliers (defined here as values lower or higher than the lower inner fence or higher inner fence, respectively) from the considered values of SIL peptide areas were excluded from median calculation. All results were stored in a local SQLite database for further evaluation.

Data Quality Assessment and Reduction

For each monitored transition, a concentration estimate was calculated based on the known amount of spiked SIL standard and the ratio between the intensity of the native peptide and that of the matching SIL standard. Importantly, the concentration estimates obtained across the patient population from all the transitions of a given peptide should be consistent to yield robust concentration values for the corresponding protein. When this is not the case, peptides should be flagged and ignored from subsequent calculations.

Internal consistency between concentration estimates obtained from the two transitions of a given peptide was evaluated using Cronbach's alpha, a measure of consistency often used in social sciences and engineering. Only peptides displaying Cronbach's alpha higher than 0.8 were considered for further processing.

To mitigate biases due to variable digestion efficiencies or to partial solubility of individual SIL standards, concentration estimates for all peptides of a given protein were normalized to that of a hypothetical median peptide using central tendency normalization. Following a Log transformation of the raw concentration estimates, a virtual median peptide was created by calculating the median Log concentration of a peptide, based on all transitions of all peptides corresponding to the same protein in each analyzed sample. The corrected Log concentration estimated for each transition was then computed using the following formula (Eq. 1):

$$x_{i,j}^* = \left[\frac{x_{i,j} - \overline{x_i} + \overline{\text{median}(x_i)}}{\sigma(x_i)}\right] \cdot \sigma(\text{median}(x_i))$$

Where i represents the index of the peptide for a given protein, j the index of the transition for the peptide i, $x_{i,j}^*$ is the corrected Log concentration estimate of the transition at hand, $x_{i,j}$ its original estimate with an average $\overline{x_i}$ and a standard deviation $\sigma(x_i)$ across all patients, with $\overline{\text{median}(x_i)}$ and $\sigma(\text{median}(x_i))$ the average and standard deviation respectively of the estimated Log concentration of the virtual median transition across all patients.

Following this normalization, corrected concentration estimates for the two transitions of all peptides from a given protein were averaged for each patient to produce a single concentration estimate per protein and per patient.

Statistical Analysis

The data set was divided into two subsets in accordance with the patient categories to perform relevant statistical analysis. The first subset included incident UBC cases (36 patients) and incident urological controls (24 patients), i.e. patients with a suspicion of primary UBC that was not confirmed by cystoscopy. The second subset considered prevalent UBC cases (29 patients) and prevalent urological controls (21 patients), i.e. patient who had a prior history of UBC and who consulted for a suspicion of tumor relapse that was cleared by the cystoscopy examination. For each subset, correlation analysis was performed by calculating the Pearson coefficient of Log transformed protein concentrations across all patients of the subset for each pair of proteins. Hierarchical clustering (unstandardized Ward method) on pairwise correlation coefficients was performed for each data subset (incident and prevalent) to group proteins with correlated abundances. At this step, proteins were assembled into 8 clusters for each subset (Tables 4-7). Missing value imputation based on mean and covariance matrix was performed within each cluster. The resulting imputed datasets were used for one way analysis of variance (ANOVA) to generate an F ratio and a p-value per protein in association with risk (high, low/intermediate, urological control) or with the disease status (case or control). Proteins with p-value 0.05 were considered as discriminative. Biological functions and metabolic or signaling pathways analyses were performed within each cluster using Ingenuity Pathway Analysis (Ingenuity Systems, INC.).

Results

Convenient non-invasive urine tests to detect incidence of UBC (urinary bladder cancer), or tumor recurrence in patients having undergone bladder tumor resection, could significantly reduce the number of unnecessary surveillance cystoscopies performed each year. For instance, in the present study, the rate at which UBC diagnostic was discarded following cystoscopy was in excess of 40%. As repeatedly pointed out by various authors (e.g. Carr et al., 2014), the evaluation step constitutes a major bottleneck in all biomarker development pipelines. This is true also for urinary biomarkers of UBC, and most of the so far identified candidates have not been evaluated further. Only one study to date reported the evaluation of candidate biomarkers of probable plasmatic origin in urine, demonstrating that a panel of 6 proteins showed statistically different urinary levels between BC patients and patients with hernia or other urological disorders (Chen et al., 2012). To build on previous evaluation efforts, the evaluation of a set of candidates preselected based on their possible tumorous origin was undertaken.

Design of Large Scale SRM Experiment

Over the past years, the biomarker verification workflows have matured and several studies aiming to reduce an initial list of candidate biomarkers to the subset that truly reflects disease presence, stage or response have been published (e.g. Carr et al., 2014). However, a gap still exists between the developments of targeted proteomic assays as proofs of concept and their systematic use in translational research. In particular, two conflicting constraints hamper efficient large-scale SRM assay developments: it is desirable on the one hand to maximize the quality of the data through rigorous assay optimization in order to improve the assessment of biomarkers significance; and on the other hand to minimize the overall cost and resource investment due to the limited relevance of the sets of candidates originating from discovery findings, which typically present high false positives rates. For the latter reason, the in-depth individual optimization of acquisition parameters for each of the hundreds to thousands of transitions monitored in a large scale SRM screening is hardly conceivable. In addition, it is always necessary to find a trade-off between the redundancy (e.g., the number of peptides to be analyzed for each protein, the number of transitions monitored per peptide) required to generate robust measurements and the throughput of the SRM assays (i.e., total number of proteins monitored by acquisition), which determines the total time and cost of the study.

In the present work, a list of 134 selected candidate biomarkers resulting from an earlier bladder cancer discovery study and from literature mining was compiled. Surrogate target peptides were chosen for each protein based on their sequence uniqueness within the human proteome of interest and their responsiveness in LC-MS analysis. When available, peptides and transitions were selected directly from experimental data generated during an earlier candidates discovery study. For the other candidates, stringent peptides and transition selection criteria were followed that have been extensively reviewed previously.

Transitions were validated by analyzing the corresponding standard peptides in buffer solution to ensure that the detected signals observed during the discovery experiments truly corresponded to the targeted peptides. For that purpose, transitions were manually reviewed and the transitions of highest intensities were retained. The SRM assay was designed to optimize the multiplexing ability, which in turn maximized the throughput while guarantying the acquisition of information with some level of redundancy. Taking into account the above mentioned constraints, a "time-scheduled SRM" assay with narrow retention time (RT) windows was used to monitor the two most intense transitions of 331 pairs of endogenous and SIL peptides, corresponding to the 134 proteins of interest in less than four hours of analysis per sample. This highly multiplexed assay generated 1,322 chromatographic traces per sample, which represented ~480,000 traces for the entire study (121 patient samples in repeated analyses).

Signal Extraction from Large Scale SRM Data Set

In spite of significant efforts to develop software packages to facilitate the design and analysis of large-scale SRM experiments (e.g. Cham Mead et al., 2010), data extraction of large number of measurement values from highly multiplexed SRM screen still constitutes a significant challenge. First, analytical variability associated with the LC separation process needs to be assessed and possibly corrected. Based on the assumption that the intensities of transitions corresponding to SIL peptides spiked in a constant amount in all samples should be uniform across all MS runs, they can be used to address this point. Second, erroneous LC peak assignment, missing value due to low signal, and interference in monitored transitions are frequent sources of quantification errors that need to be taken into account (e.g. Abbatiello et al., 2010). As recently reasserted by Carr and co-workers (Carr et al., 2014), there is a definite need for metrics to flag transitions with low quality measurements since manual inspection of SRM transitions is not practical for large scale studies. Software have been developed to automatically detect interfered transitions (e.g. Abbatiello et al., 2010). Third, the replication of LC-SRM analyses for each given sample introduces additional complexity to combine information from repeated measurements. To avoid the time-intensive and errorprone nature of manual extraction for such a large scale study, an algorithm to automatically select, integrate chromatographic peaks of interest and combine replicate information was developed (see material and methods).

In the acquired data, the analytical variability was mainly associated with the LC separation process and the ionization interface, i.e., though fluctuations of injected volume and ion suppression effect. This variability was controlled by using a constant amount of SIL peptides spiked in the samples as internal standards. Thus, to improve the precision, a procedure including two levels of data correction, based on the signal measured for the SIL peptides, was implemented (see material and methods). The efficiency of the data correction procedure was verified based on inter-replicate coefficients of variation (CV). At the end of the data extraction process, the dataset featuring ~480,000 extracted transitions for the entire study (121 patient samples in repeated analyses) was reduced to ~71,000 quantitative measures.

Data Analysis of Large Scale SRM Experiments

Following data extraction and reduction, the quality of the quantitative data was further assessed by determining the consistency of target concentration estimates based on multiple transitions per peptide for each assayed protein. Data for kininogen-1 will be used as an illustration of this process. This protein had been observed as differentially abundant in urine from UBC patients in our own discovery study and has been associated with UBC in other studies (Chen et al., 2012).

Transitions Consistency Assessment

SRM is notoriously sensitive to interferences due to other components present in the sample and having precursor and fragment m/z ratios very close to the monitored transitions. In highly complex samples, the frequent occurrence of interferences is a significant problem causing inaccurate peptide quantitation (e.g. Abbatiello et al., 2010). When two transitions are monitored, it is common to sum their signals, which may hide the contributions of interfering signal. Efforts have been recently devoted to detecting the presence of interfering signal in order to improve the reliability of SRM data (e.g. Abbatiello et al., 2010). In practice, the consistency of the measurements obtained using multiple metrics (i.e. transitions) for each peptide needs to be evaluated across all the samples to identify potentially unreliable measurements. For this purpose, a measure of internal consistency between the two monitored transitions of each peptide is required. Several metrics can be used to evaluate transitions consistency such as the Pearson correlation coefficient, the slope of the regression, or Cronbach's alpha. This latter coefficient is a measure of internal consistency used in social science and engineering to estimate if multiple metrics measure the same underlying uni-dimensional property. As a rule of thumb, Cronbach's alpha greater than 0.8 are indicative of consistent measurements. These metrics were used for each assayed peptide to judge the consistency of the data obtained using the two corresponding transitions. For each transition, the concentration of the peptide (i.e. that of its parent protein) was estimated based on the ratio with the SIL standard. After logarithm transformation to minimize the effect of outliers on the regression, concentration estimated from both transitions of the same peptide were compared across all patients to evaluate consistency.

For example, four signature peptides of the protein Kininogen-1 (KNG1), were monitored in 121 urine samples. The generated plots represent the estimated protein concentration obtained using the first transition of each peptide versus the estimate obtained using the second transition of the same peptide. Ideally, both transitions should provide exactly the same concentration estimate for each patient and the plots should display a line of slope 1 and intercept 0. This in turn would result in a Pearson correlation coefficients equal to 1, and a Cronbach's alpha equal to 1. For three out of four KNG1 peptides (TVGSDTFYSFK, YFIDFVAR, and YNSQNQSN-NQFVLYR), concentration estimates obtained using the two monitored transitions were consistent throughout the 121 samples, and all consistency estimators yielded acceptable values. In the case of the peptide LNAENNATFYFK, however, estimates obtained with the two transitions, showed inconsistencies of the acquired data, and consistency estimators were far from ideal. This suggests that the two transitions did not capture the same underlying property of the sample, namely KNG1 concentration. Measurements for this peptide should therefore be flagged as inconsistent and removed from further consideration.

When using a Cronbach's alpha >0.8 filter, manual assessment of the data indicated that no incoherent transition pairs were kept as estimators of a protein concentration. A plot of Cronbach's alpha versus Log of regression slope color coded for Pearson coefficient confirmed that the peptide rejected by the Cronbach's alpha-based filter showed either low Pearson coefficients or slopes very different from 1. Thus, Cronbach's alpha seemed to be a good compromise as a measure of consistency of the two monitored responses per peptide.

Out of 331 monitored peptides, 225 peptides representative of 109 proteins present a good internal consistency (alpha 0.80) between the two monitored transitions through all samples. Conversely, almost one third of the monitored peptides presented unacceptable inconsistencies in their concentration estimates based on their two transitions, most likely due to interfered measurements. This was surprising since targets and their transitions had been carefully selected and tested using the SIL peptides, and also because the data had been previously filtered to avoid issues related to matrix effects. It therefore appears that the previous measures did not completely clear inconsistent measurements, stressing the need for stringent SRM data quality evaluation prior to biological interpretation.

Normalization of Peptide-Dependent Responses

After checking consistency in concentration estimates obtained by the two transitions of a given peptide, the variance of these estimates across peptides for a given target protein was analyzed. Multiple signature peptides that exhibited good transition consistency may generate estimates of different magnitudes. Nevertheless, these estimates are highly correlated, leading to the conclusion that there could be a peptide-associated bias in the SRM measurement. This phenomenon was observed for most proteins monitored by multiple peptides, and it was responsible for the high coefficients of variation (CV) for protein concentrations in each sample. Several reasons could be invoked to explain differences in concentration estimates using different peptides of the same protein. First, these differences could be due to variable cleavage efficiency by trypsin for the targeted sequences within the protein of interest. Low digestion efficiency may induce underestimations of the concentrations of the endogenous peptide. A second explanation for these differential biases could be the solubility and purity of the corresponding SIL peptides, since weakly soluble peptides or overestimated SIL peptide concentration due to low purity may yield lower reference signals that would in turn induce over-estimations of the concentration of endogenous peptides. This is not so surprising since the use of SIL peptides of limited purity (i.e. "crude peptides") precluded accurate estimates of nominal concentrations of the standard.

For these reasons, it was observed that protein concentration estimates contained a peptide-dependent bias. It is worth mentioning here that such a bias is of no major consequence at the biomarker evaluation stage, since it is strived to determine precise relative abundances across samples, and not accurate concentrations in each sample. However, to mitigate these biases, it was opted for a normalization procedure that used the median bias of all measured peptides for a protein. This was done by normalizing all the signature peptides from the same protein through the sample set on a hypothetical "median peptide" as expressed in Eq. 1 (see material and methods). The concentration estimate of this "median peptide" was chosen as the median of all concentration estimates across all patients from the various signature peptides of the protein of interest. This normalization method makes the data comparable by reducing biases at the peptide level and decreases the variance of concentration estimates in each individual patient but not across patients. Following this normalization, a unique concentration value per protein in each patient's sample with a proper confidence interval could be determined. This unique concentration was calculated by averaging the "corrected" concentration estimates of the signature peptides per protein for each patient. The selected normalization procedure reduced the median CV of protein concentration estimates from 71% to 25%.

Data Analysis Output

From an initial set of 134 protein candidates of interest monitored by 331 peptides in a highly multiplexed SRM analysis, the process described above allowed to extract consistent measurements for 224 signature peptides, representative of 109 proteins, in 121 urine samples. Among them, the protein AGO2 displayed aberrant concentration values, and was removed from further consideration.

Assessment of the Performance of Individual Markers in Detecting BC

To evaluate the significance of the 108 putative biomarkers for which reliable measurements had been obtained, their urinary levels in relation to disease status and risk factors in the cohort of patients with a suspicion of BC was assessed.

Candidate Evaluation Cohort

FIG. 1 shows the repartition of the 121 urine samples analyzed in the present study into multiple sub-populations that will be described in details. Patients and controls were first divided into two categories depending on their prior history of bladder cancer: "Incident urological control" and "Incident cancer" were patients with no prior history of UBC. "Prevalent urological control" and "Prevalent cancer" were patients with a prior history of UBC, who were followed-up to detect a potential tumor relapse, and for whom clinical examination results cleared or confirmed the UBC diagnosis respectively. It is worth noting that the distinction between incident and prevalent is usually known at the time of examination. Cancer patients were further segregated by risk of progression or recurrence according to a previously published score (Babjuk et al., 2008). Two categories were considered: patients with low or intermediate risk of progression/recurrence, and patients with high risk of progression/recurrence.

An important added value of the present cohort compared to previously published work resides in the inclusion of urine samples from heterogeneous urological controls. These control samples originated from a patient population who came to the hospital with a suspicion of UBC and for whom the cystoscopy and clinical examination resulted in the rejection of the UBC diagnostic. The discrimination between these urological controls and cancer patients is the ultimate goal of clinical examination. While this examination is now performed using cystoscopy, which is an invasive procedure, there is a hope that a biomarker would enable diagnostic based on a simple urine test. For this purpose, the cohort encompasses the actual population that such a UBC screening test would target.

Statistical Analysis

In order to subdivide the 108 evaluated candidate biomarkers into manageable subsets, it was started by evaluating the pairwise correlation of their concentrations across the incident and prevalent sub-cohort. Next, unsupervised hierarchical clustering analysis (Ward) was performed on pairwise correlation coefficients for each data subset (incident and prevalent). For each subset, proteins were arbitrarily grouped into 8 clusters. Clusters of the incident subset are shown in tables 4 and 5. Clusters of the prevalent subset are shown in tables 6 and 7. A core cluster of ~25 highly correlated proteins was found in each data subset (incident cluster #I3 and prevalent cluster #P5). Interestingly, an excellent overlap (>80%) existed between these two clusters. Ingenuity analysis of these candidates revealed a high proportion of proteins involved in metabolic diseases and inflammation. Other proteins clustered somewhat differently in the two sub-populations, suggesting that incident and prevalent cancers present distinct phenotypes.

To assess the performance of individual markers selected from previous studies, the association between their abundance and the disease status and/or the risk factor for progression and recurrence was evaluated. Patients and controls were divided into 3 categories: urological controls, for whom no risk was determined, cancer patients with high risk, and cancer patients with low or intermediate risk. The association between protein abundance and risk status (Intermediate/Low, High, or urological control) or disease state (urological control vs. disease) was tested by ANOVA for the 108 dosed proteins in order to identify prognosis or diagnosis candidate biomarkers for both the incident and the prevalent populations.

Candidate Evaluation as Incident UBC Prognosis Biomarkers.

Univariate evaluation of candidate biomarkers using data from the incident subset yielded a set of 50 proteins out of 108 that displayed significantly different levels as a function of risk factor (p-value <0.05). These proteins were mainly grouped in incident clusters #I1 through #I4, but few of them appeared also in incident clusters #I7 and #I8. Incident cluster #I3 was the most represented in this list (50% of differential proteins originated from this cluster), and almost all of its proteins showed a significant association with the risk factor. Ingenuity analysis of proteins within cluster #13 showed that it was significantly enriched in molecules involved in metabolic diseases and inflammatory response. Among risk associated proteins grouped in incident cluster #I3, up-regulation of APO-A1 (apolipoprotein-A1), APO-A4 (apolipoprotein A4), VTDB (vitamin D-binding protein) and CO3 (complement C3) have been previously reported in urine from patients with IgA nephropathy (Kalantari et al., 2013). Increased levels of these proteins are most likely related to the organism defensive response to various pathological processes and their tumorous origin is doubtful. Incident clusters #I1 and #I4 also displayed high proportions of proteins with significant level variation with the risk factor (64% and 83% respectively). Ingenuity analysis of proteins from these clusters revealed "cell to cell signaling and interaction" and "cancer, cell cycle" as two networks of incident cluster #I1 and "Organismal injury and abnormalities, and lipid metabolism" as network of the cluster #I4. Importantly, while some proteins could discriminate one risk group from the two others, only a handful were able to effectively separate the three risk groups.

Among the 50 proteins showing a significant link with the risk factor, CALR (caireticulin), K1C19 (cytokeratin-19), ES8L2 (epidermal growth factor receptor kinase substrate 8-like protein 2) and RASK (GTPase KRas) were the four most discriminating proteins. More precisely, CALR (incident cluster #I3) was able to differentiate patients from the 3 risk groups (intermediate/low, high and urological control), K1C19 and RASK (incident clusters #I2 and #I3, respectively) were discriminative of the "high risk" group vs. the two other risk groups, and ES8L2 (incident cluster #I4) to differentiate "low/intermediate" group of incident patients from the two other risk groups. These four proteins are of special interest since data for CALR, K1C19 and ES8L2 has been previously reported on their differential expression in urine samples from BC patients (e.g. Kageyama et al., 2004) and also because a possible tumorous origin has been reported for these candidates at the protein or gene level. Specifically, K1C19 was previously reported as associated with the degree of differentiation of bladder squamous cell carcinomas (Ostergaard et al., 1997). Increased production of CALR in bladder cancer tissue was previously described (Kageyama et al., 2004) as well as over-expression of CALR has been associated with cell proliferation and migration of other cancers. ES8L2 was reported as linked to the epidermal growth factor receptor (EGFR) pathway, which was found to be deregulated in bladder cancer and, increased gene expression of EPS8 was also positively correlated with the migratory potential of tumor cells in pancreatic cancer (Welsch et al 2007). Finally, RASK, encoded by KRAS gene, was reported as a critical target activating pro-cancer pathways. Mutations in the RAS oncogenes (HRAS, KRAS and NRAS) were reported in bladder tumors and occurred in all stages and grades (Jebar et al., 2005). Based on these results, these four protein candidates alone or combined in a panel appear promising as prognosis urinary biomarkers for patients with no prior medical history of BC.

Candidate Evaluation as Incident UBC Diagnostic Biomarkers.

When ANOVA was performed vs. the disease status (control vs. BC regardless of risk factor) in the incident data subset, most of the proteins that showed a link with the risk did not present significant differences. As a matter of fact, only 6 proteins among the 108 displayed significantly different levels between incident urological controls and incident cancer patients. These proteins were broadly distributed among incident clusters #I2, #I3, #I4 and #I7. With the exception of S10A6 (protein S100-A6), these discriminating proteins also showed a significant link with the risk factor (p-value <0.05). Interestingly, almost all proteins in incident cluster #I3 that showed significant differences with the risk factor failed to discriminate disease status, the only exception being PLTP (phospholipid transfer protein).

The analysis revealed that TSP1 (thrombospondin-1), UROM (uromodulin), and PLTP (Phospholipid transfer protein) showed the strongest association with the disease status (expressed by significant increased urinary levels for incident cancer patients), as well as K1C19 which was also revealed as part of the most discriminating proteins with the risk factor (vide supra). TSP1 is an anti-angiogenic protein, and its expression has been previously associated with clinicopathological features and prognosis in several types of cancers (Miyata et al., 2013). As of today, there is no consensus on its specific role in urological cancers since its biological activity varies as a function of tumor environment (Miyata et al., 2013). Nevertheless, a prospective use of TSP1 as therapeutic target and prognostic factor for urological cancer has been recently considered (Miyata et al., 2013). In addition, increased levels of TSP1 in urine samples from BC cases have been previously reported when compared with urine from hernia patients (Chen et al., 2012). Based on these reports and on our results, TSP1 could be considered for further investigation as a promising diagnosis urinary candidate biomarkers for patients with no prior medical history for bladder cancer. The second most significant protein, uromodulin, is the most abundant protein secreted in urine under normal conditions. Although its exact function remains subject of debate, it is assumed to protect against urinary tract infections and stones. Even if its link with BC still remains unclear, uromodulin was previously reported as being involved in a candidate panel of four proteins to distinguish muscle-invasive and non-muscle-invasive tumors of the bladder. Finally, a significant increase in PLTP levels between BC patients and controls was found in our study. PLTP is a secreted protein involved in metabolic disease/syndrome and lipid metabolism.

Candidate Evaluation as Prevalent UBC Prognosis Biomarkers.

When considering the prevalent subset, a somewhat lower proportion of proteins (19 out of 108) presented significant differences in association with the risk factor. It is worth reminding here that all these cases and controls in the prevalent subset had a prior history of bladder cancer, and may therefore have constituted a more homogeneous population with respect to their urine protein profile. Surprisingly, only 2 out of these 19 proteins, namely OSTP and EGF, showed differential abundances with respect to risk factor in the incident subset. Over half (10) of the 19 differentially abundant proteins were grouped in prevalent cluster #P6, while the remaining proteins were distributed between prevalent clusters #P1, #P4, #P5, #P7 and #P8. Based on ingenuity analysis, proteins from prevalent cluster #P6 (58% of which were found discriminative of risk) were mainly involved in cell death and survival. Two smaller clusters (prevalent clusters #P7 and #P8) were also of particular interest, since almost all of their proteins showed a significant association with risk groups. Based on their ingenuity analysis, these clusters were significantly enriched in proteins involved in "cellular growth and proliferation, tissue development and cellular development" (prevalent cluster #P7) and "cellular movement, hematological system development and function, immune cell tracking" (prevalent cluster #P8). In prevalent cluster #P5, significant differences with respect to risk factor were only observed for a single protein, LTOR3 (Regulator complex protein LAMTOR3).

Interestingly, this cluster (prevalent cluster #P5) matched at more than 80% with the incident cluster #I3, which was found to be significantly enriched in proteins involved in metabolic diseases and inflammatory response (vide supra), and for which most proteins showed a link with risk in the incident population. This could be explained by the fact that all prevalent cases and controls considered here had a prior history of bladder cancer, a condition associated with chronic inflammation of the urothelium.

Among the 10 discriminating proteins, AMPN (aminopeptidase-N), ANAG (alphaN-acetylglucosaminidase) and TNFA (tumor necrosis factor) showed the strongest association with the risk group. More specifically, AMPN and ANAG (both from prevalent cluster #P6) were under-expressed in high risk group, and displayed the propensity to differentiate "high risk" group of prevalent patients from the two other risk groups. Conversely, TNFA (prevalent cluster #P8) was found overly abundant in the "low/intermediate risk" group of incident patients compared to the corresponding urological controls. AMPN is a metallo-protease which has been implicated in angiogenesis, an essential component of cancer growth, cell migration and cell survival (Guzman-Rojas et al., 2012). High levels of AMPN expression in tissue have been associated with tumor progression, specifically in prostate cancer (Guzman-Rojas et al., 2012). AMPN was a candidate pre-sorted from our prior discovery experiments. No bladder cancer-related association was found in the literature for this protein prior to this evaluation study. As of today, only a single study using IMAC fractionation combined to LC-MS/MS analysis and Western Blot analysis reported down-regulation of AMPN in urine samples from patients with muscle-invasive vs. non-muscle-invasive tumors, in agreement with our results that show decreased levels with increasing risk. The second most discriminating protein was ANAG. No prior association between ANAG and cancer processes has been reported. ANAG was mainly mentioned for its involvement in the degradation of heparin sulfate. TNFA is a pro-inflammatory cytokine produced by both immune and tumor cells. A previously reported cancer-related function for this protein could be to mediate tumor progression by inducing proliferation, invasion and metastasis of tumor cells. Higher levels of TNFA have been correlated with advanced tumor stage and shorter survival in several cancer studies. In particular, TNFA has been associated with tumor stage in UBC.

Candidate Evaluation as Prevalent UBC Diagnostic Biomarkers.

When considering differential abundance with respect to the disease status (control vs. UBC) in the prevalent subpopulation, 10 proteins emerged as significant. These proteins could be of particular interest to discriminate patients with prior UBC history whose examination results confirmed UBC recurrence to those for whom the examination results cleared any suspicion of UBC recurrence (prevalent urological controls). These 10 proteins were distributed between prevalent clusters #P1, #P4, #P6 and #P8. Among them, a large proportion (80%) also exhibited a significant link with the risk, similarly to what was observed in the incident population. Conversely, three proteins (KLK3, EGF and OSTP) showing significant differences with the risk group failed to discriminate disease status in prevalent cluster #P7 associated with "cellular growth and proliferation, tissue development and cellular development" network.

The strongest associations with the disease status were observed for LAMP1 (lysosome-associated membrane glycoprotein 1), TNFA, and AMPN which were also revealed as part of the most discriminating proteins with the risk factor. LAMP1 is mainly expressed in the endosome-lysosomal membrane of cells but has also been found in the plasma membrane (1-2% of total LAMP1) (Jensen et al., 2013). It has been reported that enhanced expression of LAMP1 in tumor cells may promote invasion by influencing adhesion to extracellular matrix and perhaps also binding to endothelial cells (Jensen et al., 2013). The interesting point is that its abundances significantly decreased in urine samples from prevalent cancer in the present study. No such observation has been previously reported. This finding confirms results from our prior discovery experiments. Since these three protein candidates have been previously associated with cancer, these results prompt further validation studies to confirm their clinical utility as diagnosis markers of UBC relapse.

In summary, of the 108 candidate biomarker proteins analyzed by SRM, significant changes in urinary levels in association with risk group and disease status were observed for 50 and 6 proteins in the incident subset, and 19 and 10 proteins in the prevalent subset, respectively. Overall, the strongest significant differences in urinary levels were observed for proteins that have already been reported in cancer (CALR, ES8L2, RASK, AMPN) or more specifically in UBC (K1C19, TSP1, UROM, TNFA), except for ANAG and PLTP with unknown cancer-related function reported up-to-date. Finally, different sets of candidates emerged as discriminative of UBC incidence vs. UBC recurrence, reinforcing the assumption that there could be considerable differences in the phenotypes of recurrent and incident UBC.

Table 4

ANOVA analysis of candidate biomarker proteins sorted by clusters in the incident subset associated with the risk factor (High risk incident cancer, low/intermediate risk incident cancer, and urological incident control). Proteins displaying significant differences between groups (p-value≤0.05) are marked by asterisks.

TABLE 4A

Cluster #I1

| Protein | F Ratio | p-value |
|---|---|---|
| P53_HUMAN* | 6.239 | 0.0035 |
| A1BG_HUMAN* | 5.098 | 0.0092 |
| CERU_HUMAN* | 5.000 | 0.0100 |
| CO1A2_HUMAN* | 4.885 | 0.0110 |
| ANGP2_HUMAN* | 4.013 | 0.0234 |
| IGF2_HUMAN* | 3.715 | 0.0304 |
| A2GL_HUMAN* | 3.681 | 0.0314 |
| A1AG2_HUMAN* | 3.590 | 0.0340 |
| GELS_HUMAN* | 3.283 | 0.0447 |
| ZA2G_HUMAN | 3.097 | 0.0529 |
| CATL1_HUMAN | 2.491 | 0.0918 |
| SODC_HUMAN | 1.837 | 0.1686 |
| VCAM1_HUMAN | 1.347 | 0.2681 |
| SBP1_HUMAN | 0.001 | 0.9988 |

TABLE 4B

Cluster #I2

| Protein | F Ratio | p-value |
|---|---|---|
| K1C19_HUMAN* | 12.375 | <.0001 |
| TERA_HUMAN* | 5.945 | 0.0045 |
| IBP4_HUMAN* | 5.335 | 0.0075 |
| ALDOA_HUMAN* | 4.706 | 0.0128 |
| NID2_HUMAN* | 3.580 | 0.0343 |
| AK1C4_HUMAN* | 3.238 | 0.0466 |

TABLE 4B-continued

Cluster #I2

| Protein | F Ratio | p-value |
|---|---|---|
| LDHA_HUMAN* | 3.190 | 0.0486 |
| NDKA_HUMAN | 3.149 | 0.0505 |
| S10A6_HUMAN | 2.923 | 0.0619 |
| PROF1_HUMAN | 2.417 | 0.0982 |
| SYUG_HUMAN | 1.657 | 0.1998 |
| PRDX1_HUMAN | 1.394 | 0.2565 |
| PTGDS_HUMAN | 1.331 | 0.2722 |
| KPYM_HUMAN | 1.198 | 0.3093 |
| IBP6_HUMAN | 1.083 | 0.3453 |
| S10A9_HUMAN | 1.061 | 0.3530 |
| AL1L1_HUMAN | 0.934 | 0.3989 |
| FABP4_HUMAN | 0.515 | 0.6001 |
| MUC4_HUMAN | 0.333 | 0.7182 |
| ITB1_HUMAN | 0.046 | 0.9555 |

TABLE 4C

Cluster #I3

| Protein | F Ratio | p-value |
|---|---|---|
| CALR_HUMAN* | 15.434 | <.0001 |
| RASK_HUMAN* | 11.663 | <.0001 |
| TRFE_HUMAN* | 11.474 | <.0001 |
| FCN3_HUMAN* | 11.385 | <.0001 |
| BIRC5_HUMAN* | 10.736 | 0.0001 |
| AFAM_HUMAN* | 10.510 | 0.0001 |
| CO3_HUMAN* | 10.493 | 0.0001 |
| ITIH4_HUMAN* | 10.489 | 0.0001 |
| ITIH2_HUMAN* | 10.442 | 0.0001 |
| APOA1_HUMAN* | 10.034 | 0.0002 |
| FIBG_HUMAN* | 9.769 | 0.0002 |
| FIBB_HUMAN* | 9.348 | 0.0003 |
| C4BPA_HUMAN* | 9.286 | 0.0003 |
| PLTP_HUMAN* | 9.282 | 0.0003 |
| A2MG_HUMAN* | 9.277 | 0.0003 |
| SORL_HUMAN* | 9.203 | 0.0003 |
| PDGFA_HUMAN* | 8.911 | 0.0004 |
| VTDB_HUMAN* | 7.949 | 0.0009 |
| A1AT_HUMAN* | 7.239 | 0.0016 |
| APOA4_HUMAN* | 6.432 | 0.0030 |
| PGS1_HUMAN* | 6.187 | 0.0037 |
| IGHG1_HUMAN* | 4.697 | 0.0129 |
| PTX3_HUMAN* | 4.280 | 0.0185 |
| MUC5B_HUMAN* | 4.097 | 0.0218 |
| NF2L2_HUMAN* | 3.736 | 0.0299 |
| APOE_HUMAN | 2.641 | 0.0800 |

TABLE 4D

Cluster #I4

| Protein | F Ratio | p-value |
|---|---|---|
| ES8L2_HUMAN* | 11.772 | <.0001 |
| UROM_HUMAN* | 6.545 | 0.0028 |
| RETN_HUMAN* | 6.138 | 0.0039 |
| KV201_HUMAN* | 4.615 | 0.0139 |
| MIME_HUMAN* | 3.865 | 0.0267 |
| TNFA_HUMAN | 2.636 | 0.0804 |

TABLE 4E

Cluster #I5

| Protein | F Ratio | p-value |
|---|---|---|
| HPT_HUMAN | 1.879 | 0.1621 |
| IMA2_HUMAN | 1.377 | 0.2607 |

TABLE 4E-continued

Cluster #I5

| Protein | F Ratio | p-value |
|---|---|---|
| HBB_HUMAN | 1.315 | 0.2766 |
| HBA_HUMAN | 1.230 | 0.2998 |
| LAMA4_HUMAN | 0.887 | 0.4174 |
| LTOR3_HUMAN | 0.724 | 0.4891 |
| RALA_HUMAN | 0.473 | 0.6255 |
| RASN_HUMAN | 0.436 | 0.6487 |
| MMP9_HUMAN | 0.305 | 0.7387 |

TABLE 4F

Cluster #I6

| Protein | F Ratio | p-value |
|---|---|---|
| LAMP1_HUMAN | 2.289 | 0.1106 |
| NHRF1_HUMAN | 1.299 | 0.2808 |
| CAD13_HUMAN | 1.133 | 0.3292 |
| CD59_HUMAN | 1.013 | 0.3696 |
| DPP4_HUMAN | 0.838 | 0.4379 |
| AMPN_HUMAN | 0.412 | 0.6642 |
| CADH1_HUMAN | 0.384 | 0.6832 |
| DAF_HUMAN | 0.186 | 0.8311 |
| CATD_HUMAN | 0.099 | 0.9057 |
| ANM1_HUMAN | 0.094 | 0.9108 |

TABLE 4G

Cluster #I7

| Protein | F Ratio | p-value |
|---|---|---|
| TSP1_HUMAN* | 4.310 | 0.0181 |
| CLUS_HUMAN | 2.059 | 0.1370 |
| SDF1_HUMAN | 1.132 | 0.3295 |
| MASP2_HUMAN | 0.964 | 0.3875 |
| IPSP_HUMAN | 0.886 | 0.4181 |
| TRBM_HUMAN | 0.544 | 0.5837 |
| CD44_HUMAN | 0.274 | 0.7613 |

TABLE 4H

Cluster #I8

| Protein | F Ratio | p-value |
|---|---|---|
| OSTP_HUMAN* | 4.882 | 0.0110 |
| EGF_HUMAN* | 3.366 | 0.0415 |
| PPAP_HUMAN* | 3.162 | 0.0498 |
| IBP7_HUMAN | 2.721 | 0.0743 |
| LYAG_HUMAN | 2.674 | 0.0776 |
| CO6A1_HUMAN | 2.612 | 0.0822 |
| LG3BP_HUMAN | 2.479 | 0.0928 |
| KNG1_HUMAN | 2.440 | 0.0962 |
| ATRN_HUMAN | 1.866 | 0.1641 |
| CBPE_HUMAN | 1.859 | 0.1652 |
| CUBN_HUMAN | 1.551 | 0.2209 |
| ANAG_HUMAN | 1.415 | 0.2513 |
| GGH_HUMAN | 1.362 | 0.2644 |
| LAMP2_HUMAN | 0.930 | 0.4005 |
| KLK3_HUMAN | 0.573 | 0.5672 |
| SAP_HUMAN | 0.559 | 0.5751 |

Table 5

ANOVA analysis of candidate biomarker proteins sorted by clusters in the incident subset associated with the disease status (urological incident control vs. incident cancer). Proteins displaying significant differences between groups (p-value≤0.05) are marked by asterisks.

TABLE 5A

Cluster #I1

| Protein | F Ratio | p-value |
|---|---|---|
| ANGP2_HUMAN | 3.166 | 0.0804 |
| ZA2G_HUMAN | 2.857 | 0.0964 |
| SODC_HUMAN | 2.324 | 0.1328 |
| CO1A2_HUMAN | 2.007 | 0.1619 |
| IGF2_HUMAN | 1.594 | 0.2118 |
| VCAM1_HUMAN | 1.538 | 0.2200 |
| A2GL_HUMAN | 1.191 | 0.2797 |
| A1AG2_HUMAN | 1.157 | 0.2865 |
| A1BG_HUMAN | 0.943 | 0.3356 |
| GELS_HUMAN | 0.900 | 0.3468 |
| CATL1_HUMAN | 0.711 | 0.4026 |
| P53_HUMAN | 0.289 | 0.5929 |
| CERU_HUMAN | 0.086 | 0.7701 |
| SBP1_HUMAN | 0.001 | 0.9746 |

TABLE 5B

Cluster #I2

| Protein | F Ratio | p-value |
|---|---|---|
| K1C19_HUMAN* | 7.177 | 0.0096 |
| S10A6_HUMAN* | 4.596 | 0.0363 |
| ALDOA_HUMAN | 2.520 | 0.1179 |
| PROF1_HUMAN | 2.396 | 0.1271 |
| PTGDS_HUMAN | 2.230 | 0.1408 |
| S10A9_HUMAN | 2.153 | 0.1477 |
| IBP6_HUMAN | 1.709 | 0.1963 |
| NDKA_HUMAN | 1.481 | 0.2285 |
| IBP4_HUMAN | 0.919 | 0.3417 |
| NID2_HUMAN | 0.728 | 0.3971 |
| PRDX1_HUMAN | 0.648 | 0.4242 |
| LDHA_HUMAN | 0.584 | 0.4479 |
| TERA_HUMAN | 0.548 | 0.4622 |
| AK1C4_HUMAN | 0.295 | 0.5891 |
| KPYM_HUMAN | 0.196 | 0.6594 |
| MUC4_HUMAN | 0.136 | 0.7135 |
| AL1L1_HUMAN | 0.100 | 0.7535 |
| FABP4_HUMAN | 0.096 | 0.7582 |
| SYUG_HUMAN | 0.033 | 0.8574 |
| ITB1_HUMAN | 0.008 | 0.9273 |

TABLE 5C

Cluster #I3

| Protein | F Ratio | p-value |
|---|---|---|
| PLTP_HUMAN* | 6.699 | 0.0122 |
| APOE_HUMAN | 3.150 | 0.0812 |
| FIBB_HUMAN | 2.426 | 0.1248 |
| CO3_HUMAN | 2.064 | 0.1562 |
| FIBG_HUMAN | 1.993 | 0.1634 |
| FCN3_HUMAN | 1.561 | 0.2166 |
| C4BPA_HUMAN | 1.504 | 0.2251 |
| ITIH2_HUMAN | 1.373 | 0.2461 |
| APOA1_HUMAN | 1.205 | 0.2769 |
| ITIH4_HUMAN | 0.886 | 0.3505 |
| VTDB_HUMAN | 0.751 | 0.3896 |
| A2MG_HUMAN | 0.522 | 0.4730 |
| APOA4_HUMAN | 0.503 | 0.4810 |
| NF2L2_HUMAN | 0.448 | 0.5059 |
| SORL_HUMAN | 0.431 | 0.5140 |
| PGS1_HUMAN | 0.402 | 0.5285 |
| AFAM_HUMAN | 0.320 | 0.5738 |
| BIRC5_HUMAN | 0.268 | 0.6064 |
| TRFE_HUMAN | 0.210 | 0.6488 |
| RASK_HUMAN | 0.155 | 0.6955 |
| A1AT_HUMAN | 0.143 | 0.7072 |
| PDGFA_HUMAN | 0.087 | 0.7692 |
| MUC5B_HUMAN | 0.085 | 0.7716 |

TABLE 5C-continued

| Cluster #I3 | | |
|---|---|---|
| Protein | F Ratio | p-value |
| PTX3_HUMAN | 0.070 | 0.7925 |
| CALR_HUMAN | 0.014 | 0.9079 |
| IGHG1_HUMAN | 0.005 | 0.9419 |

TABLE 5D

| Cluster #I4 | | |
|---|---|---|
| Protein | F Ratio | p-value |
| UROM_HUMAN* | 7.300 | 0.0090 |
| TNFA_HUMAN | 3.591 | 0.0631 |
| ES8L2_HUMAN | 2.486 | 0.1203 |
| KV201_HUMAN | 2.163 | 0.1468 |
| RETN_HUMAN | 0.636 | 0.4286 |
| MIME_HUMAN | 0.584 | 0.4477 |

TABLE 5E

| Cluster #I5 | | |
|---|---|---|
| Protein | F Ratio | p-value |
| HPT_HUMAN | 3.099 | 0.0836 |
| HBB_HUMAN | 2.497 | 0.1195 |
| HBA_HUMAN | 2.306 | 0.1343 |
| LAMA4_HUMAN | 1.730 | 0.1937 |
| LTOR3_HUMAN | 0.870 | 0.3547 |
| IMA2_HUMAN | 0.662 | 0.4190 |
| RASN_HUMAN | 0.602 | 0.4410 |
| MMP9_HUMAN | 0.465 | 0.4979 |
| RALA_HUMAN | 0.032 | 0.8590 |

TABLE 5F

| Cluster #I6 | | |
|---|---|---|
| Protein | F Ratio | p-value |
| CAD13_HUMAN | 2.073 | 0.1553 |
| CD59_HUMAN | 1.409 | 0.2401 |
| NHRF1_HUMAN | 1.086 | 0.3016 |
| CADH1_HUMAN | 0.676 | 0.4143 |
| DAF_HUMAN | 0.353 | 0.5547 |
| DPP4_HUMAN | 0.312 | 0.5788 |
| AMPN_HUMAN | 0.141 | 0.7091 |
| ANM1_HUMAN | 0.128 | 0.7215 |
| CATD_HUMAN | 0.027 | 0.8693 |
| LAMP1_HUMAN | 0.001 | 0.9787 |

TABLE 5G

| Cluster #I7 | | |
|---|---|---|
| Protein | F Ratio | p-value |
| TSP1_HUMAN* | 8.650 | 0.0047 |
| CLUS_HUMAN* | 4.185 | 0.0453 |
| IPSP_HUMAN | 1.777 | 0.1877 |
| SDF1_HUMAN | 1.169 | 0.2841 |
| TRBM_HUMAN | 0.184 | 0.6693 |
| MASP2_HUMAN | 0.076 | 0.7836 |
| CD44_HUMAN | 0.033 | 0.8564 |

TABLE 5H

| Cluster #I8 | | |
|---|---|---|
| Protein | F Ratio | p-value |
| EGF_HUMAN | 3.619 | 0.0621 |
| LG3BP_HUMAN | 3.428 | 0.0692 |
| KNG1_HUMAN | 2.905 | 0.0937 |
| IBP7_HUMAN | 2.779 | 0.1009 |
| OSTP_HUMAN | 2.776 | 0.1011 |
| CUBN_HUMAN | 1.931 | 0.1700 |
| LAMP2_HUMAN | 1.887 | 0.1749 |
| CO6A1_HUMAN | 1.850 | 0.1791 |
| GGH_HUMAN | 1.487 | 0.2277 |
| ANAG_HUMAN | 1.235 | 0.2711 |
| ATRN_HUMAN | 1.052 | 0.3094 |
| PPAP_HUMAN | 0.949 | 0.3341 |
| SAP_HUMAN | 0.747 | 0.3911 |
| LYAG_HUMAN | 0.614 | 0.4363 |
| KLK3_HUMAN | 0.386 | 0.5369 |
| CBPE_HUMAN | 0.047 | 0.8286 |

Table 6

ANOVA analysis of candidate biomarker proteins sorted by clusters in the prevalent subset associated with the risk factor (High risk prevalent cancer, low/intermediate risk prevalent cancer, and urological prevalent control). Proteins displaying significant differences between groups (p-value≤0.05) are marked by asterisks.

TABLE 6A

| Cluster #P1 | | |
|---|---|---|
| Protein | F Ratio | p-value |
| LAMP1_HUMAN* | 4.688 | 0.0139 |
| LAMA4_HUMAN* | 3.297 | 0.0457 |
| ZA2G_HUMAN | 2.454 | 0.0969 |
| A1AG2_HUMAN | 2.232 | 0.1185 |
| PTGDS_HUMAN | 2.166 | 0.1260 |
| A2GL_HUMAN | 1.992 | 0.1478 |
| VCAM1_HUMAN | 1.673 | 0.1986 |
| RETN_HUMAN | 1.488 | 0.2362 |
| ES8L2_HUMAN | 0.921 | 0.4051 |
| MIME_HUMAN | 0.827 | 0.4436 |
| KV201_HUMAN | 0.679 | 0.5122 |

TABLE 6B

| Cluster #P2 | | |
|---|---|---|
| Protein | F Ratio | p-value |
| LDHA_HUMAN | 1.325 | 0.2756 |
| A1BG_HUMAN | 1.159 | 0.3226 |
| MMP9_HUMAN | 0.842 | 0.4372 |
| TERA_HUMAN | 0.824 | 0.4447 |
| K1C19_HUMAN | 0.810 | 0.4511 |
| GELS_HUMAN | 0.802 | 0.4543 |
| HPT_HUMAN | 0.702 | 0.5007 |
| ITB1_HUMAN | 0.576 | 0.5661 |
| CO1A2_HUMAN | 0.507 | 0.6057 |
| MUC5B_HUMAN | 0.499 | 0.6106 |
| CATL1_HUMAN | 0.412 | 0.6650 |
| CERU_HUMAN | 0.389 | 0.6799 |
| PTX3_HUMAN | 0.314 | 0.7324 |
| ANGP2_HUMAN | 0.144 | 0.8663 |
| NF2L2_HUMAN | 0.128 | 0.8802 |
| NDKA_HUMAN | 0.099 | 0.9058 |
| IMA2_HUMAN | 0.068 | 0.9343 |
| IBP6_HUMAN | 0.027 | 0.9738 |

TABLE 6C

| Cluster #P3 | | |
|---|---|---|
| Protein | F Ratio | p-value |
| AL1L1_HUMAN | 2.118 | 0.1316 |
| S10A9_HUMAN | 1.385 | 0.2604 |
| IGF2_HUMAN | 0.830 | 0.4425 |
| MUC4_HUMAN | 0.783 | 0.4630 |
| P53_HUMAN | 0.782 | 0.4633 |
| PROF1_HUMAN | 0.769 | 0.4692 |
| KPYM_HUMAN | 0.427 | 0.6553 |
| APOE_HUMAN | 0.330 | 0.7209 |
| AK1C4_HUMAN | 0.310 | 0.7350 |
| SYUG_HUMAN | 0.256 | 0.7755 |
| ALDOA_HUMAN | 0.241 | 0.7869 |
| S10A6_HUMAN | 0.229 | 0.7962 |
| FABP4_HUMAN | 0.210 | 0.8111 |
| PRDX1_HUMAN | 0.072 | 0.9309 |

TABLE 6D

| Cluster #P4 | | |
|---|---|---|
| Protein | F Ratio | p-value |
| LAMP2_HUMAN* | 4.676 | 0.0141 |
| CD44_HUMAN | 3.154 | 0.0518 |
| MASP2_HUMAN | 3.085 | 0.0551 |
| CUBN_HUMAN | 2.743 | 0.0747 |
| SODC_HUMAN | 2.528 | 0.0906 |
| ATRN_HUMAN | 2.476 | 0.0950 |
| NHRF1_HUMAN | 2.433 | 0.0988 |
| SDF1_HUMAN | 1.826 | 0.1723 |
| CLUS_HUMAN | 1.447 | 0.2457 |
| IPSP_HUMAN | 1.070 | 0.3511 |
| TRBM_HUMAN | 0.935 | 0.4000 |
| TSP1_HUMAN | 0.771 | 0.4681 |
| SBP1_HUMAN | 0.516 | 0.6003 |
| RASN_HUMAN | 0.014 | 0.9862 |

TABLE 6E

| Cluster #P5 | | |
|---|---|---|
| Protein | F Ratio | p-value |
| LTOR3_HUMAN* | 3.384 | 0.0424 |
| FIBB_HUMAN | 2.589 | 0.0858 |
| FIBG_HUMAN | 2.581 | 0.0864 |
| CO3_HUMAN | 2.431 | 0.0990 |
| ITIH4_HUMAN | 2.355 | 0.1060 |
| HBA_HUMAN | 2.144 | 0.1285 |
| ITIH2_HUMAN | 2.021 | 0.1439 |
| BIRC5_HUMAN | 1.912 | 0.1601 |
| A2MG_HUMAN | 1.854 | 0.1679 |
| VTDB_HUMAN | 1.625 | 0.2078 |
| FCN3_HUMAN | 1.464 | 0.2417 |
| C4BPA_HUMAN | 1.223 | 0.3037 |
| RASK_HUMAN | 1.149 | 0.3256 |
| PLTP_HUMAN | 1.008 | 0.3727 |
| APOA1_HUMAN | 0.853 | 0.4328 |
| IGHG1_HUMAN | 0.821 | 0.4461 |
| TRFE_HUMAN | 0.798 | 0.4561 |
| HBB_HUMAN | 0.760 | 0.4735 |
| NID2_HUMAN | 0.674 | 0.5154 |
| A1AT_HUMAN | 0.419 | 0.6599 |
| AFAM_HUMAN | 0.273 | 0.7626 |
| PDGFA_HUMAN | 0.258 | 0.7738 |
| IBP4_HUMAN | 0.244 | 0.7843 |
| SORL_HUMAN | 0.238 | 0.7895 |
| APOA4_HUMAN | 0.088 | 0.9155 |
| CALR_HUMAN | 0.048 | 0.9532 |
| PGS1_HUMAN | 0.021 | 0.9790 |

TABLE 6F

| Cluster #P6 | | |
|---|---|---|
| Protein | F Ratio | p-value |
| AMPN_HUMAN* | 9.873 | 0.0003 |
| ANAG_HUMAN* | 8.523 | 0.0007 |
| LYAG_HUMAN* | 7.655 | 0.0013 |
| CBPE_HUMAN* | 7.512 | 0.0015 |
| DPP4_HUMAN* | 6.698 | 0.0028 |
| CO6A1_HUMAN* | 5.755 | 0.0058 |
| LG3BP_HUMAN* | 5.201 | 0.0091 |
| KNG1_HUMAN* | 4.813 | 0.0125 |
| IBP7_HUMAN* | 3.764 | 0.0304 |
| GGH_HUMAN* | 3.248 | 0.0477 |
| SAP_HUMAN | 2.416 | 0.1003 |
| DAF_HUMAN | 2.309 | 0.1106 |
| CADH1_HUMAN | 2.145 | 0.1284 |
| ANM1_HUMAN | 1.937 | 0.1555 |
| CATD_HUMAN | 1.585 | 0.2157 |
| CD59_HUMAN | 1.512 | 0.2310 |
| CAD13_HUMAN | 1.190 | 0.3132 |

TABLE 6G

| Cluster #P7 | | |
|---|---|---|
| Protein | F Ratio | p-value |
| KLK3_HUMAN* | 4.682 | 0.0140 |
| EGF_HUMAN* | 4.331 | 0.0188 |
| OSTP_HUMAN* | 3.697 | 0.0323 |
| PPAP_HUMAN | 1.889 | 0.1625 |

TABLE 6H

| Cluster #P8 | | |
|---|---|---|
| Protein | F Ratio | p-value |
| TNFA_HUMAN* | 4.503 | 0.0162 |
| RALA_HUMAN* | 3.864 | 0.0280 |
| UROM_HUMAN | 2.263 | 0.1153 |

Table 7

ANOVA analysis of candidate biomarker proteins sorted by clusters in the prevalent subset associated with the disease status (urological prevalent control vs. prevalent cancer). Proteins displaying significant differences between groups (p-value≤0.05) are marked by asterisks.

TABLE 7A

| Cluster #P1 | | |
|---|---|---|
| Protein | F Ratio | p-value |
| LAMP1_HUMAN* | 8.118 | 0.0064 |
| LAMA4_HUMAN* | 6.716 | 0.0126 |
| ZA2G_HUMAN* | 4.269 | 0.0442 |
| A2GL_HUMAN | 3.791 | 0.0574 |
| A1AG2_HUMAN | 3.641 | 0.0624 |
| VCAM1_HUMAN | 3.246 | 0.0779 |
| RETN_HUMAN | 3.010 | 0.0891 |
| PTGDS_HUMAN | 2.915 | 0.0942 |
| ES8L2_HUMAN | 0.516 | 0.4761 |
| KV201_HUMAN | 0.249 | 0.6198 |
| MIME_HUMAN | 0.236 | 0.6293 |

TABLE 7B

Cluster #P2

| Protein | F Ratio | p-value |
| --- | --- | --- |
| LDHA_HUMAN | 2.639 | 0.1108 |
| A1BG_HUMAN | 2.118 | 0.1520 |
| MMP9_HUMAN | 1.720 | 0.1960 |
| TERA_HUMAN | 1.418 | 0.2396 |
| GELS_HUMAN | 1.323 | 0.2558 |
| CO1A2_HUMAN | 0.998 | 0.3228 |
| CERU_HUMAN | 0.773 | 0.3836 |
| MUC5B_HUMAN | 0.526 | 0.4717 |
| NF2L2_HUMAN | 0.258 | 0.6136 |
| CATL1_HUMAN | 0.241 | 0.6260 |
| K1C19_HUMAN | 0.205 | 0.6526 |
| NDKA_HUMAN | 0.152 | 0.6980 |
| IMA2_HUMAN | 0.139 | 0.7109 |
| ITB1_HUMAN | 0.132 | 0.7179 |
| ANGP2_HUMAN | 0.103 | 0.7494 |
| PTX3_HUMAN | 0.078 | 0.7808 |
| IBP6_HUMAN | 0.038 | 0.8472 |
| HPT_HUMAN | 0.005 | 0.9466 |

TABLE 7C

Cluster #P3

| Protein | F Ratio | p-value |
| --- | --- | --- |
| S10A9_HUMAN | 1.647 | 0.2055 |
| IGF2_HUMAN | 1.368 | 0.2480 |
| PROF1_HUMAN | 1.291 | 0.2615 |
| AK1C4_HUMAN | 0.454 | 0.5039 |
| KPYM_HUMAN | 0.429 | 0.5157 |
| FABP4_HUMAN | 0.345 | 0.5597 |
| SYUG_HUMAN | 0.335 | 0.5652 |
| P53_HUMAN | 0.301 | 0.5858 |
| APOE_HUMAN | 0.209 | 0.6496 |
| S10A6_HUMAN | 0.169 | 0.6832 |
| PRDX1_HUMAN | 0.124 | 0.7259 |
| ALDOA_HUMAN | 0.070 | 0.7926 |
| AL1L1_HUMAN | 0.010 | 0.9212 |
| MUC4_HUMAN | 0.004 | 0.9505 |

TABLE 7D

Cluster #P4

| Protein | F Ratio | p-value |
| --- | --- | --- |
| LAMP2_HUMAN* | 6.157 | 0.0166 |
| CD44_HUMAN* | 4.954 | 0.0308 |
| MASP2_HUMAN | 3.750 | 0.0587 |
| TRBM_HUMAN | 1.692 | 0.1995 |
| SODC_HUMAN | 1.634 | 0.2074 |
| CUBN_HUMAN | 1.496 | 0.2273 |
| CLUS_HUMAN | 1.447 | 0.2350 |
| ATRN_HUMAN | 1.138 | 0.2915 |
| SBP1_HUMAN | 0.901 | 0.3473 |
| TSP1_HUMAN | 0.427 | 0.5166 |
| IPSP_HUMAN | 0.191 | 0.6638 |
| SDF1_HUMAN | 0.074 | 0.7865 |
| RASN_HUMAN | 0.022 | 0.8816 |
| NHRF1_HUMAN | 0.017 | 0.8968 |

TABLE 7E

Cluster #P5

| Protein | F Ratio | p-value |
| --- | --- | --- |
| LTOR3_HUMAN | 1.950 | 0.1690 |
| RASK_HUMAN | 1.750 | 0.1922 |

TABLE 7E-continued

Cluster #P5

| Protein | F Ratio | p-value |
| --- | --- | --- |
| IGHG1_HUMAN | 0.611 | 0.4383 |
| A1AT_HUMAN | 0.582 | 0.4493 |
| IBP4_HUMAN | 0.500 | 0.4833 |
| PLTP_HUMAN | 0.369 | 0.5462 |
| FIBB_HUMAN | 0.339 | 0.5633 |
| TRFE_HUMAN | 0.270 | 0.6055 |
| HBB_HUMAN | 0.259 | 0.6129 |
| AFAM_HUMAN | 0.248 | 0.6207 |
| SORL_HUMAN | 0.243 | 0.6245 |
| C4BPA_HUMAN | 0.206 | 0.6521 |
| PDGFA_HUMAN | 0.114 | 0.7369 |
| ITIH4_HUMAN | 0.089 | 0.7663 |
| HBA_HUMAN | 0.083 | 0.7741 |
| CO3_HUMAN | 0.082 | 0.7762 |
| CALR_HUMAN | 0.055 | 0.8165 |
| A2MG_HUMAN | 0.039 | 0.8446 |
| NID2_HUMAN | 0.037 | 0.8493 |
| FCN3_HUMAN | 0.030 | 0.8629 |
| ITIH2_HUMAN | 0.022 | 0.8821 |
| VTDB_HUMAN | 0.014 | 0.9076 |
| APOA4_HUMAN | 0.010 | 0.9224 |
| PGS1_HUMAN | 0.009 | 0.9250 |
| BIRC5_HUMAN | 0.001 | 0.9724 |
| FIBG_HUMAN | 0.000 | 0.9885 |
| APOA1_HUMAN | 0.000 | 0.9979 |

TABLE 7F

Cluster #P6

| Protein | F Ratio | p-value |
| --- | --- | --- |
| AMPN_HUMAN* | 7.051 | 0.0107 |
| DPP4_HUMAN* | 6.982 | 0.0111 |
| LYAG_HUMAN* | 4.485 | 0.0394 |
| ANAG_HUMAN | 3.888 | 0.0544 |
| DAF_HUMAN | 3.815 | 0.0566 |
| CO6A1_HUMAN | 3.331 | 0.0742 |
| KNG1_HUMAN | 3.291 | 0.0759 |
| CBPE_HUMAN | 2.758 | 0.1033 |
| CADH1_HUMAN | 2.615 | 0.1124 |
| LG3BP_HUMAN | 2.500 | 0.1204 |
| CATD_HUMAN | 1.417 | 0.2398 |
| GGH_HUMAN | 1.305 | 0.2589 |
| CAD13_HUMAN | 1.061 | 0.3082 |
| SAP_HUMAN | 0.984 | 0.3262 |
| IBP7_HUMAN | 0.501 | 0.4824 |
| ANM1_HUMAN | 0.059 | 0.8094 |
| CD59_HUMAN | 0.035 | 0.8531 |

TABLE 7G

Cluster #P7

| Protein | F Ratio | p-value |
| --- | --- | --- |
| EGF_HUMAN | 2.219 | 0.1428 |
| KLK3_HUMAN | 0.722 | 0.3998 |
| OSTP_HUMAN | 0.498 | 0.4839 |
| PPAP_HUMAN | 0.017 | 0.8971 |

TABLE 7H

Cluster #P8

| Protein | F Ratio | p-value |
| --- | --- | --- |
| TNFA_HUMAN* | 8.858 | 0.0046 |
| RALA_HUMAN* | 7.135 | 0.0103 |
| UROM_HUMAN | 3.119 | 0.0837 |

In a preceding analysis, further biomarker proteins were identified (table 8) which were not included in the 134 bladder cancer candidate biomarker proteins of the above study (SRM screening), but which were also found to be present in significantly deviating amounts in the urine of patients having bladder cancer or with an elevated risk of bladder cancer progression and recurrence.

TABLE 8

| Protein |
| --- |
| CATB_HUMAN |
| COX7R_HUMAN |
| CUBN_HUMAN |
| CYTM_HUMAN |
| GDF15_HUMAN |
| HEPC_HUMAN |
| IPSP_HUMAN |
| PIP_HUMAN |
| RET4_HUMAN |
| S100P_HUMAN |

Second Study
Material and Methods
Protein Extraction from Human Urine Samples and Trypsin Cleavage
Samples Fresh urine samples are mixed immediately with protease inhibitor and stored up to 4 h at 4° C. After centrifugation to remove cells, the protein concentration of the supernatant is determined with a Bradford assay according to the instructions of the manufacturer. The supernatant is stored at −80° C. until analysis.
Precipitation Total protein is precipitated from supernatant of centrifuged urine adding Trichloroacetic Acid (TCA, final concentration 6%). The pellet is centrifuged, washed twice with ice cold acetone and vacuum dried. Then the pellet is resuspended in 8M urea, 100 mM Ammonium Bicarbonate and the protein concentration is determined with a Bradford assay according to the instructions of the manufacturer.
Trypsin Cleavage The resuspended proteins are mixed with protein quantification standard (stable isotope labelled concatemer for protein quantification, PolyQuant GmbH) and HPLC-retention time standard (PolyQuant GmbH). After reduction with DTT (12 mM, 30 min), the proteins are alkylated with Iodoacetamide (40 mM, 30 min, darkness). To minimize the urea concentration, the solution is diluted with 0.1M Ammonium Bicarbonate. For protease cleavage, Trypsin (sequencing grade porcine Trypsin, Promega) is added (enzyme: protein=1:50) and the solution is incubated at 37° C., overnight. The reaction is stopped with formic acid (final concentration 1%) and the samples are vacuum dried.
Production of Stable Isotope Labelled QconCAT
QConCAT Expression An expression-plasmid, harbouring the sequence of the concatemer for protein quantification (QconCAT) is transformed into an *E. coli* strain optimized for protein expression. The expression level and the solubility of the expressed protein are tested in small scale cultures. After evaluation via sodium dodecyl sulfate polyacrylamide gel electrophoresis (SDS-PAGE) the most suitable clone is selected for further protein production.
Expression and Purification of Stable Isotope Labelled QconCAT The selected clone is grown in labelling medium. This is a minimal medium containing either $^{15}$N-Ammoniumchloride for complete $^{15}$N-labelling or labelled Arginine and Lysine ($^{13}$C or $^{13}$C, $^{15}$N) for single amino acid labelling (Pratt et al. 2006). After protein expression for 6 h, cells are harvested by centrifugation and lysed by sonication (30% amplitude, 3×30 sec, on ice). As the sequence contains a poly Histidin tag, the target protein is purified by ion metal affinity chromatography (IMAC) under denaturing conditions (50 mM NaP, pH 7.4, 6M GdnHCl, 300 mM NaCl, gradient: 20 mM-500 mM Imidazole). Purity and amount are verified by SDS-PAGE. The purified stable isotope labelled QconCAT is dialyzed against a selected buffer (e.g. 0.5% Acetic acid), centrifuged (16000×g, 10 min) and the supernatant is stored at 4° C. upon use.
Quality Control The protein concentration of the QConCAT is determined by amino acid analysis. Purity and molecular weight of the QconCAT are verified by SDS-PAGE. An aliquot of the QconCAT is cleaved by Trypsin and the resulting peptides are analysed by Matrix-assisted laser desorption/ionization-time-of flight mass spectrometry (MALDI-TOF MS).
Sample Preparation for Mass Spectrometry 25 μg of the digested peptide sample are desalted using the STageTip approach with six plugs of reversed phase C18 material (3M Empore C18). Peptides are loaded on the activated and equilibrated material and washed once using 0.1% FA/H$_2$O. Peptide are finally eluted using 60% ACN/H$_2$O and dried to completeness.
LC-MS/MS Analysis Peptides are re-hydrated in 50 μl 0.1% formic acid (FA) and 2 μl (=1 μg) are used for LC-MS/MS analysis in positive mode. All samples are measured on a QE Plus mass spectrometer online coupled to an UltiMate3000 LC system (both Thermo Fisher Scientific). A chromatographic gradient of 70 min is used with a 51 min gradient from 4 to 32% ACN (Loading Buffer: 0.1% FA/H$_2$O; Solvent A: 0.1% FA/H$_2$O, 5% DMSO; Solvent B: 0.1% FA/ACN, 5% DMSO). A PRM MS method is used with a cycle of one MS1 followed by 25 parallel-reaction monitoring (PRM) events. MS1 settings: 17.5K resolution, 3e6 ions, 10 ms maximum filling time, mass range 360-1300 m/z. PRM settings: 17.5K resolution, 1e6 ions, 110 ms maximum filling times, 1.7 Thompson isolation window. Retention times for the PRM inclusion list of 500 masses were derived beforehand from a datadependent acquisition of the QconCAT peptide mix (15N labelled; 20 ng; same 70 min gradient as for the PRM method) and are limited to a 5 min retention time window. General MS settings are as follows: 2.0 kV spray voltage, 275° C. capillary temperature and S-Lens RF Level 50.

.RAW files are analysed with the Skyline Software to reveal elution profiles of MS2 fragments. Ratios are calculated based on the heavy and light fragment elution profiles and absolute peptide amounts in the sample are calculated.
Data Analysis Using Skyline Software Definition of the isolation window for the signal peak of the unlabelled target peptide (light) and the 15N/labelled standard peptide (heavy);

calculation of the area under the curve (AUC) for the signal peaks of all fragments of the target peptide;

areas are corrected by a factor (Library.Dot.Product), representing the identity of the elution profile to the library spectrum;

calculation of ratio light/heavy, and calculation of amount of the target peptide, using the known amount of standard peptide.

Example

Quantification of signature peptide DGAGDVAFVK (SEQ ID NO.: 274) from target biomarker protein TRFE_HUMAN in urine sample no. 26

| | |
|---|---|
| total area light | 322194944 |
| total area heavy | 1536107 |
| Library.Dot.Product.light | 0.9858 |
| Library.Dot.Product.heavy | 0.6864 |

$$\text{Ratio light/heavy} = \frac{322194944*0.9858}{1536107*0.6864} = 301.24$$

Molecular Weight of standard: 70.3 kDa
Ratio standard/total protein: 1 ng standard/1 μg total protein
Amount of standard in sample: 1 ng/70300 ng/nmol=14.225 fmol Amount of target peptide in sample:
Light=301.24*heavy=4.29 pmol Result: 4.29 pmol peptide DGAGDVAFVK and therefore 4.29 pmol protein TRFE_HUMAN are quantified in 1 μg protein extract from urine sample no. 26.

Production of Artificial Proteins (QconCATs)

Five different artificial proteins of the invention comprising 41-68 signature peptides were produced using the QconCAT technology (QconCATs no. 1-5). The QconCATs are stable isotope labelled concatemers of the peptides. The peptides of each QconCAT represent 17 (QconCAT no. 1) or more (QconCATs no. 2-5) proteins selected from the group 1. Consecutive signature peptides are separated by a trypsin cleavage sequence.

The QconCATs were successfully used for protein quantification in urine samples by mass spectrometry.

The amino acid sequences of the QconCATs are as follows:

QconCAT no. 1:
(SEQ ID NO.: 941)
MAGRWSHPQFEKEGVNDNEEGFFSARDIVLVAHSALGTQRHIDSAYLYNNEEQ

VGLAIRELEGWEPDDDPIEEHKQFEELTLGEFLKLVDQNIFSFYLSRVSTLPAITLK

YSQAVPAVTEGPIPEVLKVFQEPLFYEAPRAVATVGPISVAIDAGHESFLFYKYSV

ANDTGFVDIPKAGLQVYNKFEHCNFNDVTIRTSFPEDTVITYKTTTPNAQATRVP

PTVQKPTTVNVPTTEVSPTSQKLLDIESQEELEDFPLPTVQRLAINLLAKSQPVSQ

PLTYESGPDEVREVGVGFATRNTEISFILGQEFDEVTADDRSTITLDGGVLVHVQ

KTAFYLAEFFVNEARYPVYGVQWHPEKAPAVAEENPKHLDSVLQQLQTEVYRH

EVTGWVLVSPLSKITVVDALHEIPVKLKPEDITQIQPQQLVLRLLVFSTDAGFHFA

GDGKLGVYELLLKSPEQQETVLDGNLIIRLNAENNATFYFKTVGSDTFYSFKALGF

EDATQALGRGLDLTEDTYKPRLADGGATNQGRQQQHLFGSDVTDCSGNFCLFR

DGAGDVAFVKQDFDITDISLLEHRDETHATYSNTLYLADEIIIRDWVSVVTPARGV

NDNEEGFFSARLAAALEHHHHHH

QconCAT no. 2:
(SEQ ID NO.: 942)
MAGRWSHPQFEKEGVNDNEEGFFSARYFIDFVARYNSQNQSNNQFVLYRAGQ

SPQLLIYTLSYRLEIPYTFGQGTKGHTLTLNFTRALQATVGNSYKFFLQGIQLNTIL

PDARGELFWDDGESLEVLERWGYSSTAITRSLEPFTLEILARIGLASALQPRDRP

FFAGLVKNIIHGSDSVESAEKAIPVAQDLNAPSDWDSRANDESNEHSDVIDSQEL

SKYPDAVATWLNPDPSQKIPLLSDLTHQISKVSVADHSLHLSKAQGFTEDTIVFLP

QTDKWFSAGLASNSSWLRAHAWPSPYKTNVNVFSELSAPRAEQWNVNYVETS

AKEDENVPFLLVGNKIQEVAGSLIFREIVDSYLPVILDIIKQEILAALEKFFESHVAR

WIQEYLEKTVEEAENIAVTSGVVREQANAVSEAVVSSVNTVATKELQELVQYPVE

HPDKLIVDEAINEDNSVVSLSQPKIELPTTVKTIVLQESIGKEVVLQHVRSSVAADV

ISLLLNGDGGVGRTIVTTLQDSIRGGVNDNFQGVLQNVRLTFDSSFSPNTGKVNN

SSLIGLGYTQTLKPGIIPSALDTDSSKSDLAVPSELALLKFAGVFHVEKDPDH

SEGSTTLLEGYTSHYPHTKYGFIEGHVVIPRLLQVVYLHSNNITKIQAIELEDLLRG

VNDNEEGFFSARLAAALEHHHHHH

QconCAT no. 3:
(SEQ ID NO.: 943)
MAGRWSHPQFEKEGVNDNEEGFFSARFNWYVDGVEVHNAKGPSVFPLAPSSK

TTPPVLDSDGSFFLYSKQLSFEEFIMLMARLTWASHEKVIEHIMEDLDTNADKLVL

-continued

PSLISSRAADLLLHSKTNVYISSSAGARITTVSLSAPDALKEDFTSLSLVLYSRYTF

ELSRTHLPEVFLSKEATDVIIIHSKSIQLPTTVRFSTEYELQQLEQFKALYLQYTDE

TFRGAYPLSIEPIGVRNNEGTYYSPNYNPQSRGIPGPVGAAGATGARGEPGNIG

FPGPKVLEDNSALDKLGTFEVEDQIEAARWEYYDSVYTERTLVLLMGKSTGGAP

TFNVTVTKVAAGAFQGLRGQTLLAVAKDLLLPQPDLRIDSLLENDRELDESLQVA

ERASSIIDELFQDRSLSQQIENIRGANGAPGIAGAPGFPGARFVTDGSVTASGFR

EQLANPIVSSGNSLFLRDFVEILDGGHEDAPLRIESSSLQGLGRNQVTPLDILSKIY

WVDLERQDGSVDFFRYGIDWASGRFADGDLDAVLSRAGLILFGNDDKDLGEAA

LNEYLRLGVYELLLKSPEQQETVLDGNLIIRFAHTVVTSRYSSDYFQAPSDYRIDIT

LSSVKELSEALGQIFDSQRFQTFEGDLKQSTLVLFPGDLRLGLGADVAQVTGALR

AAYEDFNVQLRAVTLSLDGGDTAIRYPDAVATWLNPDPSQKAIPVAQDLNAPSD

WDSRISHELDSASSEVNSAVTALWGKVNVDEVGGEALGRFFESFGDLSTPDAV

MGNPKGVNDNEEGFFSARLAAALEHHHHHH

QconCAT no. 4: (SEQ ID NO.: 944)

MAGRWSHPQFEKEGVNDNEEGFFSARSDVMYTDWKNWGLSFYADKPETTKE

HVAHLLFLRLQHLENELTHDIITKSVLGQLGITKITPNLAEFAFSLYRQGIPFFGQV

RNEDSLVFVQTDKLVHVEEPHTETVRDADPDTFFAKFTFEYSRIAPQLSTEELVS

LGEKGILAADESTGSIAKADDGRPFPQVIKVSFLSALEEYTKATEHLSTLSEKVQP

YLDDFQKLGEVNTYAGDLQKSLAPYAQDTQEKSELTQQLNALFQDKLGPLVEQG

RSELEEQLTPVAEETRAFDSDGDGRYSFLELRHDLGHFMLRSNLDEDIIAEENIV

SRIHWESASLLRTIYTPGSTVLYRTYFPHFDLSHGSAQVKVGAHAGEYGAEALER

MFLSFPTTKGDGPVQGIINFEQKLMEDLDRLQDAEIARDNENVVNEYSSELEKHQ

LYIDETVNSNIPTNLRIRPFFPQQIHLISTQSAIPYALRYEASILTHDSSIRQSGLYFI

KPLKTEVNVLPGAKIQPSGGTNINEALLRFYNQVSTPLLRIYVDDGLISLQVKLDID

SPPITARGADFLVTEVENGGSLGSKSADTLWGIQKVTLTSEEEARDLADELALVD

VIEDKSVDPDSPAEASGLRQGGLGPMNIPLVSDPKATAVMPDGQFKDISLSDYK

SLEVTFTPVIEDIGKELQVYISPKAGALNSNDAFVLKQTQVSVLPEGGETPLFKYIE

TDPANRDFADIPNLRLSLEIEQLELQREDVYVVGTVLRGYILVGQAKGVNDNEEG

FFSARLAAALEHHHHHH

QconCAT no. 5: (SEQ ID NO.: 945)

MWSHPQFEKEGVNDNEEGFFSARSASDLTWDNLKLLGNVLVCVLAHHFGKGEV

TYTTSQVSKYSLTYIYTGLSKHINPVAASLIQKLSITGTYDLKSSGPGGQNVNKEG

HFYYNISEVKILGATIENSREIPAWVPFDPAAQITKSFEDIHHYRAQGYSGLSVKG

LQTSQDARQIDNPDYKIVTATVNNSVLQKDYQPGITFIVVQKHAQAQYAYPGARN

HLVEIPPNLPSSLVELRLDHVVTIIKATWSGAVLAGRTGFSTSPESPYTHWKGTF

ATLSELHCDKLPDTPQGLLGEARDAPSWDPVALKLGELILTSESSRGPDVLTATV

SGKEALAENNLNLPKGDDLSTAILKLILYNDGDSLQYIERSVVAPATDGGLNLTST

FLRVELEVTLPGEGKEQYAVVGHSAHIVTLKDVSTPPTVLPDNFPRSVSCPLLSR

DGVVSVNKADGVPVYLKVEDAFYTLVREFTPPVQAAYQKVPVILVGNKFGSDDE

GRTQILEWAAERATYFGSIVLLSPAVIDSPLKIPFTFWARTELLPGDRFFNVLTTN

-continued

```
TDGKAGALQLLLVGDKGAYTQVIFLARGLPDQMLYREFLQSSLRHDSATDTIDIA

PNHRLYHSEAFTVNFGDTEEAKQILDQTSEINKLGNLFLNEDLEVKDSTIQVVENG

ESSQGRDYGVYLEDSGHTLRQVMNGFQNRLTSDSTVYDYAGKTHLAPYSDELR

LITEEANREGYYGYTGAFRDYVSQFEGSALGKATLYVTAIEDRGQNSLALHKESY

NVQLQLPARWEAEPVYVQRFESSEEQARAKPALEDLRSGVLSVSSGAAAHRLA

AALEHHHHHH
```

The individual peptides of the QconCATs are as follows (GluFib: Glu-1-Fibrinopeptide B):

| QconCAT no. 1: | | | |
|---|---|---|---|
| Peptide sequence | protein | description | SEQ ID NO. |
| MAGR | | Start | 935 |
| WSHPQFEK | | Tag | 936 |
| EGVNDNEEGFFSAR | | GluFib | 937 |
| DIVLVAHSALGTQR | AK1C4_HUMAN | | 20 |
| HIDSAYLYNNEEQVGLAIR | AK1C4_HUMAN | | 21 |
| ELEGWEPDDDPIEEHK | BIRC5_HUMAN | | 41 |
| QFEELTLGEFLK | BIRC5_HUMAN | | 42 |
| LVDQNIFSFYLSR | CATD_HUMAN | | 336 |
| VSTLPAITLK | CATD_HUMAN | | 337 |
| YSQAVPAVTEGPIPEVLK | CATD_HUMAN | | 335 |
| VFQEPLFYEAPR | CATL1_HUMAN | | 344 |
| AVATVGPISVAIDAGHESFLFYK | CATL1_HUMAN | | 343 |
| YSVANDTGFVDIPK | CATL1_HUMAN | | 345 |
| AGLQVYNK | CD59_HUMAN | | 350 |
| FEHCNFNDVTTR | CD59_HUMAN | | 351 |
| TSFPEDTVITYK | DAF_HUMAN | | 722 |
| TTTPNAQATR | DAF_HUMAN | | 723 |
| VPPTVQKPTTVNVPTTEVSPTSQK | DAF_HUMAN | | 724 |
| LLDIESQEELEDFPLPTVQR | ES8L2_HUMAN | | 110 |
| LAINLLAK | ES8L2_HUMAN | | 109 |
| SQPVSQPLTYESGPDEVR | ES8L2_HUMAN | | 111 |
| EVGVGFATR | FABP4_HUMAN | | 381 |
| NTEISFILGQEFDEVTADDR | FABP4_HUMAN | | 380 |
| STITLDGGVLVHVQK | FABP4_HUMAN | | 382 |
| TAFYLAEFFVNEAR | GGH_HUMAN | | 139 |
| YPVYGVQWHPEK | GGH_HUMAN | | 140 |
| APAVAEENPK | IBP6_HUMAN | | 411 |
| HLDSVLQQLQTEVYR | IBP6_HUMAN | | 412 |
| HEVTGWVLVSPLSK | IBP7_HUMAN | | 146 |

-continued

| Peptide sequence | protein | description | SEQ ID NO. |
|---|---|---|---|
| ITVVDALHEIPVK | IBP7_HUMAN | | 147 |
| LKPEDITQIQPQQLVLR | ITB1_HUMAN | | 771 |
| LLVFSTDAGFHFAGDGK | ITB1_HUMAN | | 773 |
| LGVYELLLK | ITIH4_HUMAN | | 161 |
| SPEQQETVLDGNLIIR | ITIH4_HUMAN | | 162 |
| LNAENNATFYFK | KNG1_HUMAN | | 167 |
| TVGSDTFYSFK | KNG1_HUMAN | | 168 |
| ALGFEDATQALGR | LG3BP_HUMAN | | 905 |
| GLDLTEDTYKPR | LG3BP_HUMAN | | 906 |
| LADGGATNQGR | LG3BP_HUMAN | | 186 |
| QQQHLFGSDVTDCSGNFCLFR | TRFE_HUMAN | | 907 |
| DGAGDVAFVK | TRFE_HUMAN | | 274 |
| QDFDITDISLLEHR | UROM_HUMAN | | 908 |
| DETHATYSNTLYLADEIIIR | UROM_HUMAN | | 909 |
| DWVSVVTPAR | UROM_HUMAN | | 280 |
| GVNDNEEGFFSAR | | GluFib 2 | 938 |
| LAAALEHHHHHH | | Tag 2 | 939 |

QconCAT no. 2:

| Peptide sequence | protein | description | SEQ ID NO. |
|---|---|---|---|
| MAGR | | Start | 935 |
| WSHPQFEK | | Tag | 936 |
| EGVNDNEEGFFSAR | | GluFib | 937 |
| YFIDFVAR | KNG1_HUMAN | | 169 |
| YNSQNQSNNQFVLYR | KNG1_HUMAN | | 170 |
| AGQSPQLLIYTLSYR | KV201_HUMAN | | 171 |
| LEIPYTFGQGTK | KV201_HUMAN | | 172 |
| GHTLTLNFTR | LAMP1_HUMAN | | 178 |
| ALQATVGNSYK | LAMPLHUMAN | | 176 |
| FFLQGIQLNTILPDAR | LAMP1_HUMAN | | 177 |
| GELFWDDGESLEVLER | LYAG_HUMAN | | 192 |
| WGYSSTAITR | LYAG_HUMAN | | 193 |
| SLEPFTLEILAR | MUC4_HUMAN | | 825 |
| IGLASALQPR | MUC_HUMAN | | 823 |
| DRPFFAGLVK | NDKA_HUMAN | | 910 |
| NIIHGSDSVESAEK | NDKA_HUMAN | | 828 |
| AIPVAQDLNAPSDWDSR | OSTP_HUMAN | | 202 |
| ANDESNEHSDVIDSQELSK | OSTP_HUMAN | | 203 |
| YPDAVATWLNPDPSQK | OSTP_HUMAN | | 204 |
| IPLLSDLTHQISK | PRDX4_HUMAN | | 525 |

-continued

| Peptide sequence | protein | | SEQ ID NO. |
|---|---|---|---|
| VSVADHSLHLSK | PRDX4_HUMAN | | 526 |
| AQGFTEDTIVFLPQTDK | PTGDS_HUMAN | | 537 |
| WFSAGLASNSSWLR | PTGDS_HUMAN | | 539 |
| AHAWPSPYK | RAI3_HUMAN | | 545 |
| TNVNVFSELSAPR | RAI3_HUMAN | | 546 |
| AEQWNVNYVETSAK | RALA_HUMAN | | 233 |
| EDENVPFLLVGNK | RALA_HUMAN | | 234 |
| IQEVAGSLIFR | RETN_HUMAN | | 255 |
| EIVDSYLPVILDIIK | SAP_HUMAN | | 870 |
| QEILAALEK | SAP_HUMAN | | 873 |
| FFESHVAR | SDF1_HUMAN | | 879 |
| WIQEYLEK | SDF1_HUMAN | | 881 |
| TVEEAENIAVTSGVVR | SYUG_HUMAN | | 584 |
| EQANAVSEAVVSSVNTVATK | SYUG_HUMAN | | 583 |
| ELQELVQYPVEHPDK | TERA_HUMAN | | 269 |
| LIVDEAINEDNSVVSLSQPK | TERA_HUMAN | | 271 |
| IELPTTVK | TGFR1_HUMAN | | 597 |
| TIVLQESIGK | TGFR1_HUMAN | | 884 |
| EVVLQHVR | TRBM_HUMAN | | 602 |
| SSVAADVISLLLNGDGGVGR | TRBM_HUMAN | | 603 |
| TIVTTLQDSIR | TSP1_HUMAN | | 278 |
| GGVNDNFQGVLQNVR | TSP1_HUMAN | | 277 |
| LTFDSSFSPNTGK | VDAC1_HUMAN | | 614 |
| VNNSSLIGLGYTQTLKPGIK | VDAC1_HUMAN | | 615 |
| AAIPSALDTDSSK | LG3BP_HUMAN | | 911 |
| SDLAVPSELALLK | LG3BP_HUMAN | | 187 |
| FAGVFHVEK | CD44_HUMAN | | 67 |
| DPDHSEGSTTLLEGYTSHYPHTK | CD44_HUMAN | | 912 |
| YGFIEGHWIPR | CD44_HUMAN | | 68 |
| LLQVVYLHSNNITK | PGS1_HUMAN | | 209 |
| IQAIELEDLLR | PGS1_HUMAN | | 208 |
| GVNDNEEGFFSAR | | GluFib 2 | 938 |
| LAAALEHHHHHH | | Tag 2 | 939 |

QconCAT no. 3:

| Peptide sequence | protein | description | SEQ ID NO. |
|---|---|---|---|
| MAGR | | Start | 935 |
| WSHPQFEK | | Tag | 936 |
| EGVNDNEEGFFSAR | | GluFib | 937 |
| FNWYVDGVEVHNAK | IGHG1_HUMAN | | 150 |

| | | |
|---|---|---|
| GPSVFPLAPSSK | IGHG1_HUMAN | 151 |
| TTPPVLDSDGSFFLYSK | IGHG1_HUMAN | 152 |
| QLSFEEFIMLMAR | S10A9_HUMAN | 569 |
| LTWASHEK | S10A9_HUMAN | 568 |
| VIEHIMEDLDTNADK | S10A9_HUMAN | 567 |
| LVLPSLISSR | SBP1_HUMAN | 877 |
| AADLLLHSK | SORL_HUMAN | 266 |
| TNVYISSSAGAR | SORL_HUMAN | 268 |
| ITTVSLSAPDALK | SORL_HUMAN | 267 |
| EDFTSLSLVLYSR | VTDB_HUMAN | 281 |
| YTFELSR | VTDB_HUMAN | 283 |
| THLPEVFLSK | VTDB_HUMAN | 282 |
| EATDVIIIHSK | AMPN_HUMAN | 24 |
| SIQLPTTVR | AMPN_HUMAN | 26 |
| FSTEYELQQLEQFK | AMPN_HUMAN | 25 |
| ALYLQYTDETFR | CERU_HUMAN | 70 |
| GAYPLSIEPIGVR | CERU_HUMAN | 71 |
| NNEGTYYSPNYNPQSR | CERU_HUMAN | 72 |
| GIPGPVGAAGATGAR | CO1A2_HUMAN | 78 |
| GEPGNIGFPGPK | CO1A2_HUMAN | 77 |
| VLEDNSALDK | DPP4_HUMAN | 103 |
| LGTFEVEDQIEAAR | DPP4_HUMAN | 102 |
| WEYYDSVYTER | DPP4_HUMAN | 104 |
| TLVLLMGK | PROF1_HUMAN | 532 |
| STGGAPTFNVTVTK | PROF1_HUMAN | 531 |
| VAAGAFQGLR | A2GL_HUMAN | 13 |
| GQTLLAVAK | A2GL_HUMAN | 12 |
| DLLLPQPDLR | A2GL_HUMAN | 11 |
| IDSLLENDR | CLUS_HUMAN | 75 |
| ELDESLQVAER | CLUS_HUMAN | 74 |
| ASSIIDELFQDR | CLUS_HUMAN | 73 |
| SLSQQIENIR | CO1A1_HUMAN | 356 |
| GANGAPGIAGAPGFPGAR | CO1A1_HUMAN | 355 |
| FVTDGSVTASGFR | CUBN_HUMAN | 88 |
| EQLANPIVSSGNSLFLR | CUBN_HUMAN | 87 |
| DFVEILDGGHEDAPLR | CUBN_HUMAN | 86 |
| IESSSLQGLGR | EGF_HUMAN | 105 |
| NQVTPLDILSK | EGF_HUMAN | 108 |
| IYWVDLER | EGF_HUMAN | 106 |
| QDGSVDFFR | FCN3_HUMAN | 112 |

-continued

| Peptide | Protein | SEQ ID NO. |
|---|---|---|
| YGIDWASGR | FCN3_HUMAN | 113 |
| FADGDLDAVLSR | AL1L1_HUMAN | 652 |
| AGLILFGNDDK | AL1L1_HUMAN | 649 |
| DLGEAALNEYLR | AL1L1_HUMAN | 651 |
| LGVYELLLK | ITIH4_HUMAN | 161 |
| SPEQQETVLDGNLIIR | ITIH4_HUMAN | 162 |
| FAHTVVTSR | ITIH4_HUMAN | 159 |
| YSSDYFQAPSDYR | LG3BP_HUMAN | 188 |
| IDITLSSVK | LG3BP_HUMAN | 185 |
| ELSEALGQIFDSQR | LG3BP_HUMAN | 184 |
| FQTFEGDLK | MMP9_HUMAN | 473 |
| QSTLVLFPGDLR | MMP9_HUMAN | 476 |
| LGLGADVAQVTGALR | MMP9_HUMAN | 474 |
| AAYEDFNVQLR | MUC5B_HUMAN | 195 |
| AVTLSLDGGDTAIR | MUC5B_HUMAN | 196 |
| YPDAVATWLNPDPSQK | OSTP_HUMAN | 204 |
| AIPVAQDLNAPSDWDSR | OSTP_HUMAN | 202 |
| ISHELDSASSEVNSAVTALWGK | HBB_HUMAN | 913 |
| VNVDEVGGEALGR | HBB_HUMAN | 399 |
| FFESFGDLSTPDAVMGNPK | HBB_HUMAN | 397 |
| GVNDNEEGFFSAR | | GluFib 2 | 938 |
| LAAALEHHHHHH | | Tag 2 | 939 |

QconCAT no. 4:

| Peptide sequence | protein | description | SEQ ID NO. |
|---|---|---|---|
| MAGR | | Start | 935 |
| WSHPQFEK | | Tag | 936 |
| EGVNDNEEGFFSAR | | GluFib | 937 |
| SDVMYTDWK | A1AG2_HUMAN | | 3 |
| NWGLSFYADKPETTK | A1AG2_HUMAN | | 2 |
| EHVAHLLFLR | A1AG2_HUMAN | | 1 |
| LQHLENELTHDIITK | A1AT_HUMAN | | 5 |
| SVLGQLGITK | A1AT_HUMAN | | 8 |
| ITPNLAEFAFSLYR | A1AT_HUMAN | | 4 |
| QGIPFFGQVR | A2MG_HUMAN | | 16 |
| NEDSLVFVQTDK | A2MG_HUMAN | | 15 |
| LVHVEEPHTETVR | A2MG_HUMAN | | 14 |
| DADPDTFFAK | AFAM_HUMAN | | 17 |
| FTFEYSR | AFAM_HUMAN | | 18 |
| IAPQLSTEELVSLGEK | AFAM_HUMAN | | 19 |

-continued

| | | |
|---|---|---|
| GILAADESTGSIAK | ALDOA_HUMAN | 23 |
| ADDGR | ALDOA_HUMAN | 914 |
| PFPQVIK | ALDOA_HUMAN | 915 |
| VSFLSALEEYTK | APOA1_HUMAN | 37 |
| ATEHLSTLSEK | APOA1_HUMAN | 31 |
| VQPYLDDFQK | APOA1_HUMAN | 36 |
| LGEVNTYAGDLQK | APOA4_HUMAN | 38 |
| SLAPYAQDTQEK | APOA4_HUMAN | 40 |
| SELTQQLNALFQDK | APOA4_HUMAN | 39 |
| LGPLVEQGR | APOE_HUMAN | 311 |
| SELEEQLTPVAEETR | APOE_HUMAN | 312 |
| AFDSDGDGR | EFC14_HUMAN | 445 |
| YSFLELR | EFC14_HUMAN | 446 |
| HDLGHFMLR | BLVRB_HUMAN | 317 |
| SNLDEDIIAEENIVSR | CO3_HUMAN | 80 |
| IHWESASLLR | CO3_HUMAN | 79 |
| TIYTPGSTVLYR | CO3_HUMAN | 81 |
| TYFPHFDLSHGSAQVK | HBA_HUMAN | 394 |
| VGAHAGEYGAEALER | HBA_HUMAN | 395 |
| MFLSFPTTK | HBA_HUMAN | 393 |
| GDGPVQGIINFEQK | SODC_HUMAN | 571 |
| LMEDLDR | S10A6_HUMAN | 264 |
| LQDAEIAR | S10A6_HUMAN | 265 |
| DNENVVNEYSSELEK | FIBB_HUMAN | 114 |
| HQLYIDETVNSNIPTNLR | FIBB_HUMAN | 115 |
| IRPFFPQQIHLISTQSAIPYALR | FIBG_HUMAN | 916 |
| YEASILTHDSSIR | FIBG_HUMAN | 119 |
| QSGLYFIKPLK | FIBG_HUMAN | 118 |
| TEVNVLPGAK | ITIH2_HUMAN | 158 |
| IQPSGGTNINEALLR | ITIH2_HUMAN | 157 |
| FYNQVSTPLLR | ITIH2_HUMAN | 156 |
| IYVDDGLISLQVK | KPYM_HUMAN | 793 |
| LDIDSPPITAR | KPYM_HUMAN | 795 |
| GADFLVTEVENGGSLGSK | KPYM_HUMAN | 792 |
| SADTLWGIQK | LDHA_HUMAN | 182 |
| VTLTSEEEAR | LDHA_HUMAN | 183 |
| DLADELALVDVIEDK | LDHA_HUMAN | 181 |
| SVDPDSPAEASGLR | NHRF1_HUMAN | 494 |
| QGGLGPMNIPLVSDPK | PRDX1_HUMAN | 520 |

-continued

| Peptide sequence | protein | | SEQ ID NO. |
|---|---|---|---|
| ATAVMPDGQFK | PRDX1_HUMAN | | 519 |
| DISLSDYK | PRDX1_HUMAN | | 517 |
| SLEVTFTPV1EDIGK | VCAM1_HUMAN | | 898 |
| ELQVYISPK | VCAM1_HUMAN | | 894 |
| AGALNSNDAFVLK | GELS_HUMAN | | 135 |
| QTQVSVLPEGGETPLFK | GELS_HUMAN | | 136 |
| YIETDPANR | GELS_HUMAN | | 137 |
| DFADIPNLR | MIME_HUMAN | | 194 |
| LSLE1EQLELQR | C4BPA_HUMAN | | 45 |
| EDVYVVGTVLR | C4BPA_HUMAN | | 43 |
| GYILVGQAK | C4BPA_HUMAN | | 44 |
| GVNDNEEGFFSAR | | GluFib 2 | 938 |
| LAAALEHHHHHH | | Tag 2 | 939 |

QconCAT no. 5:

| Peptide sequence | protein | description | SEQ ID NO. |
|---|---|---|---|
| MWSHPQFEK | | Start/Tag | 940 |
| EGVNDNEEGFFSAR | | GluFib | 937 |
| SASDLTWDNLK | TRFE_HUMAN | | 276 |
| LLGNVLVCVLAHHFGK | HBB_HUMAN | | 917 |
| GEVTYTTSQVSK | EGLN_HUMAN | | 730 |
| YSLTYIYTGLSK | ZA2G_HUMAN | | 286 |
| HINPVAASLIQK | PLK1_HUMAN | | 509 |
| LSITGTYDLK | A1AT_HUMAN | | 6 |
| SSGPGGQNVNK | ICT1_HUMAN | | 421 |
| EGHFYYNISEVK | PLTP_HUMAN | | 226 |
| ILGATIENSR | K1C19_HUMAN | | 164 |
| EIPAWVPFDPAAQITK | ZA2G_HUMAN | | 284 |
| SFEDIHHYR | RASK_HUMAN | | 236 |
| AQGYSGLSVK | TSP1_HUMAN | | 918 |
| GLQTSQDAR | CALR_HUMAN | | 46 |
| QIDNPDYK | CALR_HUMAN | | 47 |
| IVTATVNNSVLQK | ANGP2_HUMAN | | 28 |
| DYQPGITFIVVQK | AGO2_HUMAN | | 644 |
| HAQAQYAYPGAR | NID2_HUMAN | | 201 |
| NHLVEIPPNLPSSLVELR | PGS1_HUMAN | | 210 |
| LDHWTIIK | ANM1_HUMAN | | 671 |
| ATWSGAVLAGR | A1BG_HUMAN | | 9 |
| TGFSTSPESPYTHWK | ANM1_HUMAN | | 673 |
| GTFATLSELHCDK | HBB_HUMAN | | 401 |

| | | |
|---|---|---|
| LPDTPQGLLGEAR | EGLN_HUMAN | 732 |
| DAPSWDPVALK | LAMA4_HUMAN | 173 |
| LGELILTSESSR | ICT1_HUMAN | 417 |
| GPDVLTATVSGK | ITIH4_HUMAN | 160 |
| EALAENNLNLPK | IL6_HUMAN | 423 |
| GDDLSTAILK | TERA_HUMAN | 270 |
| LILYNDGDSLQYIER | PLK1_HUMAN | 511 |
| SVVAPATDGGLNLTSTFLR | PTGDS_HUMAN | 538 |
| VELEVTLPGEGK | AGO2_HUMAN | 647 |
| EQYAVVGHSAHIVTLK | ATRN_HUMAN | 675 |
| DVSTPPTVLPDNFPR | IGF2_HUMAN | 149 |
| SVSCPLLSR | ES8L2_HUMAN | 919 |
| DGVVSVNK | NID2_HUMAN | 199 |
| ADGVPVYLK | COX7R_HUMAN | 83 |
| VEDAFYTLVR | RASK_HUMAN | 237 |
| EFTPPVQAAYQK | HBB_HUMAN | 400 |
| VPVILVGNK | RAP2A_HUMAN | 553 |
| FGSDDEGR | PTHR_HUMAN | 920 |
| TQILEWAAER | EGLN_HUMAN | 734 |
| ATYFGSIVLLSPAVIDSPLK | PLTP_HUMAN | 225 |
| IPFTFWAR | MAGD1_HUMAN | 921 |
| TELLPGDR | IBP7_HUMAN | 148 |
| FFNVLTTNTDGK | GGH_HUMAN | 138 |
| AGALQLLLVGDK | PLTP_HUMAN | 224 |
| GAYTQVIFLAR | LYAG_HUMAN | 191 |
| GLPDQMLYR | COX7R_HUMAN | 84 |
| EFLQSSLR | IL6_HUMAN | 424 |
| HDSATDTIDIAPNHR | TGFR1_HUMAN | 883 |
| LYHSEAFTVNFGDTEEAK | A1AT_HUMAN | 7 |
| QILDQTSEINK | ANGP2_HUMAN | 29 |
| LGNLFLNEDLEVK | PLK1_HUMAN | 510 |
| DSTIQWENGESSQGR | UROM_HUMAN | 279 |
| DYGVYLEDSGHTLR | PRDX4_HUMAN | 524 |
| QVMNGFQNR | CATL1_HUMAN | 342 |
| LTSDSTVYDYAGK | COX7R_HUMAN | 85 |
| THLAPYSDELR | APOA1_HUMAN | 35 |
| LITEEANR | LAMA4_HUMAN | 174 |
| EGYYGYTGAFR | TRFE_HUMAN | 275 |
| DYVSQFEGSALGK | APOA1_HUMAN | 32 |
| ATLYVTAIEDR | ANM1_HUMAN | 668 |

-continued

| | | |
|---|---|---|
| GQNSLALHK | RALA_HUMAN | 235 |
| ESYNVQLQLPAR | NID2_HUMAN | 200 |
| WEAEPVYVQR | ZA2G_HUMAN | 285 |
| FESSEEQAR | IL6_HUMAN | 425 |
| AKPALEDLR | APOA1_HUMAN | 30 |
| SGVLSVSSGAAAHR | LAMA4_HUMAN | 175 |
| LAAALEHHHHHH | Tag 2 | 939 |

Results

Table 9 shows the protein concentrations determined in the protein extracts of urine samples of a healthy individual, a bladder cancer stage I patient and a bladder cancer stage IV patient. Protein concentrations are given in pmol/100 μg protein extract. Protein concentrations were determined by mass spectrometry using a mixture of the five QconCATs described above (n.d. not determined).

TABLE 9

| Protein | Protein concentration in pmol/100 μg in a healthy individual | Protein concentration in pmol/100 μg in a bladder cancer stage I patient | Protein concentration in pmol/100 μg in a bladder cancer stage IV patient |
|---|---|---|---|
| A1AG2_HUMAN | 32.9333709981 | 40.2419585700 | n.d. |
| A1BG_HUMAN | 5.4300756781 | 8.2478876530 | 3.5494450482 |
| A2GL_HUMAN | n.d. | 6.6308014470 | n.d. |
| AFAM_HUMAN | 1.0704331450 | n.d. | n.d. |
| ALDOA_HUMAN | 0.1350282486 | 0.5948022600 | 2.6794350282 |
| AMPN_HUMAN | 1.3382448125 | 2.8640776700 | n.d. |
| APOA4_HUMAN | 3.5590207156 | 0.4228248590 | 0.7482485876 |
| CD44_HUMAN | n.d. | 55.8797957300 | n.d. |
| CO3_HUMAN | 0.9498681733 | 0.8812052730 | 5.8175141243 |
| DPP4_HUMAN | n.d. | 2.9388920620 | n.d. |
| FIBB_HUMAN | n.d. | 1.6040112990 | n.d. |
| FIBG_HUMAN | n.d. | 1.1130427420 | 17.4795029163 |
| GGH_HUMAN | n.d. | 2.1542453020 | n.d. |
| IBP4_HUMAN | n.d. | n.d. | 1.8208829622 |
| IBP7_HUMAN | n.d. | 6.1584879520 | n.d. |
| ITIH2_HUMAN | 0.3296045198 | 0.4775517890 | 5.3120903955 |
| ITIH4_HUMAN | 0.3155003128 | n.d. | 1.9801342793 |
| KLK3_HUMAN | 0.7399663387 | n.d. | n.d. |
| KNG1_HUMAN | n.d. | n.d. | 19.8805503922 |
| KV201_HUMAN | 0.0233730522 | n.d. | n.d. |
| LAMP2_HUMAN | 0.1700543760 | 0.2623640600 | 0.1898627654 |
| LG3BP_HUMAN | n.d. | 13.4090507700 | 11.6313337187 |
| LYAG_HUMAN | 11.7670180096 | 6.3247095550 | 5.6678066571 |
| MUC5B_HUMAN | n.d. | 0.0081096516 | 0.4245573958 |
| PDGFA_HUMAN | n.d. | n.d. | 0.2016182081 |
| RETN_HUMAN | 8.9842949136 | 4.0934370080 | 8.8979530460 |
| S10A6_HUMAN | 6.9236723164 | 5.9683615820 | n.d. |
| S10A9_HUMAN | n.d. | 11.5546925600 | 6.5590329336 |
| SORL_HUMAN | 0.2615077099 | 0.1739577380 | n.d. |
| SYUG_HUMAN | n.d. | n.d. | 1.0587272489 |
| TRFE_HUMAN | 19.2983897929 | 51.6616285800 | 44.8804274861 |
| TSP1_HUMAN | n.d. | 0.1073136310 | n.d. |
| UROM_HUMAN | 305.6265623630 | 79.3431623700 | 32.4471083566 |
| ZA2G_HUMAN | 100.6877499091 | 53.0432206500 | 34.0504180298 |

REFERENCES

Abbatiello, S. E.; Mani, D. R.; Keshishian, H.; Carr, S. A., Clin Chem 2010, 56, (2), 291-305.

Babjuk, M.; Oosterlinck, W.; Sylvester, R.; Kaasinen, E.; Bohle, A.; Palou-Redorta, J.; European Association of Urology (EAU), Eur Urol 2008, 54, (2), 303-14.

Carr, S. A.; Abbatiello, S. E.; Ackermann, B. L.; Borchers, C.; Domon, B.; Deutsch, E. W.; Grant, R. P.; Hoofnagle, A. N.; Huttenhain, R.; Koomen, J. M.; Liebler, D. C.; Liu, T.; Maclean, B.; Mani, D. R.; Mansfield, E.; Neubert, H.; Paulovich, A. G.; Reiter, L.; Vitek, O.; Aebersold, R.; Anderson, L.; Bethem, R.; Blonder, J.; Boja, E.; Botelho, J.; Boyne, M.; Bradshaw, R. A.; Burlingame, A. L.; Chan, D.; Keshishian, H.; Kuhn, E.; Kinsinger, C.; Lee, J. S.; Lee, S. W.; Moritz, R.; OsesPrieto, J.; Rifai, N.; Ritchie, J.; Rodriguez, H.; Srinivas, P. R.; Townsend, R. R.; Van Eyk, J.; Whiteley, G.; Wiita, A.; Weintraub, S., Mol Cell Proteomics 2014, 13, (3), 907-17.

Cham Mead, J. A.; Bianco, L.; Bessant, C., Proteomics 2010, 10, (6), 1106-26.

Chen, Y. T.; Chen, H. W.; Domanski, D.; Smith, D. S.; Liang, K. H.; Wu, C. C.; Chen, C. L.; Chung, T.; Chen, M. C.; Chang, Y. S.; Parker, C. E.; Borchers, C. H.; Yu, J. S., J Proteomics 2012, 75, (12), 3529-45.

Court, M.; Selevsek, N.; Matondo, M.; Allory, Y.; Garin, J.; Masselon, C. D.; Domon, B., Proteomics 2011, 11, (6), 1160-71.

Guzman-Rojas, L.; Rangel, R.; Salameh, A.; Edwards, J. K.; Dondossola, E.; Kim, Y. G.; Saghatelian, A.; Giordano, R. J.; Kolonin, M. G.; Staquicini, F. I.; Koivunen, E.; Sidman, R. L.; Arap, W.; Pasqualini, R., Proc Natl Acad Sci USA 2012, 109, (5), 1637-42.

Holman S. W.; Sims P. F.; Eyers C. E., Bioanalysis 2012, 4, (14), 1763-86.

Jebar, A. H.; Hurst, C. D.; Tomlinson, D. C.; Johnston, C.; Taylor, C. F.; Knowles, M. A., Oncogene 2005, 24, (33), 5218-25.

Jensen, S. S.; Aaberg-Jessen, C.; Christensen, K. G.; Kristensen, B., Int J Clin Exp Pathol 2013, 6, (7), 1294-305.

Kageyama, S.; Isono, T.; Iwaki, H.; Wakabayashi, Y.; Okada, Y.; Kontani, K.; Yoshimura, K.; Terai, A.; Arai, Y.; Yoshiki, T., Clin Chem 2004, 50, (5), 857-66.

Kalantari, S.; Rutishauser, D.; Samavat, S.; Nafar, M.; Mahmudieh, L.; RezaeiTavirani, M.; Zubarev, R. A., PLoS One 2013, 8, (12), e80830.

Miyata, Y.; Sakai, H., Int J Mol Sci 2013, 14, (6), 12249-72.

Ostergaard, M.; Rasmussen, H. H.; Nielsen, H. V.; Vorum, H.; Orntoft, T. F.; Wolf, H.; Celis, J. E., Cancer Res 1997, 57, (18), 4111-7.

Peterson A. C.; Russell J. D.; Bailey D. J.; Westphall M. S.; Coon J. J., Mol Cell Proteomics 2012, 11, (11), 1475-88.

Pratt J. M.; Simpson D. M.; Doherty M. K.; Rivers J.; Gaskell S. J.; Beynon R. J., Nat Protoc 2006, 1, (2), 1029-43.

Welsch, T.; Endlich, K.; Giese, T.; Buchler, M. W.; Schmidt, J., Cancer Lett 2007, 255, (2), 205-18.

Zhao Y.; Brasier A. R., Methods 2013, 61, (3), 313-22.

The invention claimed is:

1. An artificial protein comprising at least 10 signature peptides representing at least 10 proteins selected from the group consisting of
- A1AT_HUMAN (Alpha-1-antitrypsin)
- A2MG_HUMAN (Alpha-2-macroglobulin)
- ALDOA_HUMAN (Fructose-bisphosphate aldolase A)
- DPP4_HUMAN (Dipeptidyl peptidase 4)
- EGF_HUMAN (Pro-epidermal growth factor)
- ITIH2_HUMAN (Inter-alpha-trypsin inhibitor heavy chain H2)
- LG3BP_HUMAN (Galectin-3-binding protein)
- PIP_HUMAN (Prolactin-inducible protein)
- SORL_HUMAN (Sortilin-related receptor)
- TRFE_HUMAN (Serotransferrin)
- VTDB_HUMAN (Vitamin D-binding protein)
- ES8L2_HUMAN (Epidermal growth factor receptor kinase substrate 8-like protein 2)
- HBA_HUMAN (Hemoglobin subunit alpha)
- HBB_HUMAN (Hemoglobin subunit beta)
- HPT_HUMAN (Haptoglobin)
- K1C17_HUMAN (Keratin, type I cytoskeletal 17)
- PRDX4_HUMAN (Peroxiredoxin-4)
- RAI3_HUMAN (Retinoic acid-induced protein 3)
- RAP2A_HUMAN (Ras-related protein Rap-2a) and
- RAP2B_HUMAN (Ras-related protein Rap-2b), wherein the signature peptides consist of sequences selected from the group consisting of:
ITPNLAEFAFSLYR (SEQ ID NO: 4, representing A1AT_HUMAN), LQHLENELTHDIITK (SEQ ID NO: 5, representing A1AT_HUMAN),
LSITGTYDLK (SEQ ID NO: 6, representing A1AT_HUMAN),
SVLGQLGITK (SEQ ID NO: 8, representing A1AT_HUMAN),
LVHVEEPHTETVR (SEQ ID NO: 14, representing A2MG_HUMAN),
NEDSLVFVQTDK (SEQ ID NO: 15, representing A2MG_HUMAN),
QGIPFFGQVR (SEQ ID NO: 16, representing A2MG_HUMAN),
GILAADESTGSIAK (SEQ ID NO: 23, representing ALDOA_HUMAN),
VLEDNSALDK (SEQ ID NO: 103, representing DPP4_HUMAN),
WEYYDSVYTER (SEQ ID NO: 104, representing DPP4_HUMAN),
IESSSLQGLGR (SEQ ID NO: 105, representing EGF_HUMAN),
IYWVDLER (SEQ ID NO: 106, representing EGF_HUMAN),
LFWIQYNR (SEQ ID NO: 107, representing EGF_HUMAN),
FYNQVSTPLLR (SEQ ID NO: 156, representing ITIH2_HUMAN),
IQPSGGTNINEALLR (SEQ ID NO: 157, representing ITIH2_HUMAN),
TEVNVLPGAK (SEQ ID NO: 158, representing ITIH2_HUMAN),
ELSEALGQIFDSQR (SEQ ID NO: 184, representing LG3BP_HUMAN),
SDLAVPSELALLK (SEQ ID NO: 187, representing LG3BP_HUMAN),
ELGICPDDAAVIPIK (SEQ ID NO: 212, representing PIP_HUMAN),
TFYWDFYTNR (SEQ ID NO: 220, representing PIP_HUMAN),
TVQIAAVVDVIR (SEQ ID NO: 221, representing PIP_HUMAN),
TYLISSIPLQGAFNYK (SEQ ID NO: 222, representing PIP_HUMAN),
YTACLCDDNPK (SEQ ID NO: 223, representing PIP_HUMAN),
AADLLLHSK (SEQ ID NO: 266, representing SORL_HUMAN),
TNVYISSSAGAR (SEQ ID NO: 268, representing SORL_HUMAN),
SASDLTWDNLK (SEQ ID NO: 276, representing TRFE_HUMAN),
THLPEVFLSK (SEQ ID NO: 282, representing VTDB_HUMAN),
VGPQVPLSEPGFR (SEQ ID NO: 379, representing ES8L2_HUMAN)
MFLSFPTTK (SEQ ID NO: 393, representing HBA_HUMAN),
TYFPHFDLSHGSAQVK (SEQ ID NO: 394, representing HBA_HUMAN),
VGAHAGEYGAEALER (SEQ ID NO: 395, representing HBA_HUMAN),
FLASVSTVLTSK (SEQ ID NO: 396, representing HBA_HUMAN),
SAVTALWGK (SEQ ID NO: 398, representing HBB_HUMAN),
VNVDEVGGEALGR (SEQ ID NO: 399, representing HBB_HUMAN),
EFTPPVQAAYQK (SEQ ID NO: 400, representing HBB_HUMAN),
VGYVSGWGR (SEQ ID NO: 402, representing HPT_HUMAN),
VTSIQDWVQK (SEQ ID NO: 403, representing HPT_HUMAN),
VVLHPNYSQVDIGLIK (SEQ ID NO: 404, representing HPT_HUMAN),
DYAEVGR (SEQ ID NO: 405, representing HPT_HUMAN),
VQFELHYQEVK (SEQ ID NO: 444, representing ITIH2_HUMAN),
ALEEANTELEVK (SEQ ID NO: 451, representing K1C17_HUMAN),
TIEELQNK (SEQ ID NO: 453, representing K1C17_HUMAN),
DYGVYLEDSGHTLR (SEQ ID NO: 524, representing PRDX4_HUMAN),
IPLLSDLTHQISK (SEQ ID NO: 525, representing PRDX4_HUMAN),
VSVADHSLHLSK (SEQ ID NO: 526, representing PRDX4_HUMAN)
QITLNDLPVGR (SEQ ID NO: 528, representing PRDX4_HUMAN),
AHAWPSPYK (SEQ ID NO: 545, representing RAI3_HUMAN),
TNVNVFSELSAPR (SEQ ID NO: 546, representing RAI3_HUMAN),
VPVILVGNK (SEQ ID NO: 553, representing RAP2A_HUMAN),
ASVDELFAEIVR (SEQ ID NO: 556, representing RAP2B_HUMAN),
ASNLLLGFDR (SEQ ID NO: 575, representing SORL_HUMAN),
LLGNVLVCVLAHHFGK (SEQ ID NO: 917, representing HBB_HUMAN), and
SVSCPLLSR (SEQ ID NO: 919, representing ES8L2_HUMAN), and
wherein each signature peptide represents a single protein.

2. The artificial protein of claim 1, wherein the artificial protein comprises each signature peptide in a stoichiometry of 1:1.

3. An artificial protein comprising at least 10 signature peptides,
wherein the signature peptides consist of sequences selected from the group consisting of:

```
                                    (SEQ ID NO: 4)
          ITPNLAEFAFSLYR, (SEQ ID NO: 5)
          LQHLENELTHDIITK, (SEQ ID NO: 6)
          LSITGTYDLK, (SEQ ID NO: 8)
          SVLGQLGITK, (SEQ ID NO: 14)
          LVHVEEPHTETVR, (SEQ ID NO: 15)
          NEDSLVFVQTDK, (SEQ ID NO: 16)
          QGIPFFGQVR,
```

-continued

GILAADESTGSIAK, (SEQ ID NO: 23)

VLEDNSALDK, (SEQ ID NO: 103)

WEYYDSVYTER, (SEQ ID NO: 104)

IESSSLQGLGR, (SEQ ID NO: 105)

IYWVDLER, (SEQ ID NO: 106)

LFWIQYNR, (SEQ ID NO: 107)

FYNQVSTPLLR, (SEQ ID NO: 156)

IQPSGGTNINEALLR, (SEQ ID NO:m157)

TEVNVLPGAK, (SEQ ID NO: 158)

ELSEALGQIFDSQR, (SEQ ID NO: 184)

SDLAVPSELALLK, (SEQ ID NO: 187)

ELGICPDDAAVIPIK, (SEQ ID NO: 212)

TFYWDFYTNR, (SEQ ID NO: 220)

TVQIAAVVDVIR, (SEQ ID NO: 221)

TYLISSIPLQGAFNYK, (SEQ ID NO: 222)

YTACLCDDNPK, (SEQ ID NO: 223)

AADLLLHSK, (SEQ ID NO: 266)

TNVYISSSAGAR, (SEQ ID NO: 268)

SASDLTWDNLK, (SEQ ID NO: 276)

THLPEVFLSK, (SEQ ID NO: 282)

VGPQVPLSEPGFR (SEQ ID NO: 379)

MFLSFPTTK, (SEQ ID NO: 393)

TYFPHFDLSHGSAQVK, (SEQ ID NO: 394)

-continued

VGAHAGEYGAEALER, (SEQ ID NO: 395)

FLASVSTVLTSK, (SEQ ID NO: 396)

SAVTALWGK, (SEQ ID NO: 398)

VNVDEVGGEALGR, (SEQ ID NO: 399)

EFTPPVQAAYQK, (SEQ ID NO: 400)

VGYVSGWGR, (SEQ ID NO: 402)

VTSIQDWVQK, (SEQ ID NO: 403)

VVLHPNYSQVDIGLIK (SEQ ID NO: 404)

DYAEVGR, (SEQ ID NO: 405)

VQFELHYQEVK, (SEQ ID NO: 444)

ALEEANTELEVK, (SEQ ID NO: 451)

TIEELQNK, (SEQ ID NO: 453)

DYGVYLEDSGHTLR, (SEQ ID NO: 524)

IPLLSDLTHQISK, (SEQ ID NO: 525)

VSVADHSLHLSK (SEQ ID NO: 526)

QITLNDLPVGR, (SEQ ID NO: 528)

AHAWPSPYK, (SEQ ID NO: 545)

TNVNVFSELSAPR, (SEQ ID NO: 546)

VPVILVGNK, (SEQ ID NO: 553)

ASVDELFAEIVR, (SEQ ID NO: 556)

ASNLLLGFDR, (SEQ ID NO: 575)

LLGNVLVCVLAHHFG , and (SEQ ID NO: 917)

SVSCPLLSR. (SEQ ID NO: 919)

\* \* \* \* \*